US012797542B2

(12) United States Patent
Pikan et al.

(10) Patent No.: US 12,797,542 B2
(45) **Date of Patent: *Nov. 17, 2026**

(54) MULTIPLE USE COMPUTERIZED INJECTOR

(71) Applicant: E3D A.C.A.L., Merom Hagalil (IL)

(72) Inventors: Tal Pikan, Upper Galilee (IL); Menachem Zucker, Haifa (IL); Michael Segev, Lower Galilee (IL)

(73) Assignee: E3D AGRICULTURAL COOPERATIVE ASSOCIATION LTD., Merom Hagalil (IL)

( * ) Notice: Subject to any disclaimer, the term of this patent is extended or adjusted under 35 U.S.C. 154(b) by 840 days.

This patent is subject to a terminal disclaimer.

(21) Appl. No.: 18/089,942

(22) Filed: Dec. 28, 2022

(65) Prior Publication Data

US 2023/0201460 A1 Jun. 29, 2023

Related U.S. Application Data

(63) Continuation of application No. 16/307,049, filed as application No. PCT/IL2017/050607 on Jun. 1, 2017, now Pat. No. 11,571,516.
(Continued)

(51) Int. Cl.
*A61M 5/20* (2006.01)
*A61B 34/10* (2016.01)
(Continued)

(52) U.S. Cl.
CPC ............... *A61M 5/20* (2013.01); *A61B 34/10* (2016.02); *A61M 5/3146* (2013.01);
(Continued)

(58) Field of Classification Search
CPC .. A61M 5/20; A61M 5/3146; A61M 5/31546; A61M 5/31578; A61M 5/31593;
(Continued)

(56) References Cited

U.S. PATENT DOCUMENTS 5,868,710 A 2/1999 Battiato
7,621,893 B2 11/2009 Moberg
(Continued)

FOREIGN PATENT DOCUMENTS

EP 1240913 B1 12/2004
EP 1998751 A2 12/2008
(Continued)

*Primary Examiner* — Tasnim Mehjabin Ahmed
(74) *Attorney, Agent, or Firm* — Sughrue Mion, PLLC

(57) ABSTRACT

A computer-controlled injector for use with a medicament cartridge and including a housing having a medicament cartridge receiving volume and a medicament cartridge insertion and removal opening communicating with the medicament cartridge receiving volume; a pivot mount element mounted onto the housing for selectably enabling access to the medicament cartridge receiving volume via the opening; a mechanical latch selectably locking the pivot mount element in a closed operative orientation; and an injection drive mechanism including a computer-controlled motor for driving a piston, forming part of the medicament cartridge, for injecting a medicament, the computer-controlled motor also being operative for operating the mechanical latch.

20 Claims, 113 Drawing Sheets

Related U.S. Application Data

(60) Provisional application No. 62/345,897, filed on Jun. 6, 2016.

(51) Int. Cl.

| | |
|---|---|
| ***A61M 5/31*** | (2006.01) |
| ***A61M 5/315*** | (2006.01) |
| ***A61M 5/48*** | (2006.01) |
| *A61B 34/20* | (2016.01) |
| *A61M 5/24* | (2006.01) |

(52) U.S. Cl.

CPC .... *A61M 5/31546* (2013.01); *A61M 5/31578* (2013.01); *A61M 5/31593* (2013.01); *A61M 5/482* (2013.01); *A61B 2034/2048* (2016.02); *A61M 2005/2414* (2013.01); *A61M 2005/244* (2013.01); *A61M 2005/3125* (2013.01); *A61M 2005/31588* (2013.01); *A61M 2205/14* (2013.01); *A61M 2205/3569* (2013.01); *A61M 2205/50* (2013.01); *A61M 2205/581* (2013.01); *A61M 2205/8206* (2013.01)

(58) Field of Classification Search

CPC .......... A61M 5/482; A61M 2005/2414; A61M 2005/244; A61M 2005/3125; A61M 2005/31588; A61M 2205/14; A61M 2205/3569; A61M 2205/50; A61M 2205/581; A61M 2205/8206; A61B 34/10; A61B 2034/2048

See application file for complete search history.

(56) References Cited

U.S. PATENT DOCUMENTS

| | | | |
|---|---|---|---|
| 7,704,231 | B2 | 4/2010 | Pongpairochana et al. |
| 7,749,194 | B2 | 7/2010 | Edwards |
| 7,766,873 | B2 | 8/2010 | Mobeg |
| 7,922,699 | B2 | 4/2011 | Baba et al. |
| 7,967,784 | B2 | 6/2011 | Pongpairochana |
| 8,206,360 | B2 | 6/2012 | Edwards |
| 8,287,500 | B2 | 10/2012 | Baba et al. |
| 8,361,026 | B2 | 1/2013 | Edwards |
| 8,376,985 | B2 | 2/2013 | Pongpairochana et al. |
| 8,544,645 | B2 | 10/2013 | Edwards |
| 8,622,973 | B2 | 1/2014 | Edwards et al. |
| 8,690,827 | B2 | 4/2014 | Edwards et al. |
| 8,870,827 | B2 | 10/2014 | Young et al. |
| 8,920,374 | B2 | 12/2014 | Bokelman et al. |
| 8,926,594 | B2 | 1/2015 | Edwards |
| 8,932,252 | B2 | 1/2015 | Edwards et al. |
| 8,974,413 | B2 | 3/2015 | Baba |
| 9,022,980 | B2 | 5/2015 | Edwards et al. |
| 9,024,768 | B2 | 5/2015 | Mandro et al. |
| 9,063,552 | B2 | 6/2015 | Gaudet |
| 9,149,579 | B2 | 10/2015 | Edwards |
| 9,155,835 | B2 | 10/2015 | Watanabe et al. |
| 9,192,728 | B2 | 11/2015 | Gilmore |
| 9,238,108 | B2 | 1/2016 | Edwards |
| 9,278,177 | B2 | 3/2016 | Edwards |
| 9,297,370 | B2 | 3/2016 | Ulrich |
| 9,381,300 | B2 | 7/2016 | Smith |
| 9,474,857 | B2 | 10/2016 | Riley |
| 9,492,618 | B2 | 11/2016 | Day |
| 9,504,793 | B2 | 11/2016 | Eggert |
| 9,514,131 | B1 | 12/2016 | Bochenko |
| 9,572,932 | B2 | 2/2017 | Eggert |
| 9,579,459 | B2 | 2/2017 | Jennings et al. |
| 9,750,875 | B2 | 9/2017 | Smith et al. |
| 9,805,620 | B2 | 10/2017 | Edwards et al. |
| 9,867,938 | B2 | 1/2018 | Edwards et al. |
| 9,956,343 | B2 | 5/2018 | Murakami et al. |
| 10,052,442 | B2 | 8/2018 | Watanabe et al. |
| 10,463,800 | B2 | 11/2019 | Baba et al. |
| 10,695,506 | B2 | 6/2020 | Shultz |
| 10,796,604 | B2 | 10/2020 | Edwards et al. |
| 11,090,435 | B2 | 8/2021 | Day et al. |
| 11,213,626 | B2 | 1/2022 | Paramanandam et al. |
| 11,571,516 | B2 * | 2/2023 | Pikan ................ A61M 5/31546 |
| 2004/0024364 | A1 | 2/2004 | Langley |
| 2005/0182323 | A1 | 8/2005 | Grispo |
| 2012/0116311 | A1 | 5/2012 | Ulrich |
| 2012/0203178 | A1 | 8/2012 | Tverskoy |
| 2013/0184649 | A1 | 7/2013 | Edwards |
| 2014/0012229 | A1 | 1/2014 | Marlin |
| 2014/0142544 | A1 | 5/2014 | Atterbury |
| 2014/0155827 | A1 | 6/2014 | Ostrander |
| 2014/0249412 | A1 | 9/2014 | Yamamoto |
| 2014/0276414 | A1 | 9/2014 | Baker |
| 2014/0296824 | A1 | 10/2014 | Edwards |
| 2014/0379874 | A1 | 12/2014 | Starr |
| 2015/0011973 | A1 | 1/2015 | Edwards |
| 2015/0051580 | A1 | 2/2015 | Shain |
| 2015/0078536 | A1 | 3/2015 | Denny |
| 2015/0105903 | A1 | 4/2015 | Denny |
| 2015/0133855 | A1 | 5/2015 | Smith |
| 2015/0157803 | A1 | 6/2015 | Radmer |
| 2015/0165135 | A1 | 6/2015 | McLoughlin |
| 2015/0174326 | A1 | 6/2015 | Bokelman |
| 2015/0182691 | A1 | 7/2015 | McLoughlin |
| 2015/0202374 | A1 | 7/2015 | McLoughlin |
| 2015/0250956 | A1 | 9/2015 | Ostrander |
| 2015/0251839 | A1 | 9/2015 | Denny |
| 2015/0314073 | A1 | 11/2015 | Shang |
| 2015/0328404 | A1 * | 11/2015 | Murakami ............ A61M 5/347 604/67 |
| 2015/0343157 | A1 | 12/2015 | Basile |
| 2015/0359967 | A1 | 12/2015 | Steel |
| 2015/0359977 | A1 | 12/2015 | Watanabe |
| 2016/0001005 | A1 | 1/2016 | Bechmann |
| 2016/0015897 | A1 | 1/2016 | Swanson |
| 2016/0082195 | A1 | 3/2016 | Atterbury |
| 2016/0106927 | A1 | 4/2016 | Moeller |
| 2016/0119753 | A1 | 4/2016 | Ostrander |
| 2016/0120751 | A1 | 5/2016 | Mounce |
| 2016/0121056 | A1 | 5/2016 | Edwards |
| 2016/0166768 | A1 | 6/2016 | Edwards |
| 2016/0175515 | A1 | 6/2016 | McCullough |
| 2016/0175527 | A1 | 6/2016 | McCullough |
| 2016/0193414 | A1 | 7/2016 | McLoughlin |
| 2016/0235916 | A1 | 8/2016 | Edward |
| 2016/0243318 | A1 | 8/2016 | Despa |
| 2016/0256630 | A1 | 9/2016 | Kramer |
| 2016/0271323 | A1 | 9/2016 | Ulrich |
| 2016/0331901 | A1 | 11/2016 | Grubbe |
| 2016/0339178 | A1 | 11/2016 | Baker |
| 2016/0354553 | A1 | 12/2016 | Anderson |
| 2017/0043092 | A1 | 2/2017 | Murakami |
| 2017/0143908 | A1 | 5/2017 | Eggert |
| 2017/0266390 | A1 | 9/2017 | Baba |
| 2017/0290996 | A1 | 10/2017 | Davies |
| 2019/0381253 | A1 | 12/2019 | Baba et al. |

FOREIGN PATENT DOCUMENTS

| | | | |
|---|---|---|---|
| EP | 2125075 | | 12/2009 |
| EP | 2355858 | A1 | 8/2011 |
| EP | 2298391 | | 3/2012 |
| EP | 2319562 | B1 | 5/2012 |
| EP | 2319563 | | 5/2013 |
| EP | 2319563 | B1 | 5/2013 |
| EP | 2319561 | B1 | 7/2013 |
| EP | 2319564 | | 7/2013 |
| EP | 2714135 | | 4/2014 |
| EP | 2760506 | | 8/2014 |
| EP | 2869871 | | 5/2015 |
| EP | 2908888 | | 8/2015 |
| EP | 1715904 | | 9/2015 |
| EP | 2928526 | | 10/2015 |
| EP | 2949356 | | 12/2015 |
| EP | 2953667 | | 12/2015 |
| EP | 2965772 | | 1/2016 |
| EP | 2968760 | | 1/2016 |

(56) References Cited

FOREIGN PATENT DOCUMENTS

| | | | |
|---|---|---|---|
| EP | 2968775 | | 1/2016 |
| EP | 3003430 | | 4/2016 |
| EP | 3033127 | | 6/2016 |
| EP | 2384207 | | 3/2017 |
| EP | 2932993 | | 3/2017 |
| EP | 2714146 | | 3/2018 |
| EP | 2361647 | | 5/2018 |
| EP | 3082912 | | 5/2018 |
| EP | 3178505 | | 5/2018 |
| EP | 2714141 | | 6/2018 |
| EP | 3127569 | | 6/2018 |
| EP | 3 348 295 | A1 | 7/2018 |
| EP | 2879737 | | 9/2018 |
| EP | 2968769 | | 10/2018 |
| EP | 2879736 | | 11/2018 |
| EP | 2 767 297 | B1 | 10/2019 |
| EP | 2879735 | | 11/2019 |
| EP | 2 303 359 | B1 | 2/2020 |
| EP | 2925272 | | 2/2020 |
| EP | 2968773 | | 5/2020 |
| EP | 2926328 | | 4/2021 |
| JP | 2002272839 | | 9/2002 |
| JP | 2012081283 | | 4/2012 |
| JP | 2014012214 | | 1/2014 |
| JP | 05717649 | | 5/2015 |
| JP | 2016025934 | | 2/2016 |
| JP | 2016039906 | | 3/2016 |
| WO | 2009/083600 | A1 | 7/2009 |
| WO | 2012032411 | | 3/2012 |
| WO | 2015066522 | | 5/2015 |
| WO | 2015091555 | | 6/2015 |
| WO | 2015098399 | | 7/2015 |
| WO | 2015144606 | | 10/2015 |
| WO | 2015178961 | | 11/2015 |
| WO | 2015179015 | | 11/2015 |
| WO | 2015189700 | | 12/2015 |
| WO | 2016003813 | | 1/2016 |
| WO | 2016022865 | | 2/2016 |
| WO | 2016025634 | | 2/2016 |
| WO | 2016040512 | | 3/2016 |
| WO | 2016060908 | | 4/2016 |
| WO | 2016060986 | | 4/2016 |
| WO | 2016091978 | | 6/2016 |
| WO | 2016099934 | | 6/2016 |
| WO | 2016100781 | | 6/2016 |
| WO | 2016115372 | | 7/2016 |

* cited by examiner

MULTIPLE USE COMPUTERIZED INJECTOR

CROSS REFERENCE TO RELATED APPLICATIONS

This application is Continuation of U.S. application Ser. No. 16/307,049, filed Dec. 4, 2018, which is a National Stage of International Application No. PCT/IL2017/050607, filed Jun. 1, 2017, claiming priority based on U.S. Provisional Patent Application No. 62/345,897, filed Jun. 6, 2016, the contents of all of which are incorporated herein by reference in their entirety.

Reference is hereby made to U.S. patent application Ser. No. 14/423,834, filed Sep. 3, 2013, which has published as US20150202367 and entitled "ELECTRONIC AUTO-INJECTION DEVICE", the disclosure of which is incorporated by reference in its entirety.

FIELD OF THE INVENTION

The present invention generally relates to a computerized injector, and more specifically to a multiple-use computerized injector, adapted for administration of medication to a patient.

BACKGROUND OF THE INVENTION

Many computerized injectors adapted for administration of medication to a patient are known.

SUMMARY OF THE INVENTION

The present invention seeks to provide an improved computerized injector.

There is thus provided in accordance with an embodiment of the present invention a computer-controlled injector for use with a medicament cartridge and including a housing including a medicament cartridge receiving volume and a medicament cartridge insertion and removal opening communicating with the medicament cartridge receiving volume; a pivot mount element mounted onto the housing for selectably enabling access to the medicament cartridge receiving volume via the opening; a mechanical latch selectably locking the pivot mount element in a closed operative orientation; and an injection drive mechanism including a computer-controlled motor for driving a piston, forming part of the medicament cartridge, for injecting a medicament, the computer-controlled motor also being operative for operating the mechanical latch.

Further, in accordance with an embodiment of the present invention, a computer-controlled injector for use with a medicament cartridge includes a housing having a medicament cartridge receiving volume and a medicament cartridge insertion and removal opening communicating with the medicament cartridge receiving volume; a pivot mount element mounted onto the housing for selectably enabling access to the medicament cartridge receiving volume via the opening; and an injection drive mechanism including a computer-controlled motor for driving a piston, forming part of the medicament cartridge, for injecting a medicament, the computer-controlled motor also being operative for enabling opening of the pivot mount element when the injection drive mechanism is retracted from the medicament cartridge.

Still further, in accordance with an embodiment of the present invention a computer-controlled injector for use with a medicament cartridge and including a housing having a medicament cartridge receiving volume and a medicament cartridge insertion and removal opening communicating with the medicament cartridge receiving volume; a pivot mount element mounted onto the housing for selectably enabling access to the medicament cartridge receiving volume via the opening, the pivot mount element being normally open unless latched closed; a mechanical latch selectably locking the pivot mount element in a closed operative orientation; and an injection drive mechanism including a computer-controlled motor for driving a piston, forming part of the medicament cartridge, for injecting a medicament.

Preferably, the computer-controlled injector also includes a moveable subassembly, which is linearly displaceable by the computer-controlled motor for linearly displacing the piston, the moveable subassembly including a mechanical latch engagement portion which engages the mechanical latch when the moveable subassembly is at a predetermined linear position with respect to the medicament cartridge. Further preferably, the mechanical latch engagement portion unlatches the mechanical latch, thereby allowing opening of the pivot mount element, only when the moveable subassembly is entirely retracted from the medicament cartridge.

Further preferably, the computer-controlled injector also includes a manually operable pivot mount element opener, which is operative to permit opening of the pivot mount element under low-battery conditions and wherein the computer-controlled motor is operative under the low-battery conditions to operate the mechanical latch so as to enable opening of the pivot mount element by the manually operable pivot mount element opener. Yet further preferably, the computer-controlled motor is operative under low-battery conditions to operate the mechanical latch so as to enable opening of the pivot mount element.

According to an embodiment of the present invention, the computer-controlled injector also includes a biasing element operative to open the pivot mount element except when the pivot mount element is locked in the closed operative orientation by the mechanical latch. Preferably, the biasing element is a torsion spring. Further preferably, the pivot mount element is pivotably mounted onto the housing and also has a transparent cover.

Further preferably, the pivot mount element includes a threaded portion for mounting of a needle assembly thereon. Yet further, the computer-controlled injector includes a needle presence responsive element, configured to be coupled to the pivot mount element, and being axially displaceable, thereby indicating mounting of a needle assembly to the pivot mount element.

Advantageously, the mechanical latch is biased to be positioned in a locked operative orientation by the biasing force of a biasing element. Preferably, the biasing element is a compression spring.

Still preferably, the mechanical latch engagement portion engages a piston of the medicament cartridge when the moveable subassembly is at a predetermined linear position with respect to the medicament cartridge.

According to an embodiment of the present invention, the computer-controlled injector includes a PCB assembly having at least one of: a cartridge sensor, which is configured to indicate whether the medicament cartridge is inserted into the medicament cartridge receiving volume, a needle sensor, which is configured to indicate whether a needle assembly is mounted to the pivot mount element, and a cartridge enclosure assembly state sensor, which is configured to indicate whether the pivot mount element is disposed in an open or a closed operative orientation.

Preferably, when the moveable subassembly is disposed in a forward operative orientation, the mechanical latch is latched and urges the pivot mount element to assume the closed operative orientation; when the moveable subassembly is disposed in a rearward operative orientation, the mechanical latch is unlatched and urges the pivot mount element to assume an open operative orientation and when the moveable subassembly is disposed in an intermediate operative orientation, the mechanical latch urges the pivot mount element to assume a snapped operative orientation.

Further preferably, the computer-controlled injector includes a home position sensor, which is operative to limit rearward displacement of the moveable subassembly.

According to an embodiment of the present invention, a computer-controlled injector for use with a medicament cartridge includes a housing having a medicament cartridge receiving volume; a computer interactive user interface including a display and user input facility. The computer interactive user interface providing a prompt to the user to perform a priming function and requiring a confirmatory indication, indicating carrying out of at least part of the priming function before permitting injection to take place and an injection drive mechanism including a computer-controlled motor for driving a piston, forming part of the medicament cartridge, for injecting a medicament, the injection drive mechanism being responsive to operation of the user input facility for performing the priming function.

Further, according to an embodiment of the present invention, a computer-controlled injector for use with a medicament cartridge including a housing having a medicament cartridge receiving volume; a computer interactive user interface including a display and user input facility. The computer interactive user interface providing a prompt appearing on the display in a first orientation to the user to perform a priming function including a 180 degrees shift in the orientation of the housing and being responsive to an indication of carrying out of the 180 degree shift, providing a message to the user in a second orientation shifted by 180 degrees from the first orientation; and an injection drive mechanism including a computer-controlled motor for driving a piston, forming part of the medicament cartridge, for injecting a medicament, the injection drive mechanism being responsive to operation of the user input facility for performing the priming function.

Still further, according to an embodiment of the present invention, a computer-controlled injector for use with a medicament cartridge including a housing having a medicament cartridge receiving volume; a computer interactive user interface including a display and user input facility, and an injection drive mechanism including a computer-controlled motor for driving a piston, forming part of the medicament cartridge, for injecting a medicament. The injection drive mechanism being responsive to operation of the user input facility for performing a priming function prior to injecting the medicament, the priming function including bringing at least part of the injection drive mechanism into contact with the piston such that any linear displacement of the at least part of the injection drive mechanism produces a corresponding linear displacement of the piston.

Preferably, the computer-controlled injector also includes at least one accelerometer indicating the carrying out of part of the priming function. Further preferably, the pivot mount element includes a needle mount on a first end thereof and the accelerometer senses reorientation of the housing such that the needle mount is oriented vertically upwardly.

Further preferably, the computer-controlled injector also includes a moveable subassembly, which is linearly displaceable by the computer-controlled motor for linearly displacing the piston and wherein the priming function includes: linear displacement of the piston by the moveable subassembly by a distance sufficient to eject trapped air and a small quantity of medicament from the medicament cartridge. Yet preferably, the priming function also includes applying a force to the medicament cartridge sufficient to dislodge trapped air bubbles from the medicament cartridge. Still further preferably, the priming function also includes bringing at least part of the moveable subassembly into contact with the piston such that any linear displacement of the plunger produces a corresponding linear displacement of the piston.

Advantageously, a change in resistance to operation of the computer-controlled motor indicates the bringing the at least part of the moveable subassembly into contact with the piston such that any further forward linear displacement of the at least part of the moveable subassembly produces a corresponding linear displacement of the piston.

According to an embodiment of the present invention, a computer-controlled injector for use with a medicament cartridge including a housing having a medicament cartridge receiving volume; a computer interactive user interface including a display and user input facility which enables a user to indicate an injection dosage and a desired minimum injection duration within a range of possible durations for the injection dosage, and an injection drive mechanism including a computer-controlled motor for driving a piston, forming part of the medicament cartridge, for injecting a medicament. The computer interactive user interface being operative to ascertain whether the user indicated injection dosage can be injected within a user indicated minimum injection duration and if so, to inject the user indicated injection dosage according to the user indicated minimum injection duration; and the computer interactive user interface being operative in a case wherein the user indicated injection dosage cannot be injected within a user indicated minimum injection duration or in a case where no user indicated minimum injection duration is available, to inject the user indicated injection dosage over a duration which is the shortest possible duration for the user indicated dosage.

Further according to an embodiment of the present invention, a computer-controlled injector for use with a circularly symmetric cylindrical medicament cartridge bearing an RFID transducer and including a housing having a medicament cartridge receiving volume; an RFID communication antenna disposed within the housing for communicating with an RFID transducer on a medicament cartridge located within the medicament cartridge receiving volume; a computer controller communicating with the RFID communication antenna, and an injection drive mechanism including a computer-controlled motor for driving a piston, forming part of the medicament cartridge, for injecting a medicament.

Preferably, the RFID communication antenna is operative to communicate with the RFID transducer irrespective of the rotational orientation of the medicament cartridge within the medicament cartridge receiving volume. Further preferably, the RFID communication antenna is a V-shaped antenna.

Still further, according to an embodiment of the present invention, a computer-controlled injection method for use with a medicament cartridge and an injector including a housing having a medicament cartridge receiving volume and a medicament cartridge insertion and removal opening communicating with the medicament cartridge receiving volume; a pivot mount element mounted onto the housing for selectably enabling access to the medicament cartridge receiving volume via the opening, the pivot mount element being normally open unless latched closed; and an injection drive mechanism including a computer-controlled motor for driving a piston, forming part of the medicament cartridge, for injecting a medicament. The method includes: operating the computer-controlled motor for permitting the pivot mount element to assume a biased open operational orientation to permit insertion of the medicament cartridge into the medicament cartridge receiving volume; thereafter, manually pushing the pivot mount element to a closed position; thereafter, automatically operating the computer-controlled motor to lock the pivot mount element in the closed position, thereby preventing opening of the pivot mount element; thereafter, operating the computer-controlled motor for driving the piston.

Yet further, according to an embodiment of the present invention, a computer-controlled injection method for use with a medicament cartridge and an injector including a housing having a medicament cartridge receiving volume and a medicament cartridge insertion and removal opening communicating with the medicament cartridge receiving volume; a pivot mount element mounted onto the housing for selectably enabling access to the medicament cartridge receiving volume via the opening, the pivot mount element being normally open unless latched closed; and an injection drive mechanism including a computer-controlled motor for driving a piston, forming part of the medicament cartridge, for injecting a medicament. The method includes: operating the computer-controlled motor for permitting the pivot mount element to assume a biased open operational orientation to permit insertion of the medicament cartridge into the medicament cartridge receiving volume; thereafter, manually pushing the pivot mount element to a closed position; thereafter, automatically operating the computer-controlled motor to lock the pivot mount element in the closed position, thereby preventing opening of the pivot mount element; thereafter, operating the computer-controlled motor for driving a moveable subassembly into the medicament cartridge and into engagement with the piston for injection; thereafter, operating the computer-controlled motor for retracting the moveable subassembly and enabling opening of the pivot mount element upon full retraction of the moveable subassembly from the medicament cartridge.

Preferably, operating the computer-controlled motor includes positioning of a mechanical latch in an unlocked operative orientation for permitting the pivot mount element to assume the biased open operational orientation. Further preferably, the computer-controlled injection method also includes manually opening the pivot mount element under low-battery conditions and wherein the computer-controlled motor is operative under the low-battery conditions to enable opening of the pivot mount element. The computer-controlled motor is operative under low-battery conditions to operate the mechanical latch so as to enable opening of the pivot mount element.

Yet further preferably, the computer-controlled injection method also includes employing a biasing element operative to open the pivot mount element except when the pivot mount element is locked in the closed operative orientation by the mechanical latch. Preferably, the biasing element is a torsion spring.

Advantageously, operating the computer-controlled motor includes driving a moveable subassembly into the medicament cartridge and into engagement with the piston for injection.

Preferably, the pivot mount element is pivotably mounted onto the housing. Further preferably, the pivot mount element includes a threaded portion for mounting of a needle assembly thereon. Yet further preferably, the computer-controlled injector also includes a needle presence responsive element, configured to be coupled to the pivot mount element, and being axially displaceable, thereby indicating mounting of a needle assembly to the pivot mount element.

According to an embodiment of the present invention, the computer-controlled injector also includes a PCB assembly including at least one of a cartridge sensor, which is configured to indicate whether the medicament cartridge is inserted into the medicament cartridge receiving volume; a needle sensor, which is configured to indicate whether a needle assembly is mounted to the pivot mount element; and a cartridge enclosure assembly state sensor, which is configured to indicate whether the pivot mount element is disposed in an open or a closed operative orientation.

Preferably, when the moveable subassembly is disposed in a forward operative orientation, the mechanical latch is latched and urges the pivot mount element to assume the closed operative orientation; when the moveable subassembly is disposed in a rearward operative orientation, the mechanical latch is unlatched and urges the pivot mount element to assume an open operative orientation; and when the moveable subassembly is disposed in an intermediate operative orientation, the mechanical latch urges the pivot mount element to assume a snapped operative orientation. Preferably, the computer-controlled injector also includes a home position sensor, which is operative to limit rearward displacement of the moveable subassembly.

According to an embodiment of the present invention, a computer-controlled injection method for use with a medicament cartridge and an injector including: a housing having a medicament cartridge receiving volume; a computer interactive user interface including a display and user input facility; and an injection drive mechanism disposed within the housing and including a computer-controlled motor providing linear displacement of a moveable subassembly for driving a piston, forming part of the medicament cartridge. The method including: employing the computer interactive user interface for prompting a user to perform a priming function; and responsive to an indication related to at least partial performance of the priming function, enabling operation of the injection drive mechanism for injecting a medicament contained in the medicament cartridge.

Further, according to an embodiment of the present invention, a computer-controlled injection method for use with a medicament cartridge and an injector including: a housing having a medicament cartridge receiving volume; a computer interactive user interface including a display and user input facility; and an injection drive mechanism disposed within the housing and including a computer-controlled motor providing linear displacement of a moveable subassembly for driving a piston, forming part of the medicament cartridge. The method including: displaying a user prompt to carry out a priming function in a first orientation on the display; responsive to an indication related to at least partial performance of the priming function, displaying a further user prompt in a second orientation on the display, shifted by 180 degrees.

Preferably, the indication indicates reorientation of the housing by approximately 180 degrees. Further preferably, the priming function includes bringing at least part of the moveable subassembly into contact with the piston such that any further forward linear displacement of the moveable subassembly produces a corresponding linear displacement of the piston. Advantageously, the priming function includes linear displacement of the piston by the at least part of the moveable subassembly by a distance sufficient to eject trapped air and a small quantity of medicament from the medicament cartridge. Further advantageously, the priming function includes applying a force to the medicament cartridge sufficient to dislodge trapped air bubbles from the medicament cartridge. Yet further advantageously, a change in resistance to operation of the computer-controlled motor indicates the bringing the at least part of the moveable subassembly into contact with the piston such that any linear displacement of the moveable subassembly produces a corresponding linear displacement of the piston.

Yet preferably, the indication is provided by at least one accelerometer indicating a change in orientation of the housing. The pivot mount element includes a needle mount on a first end thereof and the at least one accelerometer senses reorientation of the housing such that the needle mount is oriented vertically upwardly.

According to an embodiment of the present invention, a computer-controlled injection method for use with a medicament cartridge and a computer controlled injector, including: a housing having a medicament cartridge receiving volume; a computer interactive user interface including a display and user input facility and an injection drive mechanism including a computer-controlled motor for driving a piston, forming part of the medicament cartridge. The method including: enabling a user to indicate an injection dosage via the computer interactive user interface; enabling the user to indicate an intention to inject the injection dosage over a minimum duration; ascertaining the minimum duration over which the user indicated injection dosage can be injected; and injecting the user-indicated injection dosage over the minimum duration.

Further, according to an embodiment of the present invention, a computer-controlled injection method for use with a circularly symmetric cylindrical medicament cartridge bearing an RFID transducer and a computer controlled injector including: a housing having a medicament cartridge receiving volume; and an injection drive mechanism including a computer-controlled motor for driving a piston, forming part of the medicament cartridge, the method including: inserting the circularly symmetric cylindrical medicament cartridge bearing an RFID transducer into the medicament cartridge receiving volume; reading information from the RFID transducer; and operating the injection drive mechanism at least partially based on the information read from the RFID transducer.

Preferably, the inserting and the reading of the circularly symmetric cylindrical medicament cartridge is independent of the rotational orientation thereof. Further preferably, the RFID communication antenna is a V-shaped antenna.

According to an embodiment of the present invention, a medicament cartridge including: a circularly cylindrical housing; a septum fixed at a first end of the circularly cylindrical housing; a sealing piston located within the circularly cylindrical housing and spaced from the septum, thereby defining a medicament-containing volume therebetween; a medicament located within the medicament-containing volume; and an RFID element fixed to the housing and containing information relating to the medicament.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS OF THE INVENTION

Figure 1A:
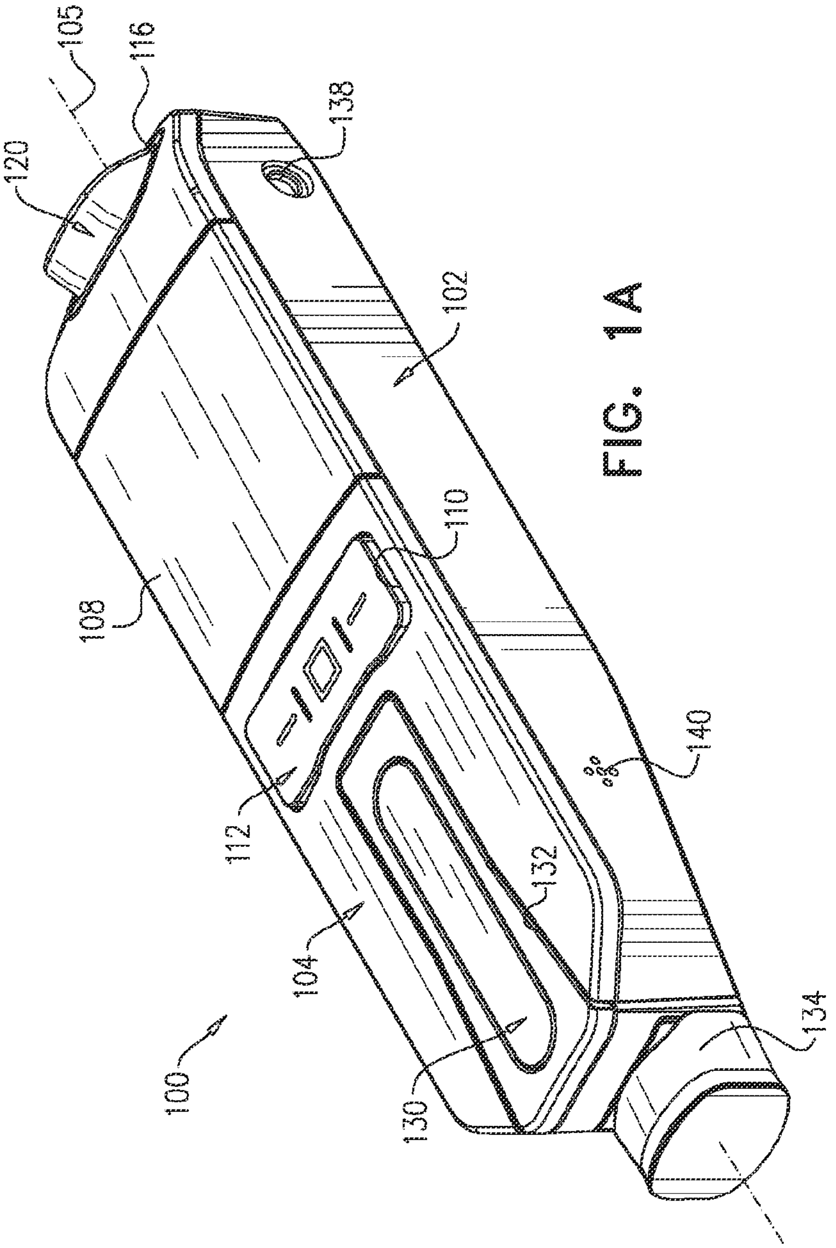
FIG. 1A is a simplified pictorial illustration of a multiple use computerized injector (MUCI) constructed and operative in accordance with a preferred embodiment of the present invention.
Figure 1B:
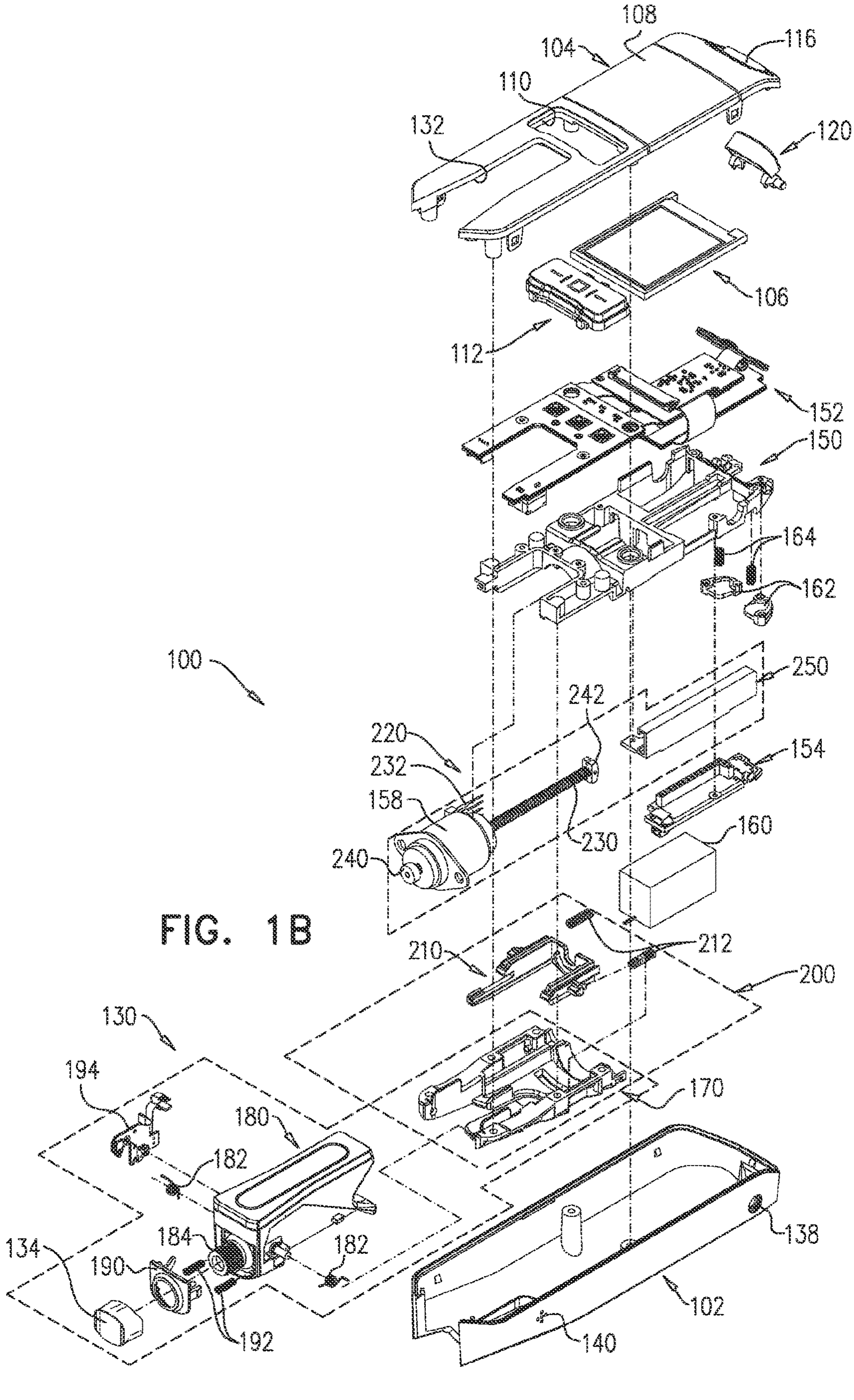
FIG. 1B is a simplified exploded view illustration of the multiple use computerized injector of FIG. 1A.
Figure 2A:
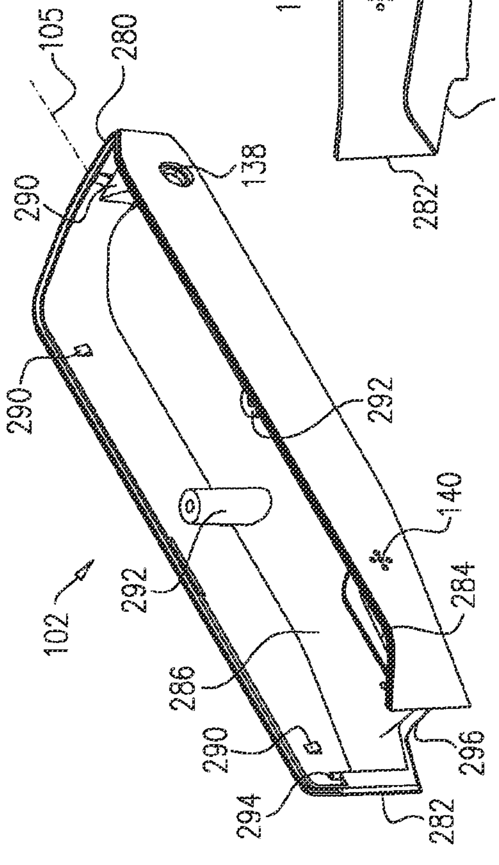
FIGS. 2A, 2B, 2C, 2D, 2E and 2F are simplified respective pictorial, side planar view, top planar view, bottom planar view, front planar view and back planar view illustrations of a main housing portion of the MUCI of FIGS. 1A & 1B.
Figure 2B:
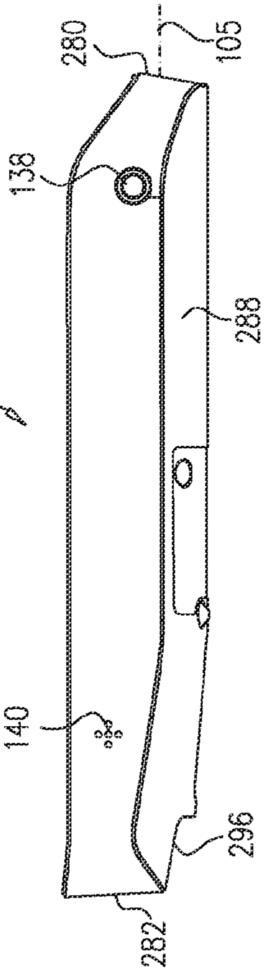
Figure 2C:
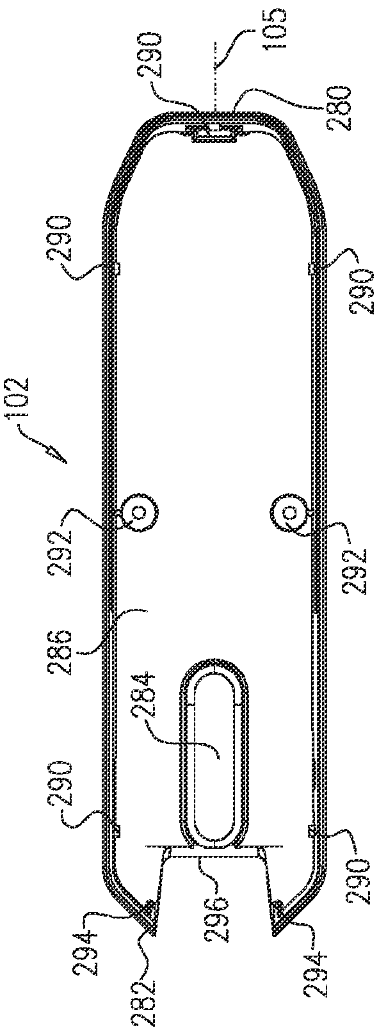
Figure 2E:
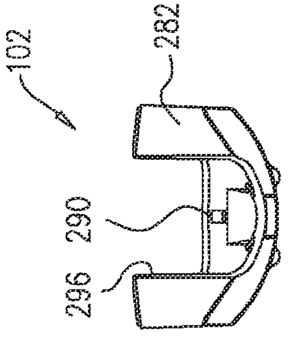
Figure 2F:
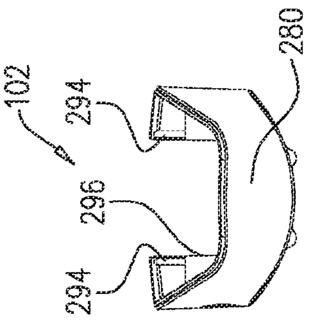
Figure 2D:
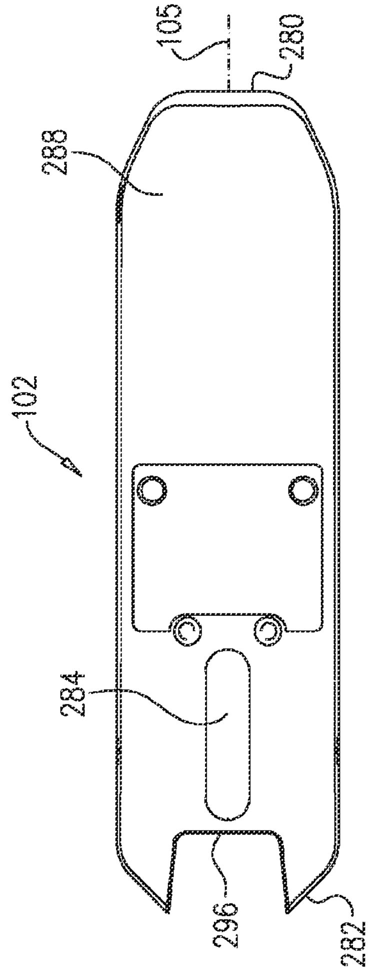

Reference is now made to FIG. 1A, which is a simplified pictorial illustration of a multiple use computerized injector (MUCI) constructed and operative in accordance with an embodiment of the present invention and to FIG. 1B, which is a simplified exploded view illustration of the multiple use computerized injector of FIG. 1A.

A multiple use computerized injector (MUCI) for cartridge insertion 100 is seen in FIGS. 1A & 1B. It is seen in FIG. 1A that the MUCI 100 includes a main housing portion 102, fixedly coupled to a top housing portion 104, both arranged along a mutual longitudinal axis 105. A display 106 is preferably disposed within the MUCI 100 and is preferably covered by a transparent window 108 formed in the top housing portion 104. The top housing portion 104 preferably has an opening 110 disposed adjacent to window 108 and configured to receive a button defining element 112 therewithin.

An opening 116 is formed at the rearward end of top housing element 104 and is configured to receive an injection button element 120 thereinto.

It is also seen particularly in FIG. 1A that a cartridge enclosure assembly 130 is mounted through an opening 132 formed in top housing portion 104 and is configured to be pivotably mounted with respect to top housing portion 104.

It is additionally seen in FIG. 1A that a cover 134 is disposed at the forward end of the MUCI 100 and is configured to cover the proximal end of the cartridge enclosure assembly 130.

It is seen in FIG. 1A that a charger inlet 138 and a speaker outlet 140 are formed in main housing portion 102.

It is particularly seen in FIG. 1B that the MUCI 100 includes a top housing portion 104 and main housing portion 102, within which a chassis element 150 is residing, being fixedly coupled to top housing portions 104.

The chassis element 150 is configured to support the internal components of the MUCI 100. A main PCB assembly 152 is seated onto the chassis element 150, and is configured to be operatively coupled with a power control PCB assembly 154 and an electrical motor 158, powered by a battery 160.

It is also seen in FIG. 1B that typically two generally identical spring support elements 162 are seated onto the underside of the chassis element 150 and two compression springs 164 are supported between each of the spring support elements 162 and the injection button element 120. The injection button element 120 can be pressed by the user against the force of the springs 164, and when the injection button element 120 is released, the button resumes its at rest operative orientation under the biasing force of springs 164.

It is seen in FIG. 1B that the cartridge enclosure assembly 130 is residing between the housing portions 102 and 104 mounted onto housing portions 102 and 104. The cartridge enclosure assembly 130 preferably includes a cartridge enclosure assembly chassis 170 and a pivot mount element 180, which is adapted to receive a medicament cartridge therewithin and is generally pivotably mounted with respect to cartridge enclosure assembly chassis 170 and configured to be biased to an open operative orientation with respect to housing portions 102 and 104, due to the biasing force of torsion springs 182. The pivot mount element 180 includes a forward generally externally threaded end 184, adapted for engagement of a needle assembly therewith.

It is noted that pivot mount element 180 is configured to be pivotably coupled to the cartridge enclosure assembly chassis 170, which is in turn configured to be fixedly coupled to chassis element 150, which is fixedly coupled to top housing portion 104.

A needle presence responsive element 190 is adapted to be coupled to the pivot mount element 180 and is configured to be axially displaceable, along longitudinal axis 105, with respect thereto. The needle presence responsive element 190 is biased to a forward position by means of the biasing force of compression springs 192.

A PCB assembly 194 is operatively coupled to the pivot mount element 180 and configured to sense the axial orientation of the needle presence responsive element 190. The PCB assembly 194 is also configured to be operatively coupled to the main PCB assembly 152.

It is further seen in FIG. 1B that a locking subassembly 200 is provided as part of the MUCI 100 and is configured for selectively retaining the pivot mount element 180 of the cartridge enclosure assembly 130 in a closed operative orientation.

The locking subassembly 200 preferably includes the cartridge enclosure assembly chassis 170, a cartridge enclosure assembly latch element 210 and typically two compression springs 212, each of which is supported at one side thereof on the cartridge enclosure assembly latch element 210 and at a second side thereof on the cartridge enclosure assembly chassis 170. The cartridge enclosure assembly latch element 210 is configured to be axially displaceable, along longitudinal axis 105, with respect to cartridge enclosure assembly chassis 170 and biased to a forward position under the biasing force of springs 212.

A piston drive subassembly 220 is provided as part of the MUCI 100. When a medicament cartridge having a piston is inserted into the MUCI 100, the piston drive assembly 220 is configured for axially displacing the piston within the medicament cartridge in order to eject fluid therefrom.

The piston drive subassembly 220 preferably includes electrical motor 158, such as a step motor or a DC motor, for example, which is mounted onto a plunger rod element 230 through a threaded nut. Electrical contacts 232 of the electrical motor 158 are adapted to be operatively coupled to power control PCB assembly 154, and following receipt of a suitable signal from the CPU of MUCI 100, the electrical motor 158 causes axial displacement of the plunger rod element 230 with respect to housing portions 102 and 104.

It is seen in FIG. 1B that a piston contact element 240 is mounted onto the forward end of plunger rod element 230 and an anti-rotation element 242 is mounted onto the distal end of plunger rod element 230. It is noted that the anti-rotation element 242 is configured to be axially displaced along a track element 250.

It is a particular feature of an embodiment of the present invention that the piston contact element 240 is configured to operatively couple the plunger rod element 230 to the cartridge enclosure assembly latch element 210, such that rearward displacement of the plunger rod element 230 causes corresponding rearward displacement of cartridge enclosure assembly latch element 210 along longitudinal axis 105. This operative coupling occurs due to the fact that piston contact element 240 pulls the cartridge enclosure assembly latch element 210 rearwardly upon rearward displacement of the plunger rod element 230 along longitudinal axis 105.

Reference is now made to FIGS. 2A, 2B, 2C, 2D, 2E and 2F, which are simplified respective pictorial, side planar view, top planar view, bottom planar view, front planar view and back planar view illustrations of a main housing portion 102 of the MUCI 100 of FIGS. 1A & 1B.

It is seen in FIGS. 2A-2F that the main housing portion 102 is arranged along longitudinal axis 105 and has a rearward end 280 and a forward end 282. It is seen that a generally transparent window 284 is located adjacent forward end 282, configured for inspection of a medicament, when a medicament cartridge is inserted into the MUCI 100.

As previously mentioned, charger inlet 138 is formed in the main housing portion 102 and disposed adjacent the rearward end 280 and speaker outlet 140 is formed in the main housing portion 102 and disposed adjacent the forward end 282.

The main housing portion 102 preferably defines an inner surface 286 and an outer surface 288.

A plurality of snaps 290 are formed on the inner surface 286 of the main housing portion 102 for fixed connection with top housing portion 104. Additionally, two generally upstanding protrusions 292 are formed generally at an intermediate location of the inner surface 286 of the main housing portion 102 for connection to top housing portion 104. Further additionally, protrusions 294 are formed at the forward end 282 of the main housing portion 102 for secure connection with top housing portion 104.

It is additionally seen that an opening 296 for mounting of cartridge enclosure assembly 130 is formed at the forward end 282 of the main housing portion 102.

Reference is now made to FIGS. 3A, 3B, 3C, 3D, 3E, 3F, 3G and 3H, which are simplified respective two pictorials views taken from different perspectives, top planar view, bottom planar view, front planar view and back planar view, first and second side view illustrations of a top housing portion 104 of the MUCI 100 of FIGS. 1A & 1B.

It is seen in FIGS. 3A-3H that top housing portion 104 is arranged along longitudinal axis 105 and has a forward end 300 and a rearward end 302.

As mentioned above, opening 116 is formed in top housing portion 104 adjacent rearward end 302. Opening 132 extends rearwardly from forward end 300 and opening 110 is formed rearwardly of opening 132.

Transparent window 108 is formed generally between opening 110 and opening 116.

Figure 3C:
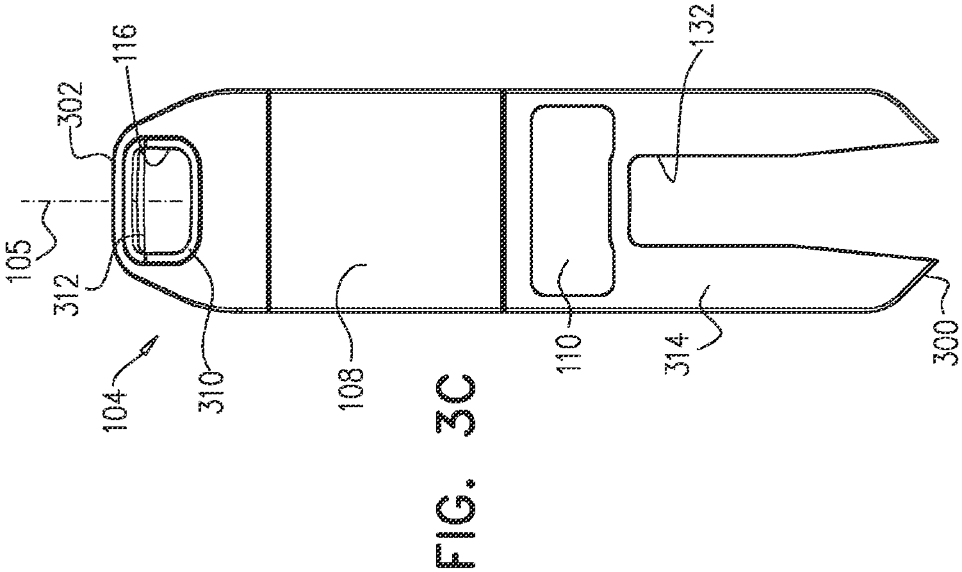
FIGS. 3A, 3B, 3C, 3D, 3E, 3F, 3G and 3H are simplified respective two pictorials views taken from different perspectives, top planar view, bottom planar view, front planar view and back planar view, first and second side view illustrations of a top housing portion of the MUCI of FIGS. 1A & 1B.
Figure 3A:
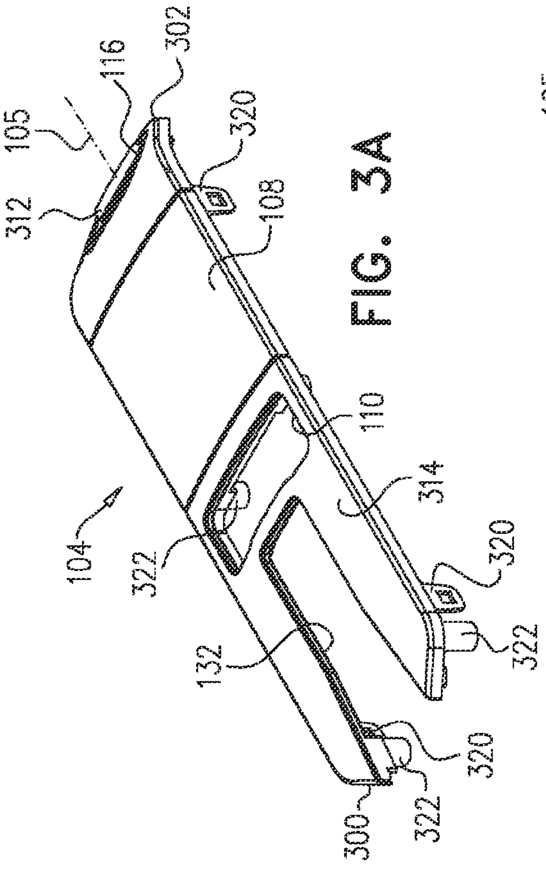
Figure 3B:
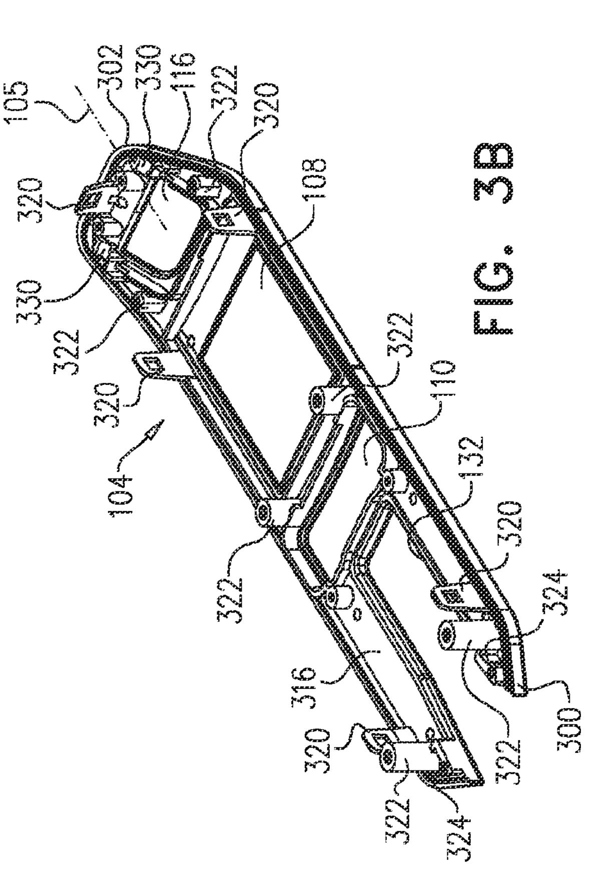
Figure 3E:
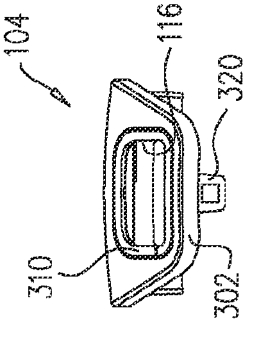
Figure 3F:
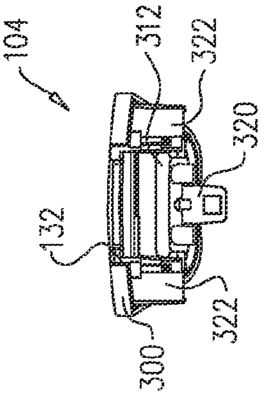
Figure 3D:
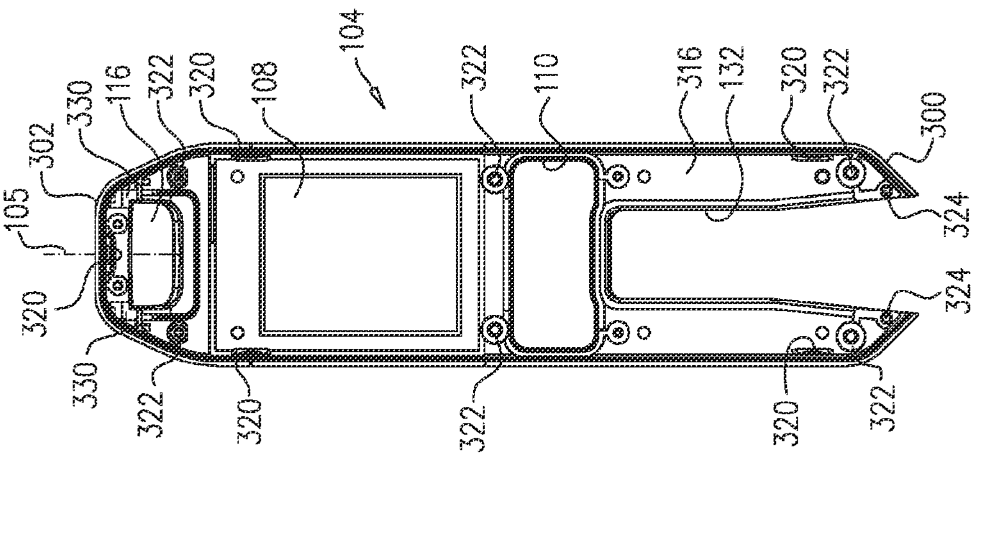
Figure 3G:
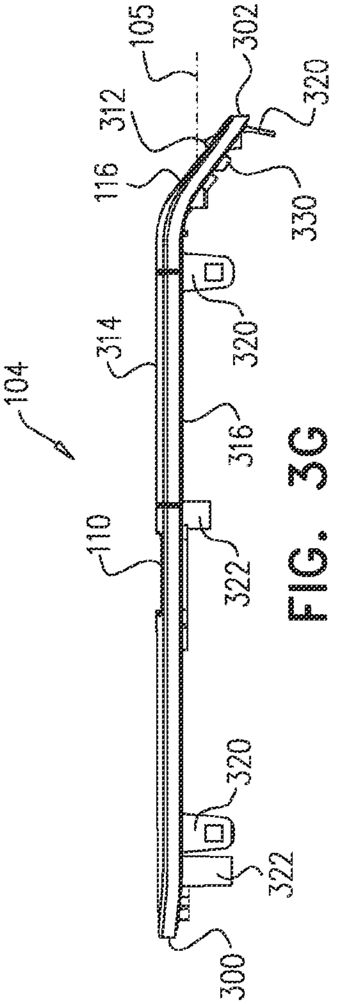
Figure 3H:
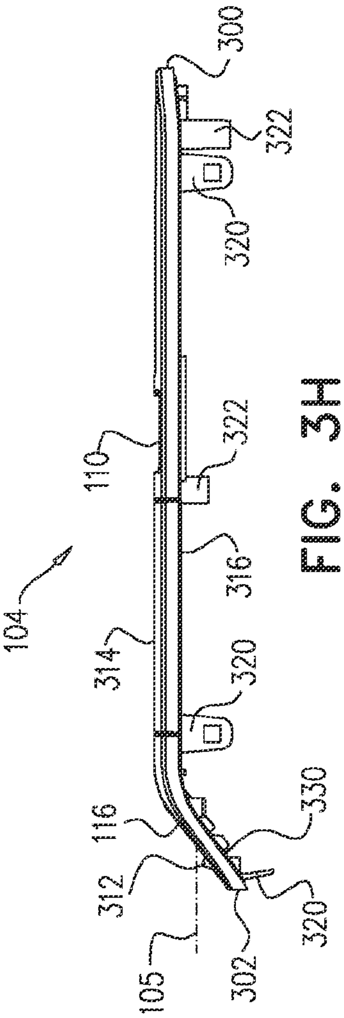
Figure 4C:
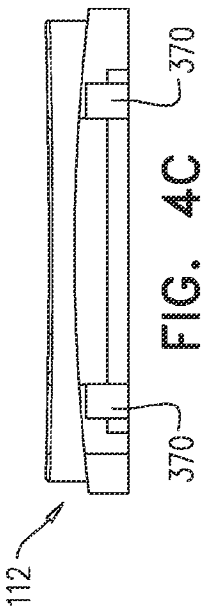
FIGS. 4A, 4B, 4C, 4D and 4E are simplified respective top and bottom pictorial, side planar view, top planar view and bottom planar view illustrations of a button defining element forming part of the MUCI of FIGS. 1A & 1B.
Figure 4D:
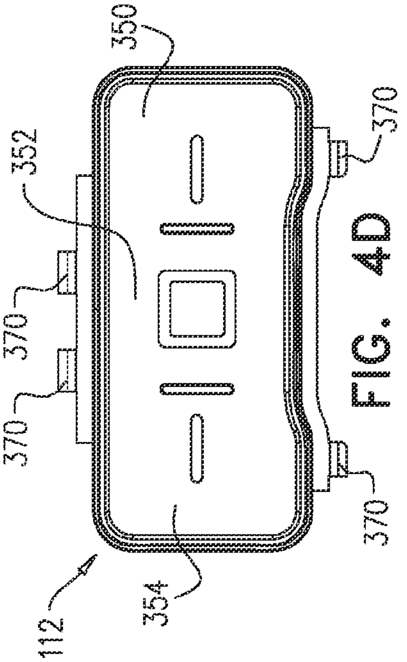
Figure 4E:
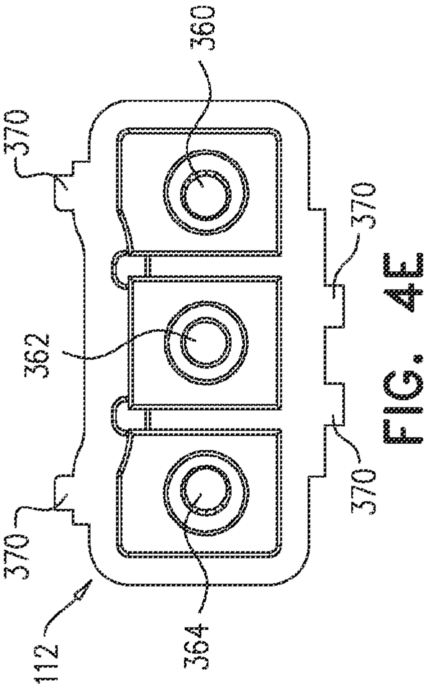
Figure 4A:
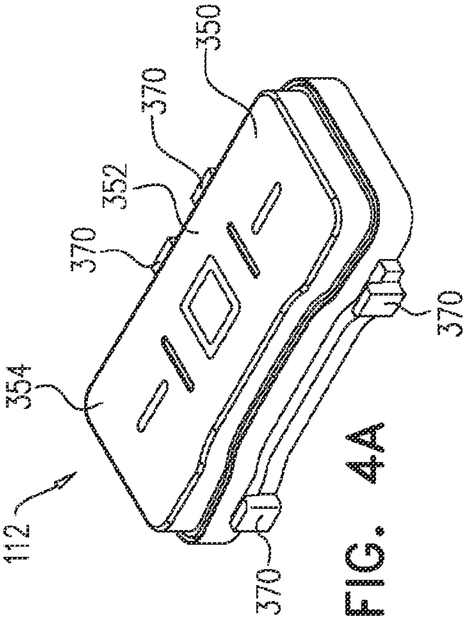
Figure 4B:
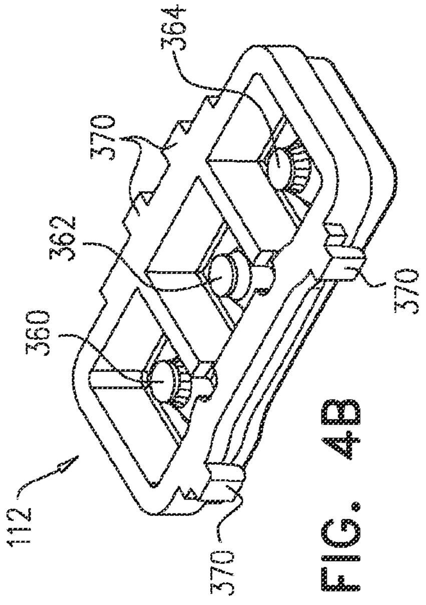
Figure 5A:
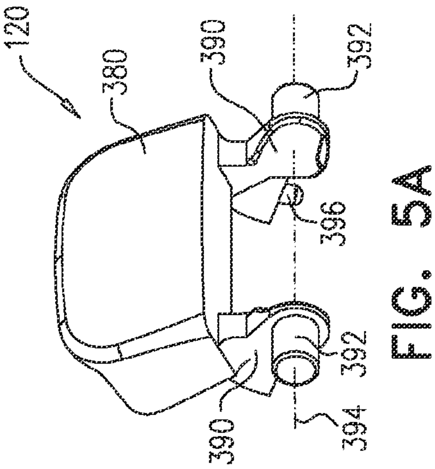
FIGS. 5A, 5B, 5C and 5D are simplified respective top and bottom pictorial, side planar view and top planar view illustrations of an injection button element forming part of the MUCI of FIGS. 1A & 1B.
Figure 5B:
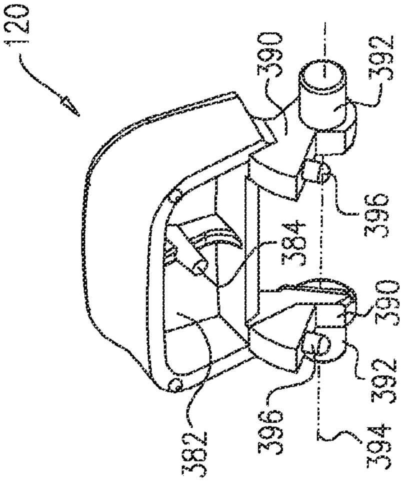
Figure 5C:
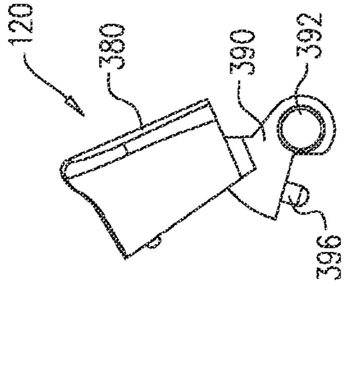
Figure 5D:
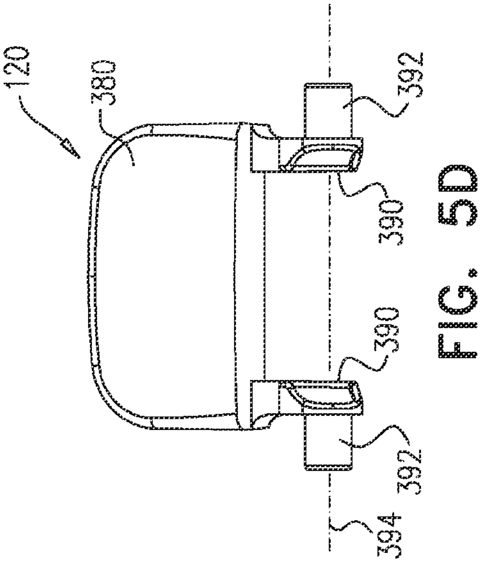

It is particularly seen in FIGS. 3C and 3E that a transparent frame 310 is formed around opening 116 enabling providing visual indication to the user, such as by LED's illuminating the injection button element 120, which is configured to be mounted through opening 116.

A flat shoulder 312 is formed on one side of the opening 116 configured to act as a stopper for the injection button element 120.

The top housing portion 104 defines an outer surface 314 and an inner surface 316.

It is seen in FIGS. 3A-3H that a plurality of snap portions 320 is formed on the inner surface 316 of the top housing portion 104 for secured connection with the snaps 290 on the main housing portion 102. There is a plurality of upstanding protrusions 322 formed on the inner surface 316 for secure connection with upstanding protrusions 292 of the main housing portion 102, top housing portion 104 and inner components of the MUCI 100. There are preferably two apertures 324 for insertion of protrusions 294 of the main housing portion 102 thereinto.

An injection button element hinge seating portion 330 is formed on the inner surface 316 adjacent the rearward end 302 of top housing portion 104.

Reference is now made to FIGS. 4A, 4B, 4C, 4D and 4E, which are simplified respective top and bottom pictorial, side planar view, top planar view and bottom planar view illustrations of button defining element 112 forming part of the MUCI 100 of FIGS. 1A & 1B.

It is seen in FIGS. 4A-4E that button defining element 112 preferably has three buttons 350, 352 and 354. Each of the buttons 350, 352 and 354 has a respective contact 360, 362, and 364 on the underside of the button defining element 112 for electrically coupling the buttons 350, 352 and 354 to the CPU of the MUCI 100.

There is a plurality of protrusions 370 on the side edges of the button defining element 112 for enabling secure mounting of the button defining element 112 in opening 110 of top housing portion 104.

Reference is now made to FIGS. 5A, 5B, 5C and 5D, which are simplified respective top and bottom pictorial, side planar view and top planar view illustrations of injection button element 120 forming part of the MUCI 100 of FIGS. 1A & 1B.

Injection button element 120 has an outer surface 380 to be engaged by a finger of a user and an inner surface 382 with a protrusion 384 extending forwardly therefrom and utilized for engaging main PCB assembly 152 once the injection button element 120 is pressed by the user. Typically, two hinge portions 390 are formed on injection button element 120. Each of hinge portions 390 includes a hinge axle 392, both of which extend along a mutual pivoting axis 394.

Injection button element 120 is configured to be pivotable about pivoting axis 394 in order to selectively activate the injection process of the MUCI 100.

Preferably two protrusions 396 extend from a location on hinge portions 390 configured to lead the springs 164 in order to enable biasing of the injection button element 120.

Figure 6B:
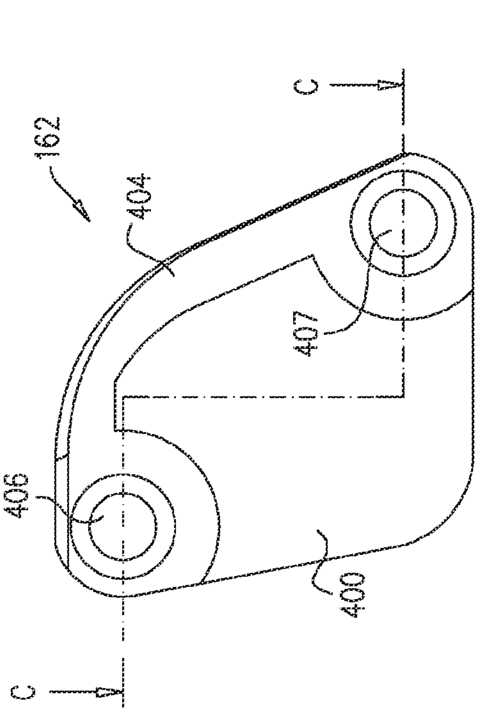
FIGS. 6A, 6B and 6C are simplified respective pictorial, planar view and section view illustrations of a spring support element forming part of the MUCI of FIGS. 1A & 1B, FIG. 6C, being taken along lines C-C in FIG. 6B.
Figure 6C:
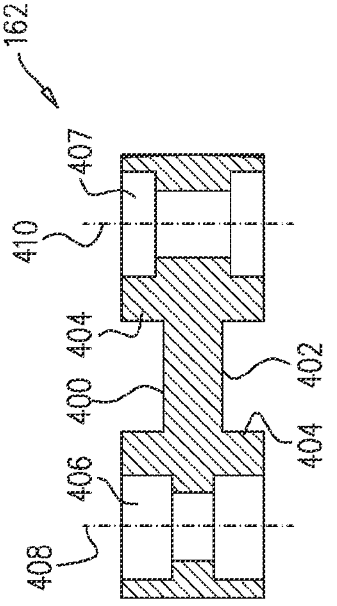
Figure 6A:
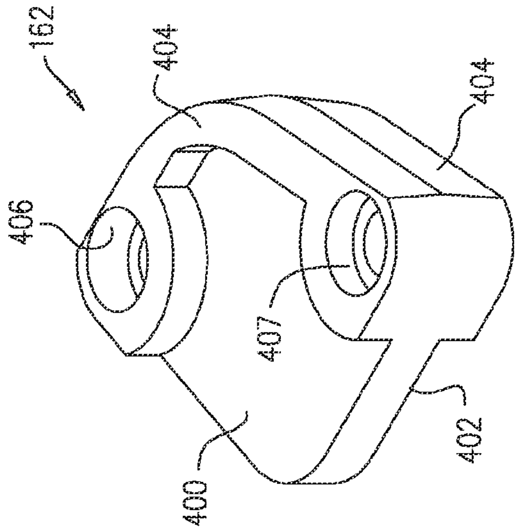

Reference is now made to FIGS. 6A, 6B and 6C, which are simplified respective pictorial, planar view and section view illustrations of spring support element 162 forming part of the MUCI 100 of FIGS. 1A & 1B, FIG. 6C, being taken along lines C-C in FIG. 6B.

There are typically two generally identical spring support elements 162. Spring support element 162 has a rearwardly facing surface 400 and a forwardly facing surface 402. Raised portions 404 are formed on both the forwardly facing surface 402 and the rearwardly facing surface 400 and preferably two bores 406 and 407 are formed through each one of raised portions 404 and extend longitudinally therethrough along axes 408 and 410, and configured for receiving screws that attach the spring support elements 162 to chassis element 150.

Reference is now made to FIGS. 7A, 7B, 7C, 7D, 7E and 7F, which are simplified respective top and bottom pictorial, first and second side planar view, top planar view and bottom planar view illustrations of chassis element 150 forming part of the MUCI 100 of FIGS. 1A & 1B.

Chassis element 150 is configured to be positioned between main housing portion 102 and top housing portion 104 and is used for carrying the piston drive subassembly 220 and to support the cartridge enclosure assembly 130, as well as to support the main PCB assembly 152 and the locking subassembly 200.

Chassis element 150 is generally arranged along longitudinal axis 105 and has an upper side 430 and an underside surface 432. Several generally upstanding protrusions 434 are formed on the upper side 430 and serve to support and align the display 106.

Figure 7A:
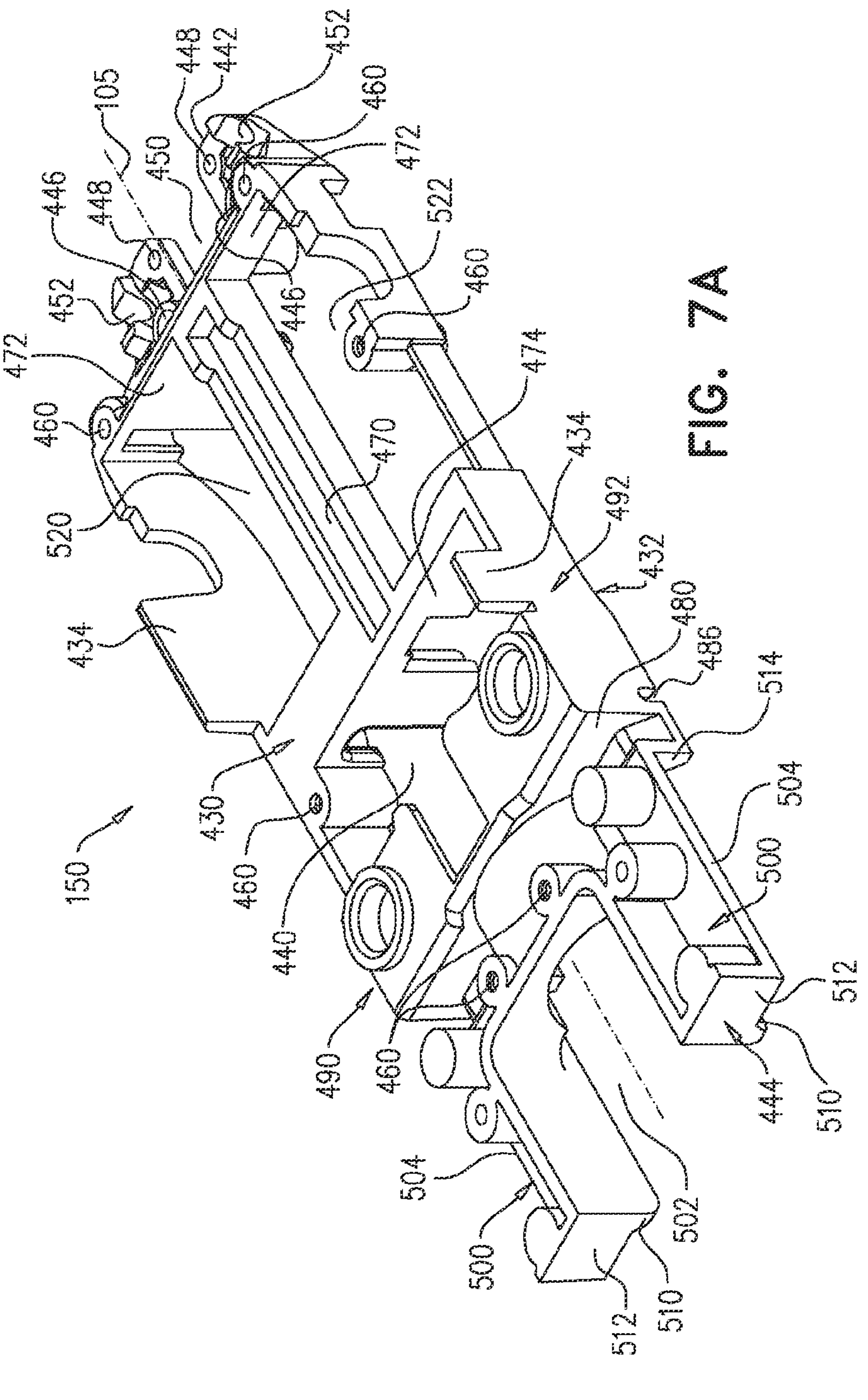
FIGS. 7A, 7B, 7C, 7D, 7E and 7F are simplified respective top and bottom pictorial, first and second side planar view, top planar view and bottom planar view illustrations of a chassis element forming part of the MUCI of FIGS. 1A & 1B.
Figure 7B:
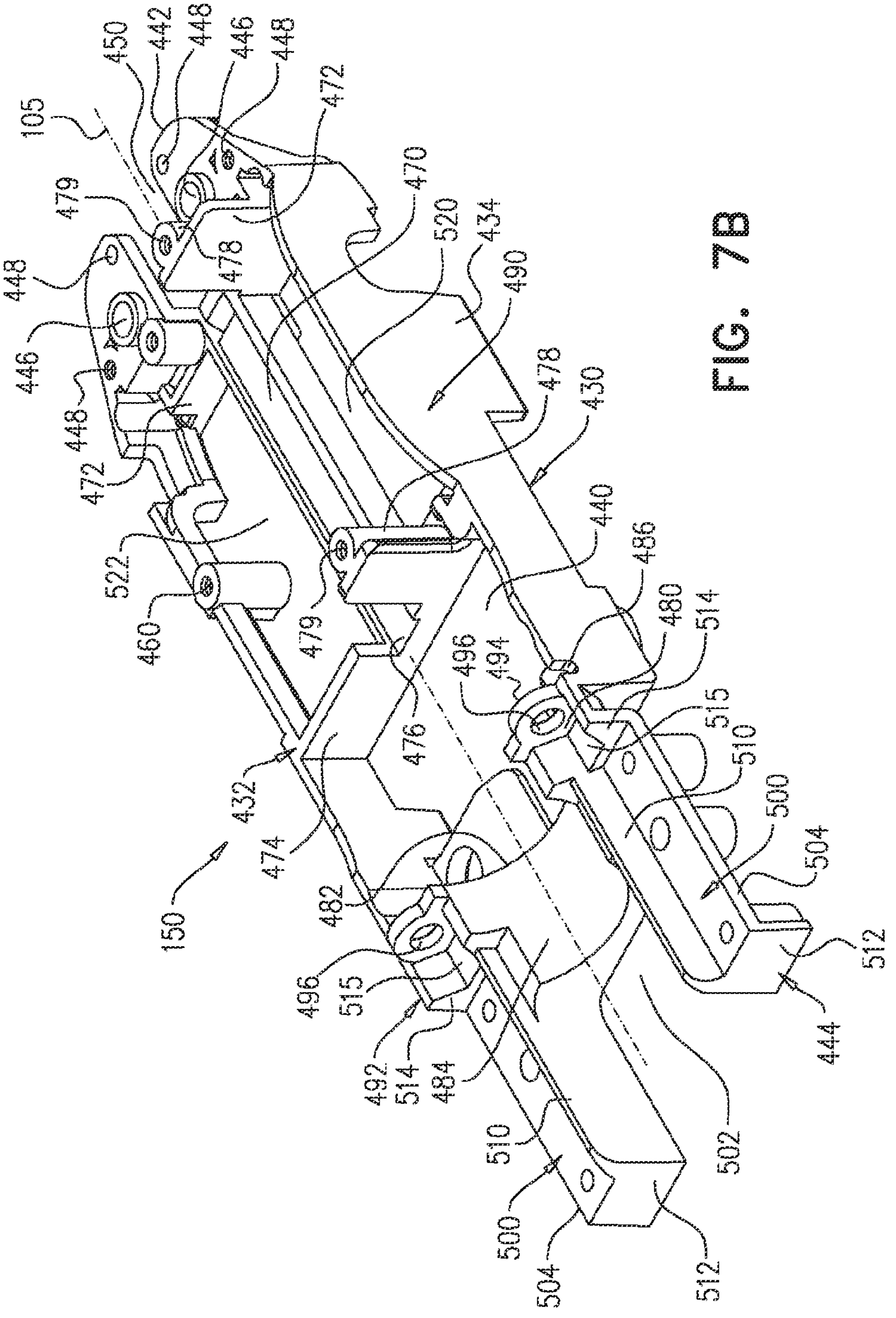
Figure 7C:
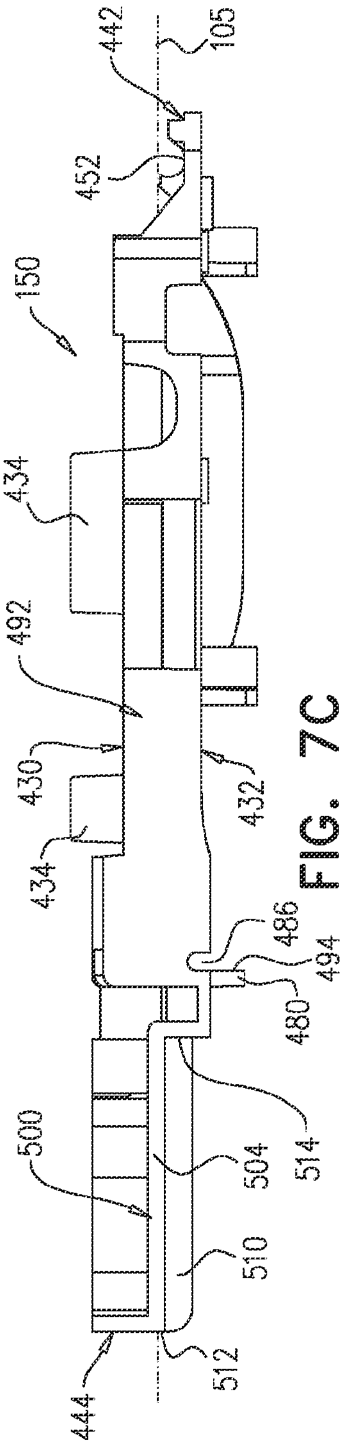
Figure 7D:
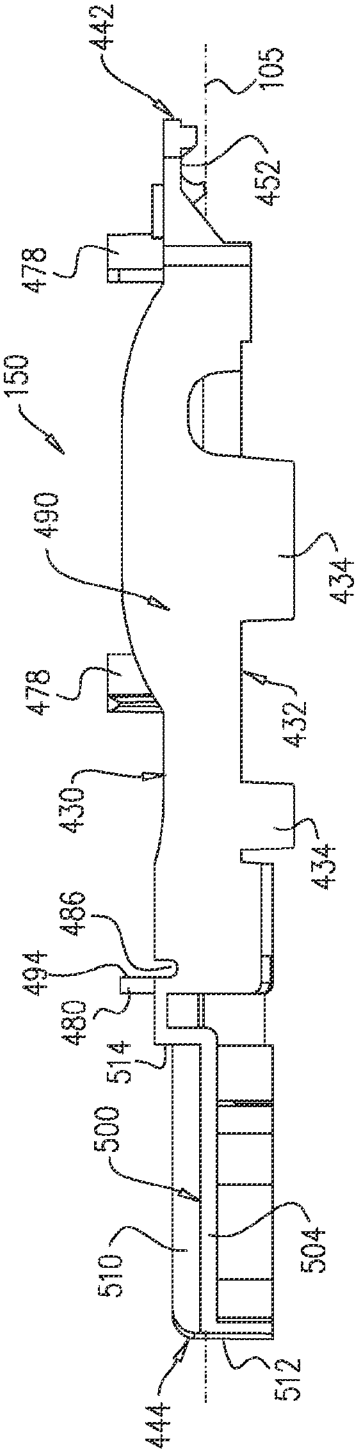
Figure 7E:
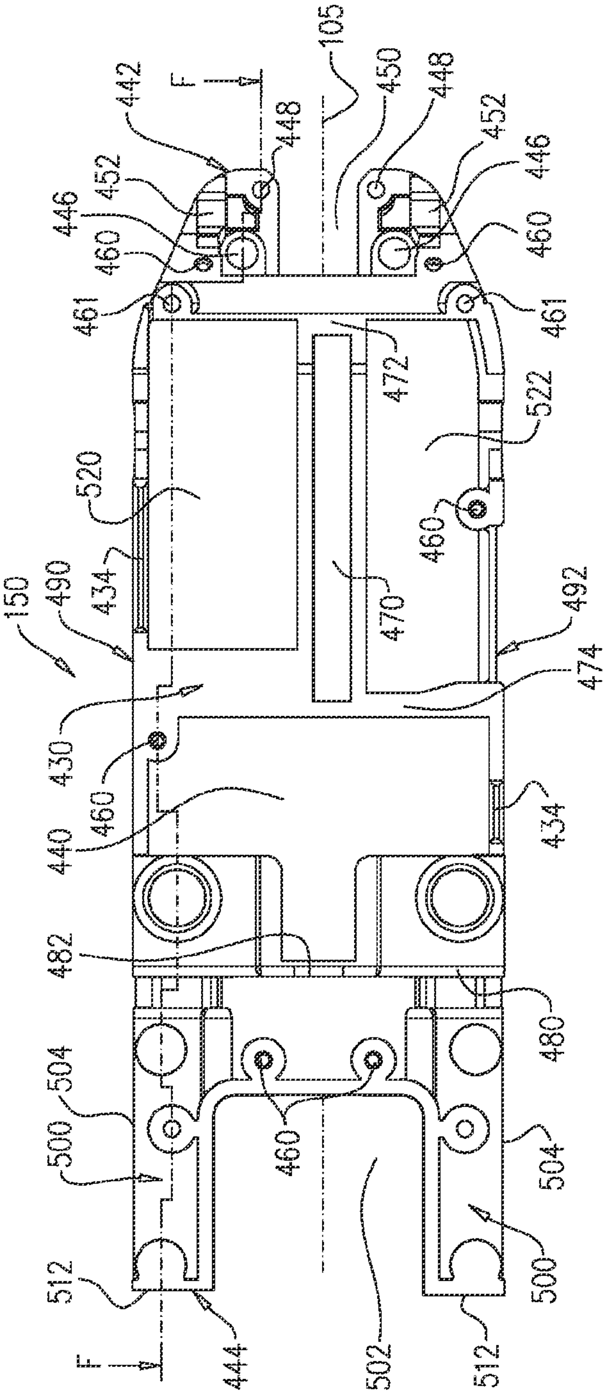
Figure 7F:
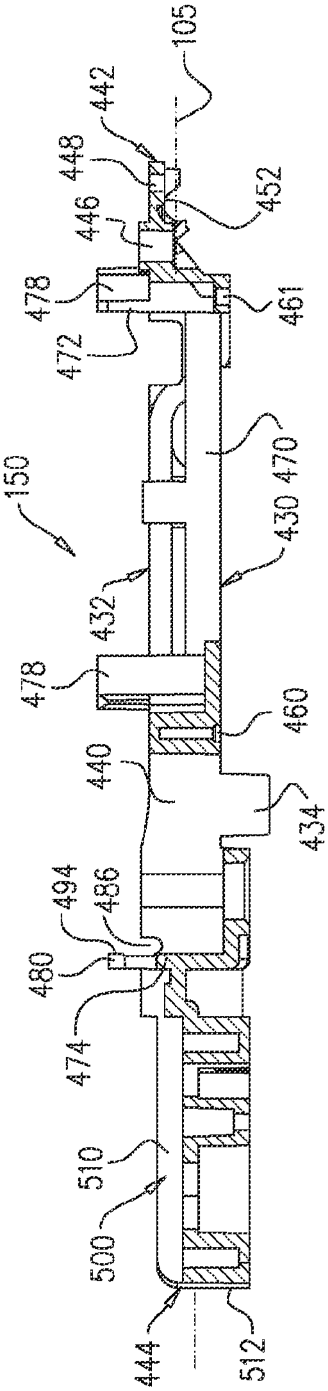

It is particularly seen in FIGS. 7A & 7B that an opening 440 for mounting the electrical motor 158 is formed in an intermediate location of chassis element 150. The electrical motor 158 is configured to be mounted onto rounded surface 484 located on the underside surface 432 of the chassis element 150.

Chassis element also defines a rearward end 442 and a forward end 444.

It is also seen in FIGS. 7A, 7B, 7E and 7F that preferably two bores 446 are formed adjacent the rearward end 442 of chassis element 150 for insertion of springs 164 therethrough. Additionally, typically four apertures 448 are formed adjacent each of bores 446, configured for insertion of screws therethrough in order to connect spring support elements 162 with chassis element 150. A recess 450 extending forwardly from the rearward end 442 is formed in chassis element 150, generally between the two bores 446.

Preferably two hinges seats 452 are formed adjacent rearward end 442 of chassis element 150, configured together with hinge seating portions 330 of the top housing portion 104 to receive hinge axles 392 of injection button element 120.

A plurality of apertures 460 are formed on the upper side 430 of the chassis element 150 and are used for insertion of screws for connection of the main PCB assembly 152 to the chassis element 150. Additional apertures 461 are formed on the upper side 430 of the chassis element 150 and are used for insertion of screws for connection of top housing portion 104 to the chassis element 150.

A longitudinal track recess 470 is formed on the underside surface 432 of the chassis element 150, separated by a transversely extending wall 472 from recess 450. Track recess 470 extends longitudinally forwardly along axis 105. A transverse wall 474 separates the track recess 470 from opening 440. A recess 476 is formed in transverse wall 474. There are two protrusions 478 formed on the underside surface 432 of the chassis element, and disposed alongside track recess 470. Protrusions 478 have recesses 479 formed therein.

Opening 440 extends between transverse wall 474 and a wall 480 parallel to wall 474. Wall 480 generally includes a rounded cut-out 482 and a rounded surface 484 extends forwardly from cut-out 482, configured to support electrical motor 158. Adjacent and slightly rearwardly of wall 480, there are two cut-outs 486 formed on a first side wall 490 and a second side wall 492 of chassis element 150, configured to enable a flange of motor 158 to be seated in cut-outs 486.

Wall 480 defines a rearwardly facing surface 494 and typically two openings 496 each formed adjacent a corresponding side wall 490 and 492.

A rearwardly extending track arm 500 extends at each side of rounded surface 484. A recess 502 is formed between track arms 500 and forwardly of rounded surface 484. It is seen that each of track arms 500 has an outwardly facing side surface 504, which joins side walls 490 and 492 respectively. Additionally, a downwardly extending protrusion 510 is formed on the inner facing side of each of track arms 500, configured to cooperate with cartridge enclosure assembly chassis 170 for guiding displacement of cartridge enclosure assembly latch element 210.

Track arms 500 are separated from opening 440 by wall 480. Each track arm 500 defines a forwardly facing edge surface 512 and terminates at a transversely extending forwardly facing surface 514. Track arms 500 are configured for engagement with the cartridge enclosure assembly latch element 210 and prevent deformation thereof.

Partially hexagonal recess 515 extends rearwardly from each of forwardly facing surfaces 514, configured for supporting nuts that are used for connection of electrical motor 158 to chassis element 150.

There is an opening 520 formed between the first side wall 490 of chassis element 150 and track recess 470. Opening 520 is configured for insertion of battery 160 therethrough. An opening 522 is formed between the second side wall 492 of chassis element 150 and track recess 470. Opening 522 is configured for insertion of power control PCB assembly 154 therethrough.

Figure 8A:
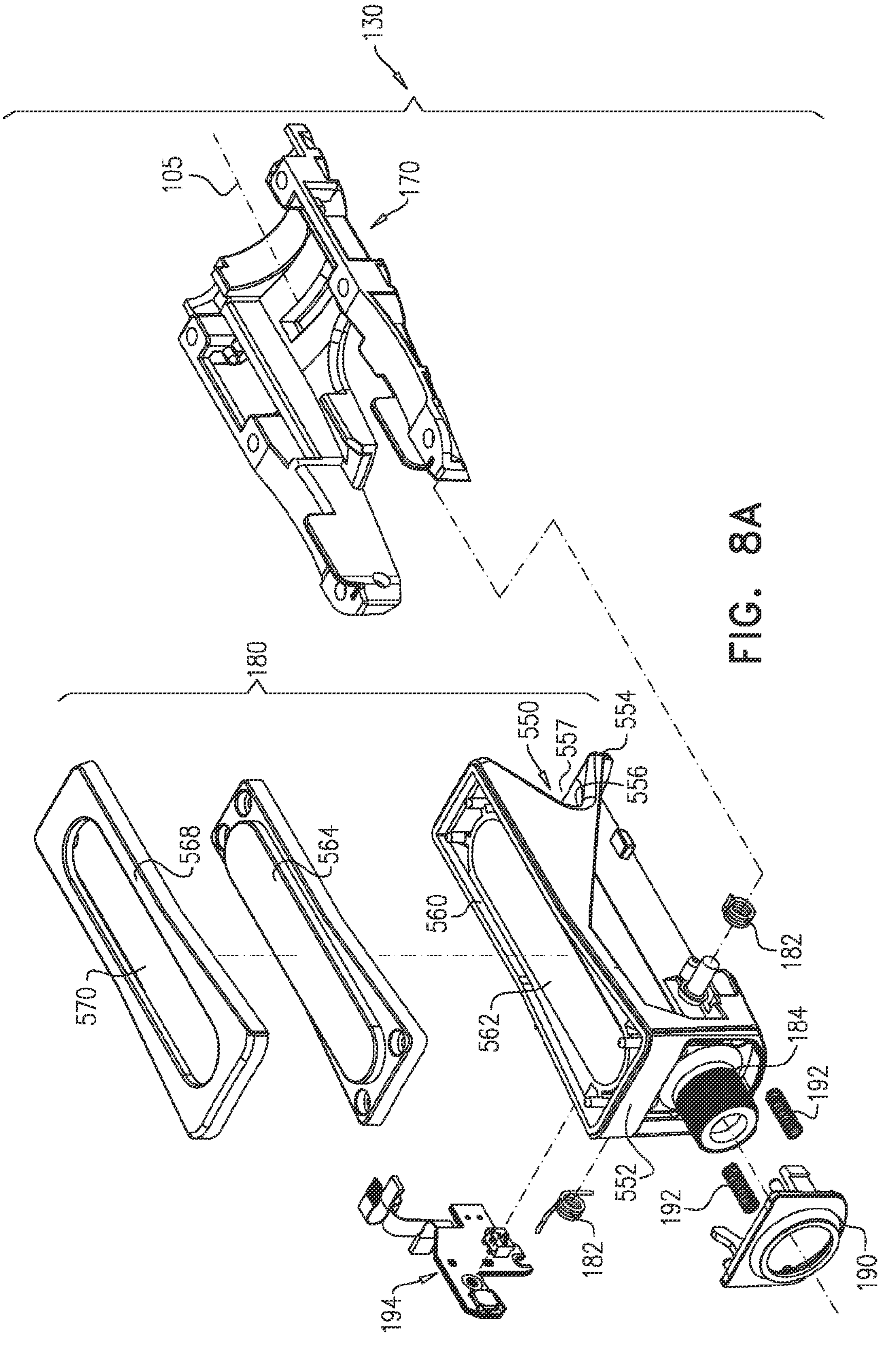
FIGS. 8A, 8B and 8C are a simplified respective first and second pictorial views and an exploded view illustration of a cartridge enclosure assembly forming part of the MUCI of FIGS. 1A & 1B.
Figure 8B:
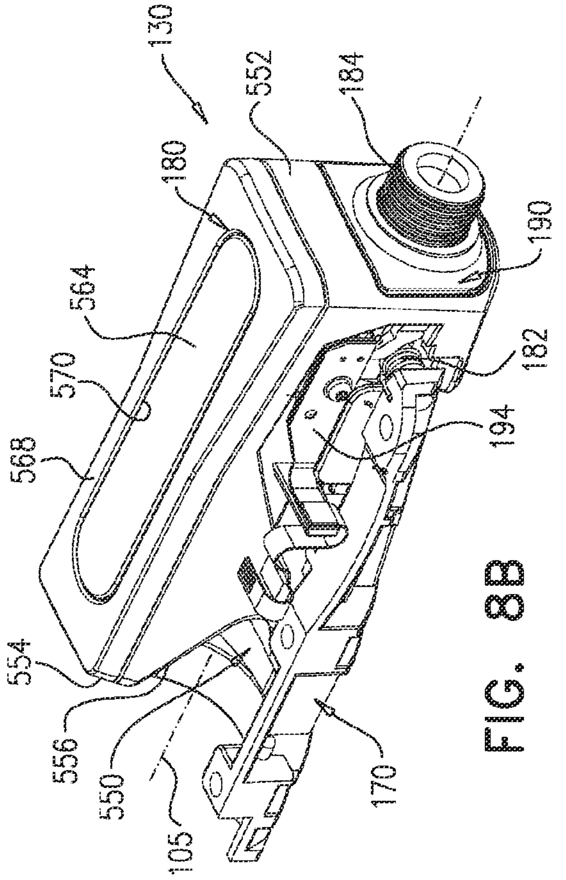
Figure 8C:
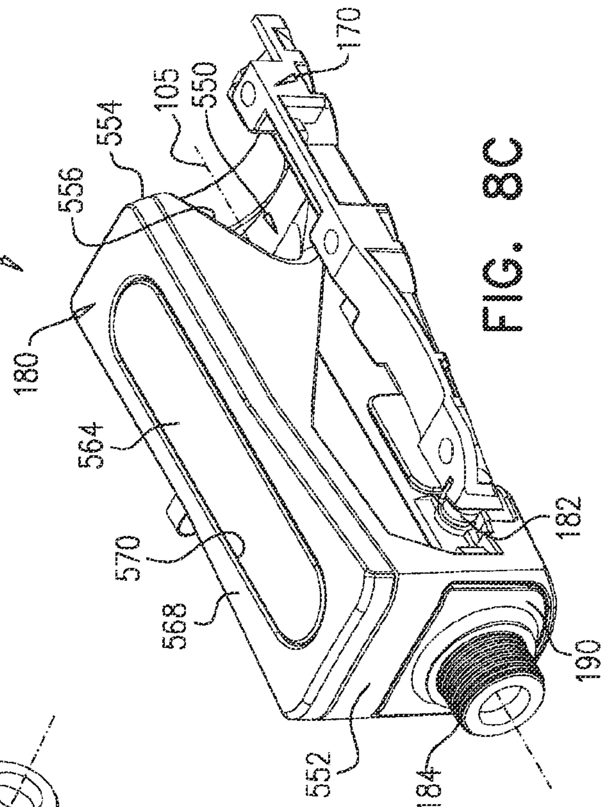

Reference is now made to FIGS. 8A, 8B and 8C, which are a simplified respective exploded view and first and second pictorial view illustrations of cartridge enclosure assembly 130 forming part of the MUCI 100 of FIGS. 1A & 1B.

As mentioned above, with reference to FIG. 1B, the cartridge enclosure assembly 130 preferably includes the cartridge enclosure assembly chassis 170 and the pivot mount element 180, which is adapted to receive a medicament cartridge therewithin and is generally pivotably mounted with respect to cartridge enclosure assembly chassis 170 and configured to be biased to an open operative orientation with respect to housing portions 102 and 104, due to the biasing force of torsion springs 182. The pivot mount element 180 includes forward generally externally threaded end 184, adapted for engagement of a needle assembly therewith.

The needle presence responsive element 190 is adapted to be coupled to the pivot mount element 180 and is configured to be axially displaceable, along longitudinal axis 105, with respect thereto. The needle presence responsive element 190 is biased to a forward position by means of the biasing force of compression springs 192.

The PCB assembly 194 is operatively coupled to the cartridge enclosure assembly 130 and configured to sense the axial orientation of the needle presence responsive element 190.

It is appreciated that both pivot mount element 180 and cartridge enclosure assembly chassis 170 are arranged along a mutual longitudinal axis 105.

Pivot mount element 180 defines an inner volume 550, which is configured for insertion of a medicament cartridge thereinto. The pivot mount element 180 has a forward end 552 and a rearward end 554. A curved edge surface 556 is formed adjacent the rearward end 554 of the pivot mount element 180, forming a cut-out 557, configured for providing firm grip for the user for inserting or removing a medicament cartridge therefrom.

It is noted that as seen in FIGS. 8A-8C the needle presence responsive element 190 is mounted onto the forward end 552 of pivot mount element 180.

Pivot mount element 180 further defines a front wall portion 560 having a central longitudinal opening 562. A generally transparent window 564 is disposed onto front wall portion 560 and is retained in place by means of mounting a cover element 568 thereupon. Cover element 568 has an opening 570 corresponding in shape to opening 562. The window 564 enables medicament inspection within a medicament cartridge by a user.

It is appreciated that window 564 and cover element 568 are formed as an integral part of pivot mount element 180.

Figure 9A:
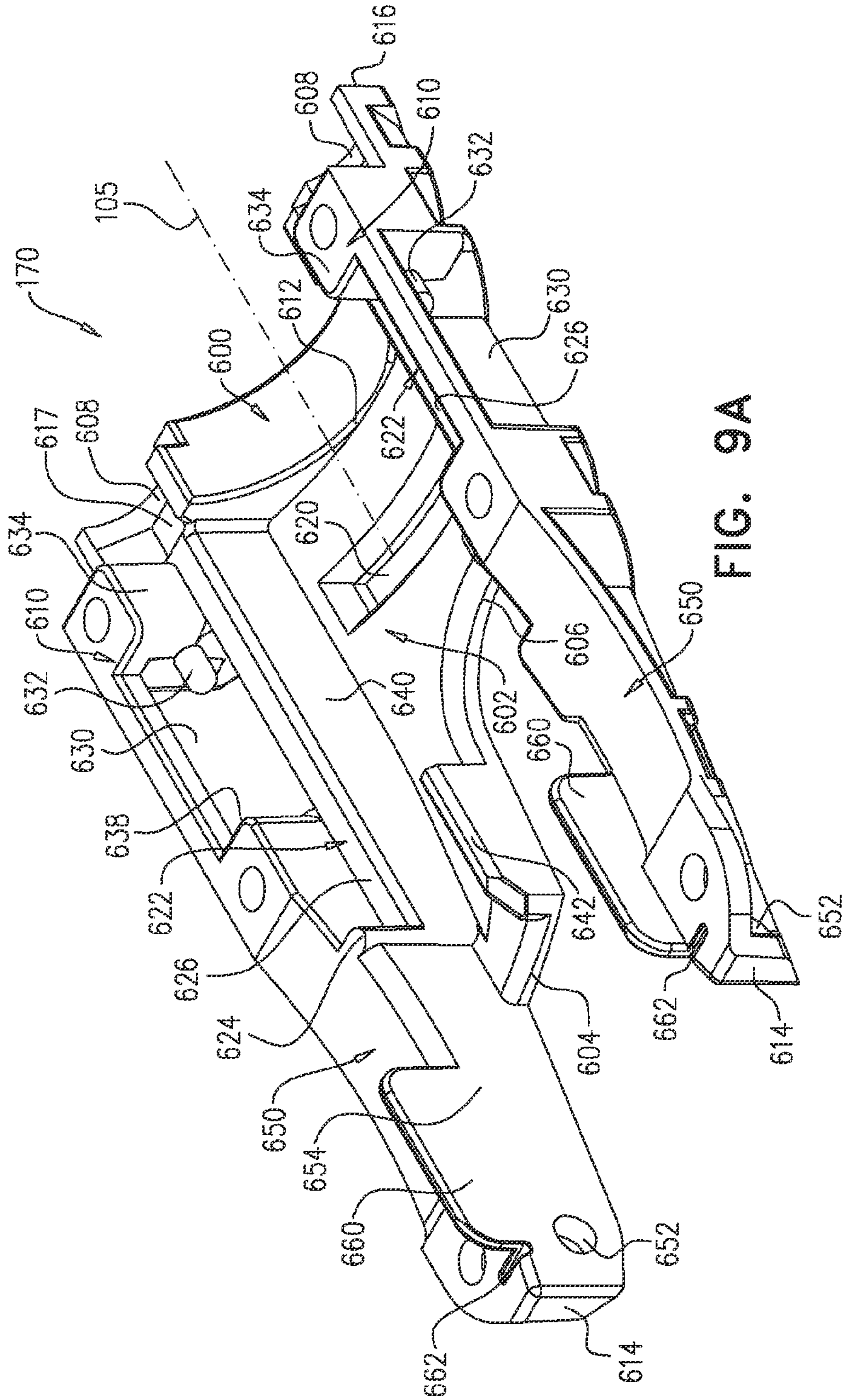
FIGS. 9A, 9B and 9C are simplified first, second and third pictorial illustrations of a cartridge enclosure assembly chassis forming part of the cartridge enclosure assembly of FIGS. 8A-8C.
Figure 9B:
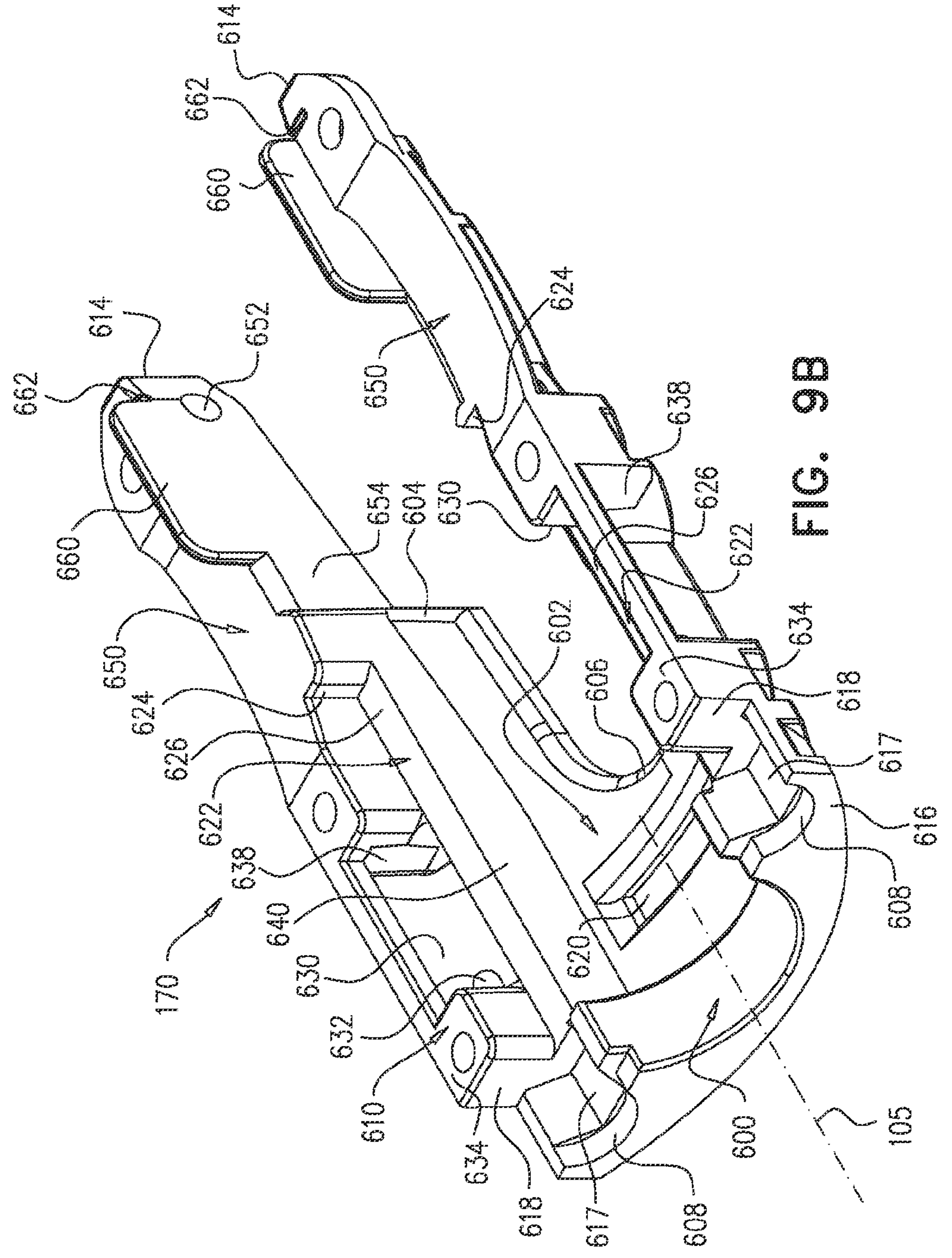
Figure 9C:
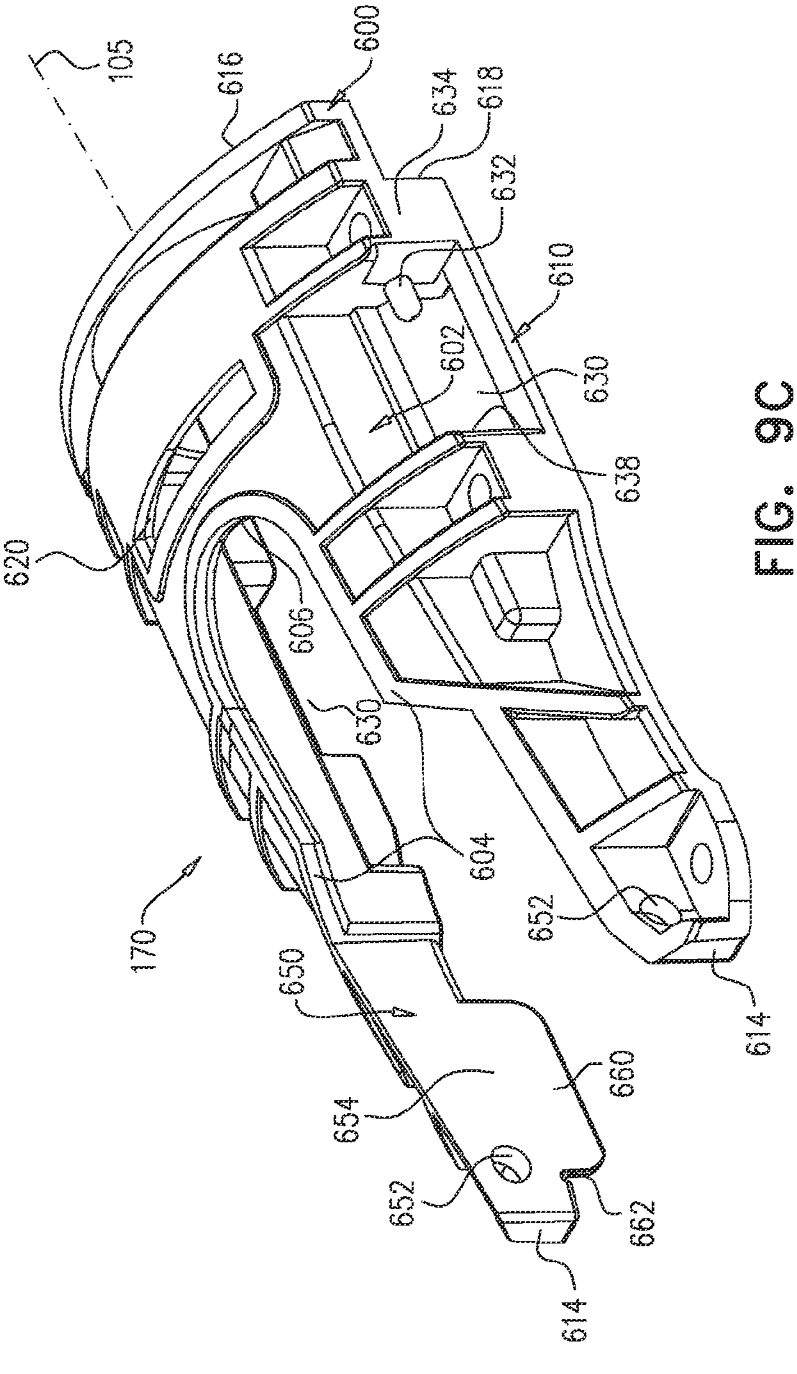
Figure 9D:
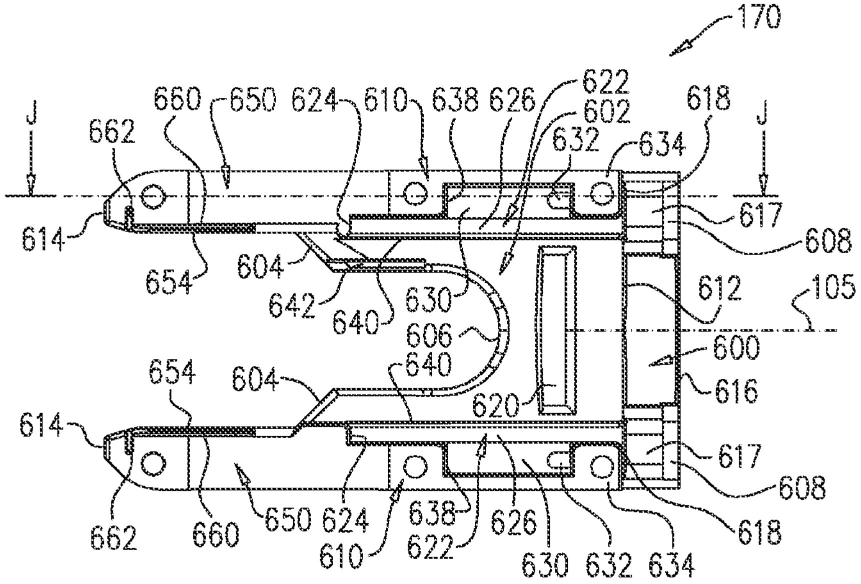
FIGS. 9D, 9E, 9F, 9G, 9H, 9I and 9J are simplified top planar view, bottom planar view, first planar side view, second planar side view, front view, back view and sectional view illustrations of the cartridge enclosure assembly chassis of FIGS. 9A-9C, the sectional view being taken along the lines J-J in FIG. 9D.
Figure 9E:
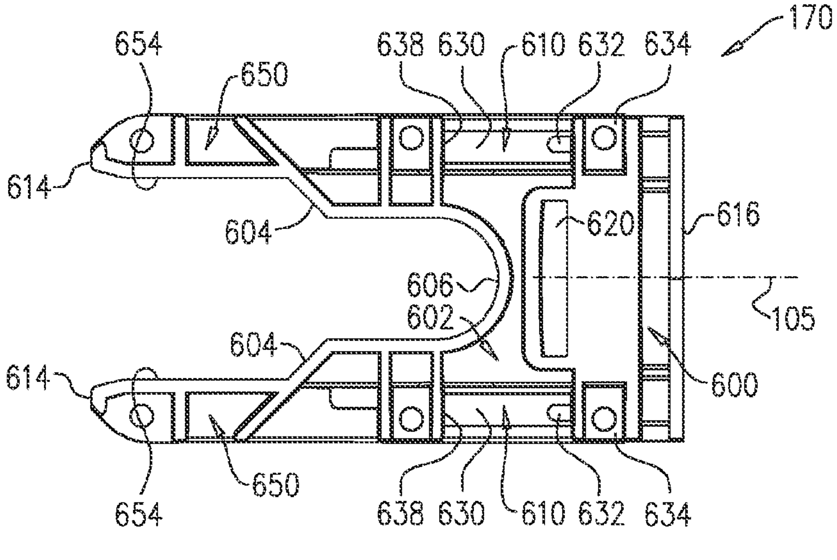
Figure 9F:
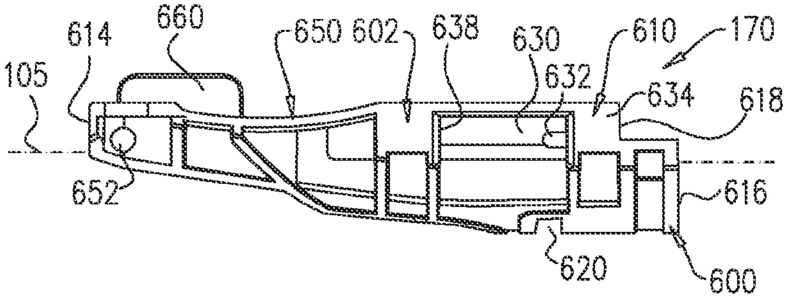
Figure 9G:
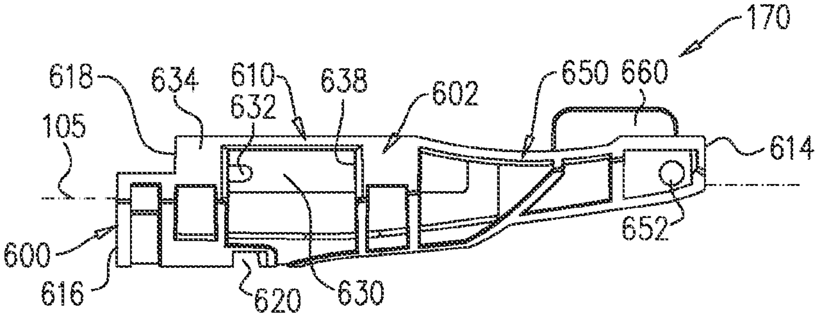
Figure 9H:
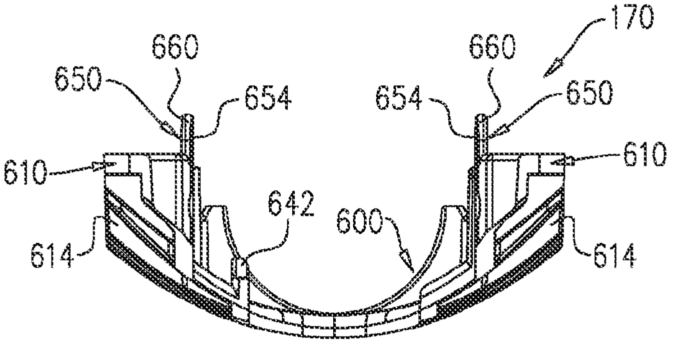
Figure 9I:
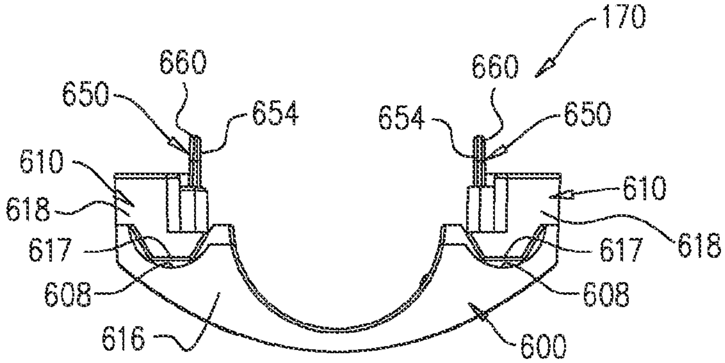
Figure 9J:
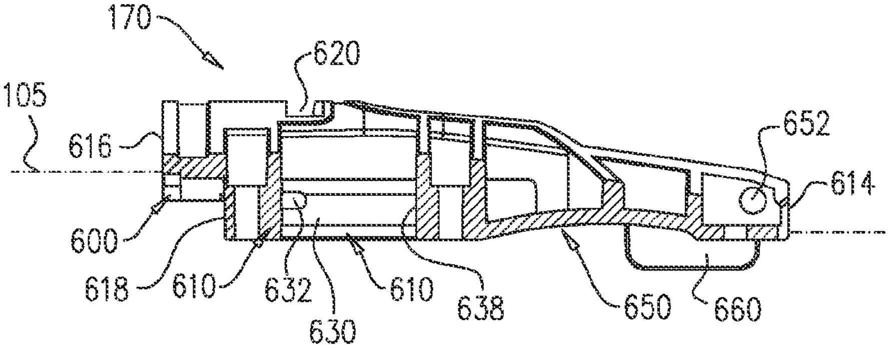

Reference is now made to FIGS. 9A, 9B and 9C, which are simplified first, second and third pictorial illustrations of the cartridge enclosure assembly chassis 170 forming part of the cartridge enclosure assembly 130 of FIGS. 8A-8C and to FIGS. 9D, 9E, 9F, 9G, 9H, 9I and 9J, which are simplified top planar view, bottom planar view, first planar side view, second planar side view, front view, back view and sectional view illustrations of the cartridge enclosure assembly chassis 170 of FIGS. 9A-9C, the sectional view being taken along the lines J-J in FIG. 9D.

It is seen in FIGS. 9A-9J that the cartridge enclosure assembly chassis 170 is arranged generally along longitudinal axis 105. The cartridge enclosure assembly chassis 170 has a rearward partially curved end portion 600 and a forward generally curved portion 602 extending forwardly therefrom. Portion 602 terminates at a forward edge 604, which has a curved cut out 606 formed therein and extending rearwardly from edge 604. Cut out 606 enables inspection of a medicament contained in the medicament cartridge once it is inserted into the MUCI 100. Portion 600 is bounded by a recessed tunnel 608 on each of its sides and portion 602 is bounded by an upwardly raised spring enclosing finger 610 on each of its sides. Spring enclosing fingers 610 extend forwardly from a forwardly facing surface 612 of portion 602 to a forward edge 614 that is disposed forwardly of forward edge 604 of portion 602. Portion 600 defines a rearwardmost edge 616. Each of recessed tunnels 608 generally terminate at partially hexagonal recess 617, which extend forwardly and terminate at a transversely extending rearwardly facing surface 618. Recesses 617 cooperate with recesses 515 of chassis element 150 to form a hexagonal channel, which is configured for supporting nuts that are used for connection of electrical motor 158 to chassis element 150.

An opening 620 is formed in portion 602, slightly rearwardly from cut out 606. Opening 620 is configured for releasably retaining the pivot mount element 180 in a closed operative orientation.

Each of spring enclosing fingers 610 has a guiding track 622 formed inwardly thereof adjacent portion 602. Guiding tracks 622 extend generally longitudinally from forwardly facing surface 612 to an upwardly extending wall portion 624, disposed in vicinity of and rearwardly from forward edge 604. Guiding tracks 622 define an upwardly facing generally flat surface 626. The guiding tracks 622 are configured for retaining a portion of the cartridge enclosure assembly latch element 210, as will be further discussed in detail.

A spring seat cut out 630 is formed in each of spring enclosing fingers 610. Spring seat cut-out 630 has a spring aligning pin 632, which is formed on and extends forwardly from a rearward end portion 634 of spring enclosing finger 610. Spring aligning pins 632 are disposed slightly outwardly with respect to guiding tracks 622. Spring seat cut-outs 630 further define a rearwardly facing end surface 638. Spring seat cut-outs 630 are configured to accommodate springs 212 (shown in FIG. 1B).

It is seen in FIGS. 9A-9J that guiding tracks 622 are generally raised above portion 602 and are joined thereto by means of inwardly facing side wall portions 640.

It is further seen particularly in FIGS. 9A, 9C, 9D and 9H that an upstanding protrusion 642 is formed on one side of the cut out 606.

Longitudinal arms 650 extend forwardly from rearwardly facing end surface 638 of spring enclosing fingers 610 to a forward edge 614. An aperture 652 is formed at each of longitudinal arms 650 and extends generally transversely to longitudinal axis 105. Apertures 652 are located adjacent forward edge 614.

Each of arms 650 defines an inwardly facing surface 654, extending from which is an upstanding protrusion 660, which is located adjacent forward edge 614 and a recess 662 formed in the vicinity of the forward end of each upstanding protrusion 660.

Figure 10A:
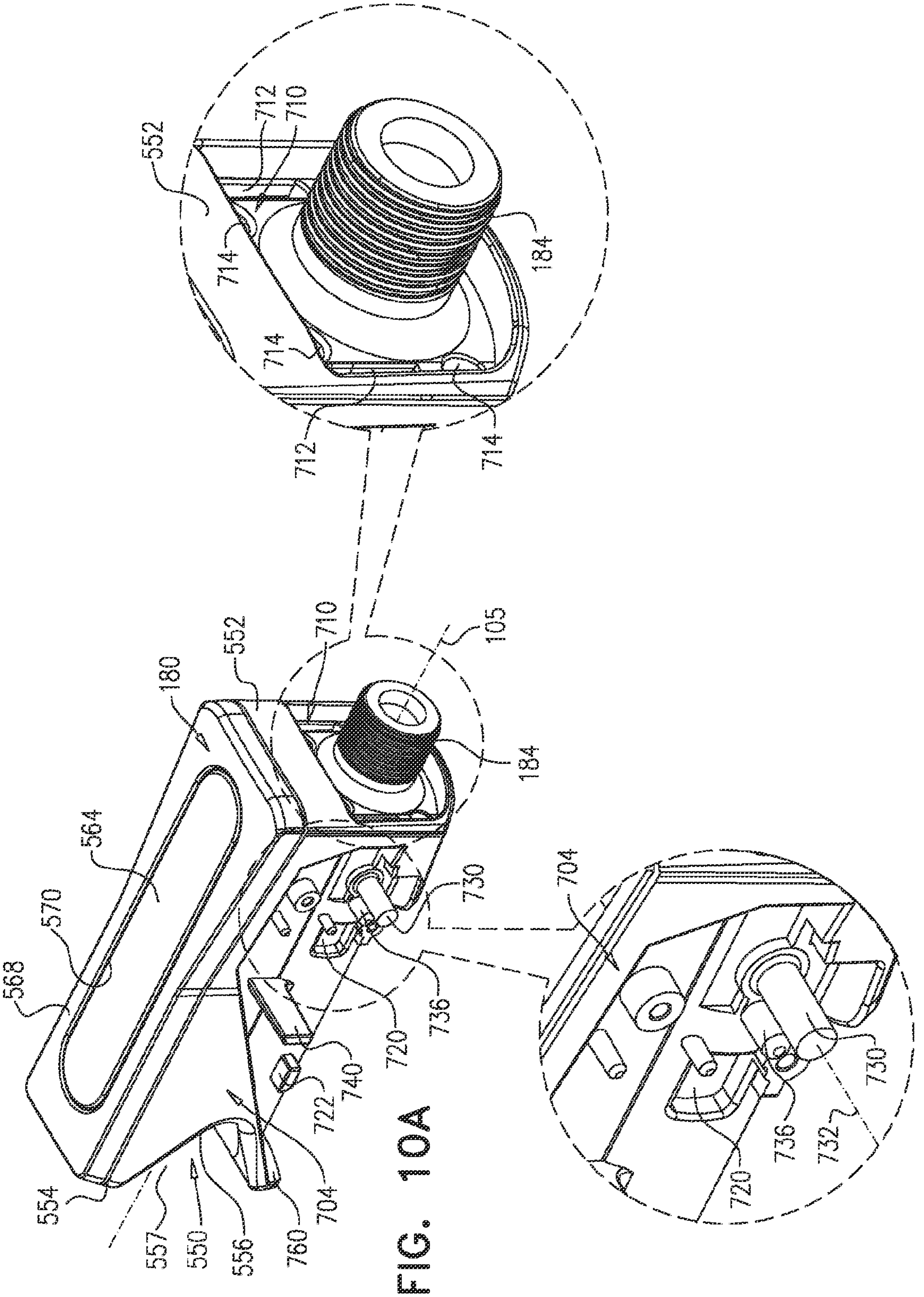
FIGS. 10A, 10B and 10C are simplified first, second and third pictorial illustrations of a pivot mount element for the cartridge enclosure assembly chassis of FIGS. 9A-9I.
Figure 10C:
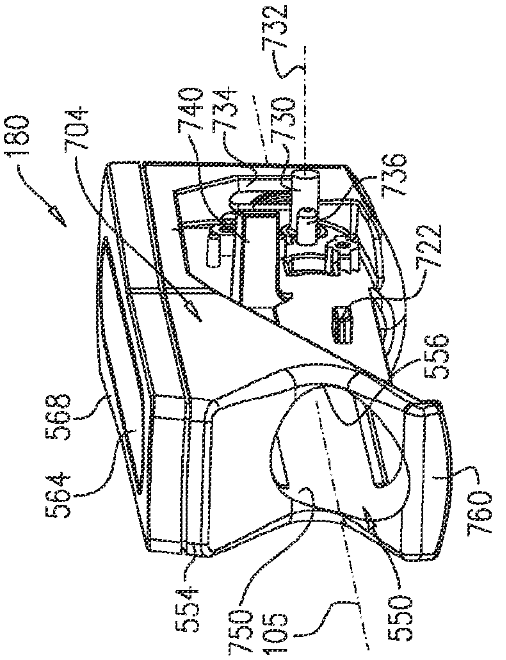
Figure 10B:
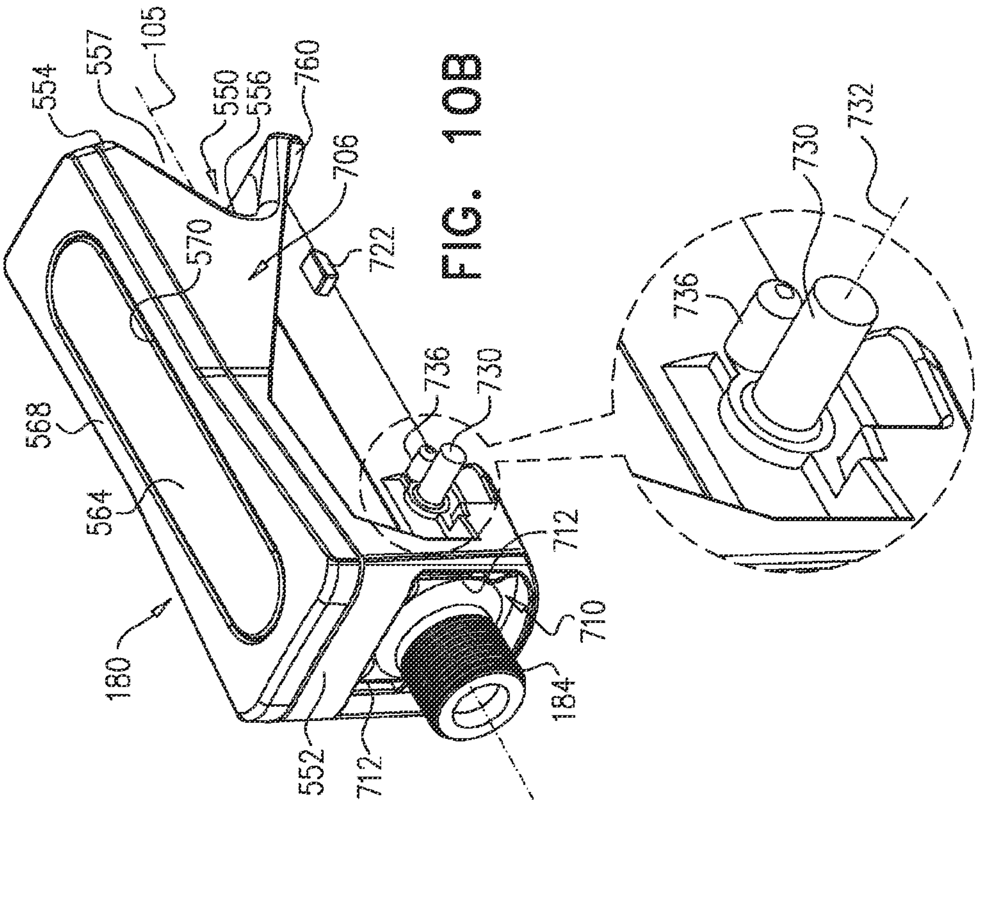
Figure 10E:
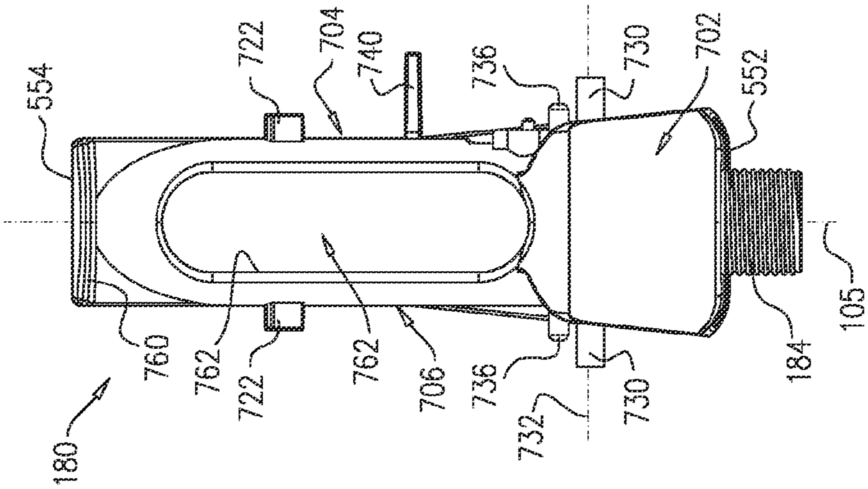
FIGS. 10D, 10E, 10F, 10G, 10H, 10I, 10J and 10K are simplified top and bottom planar views, two planar side views, front planar view, rear planar view and a sectional view illustration of the pivot mount element of FIGS. 10A-10C, the sectional views being taken along the lines J-J and K-K respectively in FIG. 10D.
Figure 10D:
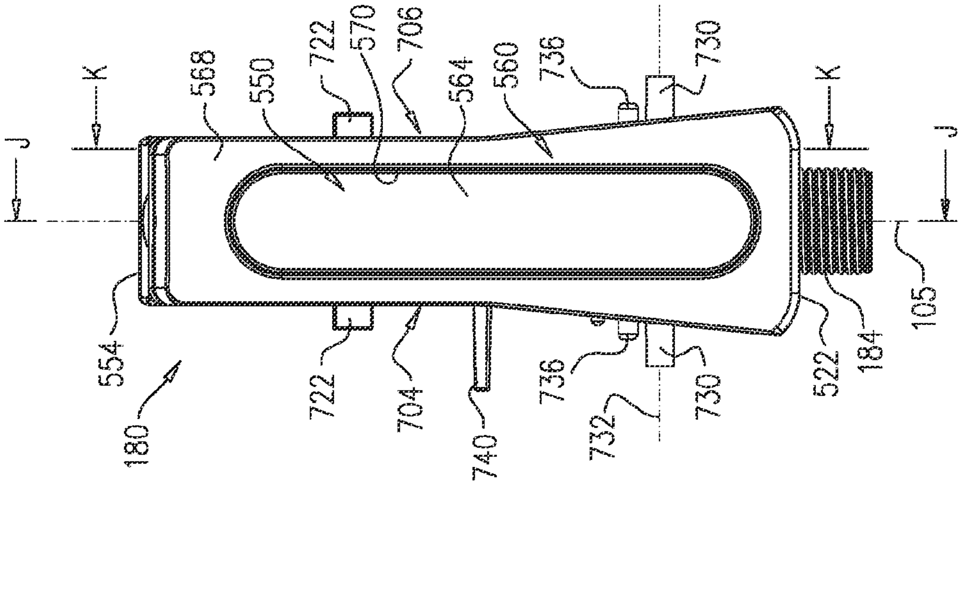

Reference is now made to FIGS. 10A, 10B and 10C, which are simplified first, second and third pictorial illustrations of pivot mount element 180 for the cartridge enclosure assembly chassis 170 of FIGS. 9A-9I and to FIGS. 10D, 10E, 10F, 10G, 10H, 10I, 10J and 10K, which are simplified top and bottom planar views, two planar side views, front planar view, rear planar view and a sectional view illustration of the pivot mount element 180 of FIGS. 10A-10C, the sectional views being taken along the lines J-J and K-K respectively in FIG. 10D.

As mentioned hereinabove, pivot mount element 180 is arranged along longitudinal axis 105 and has rearward end 554 and forward end 552 having outwardly threaded end 184 extending therefrom. The pivot mount element 180 has a front wall portion 560 having opening 562 therewithin and configured for mounting of window 564 and cover element 568 thereon. Pivot mount element 180 also has a rear wall 702, first side wall 704 and second side wall 706.

It is seen in FIGS. 10A-10J that a forwardly facing recess 710 is formed at the forward end 552 of pivot mount element 180 for mounting of needle presence responsive element 190 thereinto. Preferably two openings 712 are formed within recess 710 for insertion of a portion of the needle presence responsive element 190 therethrough.

Figure 10G:
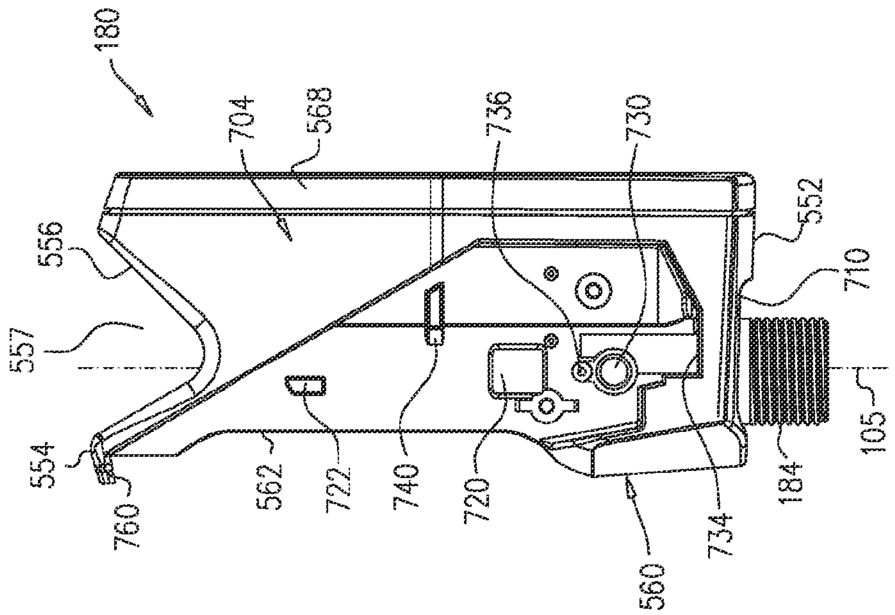
Figure 10F:
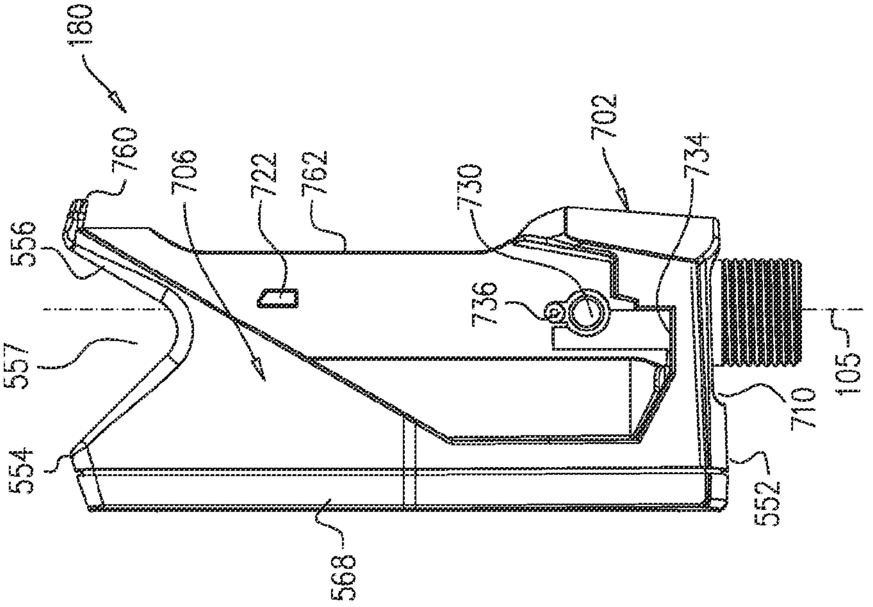
Figure 10H:
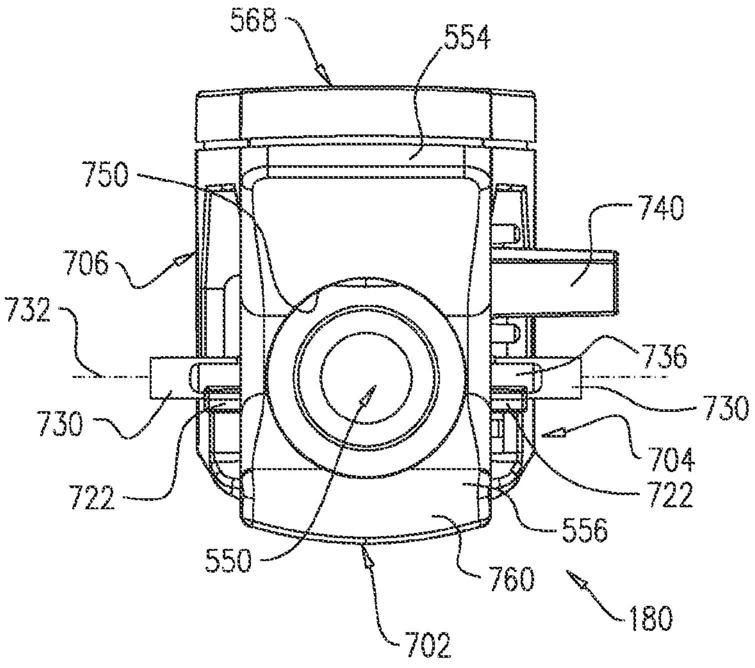
Figure 10I:
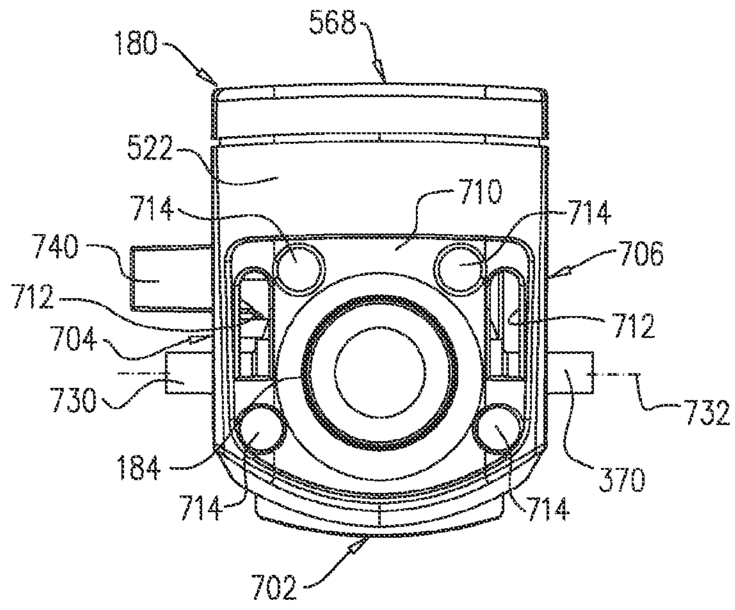
Figure 10J:
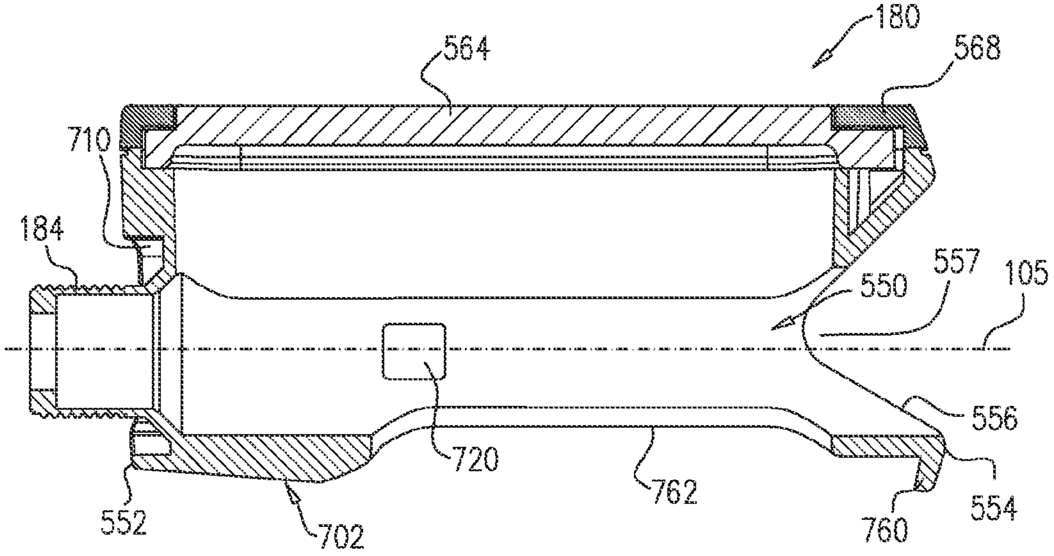

There are typically four openings 714 formed within recess 710, which are particularly seen in FIG. 10I. At least two of the openings 714 are configured to receive springs 192 thereinto.

An opening 720 is formed in side wall 704 for positioning of a portion of PCB assembly 194 therein. Preferably one locking snap element 722 is formed on each of side walls 704 and 706, each snap element 722 is configured to enable locking of pivot mount element 180 relative to top housing portion 104.

A hinge element 730 is disposed on each of side walls 704 and 706, adjacent to forward end 552 of the pivot mount element 180. Hinge elements 730 preferably extend along axis 732, which extends preferably transversely to longitudinal axis 105. Hinge elements 730 serve as the pivoting axis of the pivot mount element 180 relative to cartridge enclosure assembly chassis 170.

Rearwardly facing shoulder surfaces 734 are preferably formed slightly forwardly of each of hinge elements 730, as specifically seen in FIGS. 10C, 10F & 10G.

It is also seen in FIGS. 10A-10J that a positioning protrusion 736 is preferably disposed on each of side walls 704 and 706 for aligning the pivot mount element 180 with respect to cartridge enclosure assembly chassis 170. A protrusion 740 extends outwardly side wall 704 for positioning the connector of PCB assembly 194.

As mentioned hereinabove, rearward end 554 of the pivot mount element 180 defines curved surface 556 forming cut-outs 557, in which an opening 750 is formed, leading to inner volume 550 for insertion of a medicament cartridge thereinto. It is appreciated that cut-outs 557 are configured to provide a firm grip for the user's finger while inserting or removing a medicament cartridge to or from the inner volume 550.

A flange portion 760 is formed at the junction of curved surface 556 and rear wall 702. It is noted that flange portion 760 extends outwardly and preferably at an acute angle with respect to rear wall 702. Flange portion 760 preferably serves for two purposes: configured to engage the cartridge enclosure assembly chassis 170 in order to prevent excessive force exertion on hinge elements 730 to prevent breaking thereof. Additionally, the flange portion 760 is configured for closing the gap created between the inner volume of the MUCI 100 and the cartridge enclosure assembly 130 in order to prevent insertion of objects into the MUCI 100.

A window 762 is formed on rear wall 702 for inspection of medicament in the cartridge once it is inserted into the MUCI 100.

Figure 10K:
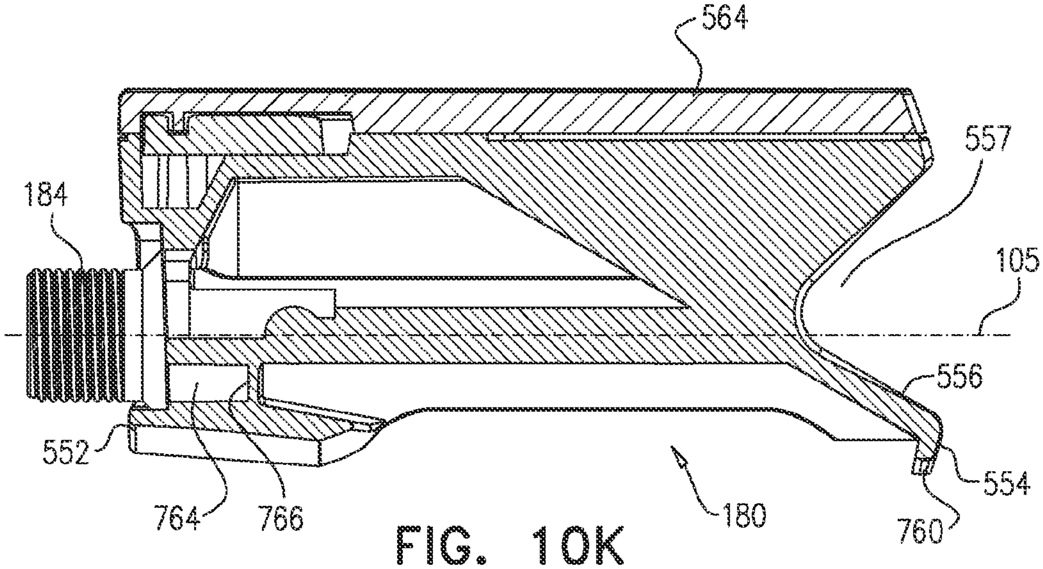
Figure 11A:
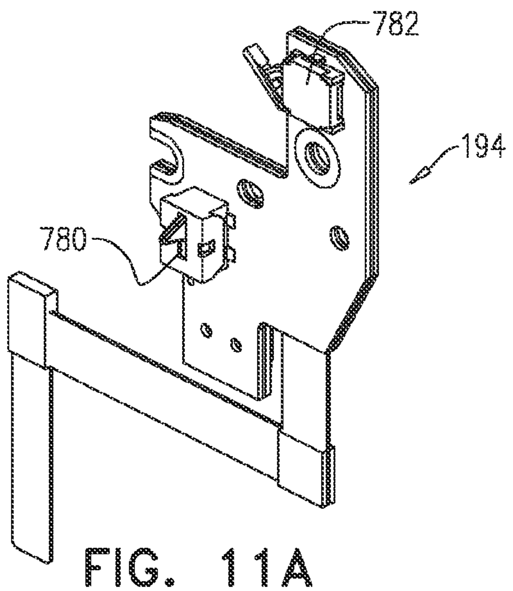
FIGS. 11A, 11B, 11C and 11D are simplified respective top and bottom pictorial, top planar view and bottom planar view illustrations of a PCB assembly forming part of the cartridge enclosure assembly of FIGS. 8A-8C.
Figure 11B:
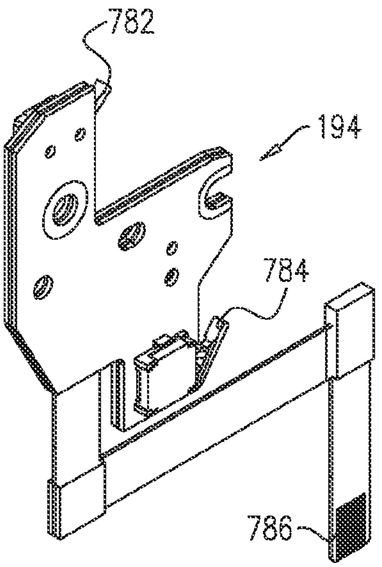
Figure 11C:
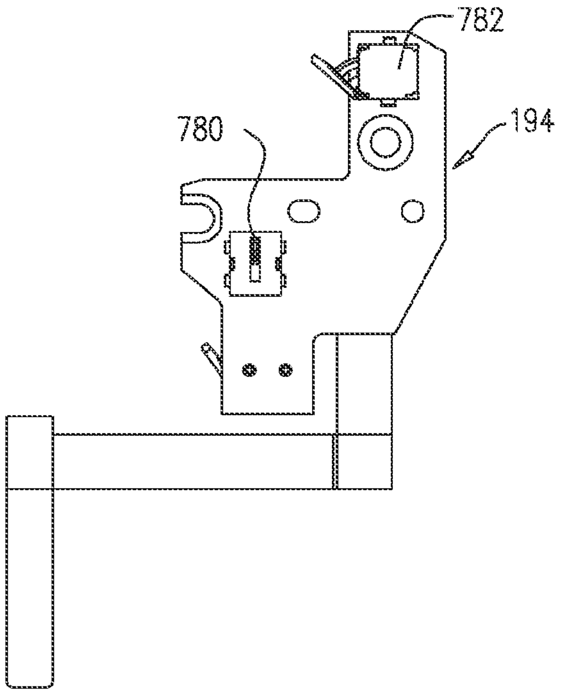
Figure 11D:
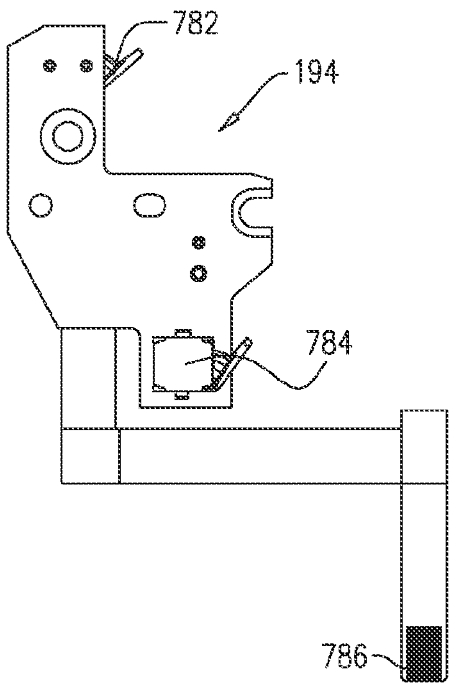
Figure 12B:
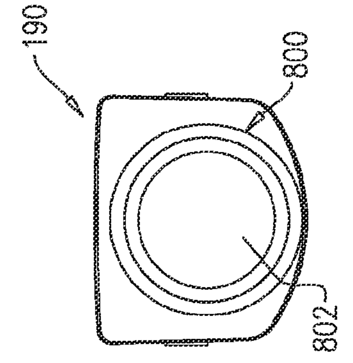
FIGS. 12A, 12B, 12C, 12D, 12E, 12F and 12G are simplified respective pictorial, top planar view, bottom planar view, first and second side view, front planar view and back planar view illustrations of a needle presence responsive element, forming part of the cartridge enclosure assembly of FIGS. 8A-8C.
Figure 12D:
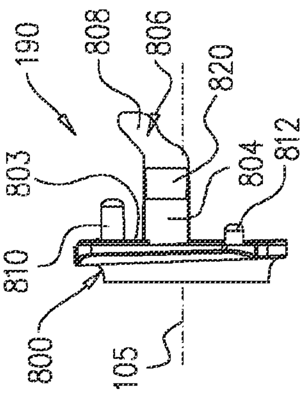
Figure 12A:
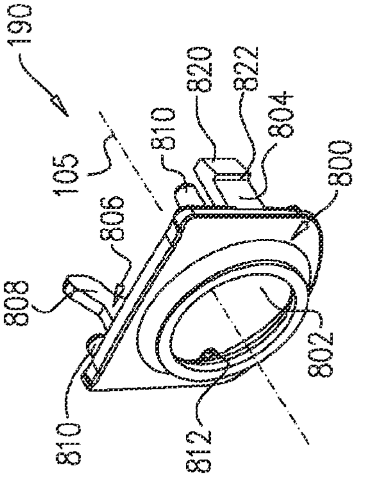
Figure 12C:
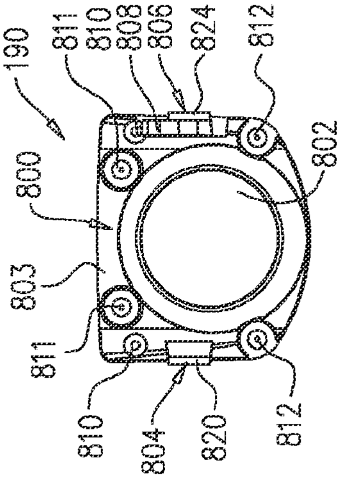
Figure 12F:
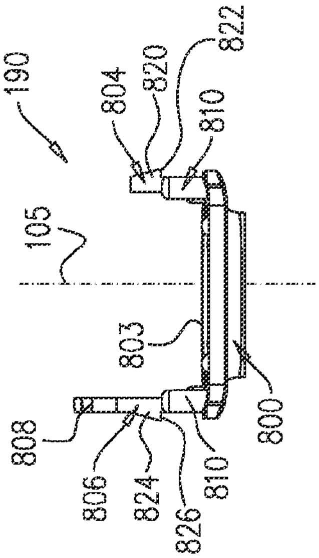
Figure 12G:
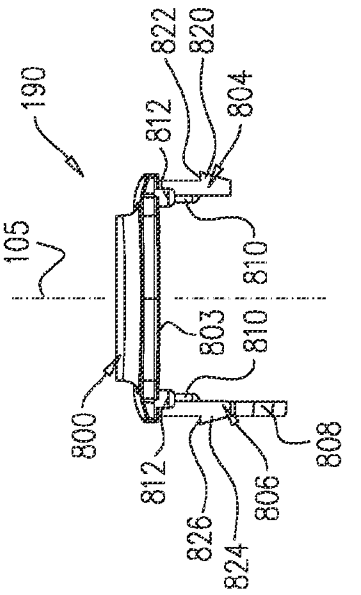
Figure 12E:
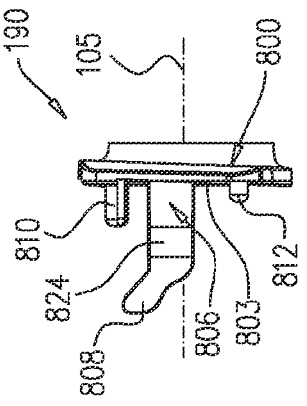

It is specifically seen in FIG. 10K that preferably two symmetrical spring receiving channels 764 are formed in pivot mount element 180 and extend axially rearwardly from forward end 552, each defining a forwardly facing edge 766 for supporting an end of spring 192.

Reference is now made to FIGS. 11A, 11B, 11C and 11D, which are simplified respective top and bottom pictorial, top planar view and bottom planar view illustrations of PCB assembly 194 forming part of the cartridge enclosure assembly 130 of FIGS. 8A-8C.

It is seen in FIGS. 11A-11D that preferably three sensors are positioned on PCB assembly 194. A cartridge sensor 780, which indicates whether a cartridge containing a medicament is inserted into the cartridge enclosure assembly 130, a needle sensor 782, which indicates whether a needle was attached to the pivot mount element 180, and a cartridge enclosure assembly state sensor 784, indicating whether the pivot mount element 180 is disposed in its open or closed operative orientation.

Additionally, contacts 786 are seen in FIGS. 11A-11D, which are adapted to enable attachment of the PCB assembly 194 to the main PCB assembly 152 of the MUCI 100.

Reference is now made to FIGS. 12A, 12B, 12C, 12D, 12E, 12F and 12G, which are simplified respective pictorial, top planar view, bottom planar view, first and second side view, front planar view and back planar view illustrations of the needle presence responsive element 190, forming part of the cartridge enclosure assembly 130 of FIGS. 8A-8C.

Needle presence responsive element 190 includes a generally flat wall portion 800 and a bore 802 formed therein for insertion of externally threaded end 184 of pivot mount element 180 therethrough. Flat wall portion defines a rearwardly facing surface 803.

Protruding rearwardly from wall portion 800 are preferably two snap protrusions 804 and 806. Snap protrusion 806 extends rearwardly further than snap protrusion 804 and includes an engagement portion 808, which is configured to engage the needle sensor 782 of PCB assembly 194.

Protrusions 810 extend rearwardly from wall portion 800 and disposed slightly rearwardly of snap protrusions 804 and 806. Protrusions 810 along with snap protrusions 804 and 806 are configured to be inserted into openings 712 of pivot mount element 180 and serve to guide the mounting of needle presence responsive element 190 onto externally threaded end 184 of pivot mount element 180. Spring seats 811 and protrusions 812 are formed on wall portion 800 and enable alignment of springs 192. At least two of the spring seats 811 and protrusions 812 are configured to bias the displacement of the needle presence responsive element 190 when needle is detached from cartridge enclosure assembly 130.

It is also seen in FIGS. 12A-12G that snap protrusion 804 preferably includes a rearwardly tapered portion 820, which terminates at a forwardly facing shoulder surface 822. Additionally, snap protrusion 806 also includes a rearwardly tapered portion 824, which terminates at a forwardly facing shoulder surface 826.

The needle presence responsive element 190 is configured to be mounted onto pivot mount element 180 of the cartridge enclosure assembly 130 and is configured to sense the attachment of a needle to the externally threaded end 184 of the pivot mount element 180.

Figure 13C:
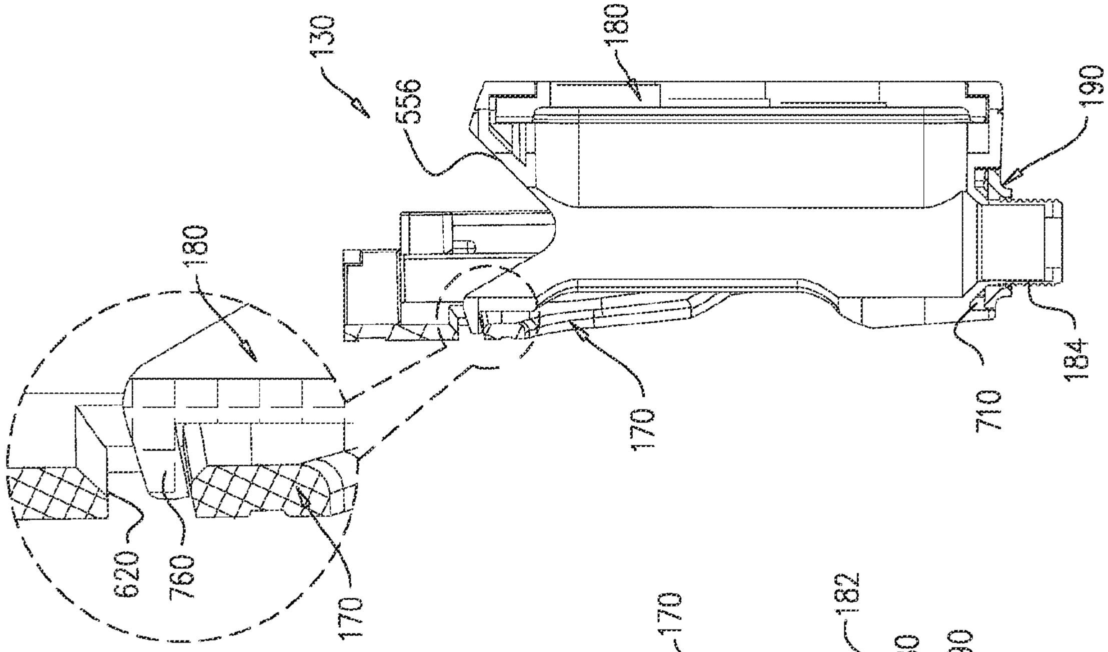
FIGS. 13A, 13B and 13C are simplified pictorial, planar top view and sectional view illustrations of the cartridge enclosure assembly of FIGS. 8A-12G in a first operative orientation thereof, the sectional view being taken along the lines C-C in FIG. 13B.
Figure 13B:
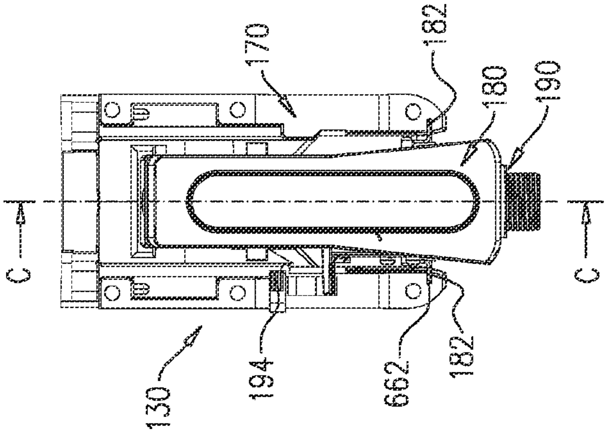
Figure 13A:
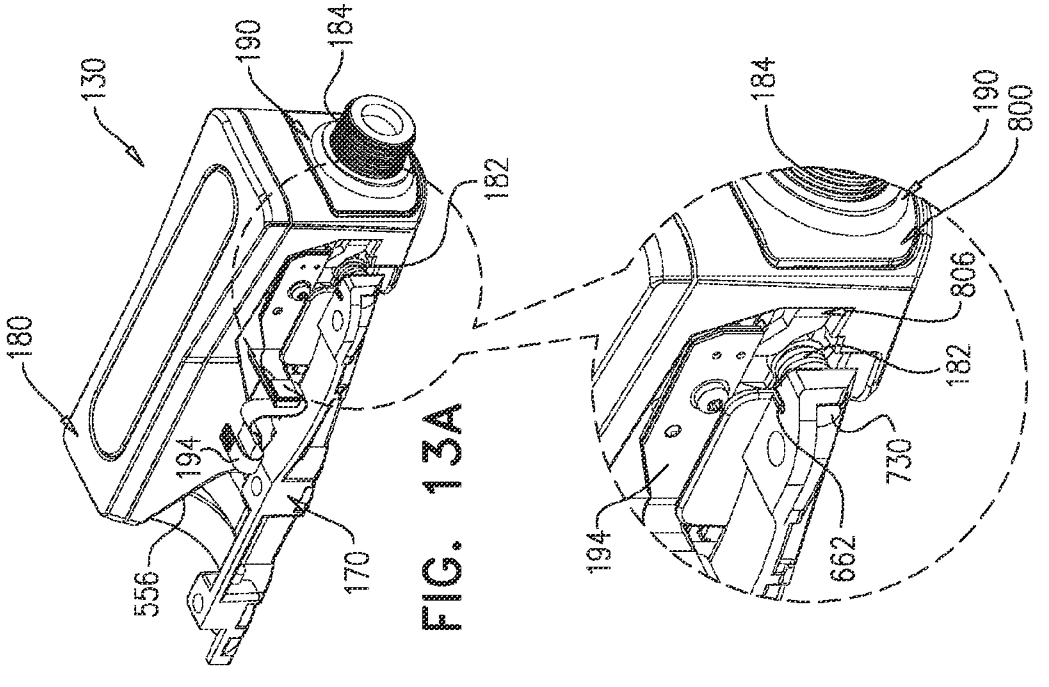
Figures 14A, 14B:
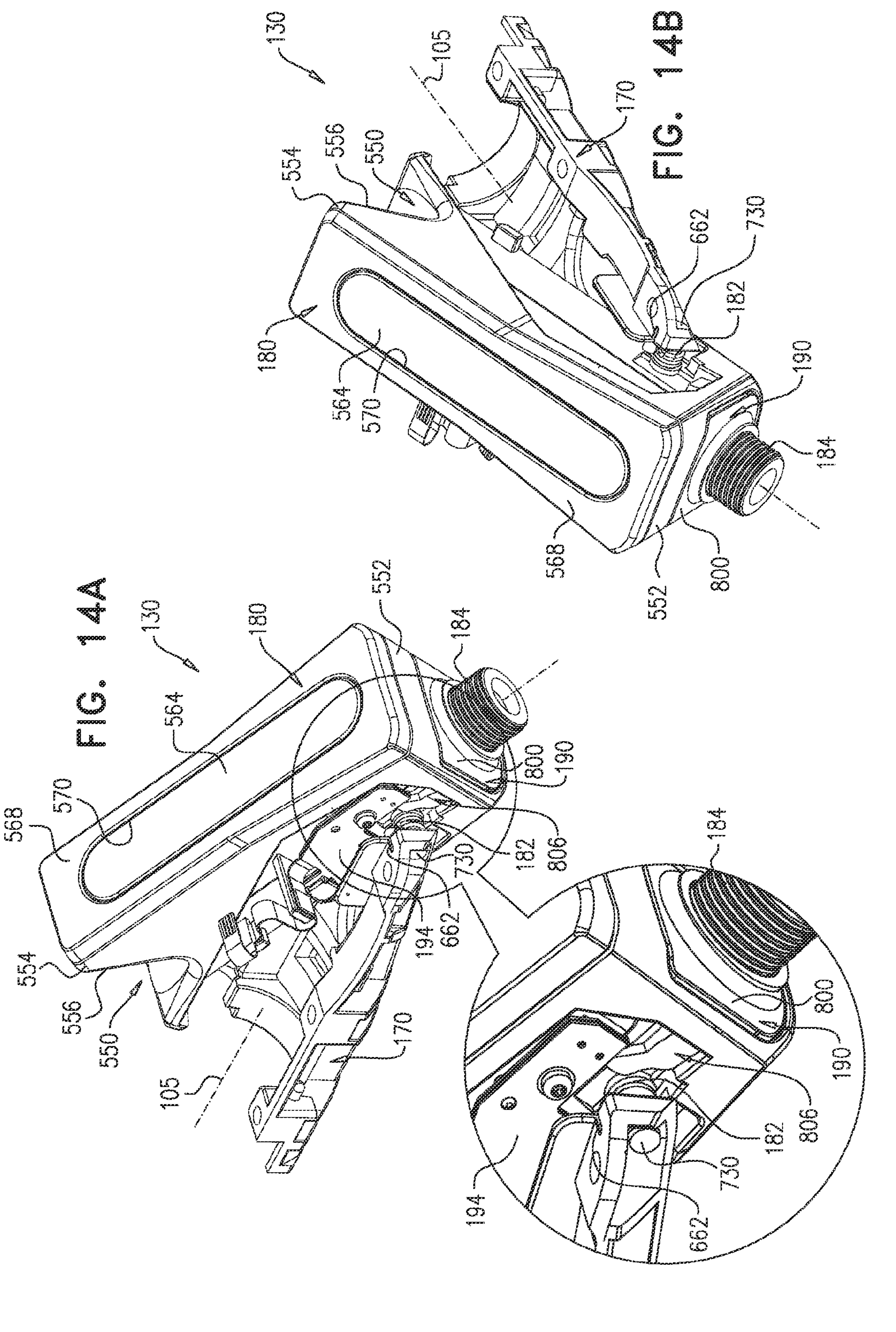
FIGS. 14A, 14B, 14C and 14D are simplified respective two pictorial views taken from different perspectives, planar top view and planar side view illustrations of the cartridge enclosure assembly of FIGS. 8A-12G in a second operative orientation thereof.
Figure 14C:
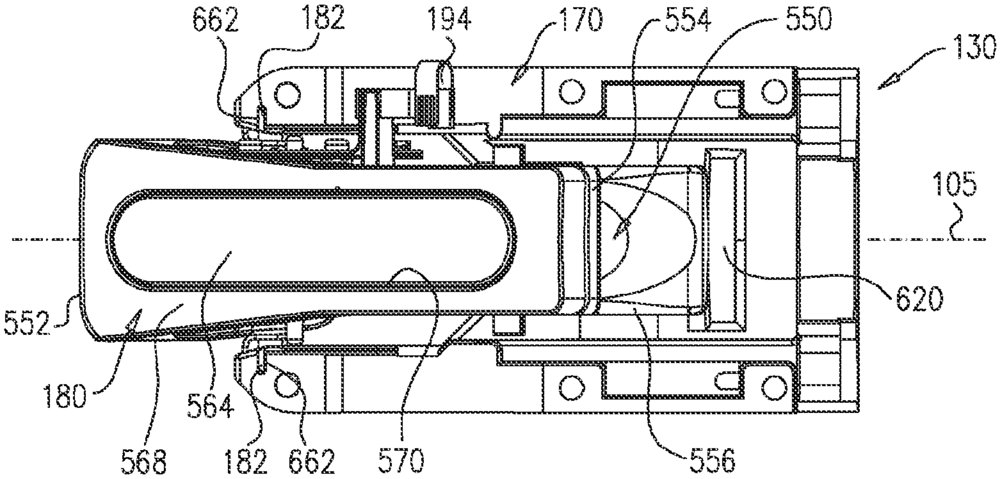
Figure 14D:
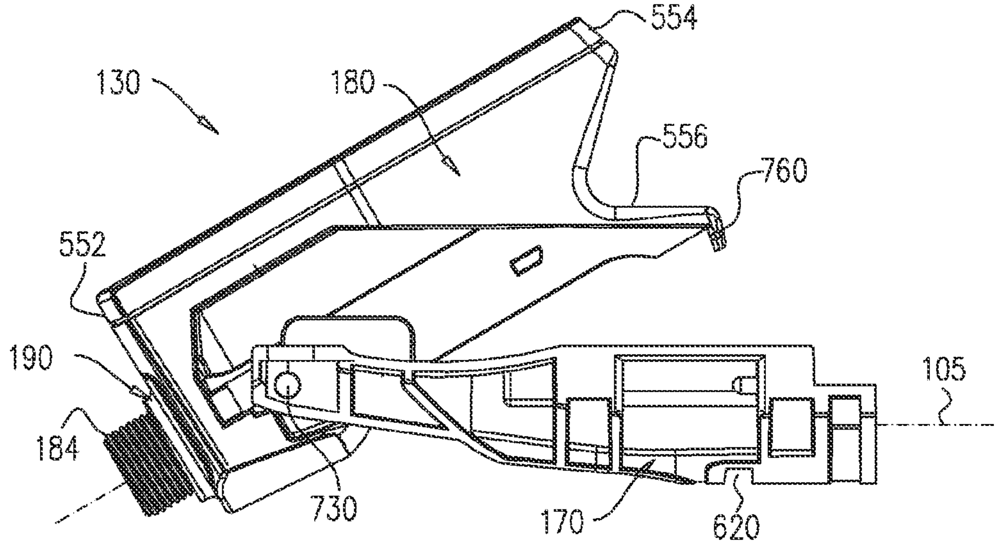
Figure 15B:
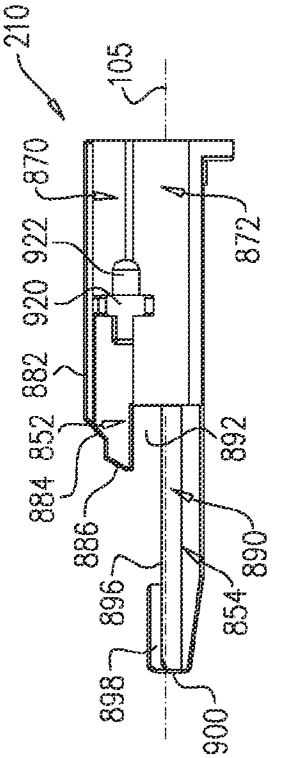
FIGS. 15A, 15B, 15C, 15D, 15E, 15F and 15G are simplified respective pictorial, first and second side views, top planar view, bottom planar view front planar view and back planar view illustrations of a cartridge enclosure assembly latch element forming part of the MUCI of FIGS. 1A & 1B.
Figure 15D:
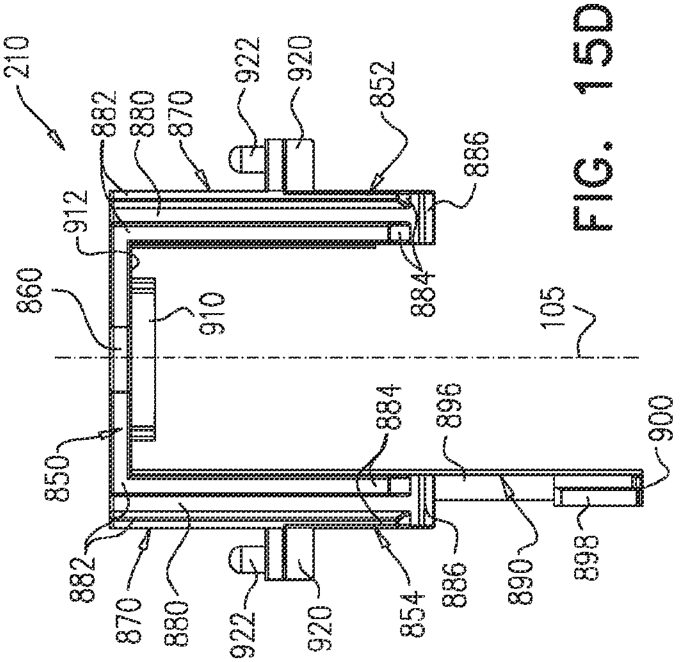
Figure 15A:
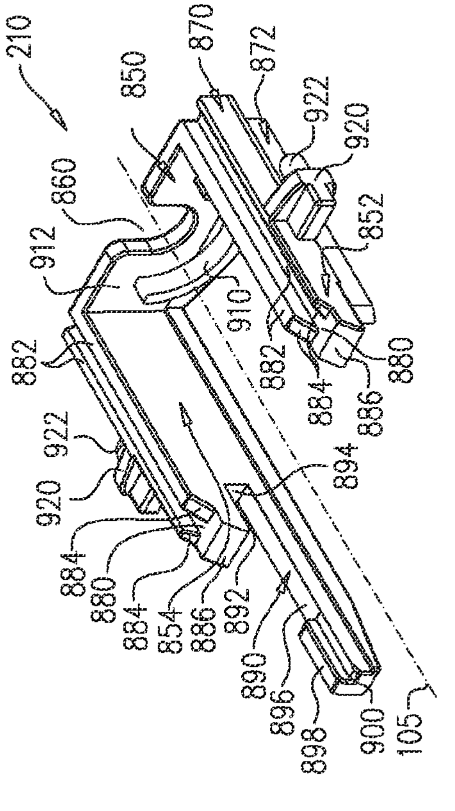
Figure 15C:
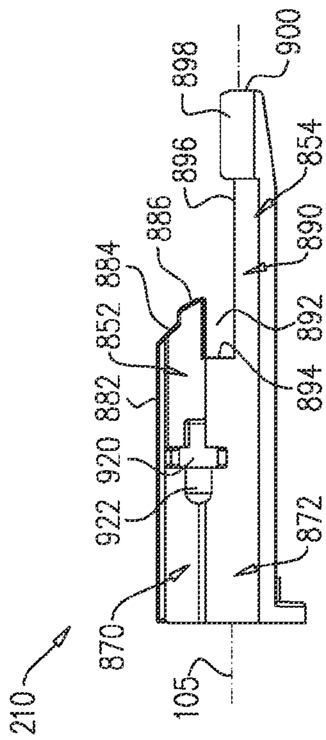
Figure 15F:
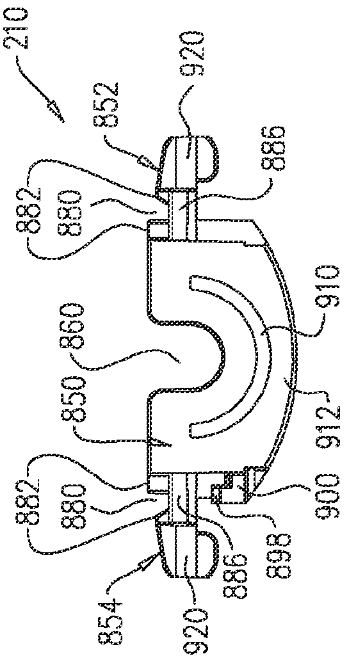
Figure 15G:
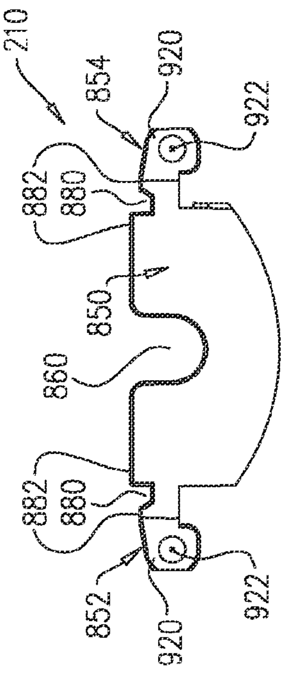
Figure 15E:
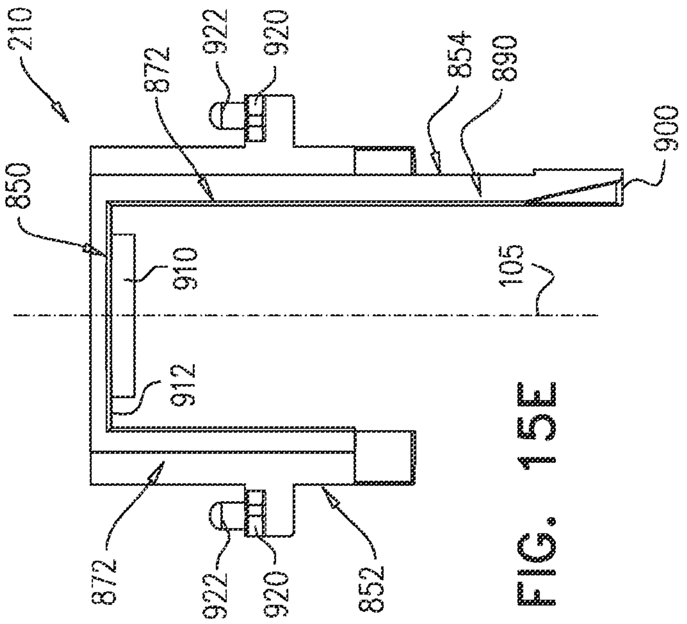
Figure 16B:
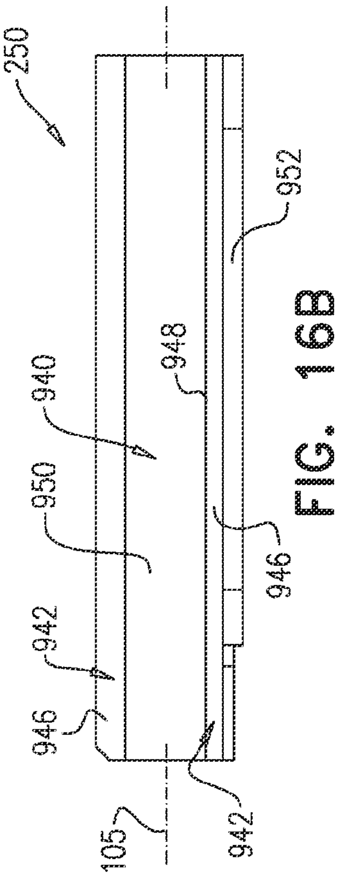
FIGS. 16A, 16B, 16C and 16D are simplified respective pictorial, planar side, planar top and planar end view illustrations of a track element forming part of the MUCI of FIGS. 1A & 1B.
Figure 16D:
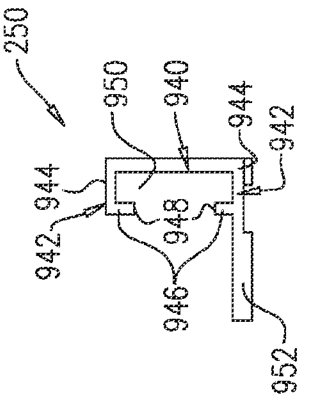
Figure 16A:
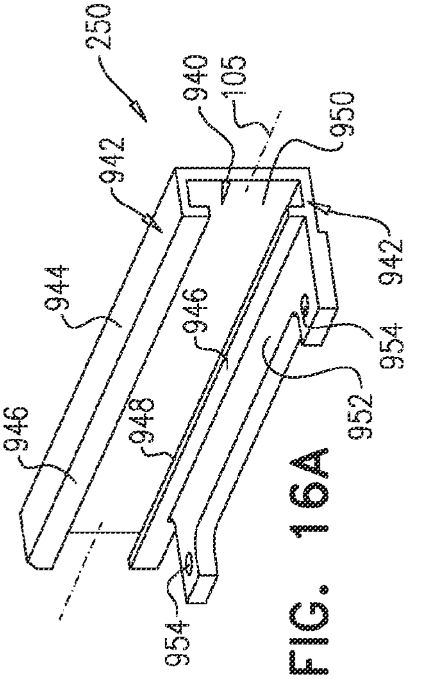
Figure 16C:
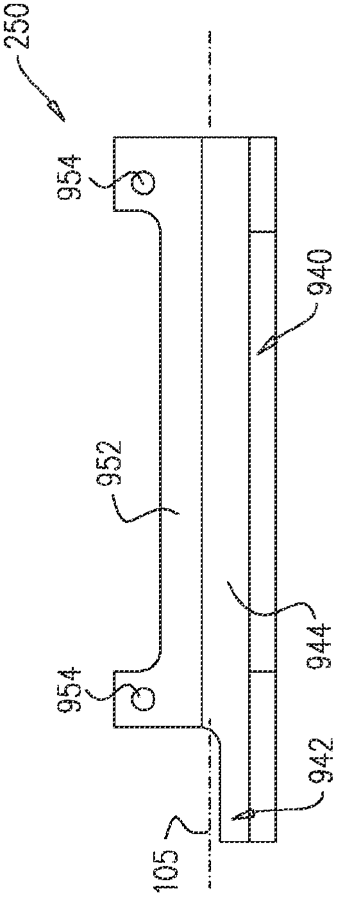
Figure 17A:
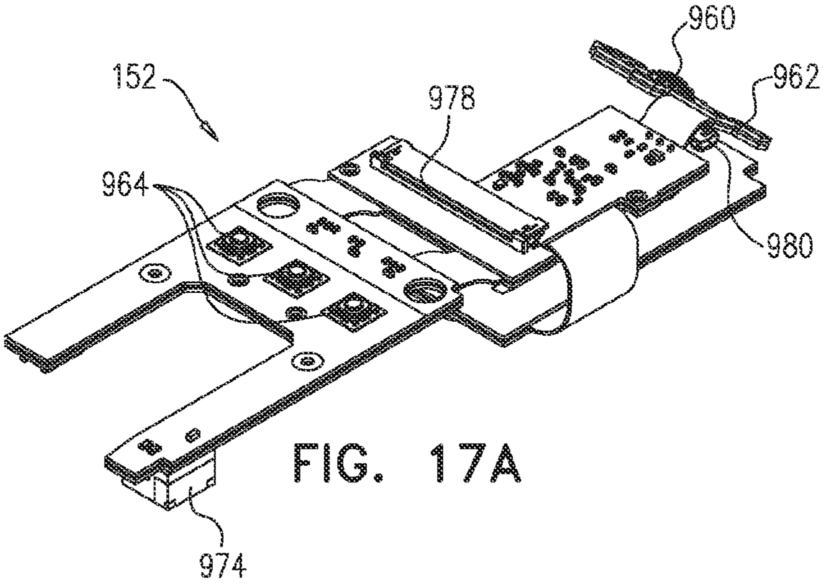
FIGS. 17A, 17B, 17C and 17D are simplified respective top and bottom pictorial, top planar view and bottom planar view illustrations of a main PCB assembly forming part of the MUCI of FIGS. 1A & 1B.
Figure 17B:
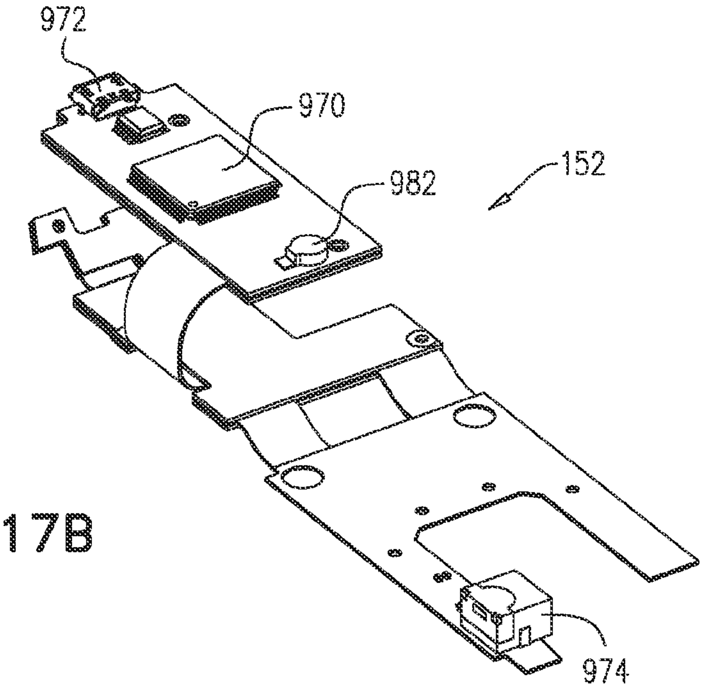
Figure 17D:
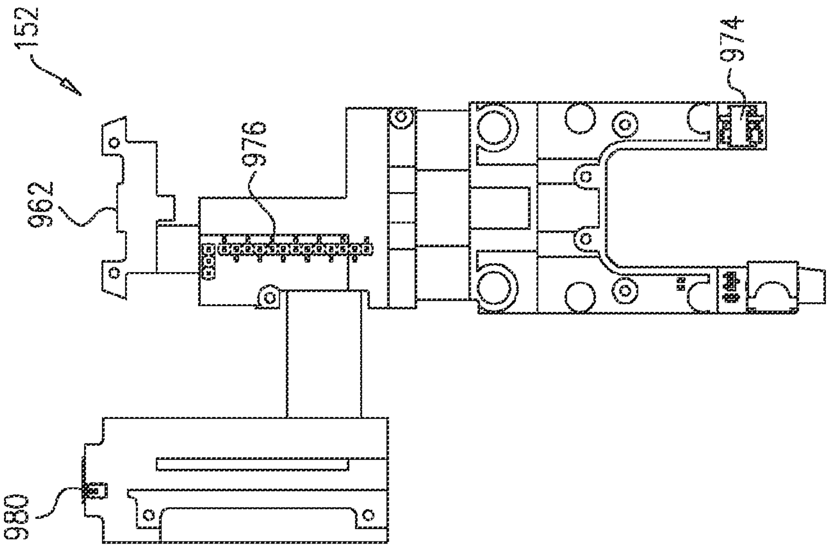
Figure 17C:
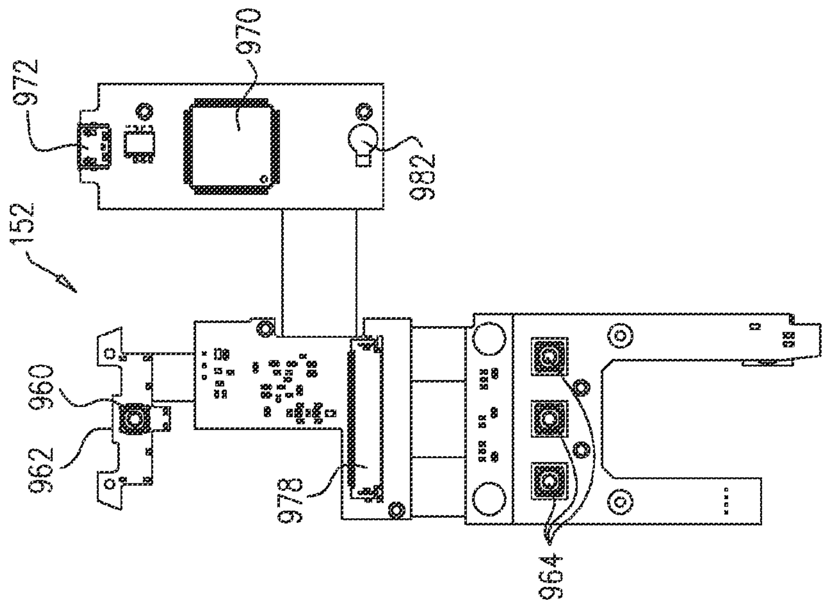

Reference is now made to FIGS. 13A, 13B and 13C, which are simplified pictorial, planar top view and sectional view illustrations of the cartridge enclosure assembly 130 of FIGS. 8A-12G in a first operative orientation thereof, the sectional view being taken along the lines C-C in FIG. 13B.

In FIGS. 13A-13C, the cartridge enclosure assembly 130 is seen in a closed operative orientation.

It is particularly seen in FIGS. 13A-13C that wall portion 800 of needle presence responsive element 190 is inserted into forwardly facing recess 710 of pivot mount element 180, such that the externally threaded end 184 of pivot mount element 180 protrudes forwardly through bore 802 of needle presence responsive element 190.

It is further seen that torsion springs 182 are mounted onto each of hinge elements 730 of pivot mount element 180 and the ends of torsion springs 182 are supported within recesses 662 formed in cartridge enclosure assembly chassis 170 for biasing the pivot mount element 180 into an open operative orientation.

It is also seen in FIGS. 13A-13C that flange portion 760 of pivot mount element 180 is inserted into opening 620 of cartridge enclosure assembly chassis 170 in this closed operative orientation.

Reference is now made to FIGS. 14A, 14B, 14C and 14D, which are simplified respective two pictorial views taken from different perspectives, planar top view and planar side view illustrations of the cartridge enclosure assembly 130 of FIGS. 8A-12G in a second operative orientation thereof.

In FIGS. 14A-14D, the cartridge enclosure assembly 130 is seen in an open operative orientation.

It is particularly seen in FIGS. 14A-14D, similar to FIGS. 13A-13C, that wall portion 800 of needle presence responsive element 190 is inserted into forwardly facing recess 710 of pivot mount element 180, such that the externally threaded end 184 of pivot mount element 180 protrudes forwardly through bore 802 of needle presence responsive element 190.

It is further seen that torsion springs 182 are mounted onto each of hinge elements 730 of pivot mount element 180 and the ends of torsion springs 182 are supported within recesses 662 formed in cartridge enclosure assembly chassis 170 for biasing the pivot mount element 180 into the open operative orientation.

It is also seen in FIGS. 14A-14D that flange portion 760 of pivot mount element 180 is disengaged from opening 620 of cartridge enclosure assembly chassis 170 in this open operative orientation.

Reference is now made to FIGS. 15A, 15B, 15C, 15D, 15E, 15F and 15G, which are simplified respective pictorial, first and second side views, top planar view, bottom planar view, front planar view and back planar view illustrations of the cartridge enclosure assembly latch element 210 forming part of the MUCI 100 of FIGS. 1A & 1B.

Cartridge enclosure assembly latch element 210 is preferably an integrally formed element, which is arranged along longitudinal axis 105. It is seen in FIGS. 15A-15G that the cartridge enclosure assembly latch element 210 generally includes a base wall portion 850, a first arm 852 of a first length and a second arm 854 of a second length, which is generally greater than the first length. Arms 852 and 854 generally extend along axes, which are parallel to longitudinal axis 105. A cut-out 860 serving for insertion of the plunger rod element 230 therethrough is formed in the base wall portion 850.

Each of the arms 852 and 854 includes an upper portion 870 and a bottom portion 872. It is noted that upper portion 870 is generally wider than base wall portion 850. An upwardly facing guiding track 880 bounded by generally two longitudinal ribs 882 is formed on each of upper portions 870. Each of ribs 882 terminate at a rearwardly tapered surface 884. Upper portions 870 terminate at a forwardly facing tapered surface 886, which is disposed generally forwardly with respect to surfaces 884.

Bottom portion 872 of arm 854 includes a forwardly extending protrusion 890. A cut-out 892 is formed between upper portion 870 and bottom portion 872 of arm 854 and protrusion 890. The cut-out 892 defines a forwardly facing surface 894. Protrusion 890 defines an upwardly facing surface 896, having an upwardly facing protrusion 898, disposed generally at a forward end 900 of protrusion 890. Protrusion 898 is configured to engage cartridge enclosure assembly state sensor 784 (shown in FIGS. 11A-11D).

An arc-shaped protrusion 910 is formed on a forwardly facing surface 912 of base wall portion 850, and is used for tight fit engagement with a rearward end of a medicament cartridge, thereby preventing displacement of the medicament cartridge relative to pivot mount element 180.

Side protrusion 920 generally extends outwardly from upper portions 870 of each of arms 852 and 854. Each side protrusion 920 has a rearwardly extending guiding pin 922. Guiding pins 922 generally serve as a seat for springs 212, complimentary to aligning pins 632 of cartridge enclosure assembly chassis 170.

It is a particular feature of an embodiment of the present invention that cartridge enclosure assembly latch element 210 is configured to electronically lock the pivot mount element 180 with respect to the top housing portion 104.

Reference is now made to FIGS. 16A, 16B, 16C and 16D, which are simplified respective pictorial, planar side, planar top and planar end view illustrations of the track element 250 forming part of the MUCI 100 of FIGS. 1A & 1B.

Track element 250 is an integrally made generally U-shaped element extending along longitudinal axis 105. Track element 250 has a base wall portion 940 and two L-shaped arms 942 extending generally transversely therefrom. A partially enclosed tunnel 950 is formed between the base wall portion 940 and arms 942. Each of arms 942 preferably includes a side wall portion 944 and an extension portion 946 extending generally transversely with respect to side wall portion 944. Each of extension portions 946 defines a longitudinal edge 948.

It is additionally seen that a generally upstanding protrusion 952 extends from one of arms 942 and is arranged generally transversely to base all portion 940. Protrusion 952 has typically two openings 954 formed thereon.

Reference is now made to FIGS. 17A, 17B, 17C and 17D, which are simplified respective top and bottom pictorial, top planar view and bottom planar view illustrations of the main PCB assembly 152 forming part of the MUCI 100 of FIGS. 1A & 1B.

The main PCB assembly 152 of the MUCI 100 preferably includes an injection button micro switch 960, which is positioned at a rearward end 962 thereof. Main PCB assembly 152 also includes menu button switches 964, CPU 970, USB slot 972 configured to engage PCB assembly 194, buzzer 974, connector 976 configured to engage power control PCB assembly 154, a display connector 978, a home position sensor 980 and a real-time battery 982, which is configured to preserve time stamp in the event of main battery power outage.

Figure 18B:
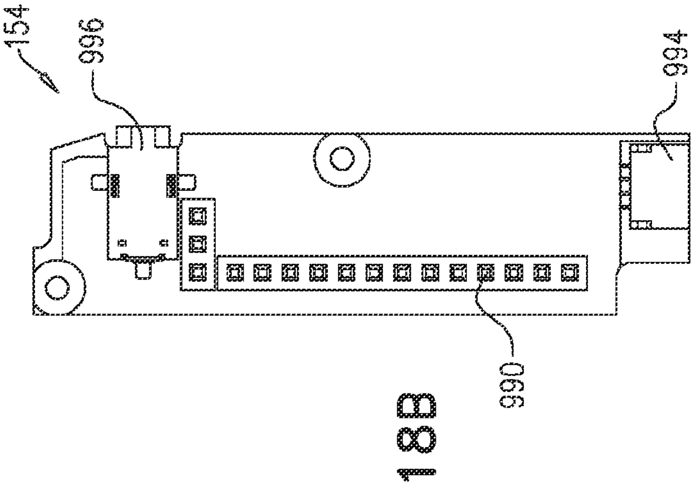
FIGS. 18A, 18B and 18C are simplified respective pictorial, top planar view and end planar view illustrations of a power control PCB assembly forming part of the MUCI of FIGS. 1A & 1B.
Figure 18C:
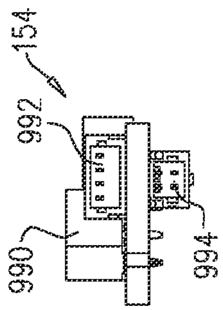
Figure 18A:
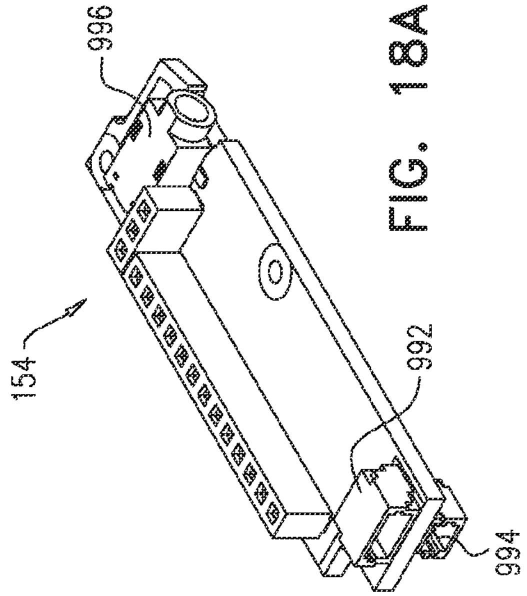

Reference is now made to FIGS. 18A, 18B and 18C, which are simplified respective pictorial, top planar view and end planar view illustrations of the power control PCB assembly 154 forming part of the MUCI 100 of FIGS. 1A & 1B.

Power control PCB assembly 154 is provided in the MUCI 100 and shown in FIGS. 18A-18C. Power control PCB assembly 154 is configured to be connected to the main PCB assembly 152 by means of a connector 990. Power control PCB assembly 154 also includes a motor connector 992, a battery connector 994 and a charging slot 996.

Figure 19A:
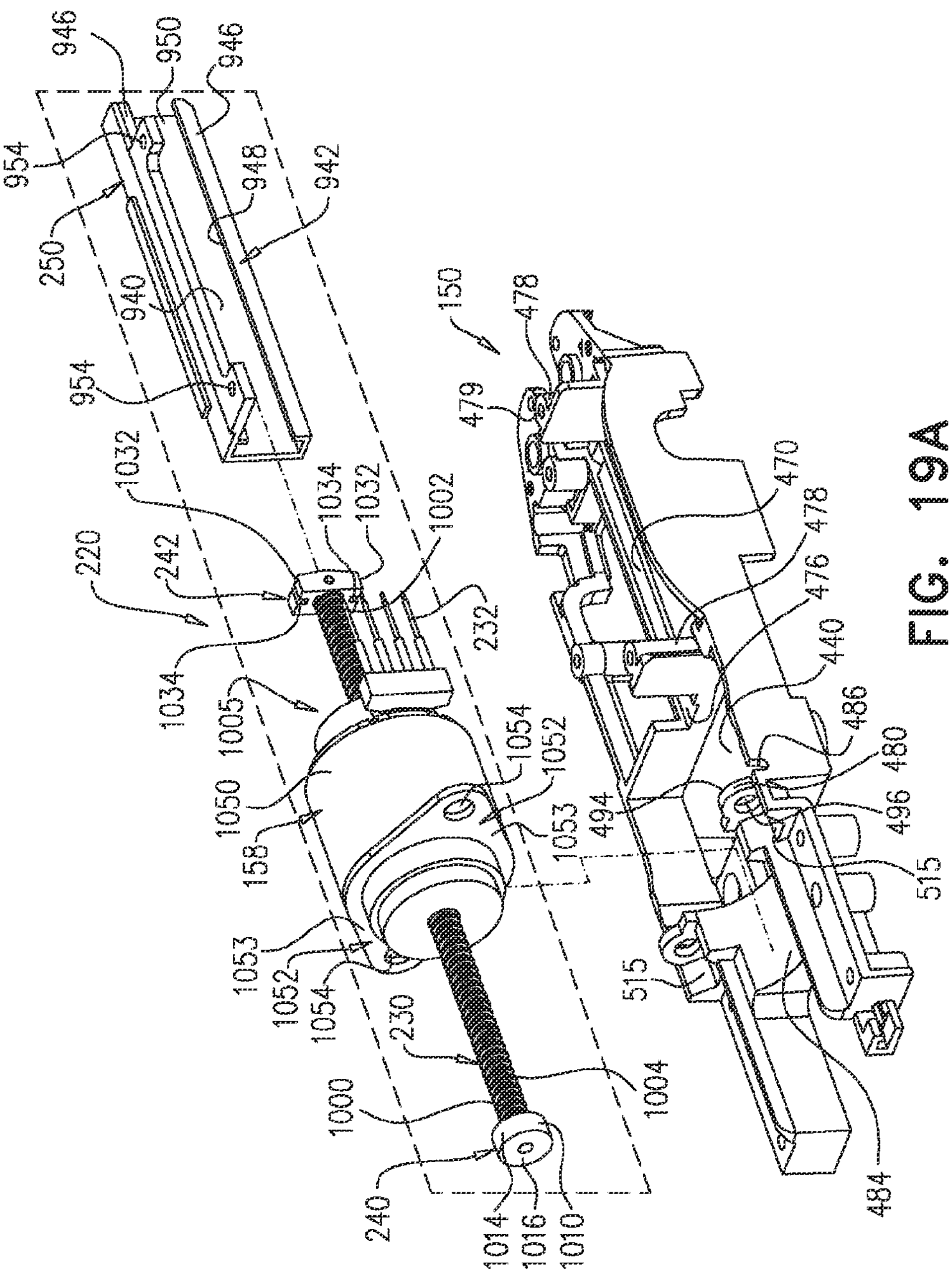
FIGS. 19A, 19B and 19C are simplified respective exploded view, pictorial view and end view illustrations of a piston drive subassembly forming part of MUCI of FIGS. 1A-18C.
Figure 19B:
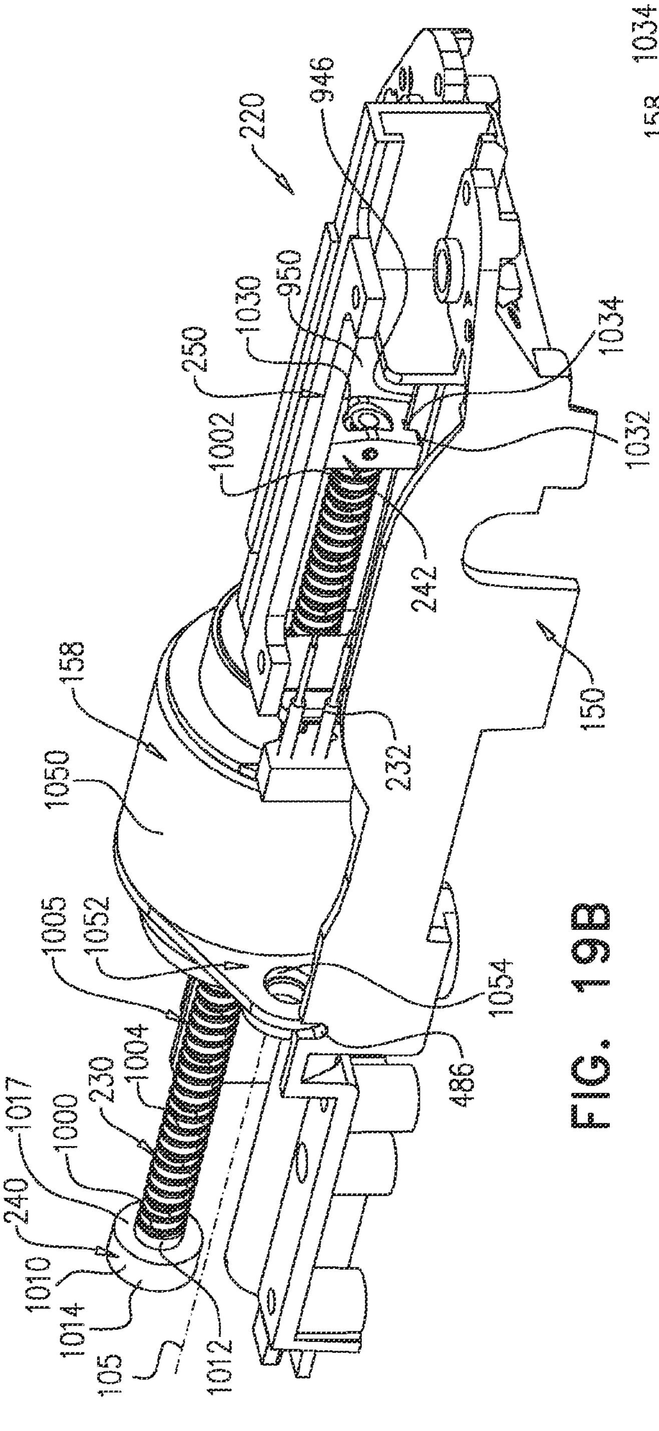
Figure 19C:
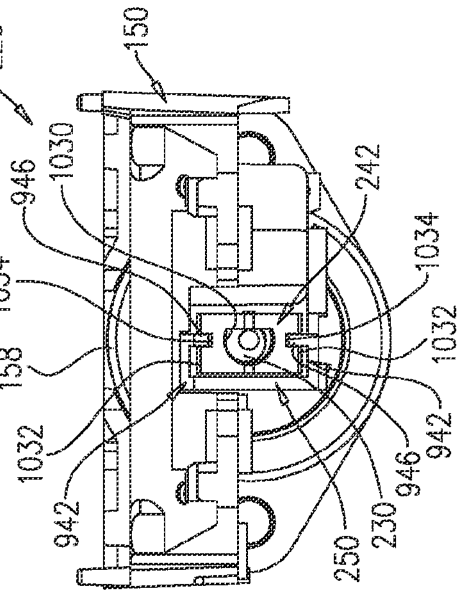

Reference is now made to FIGS. 19A, 19B and 19C, which are simplified respective exploded view, pictorial view and end view illustrations of the piston drive subassembly 220 forming part of MUCI 100 of FIGS. 1A-18C.

It is noted hereinabove that the piston drive subassembly 220 is configured for axially displacing the piston within the medicament cartridge in order to eject fluid therefrom.

The piston drive subassembly 220 preferably includes electrical motor 158, which is mounted onto the plunger rod element 230. The plunger rod element has a forward end 1000, a rearward end 1002 and an external threading 1004.

Piston contact element 240 is mounted onto the forward end 1000 of plunger rod element 230 and anti-rotation element 242 is mounted onto the distal end 1002 of plunger rod element 230. It is also noted that the anti-rotation element 242 is configured to be axially displaced along track element 250.

Piston drive sub-assembly 220 is configured to be mounted onto chassis element 150.

Piston drive sub-assembly 220 preferably includes a moveable subassembly 1005, namely the plunger rod element 230, piston contact element 240 and anti-rotation element 242. The remaining components of piston drive sub-assembly 220 are preferably static.

It is particularly seen in FIG. 19B that piston contact element 240 has a generally ring-shaped element 1010 and a generally cylindrical protrusion 1012 extending generally rearwardly therefrom. The ring-shaped element 1010 defines an outer circumferential surface 1014, a forwardly facing surface 1016 and a rearwardly facing surface 1017. Piston contact element 240 is threadably coupled to plunger rod element 230 by means of cylindrical protrusion 1012.

It is appreciated that the piston contact element 240 is operative to engage the piston within the cartridge and to enlarge the contact surface area between the plunger rod element 230 and the piston within the cartridge. Piston contact element 240 is additionally operative for engaging cartridge enclosure assembly latch element 210 to urge the displacement thereof, as will be described in detail hereinbelow.

It is seen in FIGS. 19A-19C that anti-rotation element 242 is an integrally made element having a through D-shaped bore 1030, which is operative to receive the distal end 1002 of the plunger rod element 230 thereinto and prevent rotational displacement of the plunger rod element 230 relative to 242. It is additionally seen that the anti-rotation element 242 defines a first and a second side wall 1032. A longitudinal groove 1034 is formed along each of side walls 1032. Anti-rotation element 242 is adapted to be inserted partially into tunnel 950 of track element 250, such that longitudinal grooves 1034 are operative to engage extension portions 946 of track element 250, in order to guide the plunger rod element 230 and enable its axial displacement therealong.

It is a particular feature of an embodiment of the present invention that piston drive subassembly 220 includes the plunger rod element 230, the rearward end 1002 of which is inserted into D-shaped bore 1030 of the anti-rotation element 242. Plunger rod element 230 is mounted onto motor 158, and is configured to urge axial displacement of the plunger rod element 230 in order to eject medicament out of the cartridge, upon motor activation, as is described in detail hereinbelow. Electrical contacts 232 are configured to operatively electrically couple the motor 158 to the power control PCB assembly 154.

It is seen in FIGS. 19A-19C that motor 158 has a main portion 1050 and typically two fixation flanges 1052 extending radially outwardly therefrom and defining forwardly facing surfaces 1053 and openings 1054. Main portion 1050 is seated partially within opening 440 and partially supported by surface 484 of chassis element 150. Fixation flanges 1052 are supported within cut-outs 486 of chassis element 150 and are also supported against rearwardly facing surfaces 494 of wall 480 of chassis element 150, such that forwardly facing surfaces 1053 of flanges 1052 engage rearwardly facing surfaces 494 of wall 480 and fixedly attached thereto by means of screws received in both openings 1054 of flanges 1052 and openings 496 of wall 480. It is noted that the nuts which are adapted to tighten these screws are configured to be supported in a channel formed between hexagonal recess 515 of chassis element 150 and hexagonal recess 617 of cartridge enclosure assembly chassis 170.

It is also seen that track element 250 is fixedly attached to chassis element 150 by means of screws inserted into both openings 954 in protrusion 952 of track element 250 and recesses 479 in protrusions 478 of the chassis element 150.

The rearward end 1002 of plunger rod element 230, is inserted into D-shaped opening 1030 of anti-rotating element 242 and fixedly coupled thereto, such that there is no relative movement between the plunger rod element 230 and the anti-rotating element 242. The anti-rotating element 242 is in turn inserted into tunnel 950 defined by track element 250, such only axial relative displacement is permitted between the plunger rod element 230 and the track element 250. The plunger rod element 230 extends forwardly from track element 250, through recess 476 of chassis element 150.

Figures 20A, 20B:
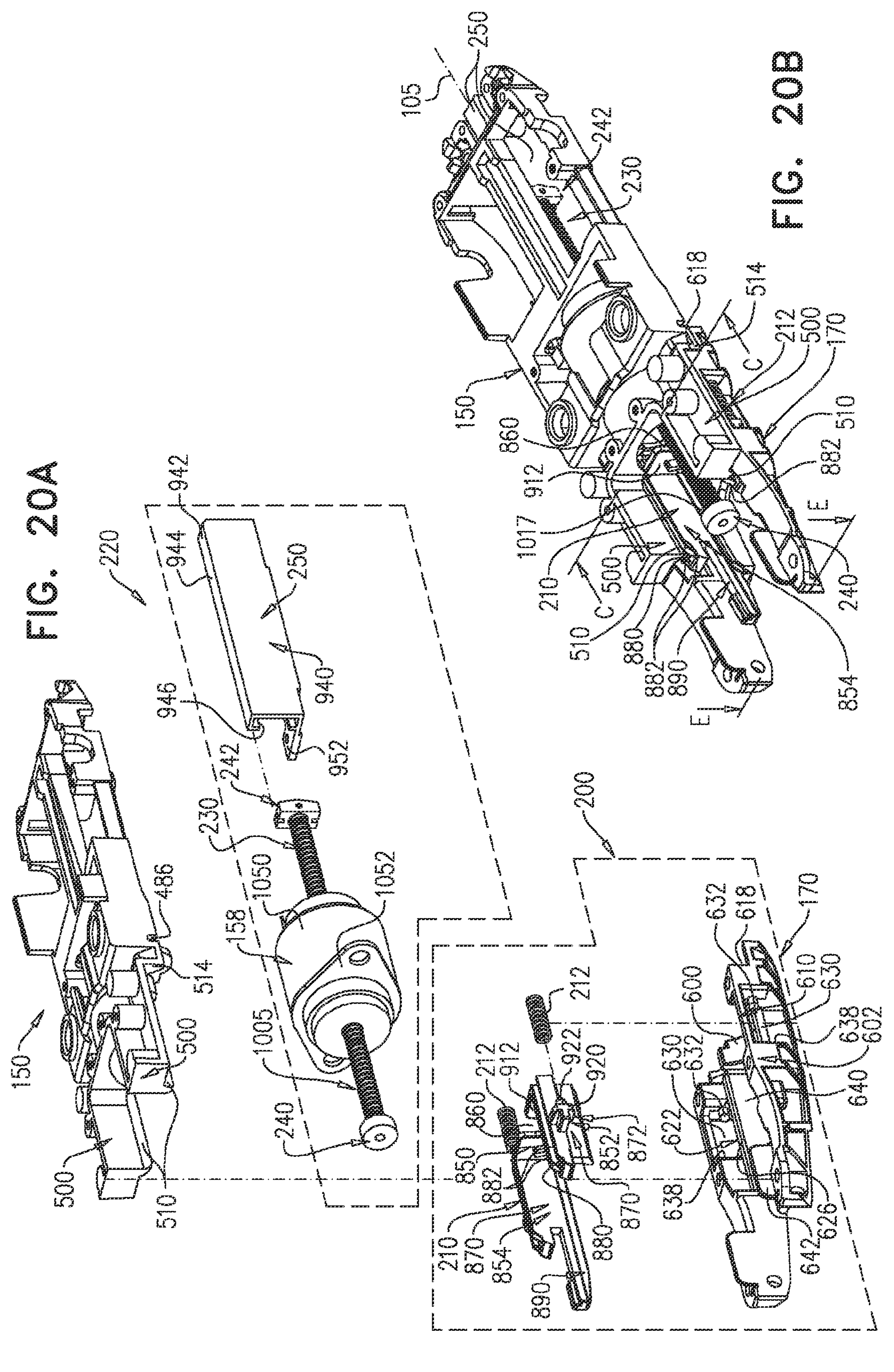
FIG. 20A is a simplified exploded view showing the chassis element, piston drive subassembly and a locking subassembly forming part of MUCI of FIGS. 1A-19C.
FIGS. 20B-20E are simplified respective pictorial view, first section view, side view and second section view of the locking subassembly assembled with the chassis element and the piston drive subassembly, where the locking subassembly being positioned in a locked operative orientation, sections being taken along lines C-C and E-E in FIG. 20B respectively.
Figure 20D:
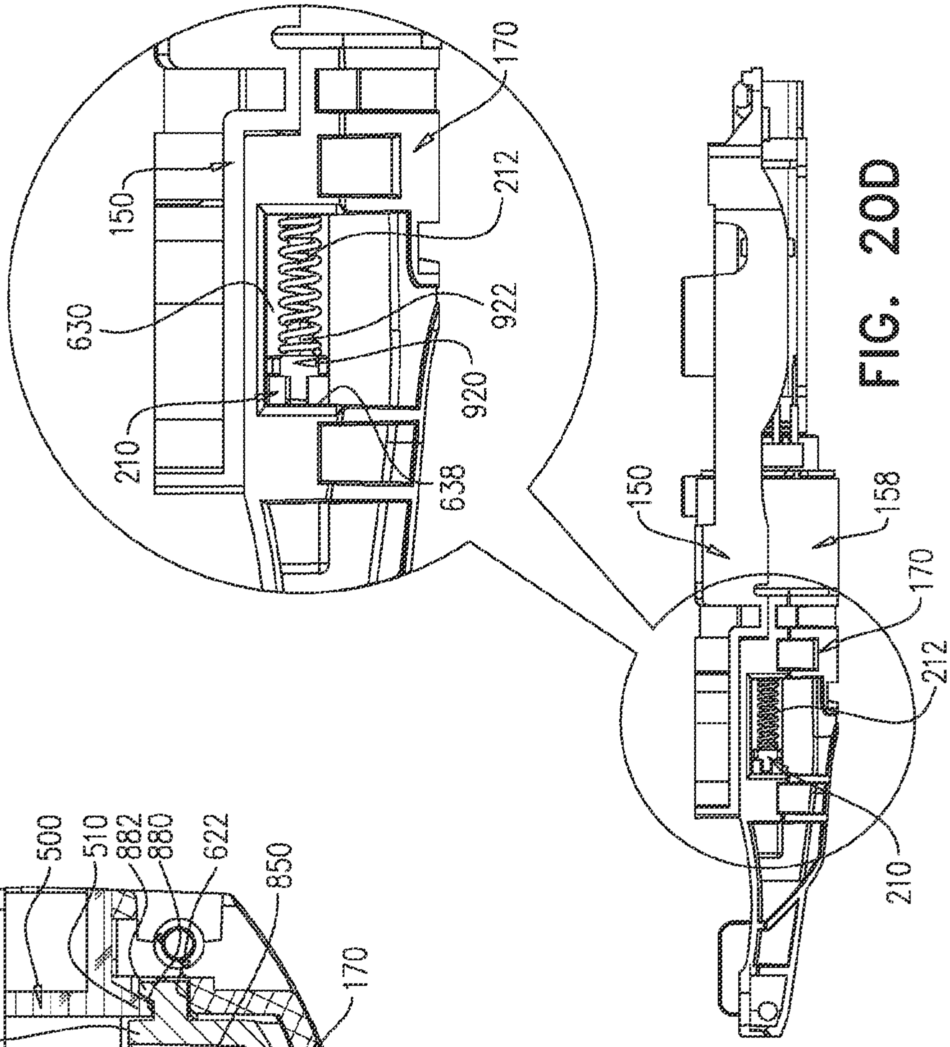
Figure 20C:
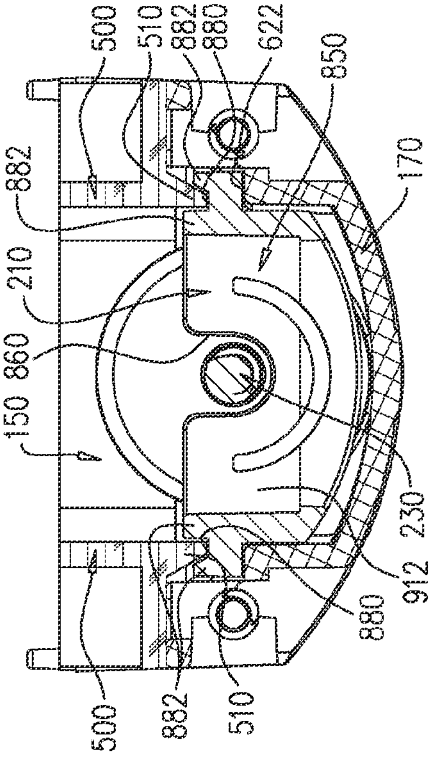
Figure 20E:
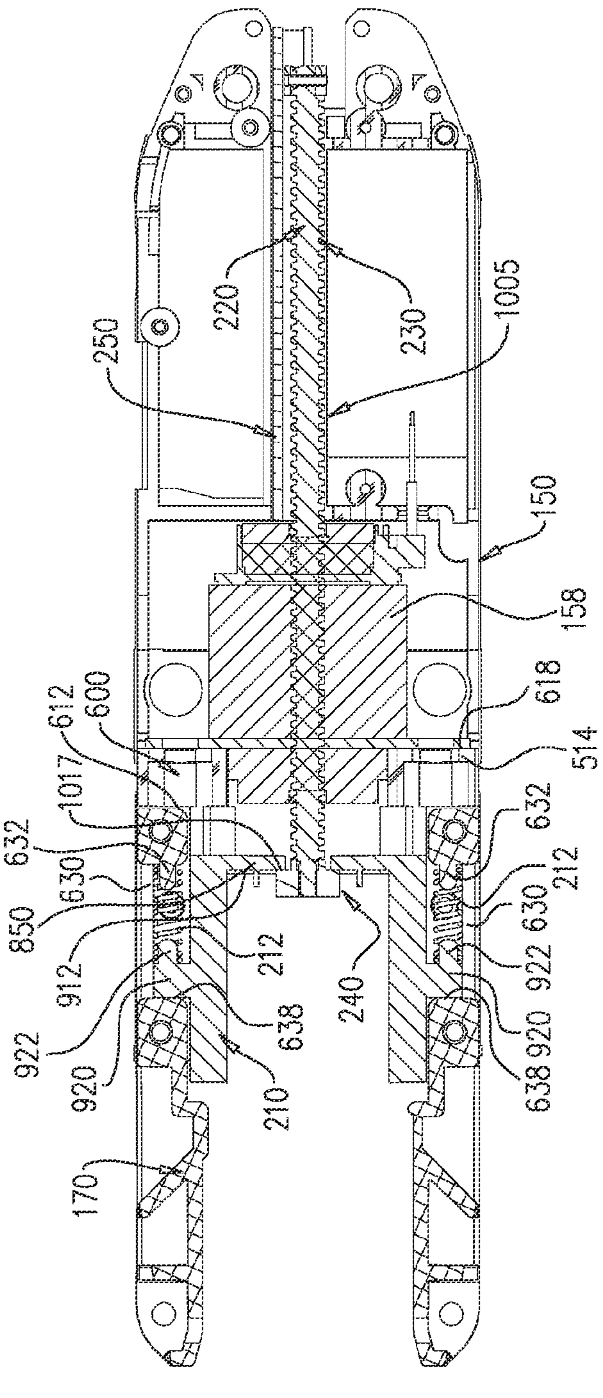

Reference is now made to FIGS. 20A, which is a simplified exploded view showing the chassis element 150, piston drive subassembly 220 and a locking subassembly 200 forming part of MUCI 100 of FIGS. 1A-19C. Reference is additionally made to FIGS. 20B-20E, which are simplified respective pictorial view, first section view, side view and second section view of the locking subassembly 200 assembled with the chassis element 150 and the piston drive subassembly 220, where the locking subassembly 200 being positioned in a locked operative orientation, sections being taken along lines C-C and E-E in FIG. 20B respectively.

It is mentioned above with reference to FIG. 1B that the locking subassembly 200 is provided as part of the MUCI 100 and is configured for selectively retaining the pivot mount element 180 of the cartridge enclosure assembly 130 in a closed operative orientation.

The locking subassembly 200 preferably includes the cartridge enclosure assembly chassis 170, cartridge enclosure assembly latch element 210 and two compression springs 212, each of which is support at one side thereof on the cartridge enclosure assembly latch element 210 and at a second side thereof on the cartridge enclosure assembly chassis 170. The cartridge enclosure assembly latch element 210 is configured to be axially displaceable, along longitudinal axis 105, with respect to cartridge enclosure assembly chassis 170 and biased to a forward position under the biasing force of springs 212.

It is a particular feature of an embodiment of the present invention that the operative orientation of the locking subassembly 200 depends on the axial position of part of the moveable subassembly 1005 of the piston drive subassembly 220, as will be further described in detail. Particularly, when the moveable subassembly 1005 of the piston drive subassembly 220 is disposed in its forward operative orientation, cartridge enclosure assembly latch element 210 is urged to be displaced axially forwardly along longitudinal axis 105, under the force of compression springs 212, and thus causing the locking subassembly 200 to assume its locked operative orientation. When the moveable subassembly 1005 of the piston drive subassembly 220 is disposed in its rearward operative orientation, the cartridge enclosure assembly latch element 210 is pulled rearwardly by piston contact element 240 and urges the locking subassembly 200 to assume its unlocked operative orientation. When the moveable subassembly 1005 of the piston drive subassembly 220 is disposed in a predetermined intermediate operative orientation, the cartridge enclosure assembly latch element 210 is not fully displaced forwardly, thus positioning the locking subassembly 200 in a snapped operative orientation.

It is specifically seen in FIGS. 20A-20E that cartridge enclosure assembly latch element 210 is mounted onto cartridge enclosure assembly chassis 170. Particularly, it is seen that base wall portion 850 of cartridge enclosure assembly latch element 210 is seated forwardly of partially curved end portion 600 of cartridge enclosure assembly chassis 170. It is a particular feature of an embodiment of the present invention that in the locked operative orientation of locking subassembly 200, base wall portion 850 of cartridge enclosure assembly latch element 210 is forwardly spaced from forwardly facing surface 612 of portion 602 of cartridge enclosure assembly chassis 170.

It is additionally seen that first and second arms 852 and 854 of cartridge enclosure assembly latch element 210 are configured to be at least partially seated within spring enclosing fingers 610 of cartridge enclosure assembly chassis 170. It is particularly seen that upper portions 870 of arms 852 and 854 are received within spring seat cut-outs 630 of spring enclosing fingers 610 of cartridge enclosure assembly chassis 170 and rearwardly extending guiding pins 922 of cartridge enclosure assembly latch element 210 are axially aligned with spring aligning pins 632 of cartridge enclosure assembly chassis 170, and both form a guiding route for springs 212.

It is a particular feature of an embodiment of the present invention that side protrusion 920 of cartridge enclosure assembly latch element 210 engages rearwardly facing end surfaces 638 of spring seat cut-outs 630 in this locked operative orientation and the springs 212, which are supported at one side on side protrusions 920 and on another side on forwardly facing surface from which spring aligning pins 632 extend, are pre-stressed in this locked operative orientation.

It is also seen that cartridge enclosure assembly latch element 210 is seated within cartridge enclosure assembly chassis 170, such that the outwardly facing surfaces of bottom portions 872 of first and second arms 852 and 854 of cartridge enclosure assembly latch element 210 engage inwardly facing side wall portions 640 of cartridge enclosure assembly chassis 170.

It is seen in FIGS. 20A-20E that locking subassembly 200 is mounted onto chassis element 150, which slidably receives piston drive sub-assembly 220. The spatial relationship between chassis element 150 and piston drive assembly 220 are described in detail hereinabove, with reference to FIGS. 19A-19C.

The cartridge enclosure assembly chassis 170 is supported on chassis element 150, such that rearwardly facing surfaces 618 of cartridge enclosure assembly chassis 170 engage forwardly facing surfaces 514 of chassis element 150 and thus prevent any relative movement between the cartridge enclosure assembly chassis 170 and the chassis element 150.

It is a particular feature of an embodiment of the present invention that cartridge enclosure assembly latch element 210 is slidably axially displaceable along longitudinal axis 105 with respect to chassis element 150. It is particularly seen that downwardly extending protrusions 510 of track arms 500 of chassis element 150 engage upwardly facing guiding track 880 formed between longitudinal ribs 882 of first and second arms 852 and 854 of cartridge enclosure assembly latch element 210, thus guiding the slidable axial displacement of the cartridge enclosure assembly latch element 210 with respect to chassis element 150.

It is additionally seen in FIGS. 20A-20E that piston drive subassembly 220 is slidably mounted onto chassis element 150 as described with reference to FIGS. 19A-19C and that typically the majority of main portion 1050 of motor 158 is seated within opening 440 of chassis element 150 and the forward end of main portion 1050 of motor 158 is seated in end portion 600 of cartridge enclosure assembly chassis 170.

It is a particular feature of an embodiment of the present invention that plunger rod element 230 extends forwardly through cut-out 860 of cartridge enclosure assembly latch element 210.

It is a further particular embodiment of the present invention that rearwardly facing surface 1017 of piston contact element 240 engages forwardly facing surface 912 of cartridge enclosure assembly latch element 210 in this locked operative orientation, when the plunger rod element 230 is positioned at its forward operative orientation.

Figure 21A:
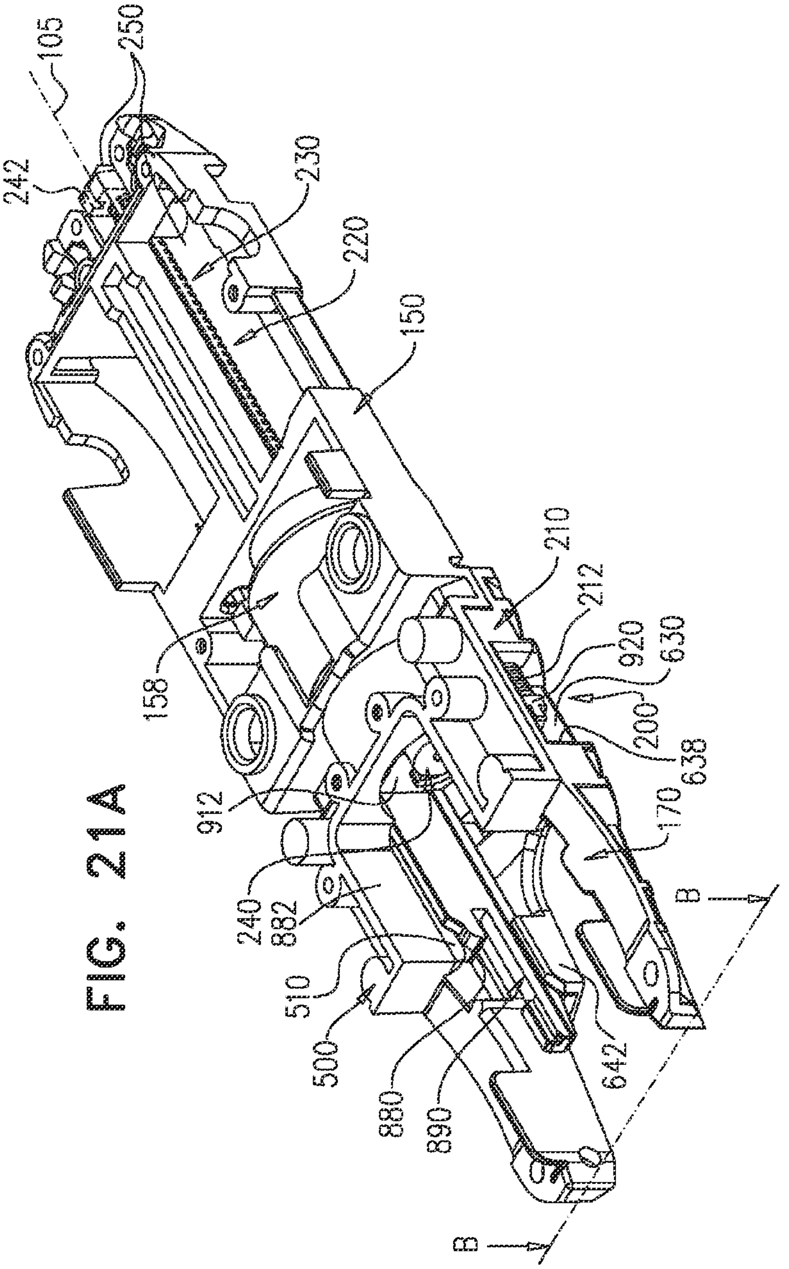
FIGS. 21A-21B are simplified respective pictorial and sectional view of the locking subassembly assembled with the chassis element and piston drive subassembly, where the locking subassembly being positioned in an unlocked operative orientation, section being taken along lines B-B in FIG. 21A.
Figure 21B:
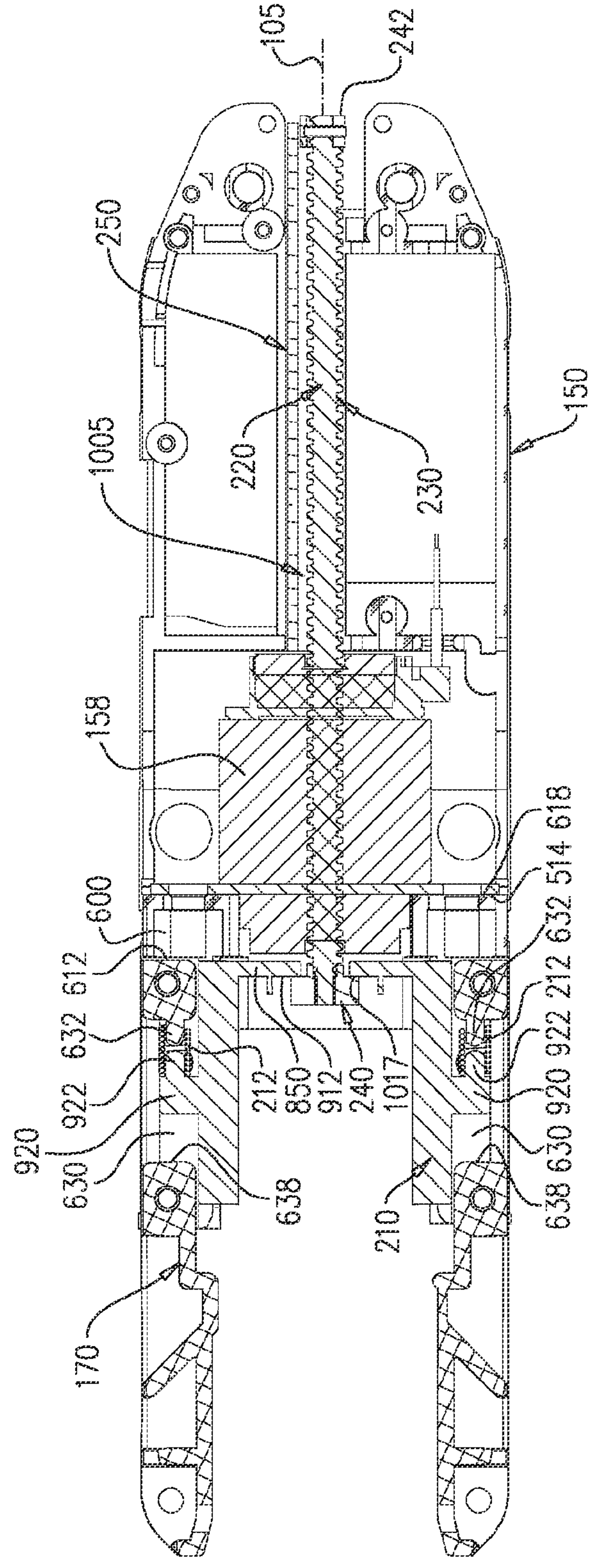

Reference is now made to FIGS. 21A-21B, which are simplified respective pictorial and sectional view of the locking subassembly 200 assembled with the chassis element 150 and piston drive subassembly 220, where the locking subassembly 200 being positioned in unlocked operative orientation, section being taken along lines B-B in FIG. 21A.

It is noted that most spatial relationships between the chassis element 150, the piston drive subassembly 220 and the locking subassembly 200 remain substantially the same as described hereinabove with reference to FIGS. 20A-20E, besides the relationships that are described hereinbelow.

It is seen in FIGS. 21A-21B that the moveable subassembly 1005 of the piston drive subassembly 220 is disposed in its rearward axial orientation, where the plunger rod element 230 is retracted rearwardly, thus the locking subassembly 200 assumes its unlocked operative orientation.

It is specifically seen in FIGS. 21A-21B that cartridge enclosure assembly latch element 210 remains mounted onto cartridge enclosure assembly chassis 170. In comparison to FIGS. 20A-20E, it is seen in FIGS. 21A-21B that base wall portion 850 of cartridge enclosure assembly latch element 210 is disposed slightly forwardly of partially curved end portion 600 of cartridge enclosure assembly chassis 170.

It is a particular feature of an embodiment of the present invention that in order to position the locking subassembly 200 in the unlocked operative orientation, the moveable subassembly 1005 of the piston drive subassembly 220 pulls the cartridge enclosure assembly latch element 210 axially rearwardly, due to activation of the electrical motor 158. The extent of rearward displacement of the plunger rod element 230 depends on pre-programmed definitions for the electrical motor 158. It is an additional particular feature of an embodiment of the present invention that the maximum extent of rearward displacement of the plunger rod element 230 is defined by engagement of anti-rotation element 242 with home position sensor 980, which serves as a safety measure that stops rearward displacement of the plunger rod element 230 in order to prevent damage to the MUCI 100.

It is a particular feature of an embodiment of the present invention that in comparison to FIGS. 20A-20E, it is seen in FIGS. 21A-21B that side protrusions 920 of cartridge enclosure assembly latch element 210 are rearwardly spaced from rearwardly facing end surfaces 638 of spring seat cut-outs 630 in this unlocked operative orientation and the springs 212, which are supported at one side on side protrusions 920 and on another side on forwardly facing surface from which spring aligning pins 632 extend, are compressed in this unlocked operative orientation.

It is a further particular embodiment of the present invention that piston drive subassembly 220 is operative for axially slidably displacing the cartridge enclosure assembly latch element 210 with respect to cartridge enclosure assembly chassis 170 due to engagement of piston contact element 240 with base wall portion 850 of cartridge enclosure assembly latch element 210. Particularly, rearwardly facing surface 1017 of piston contact element 240 is supported against forwardly facing surface 912 of cartridge enclosure assembly latch element 210, and thus upon rearward displacement of the piston drive subassembly 220 along longitudinal axis 105, piston contact element 240 displaces the cartridge enclosure assembly latch element 210 rearwardly against the force of springs 212. It is seen in FIGS. 21A-21B that in this unlocked operative orientation, the moveable subassembly 1005 of the piston drive subassembly 220 is positioned at its rearward operative orientation.

Figure 22:
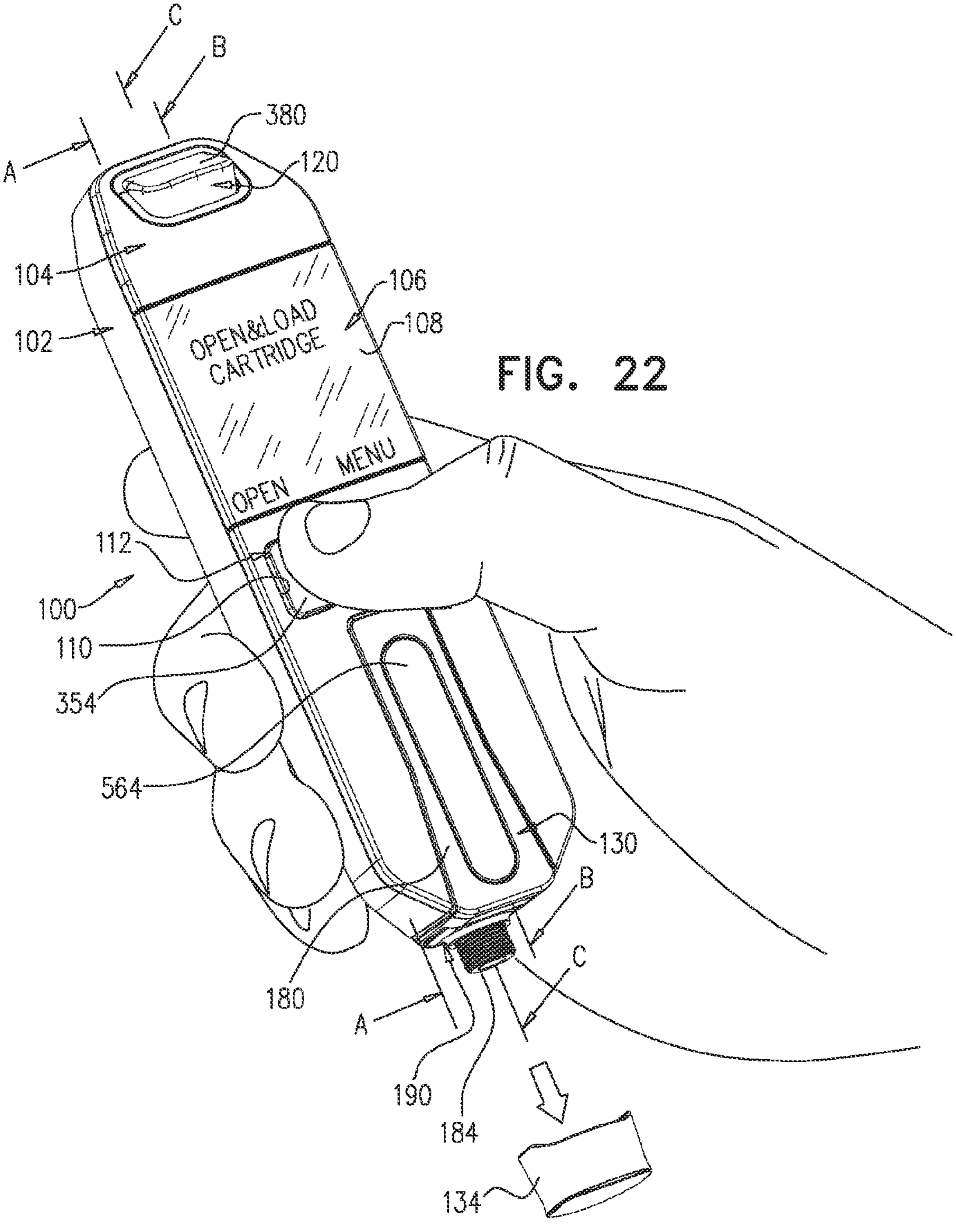
FIG. 22 is a simplified pictorial illustration of the MUCI of FIGS. 1A & 1B operated by a user, in a first pre-cartridge insertion operative orientation.
Figure 23A:
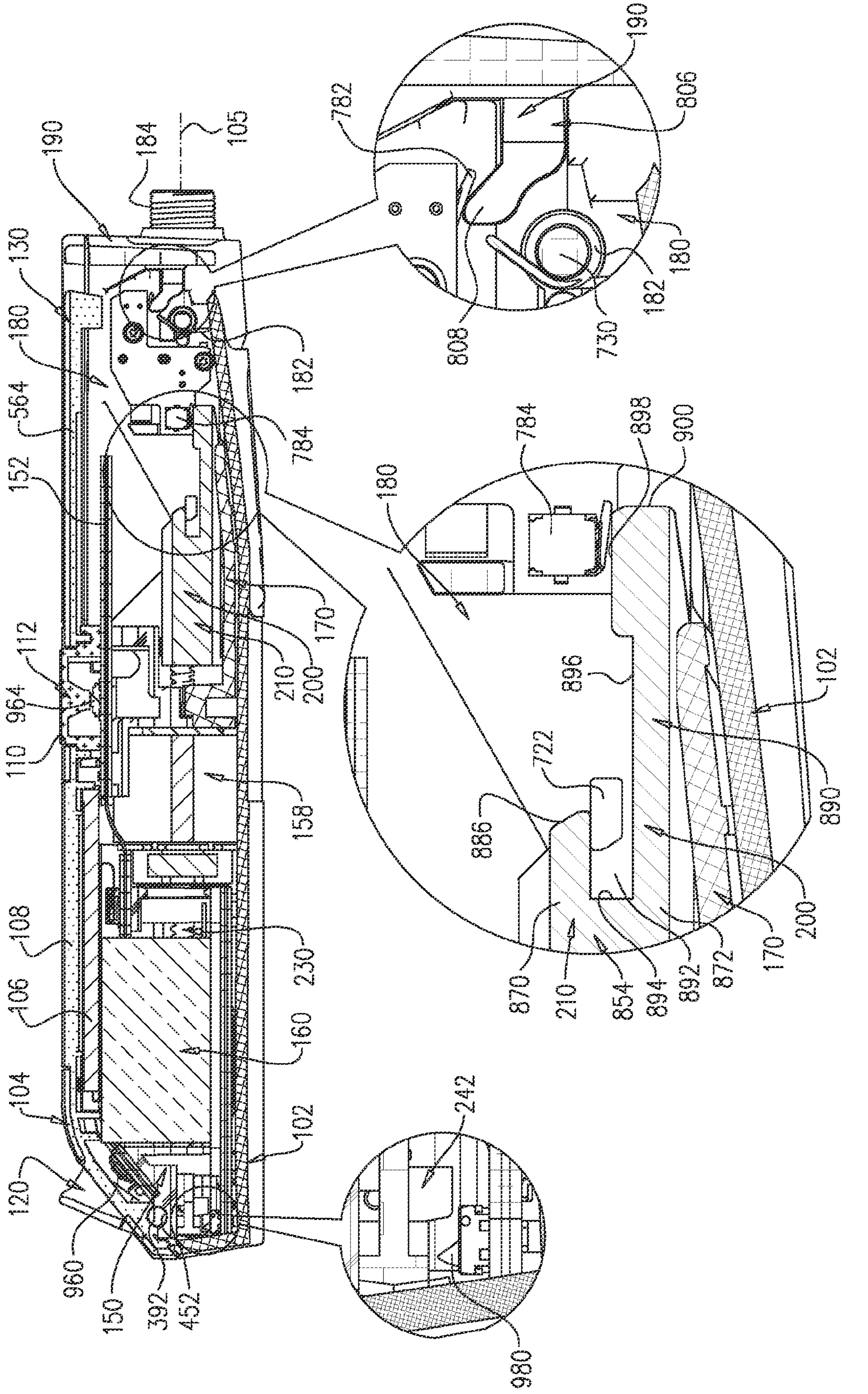
FIGS. 23A-23C are simplified sectional illustrations, taken generally along lines A-A, B-B and C-C respectively in FIG. 22 in the first pre-cartridge insertion operative orientation.
Figure 23B:
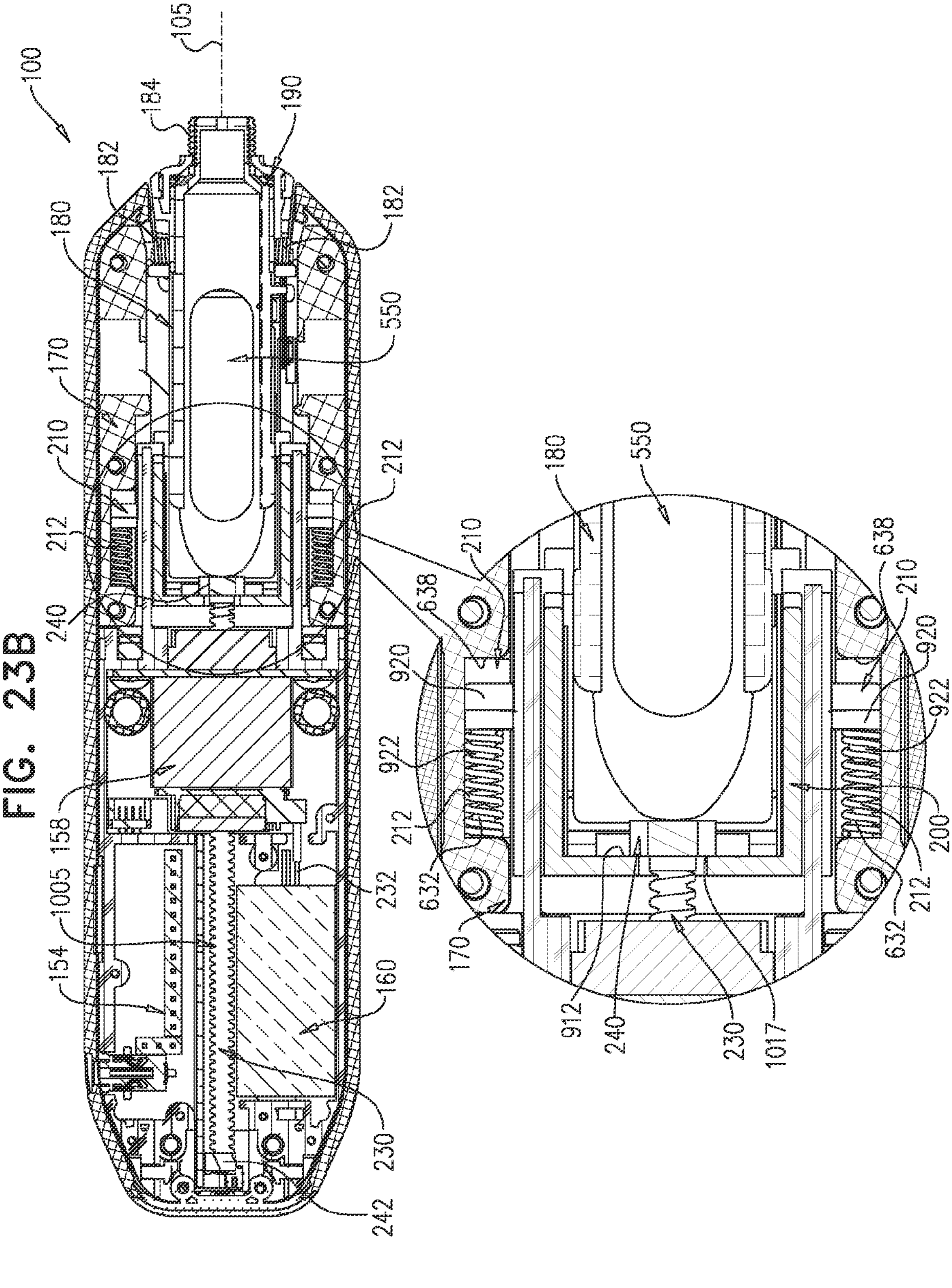
Figure 23C:
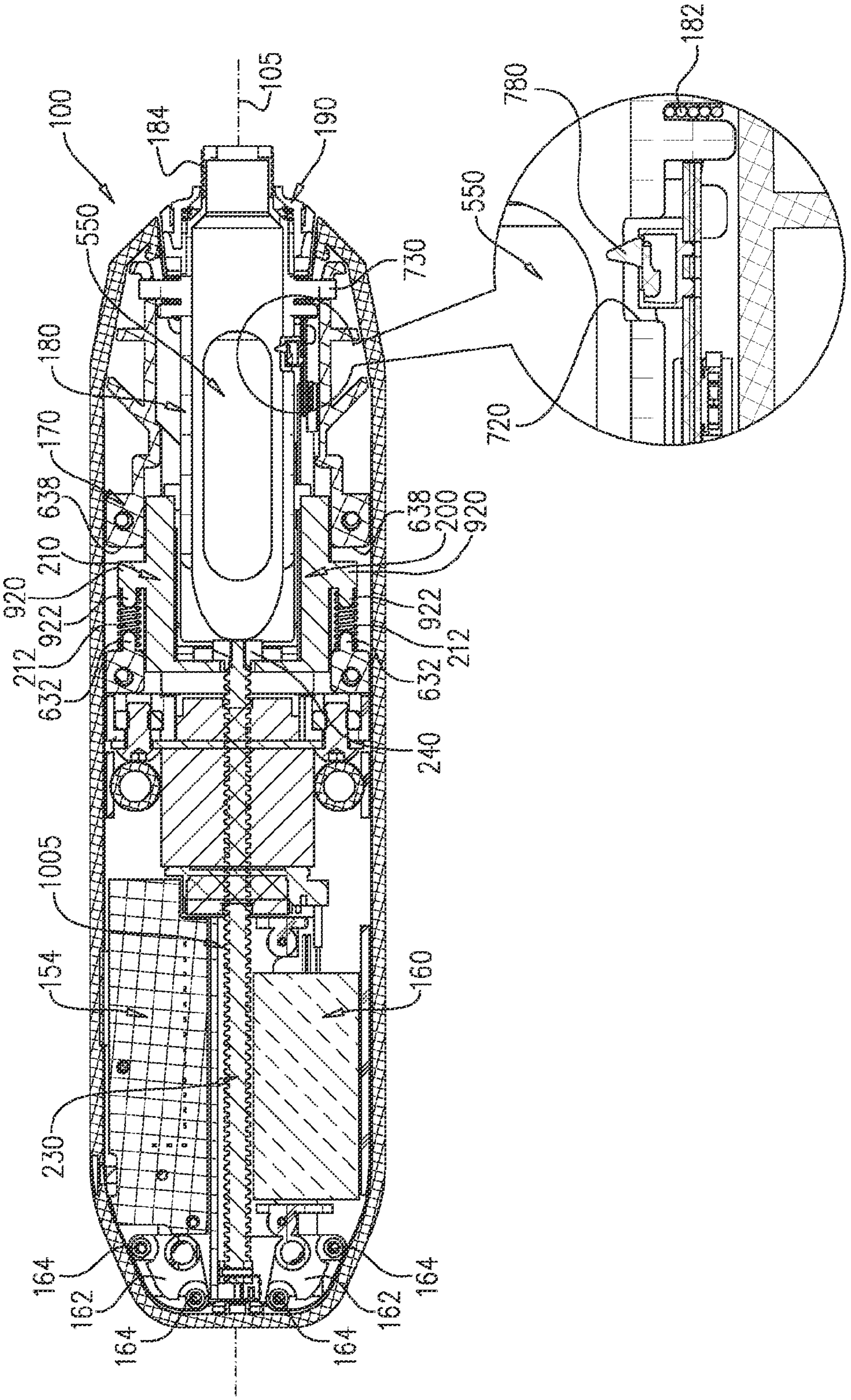

Reference is now made to FIG. 22, which is a simplified pictorial illustration of the MUCI 100 of FIGS. 1A-21B operated by a user, in a first pre-cartridge insertion operative orientation and to FIGS. 23A-23C, which are simplified sectional illustrations, taken generally along lines A-A, B-B and C-C respectively in FIG. 22 in the first pre-cartridge insertion operative orientation.

In FIG. 22, the MUCI 100 is shown in the first pre-cartridge insertion operative orientation, operated by a user. Preferably, in this first pre-cartridge insertion operative orientation, the user removes cover 134 by one hand and presses a button of the button defining element 112 by the other hand. The user can visually inspect the contents of cartridge enclosure assembly 130 through transparent window 564, which forms part of pivot mount element 180. There is no medicament cartridge mounted into the cartridge enclosure assembly 130 in this operative orientation.

As illustrated in FIG. 22, the display 106 instructs the user to open and load cartridge, by pressing button 354, which is identified on display 106 as "OPEN".

It is appreciated that in this first pre-cartridge insertion operative orientation, the cartridge enclosure assembly 130 is disposed in its closed operative orientation, as described in detail hereinabove with reference to FIGS. 13A-13C, and the following spatial relationships exist between the various elements:

It is specifically seen in FIGS. 23A-23C that injection button element 120 is seated within opening 116 of top housing portion 104 and is pivotably supported on chassis element 150, such that hinge axles 392 of injection button element 120 are seated within corresponding hinge seats 452 of chassis element 150.

Display 106 is provided under the transparent window 108 of top housing portion 104, preferably configured to provide instructions and indications to the user.

Button defining element 112 is seated within opening 110 of top hop housing portion and is disposed such that buttons 350, 352 and 354 are positioned just above menu button switches 964, thus configured to be operatively coupled therewith.

It is seen particularly in FIG. 23A that in this first pre-cartridge insertion operative orientation, the locking subassembly 200 being positioned in the locked operative orientation, as described in detail hereinabove, with reference to FIGS. 20A-20E. It is appreciated that there is a range of axial positions of the cartridge enclosure assembly latch element 210, which define the locked operative orientation of locking subassembly 200, in which the cartridge enclosure assembly 130 is disposed in its closed operative orientation.

It is a particular feature of an embodiment of the present invention that as specifically seen in FIGS. 23A & 23B, axial position of the moveable subassembly 1005 of the piston drive subassembly 220 with respect to cartridge enclosure assembly 130 defines the operative orientation of locking subassembly 200. Specifically, when the moveable subassembly 1005 is positioned in its forward operative orientation, locking subassembly 200 is urged to its locked operative orientation due to the biasing force of springs 212, which is exerted onto cartridge enclosure assembly latch element 210. When the moveable subassembly 1005 is positioned in its rearward operative orientation, it pulls cartridge enclosure assembly latch element 210 rearwardly and thus urging the locking subassembly 200 to its unlocked operative orientation.

It is appreciated that there is a range of axial positions of the moveable subassembly 1005, which define the forward and rearward operative orientations thereof, in which the locking subassembly 200 is positioned in locked and unlocked operative orientations respectively.

Locked operative orientation of the locking subassembly 200, which causes the cartridge enclosure assembly 130 to assume its closed operative orientation, is defined by the following spatial relationships:

As specifically seen in FIG. 23A, pivot mount element 180 is prevented from pivoting relative to cartridge enclosure assembly chassis 170 to assume an open operative orientation under the force of torsion springs 182, due to the fact that locking snap elements 722 of pivot mount element 180 are received within cut-out 892 formed between upper portion 870 and bottom portion 872 of first and second arms 852, 854 of cartridge enclosure assembly latch element 210.

As specifically seen in FIG. 23B, the cartridge enclosure assembly latch element 210 is slightly displaced rearwardly with respect to the operative orientation shown in FIGS. 20A-20E, which shows the locked operative orientation of the locking subassembly 200, however is still positioned in the range of axial positions, which defines the locked operative orientation of locking subassembly 200.

It is seen that cartridge enclosure assembly latch element 210 is positioned in this slightly rearwardly displaced positioned by means of force that is applied thereon by piston contact element 240, which is fixedly attached to plunger rod element 230, which is in turn displaced by means of the force applied thereon by the electrical motor 158. Specifically, rearwardly facing surface 1017 of piston contact element 240 engages forwardly facing surface 912 of base wall portion 850 of cartridge enclosure assembly latch element 210. Due to this engagement and the position of the moveable subassembly 1005 of the piston drive subassembly 220 in this operative orientation, side protrusions 920 of cartridge enclosure assembly latch element 210 are slightly spaced rearwardly from rearwardly facing end surfaces 638 of cartridge enclosure assembly chassis 170 and the springs 212 are slightly compressed.

Cartridge enclosure assembly state sensor 784 is preferably disposed in a triggered state, resulting from engagement with upwardly facing protrusion 898 of protrusion 890 of cartridge enclosure assembly latch element 210, which indicates that pivot mount element 180 is disposed in its closed operative orientation.

Additionally seen in FIG. 23A that the anti-rotation element 242 which is fixedly coupled to the rearward end 1002 of plunger rod element 230 is forwardly spaced from home position sensor 980, which is mounted onto main PCB assembly 152, thus permitting further rearward axial displacement of the plunger rod element 230, if an appropriate signal is provided to the electrical motor 158 which urges axial displacement of the plunger rod element 230.

It is additionally seen in FIG. 23A that needle sensor 782 is preferably disposed in a triggered state, resulting from engagement with engagement portion 808 of needle presence responsive element 190, which indicates that needle is not mounted onto externally threaded end 184 of pivot mount element 180 in this operative orientation.

It is particularly seen in FIG. 23C that cartridge sensor 780 preferably partially protrudes through opening 720 of pivot mount element 180 and is preferably disposed in an untriggered state, since there is no engagement with any element. Untriggered state of cartridge sensor 780 indicates that there is no medicament cartridge mounted into the cartridge enclosure assembly 130 in this operative orientation.

Figure 24B:
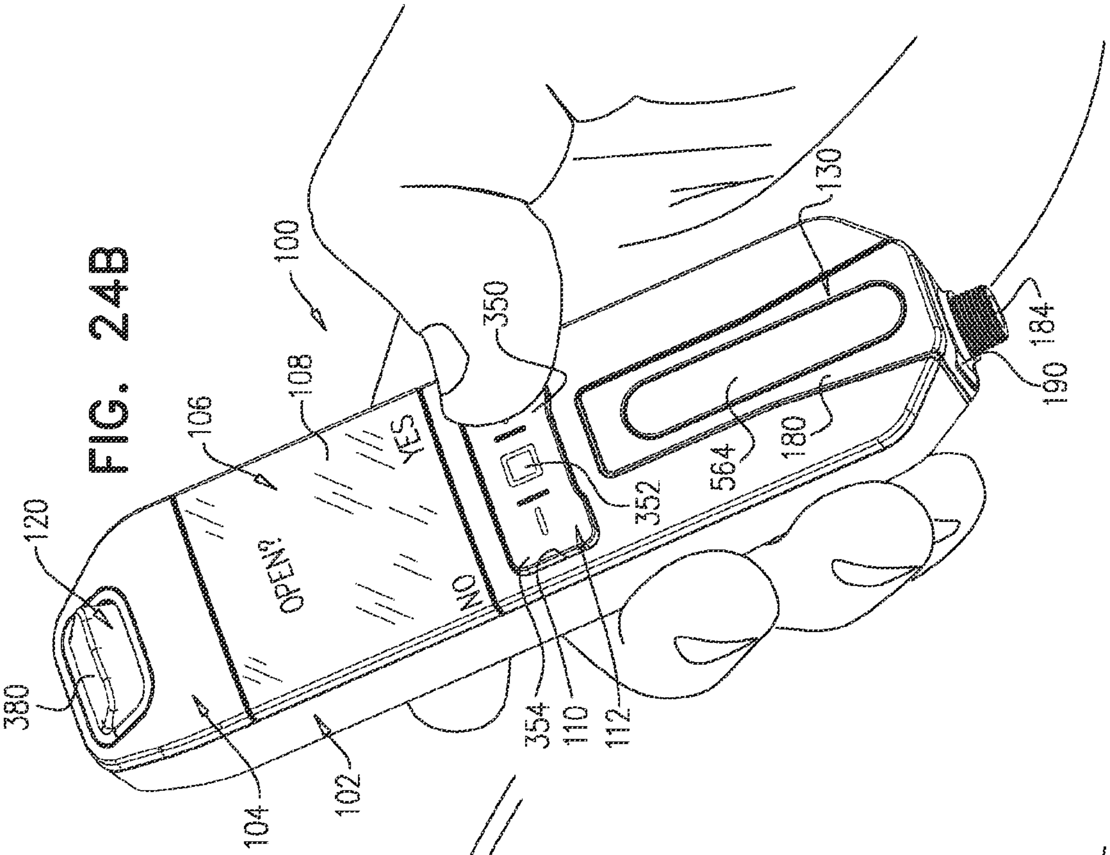
FIGS. 24A-24B are two simplified pictorial illustrations of the MUCI of FIGS. 1A & 1B operated by a user, in a second pre-cartridge insertion operative orientation.
Figure 24A:
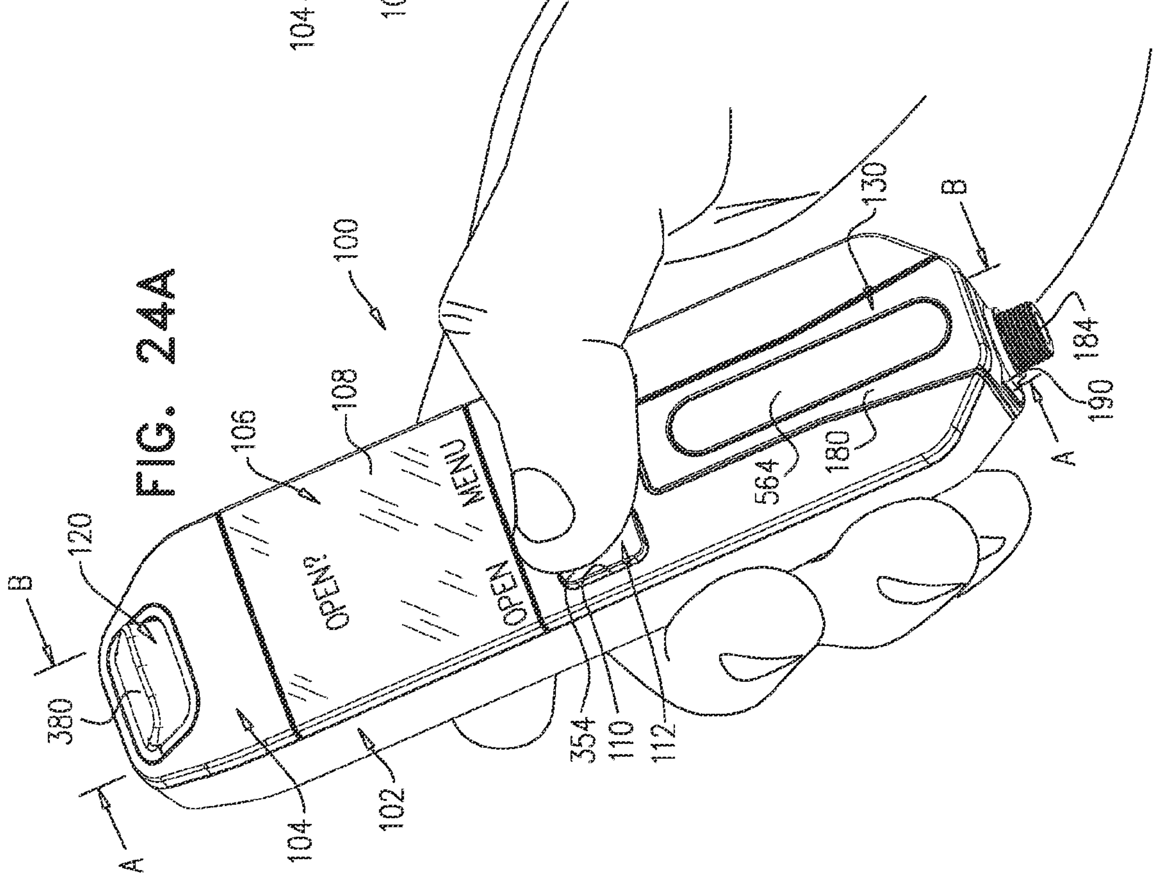
Figure 25A:
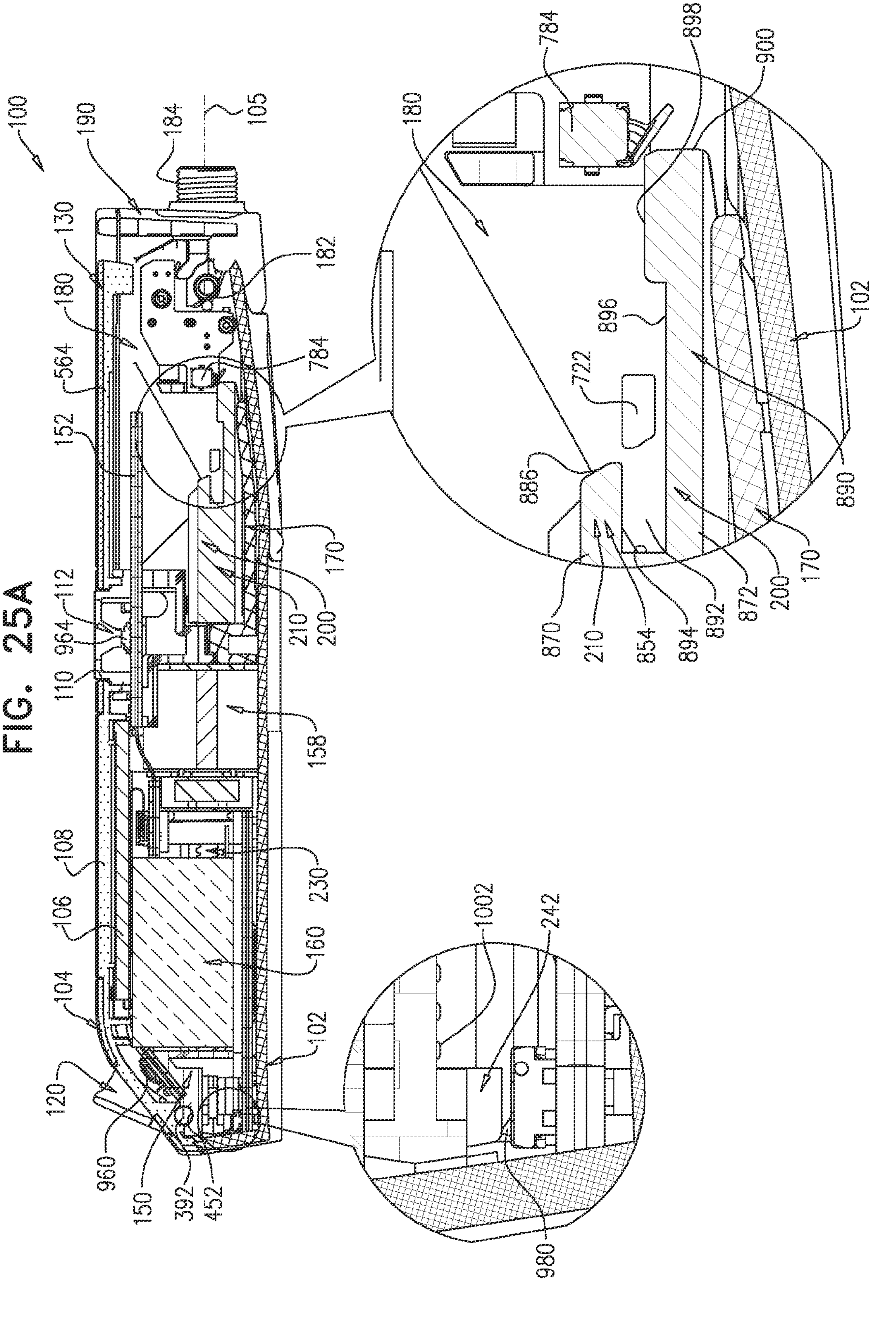
FIGS. 25A-25B are simplified sectional illustrations, taken generally along lines A-A and B-B respectively in FIG. 24A in the second pre-cartridge insertion operative orientation.
Figure 25B:
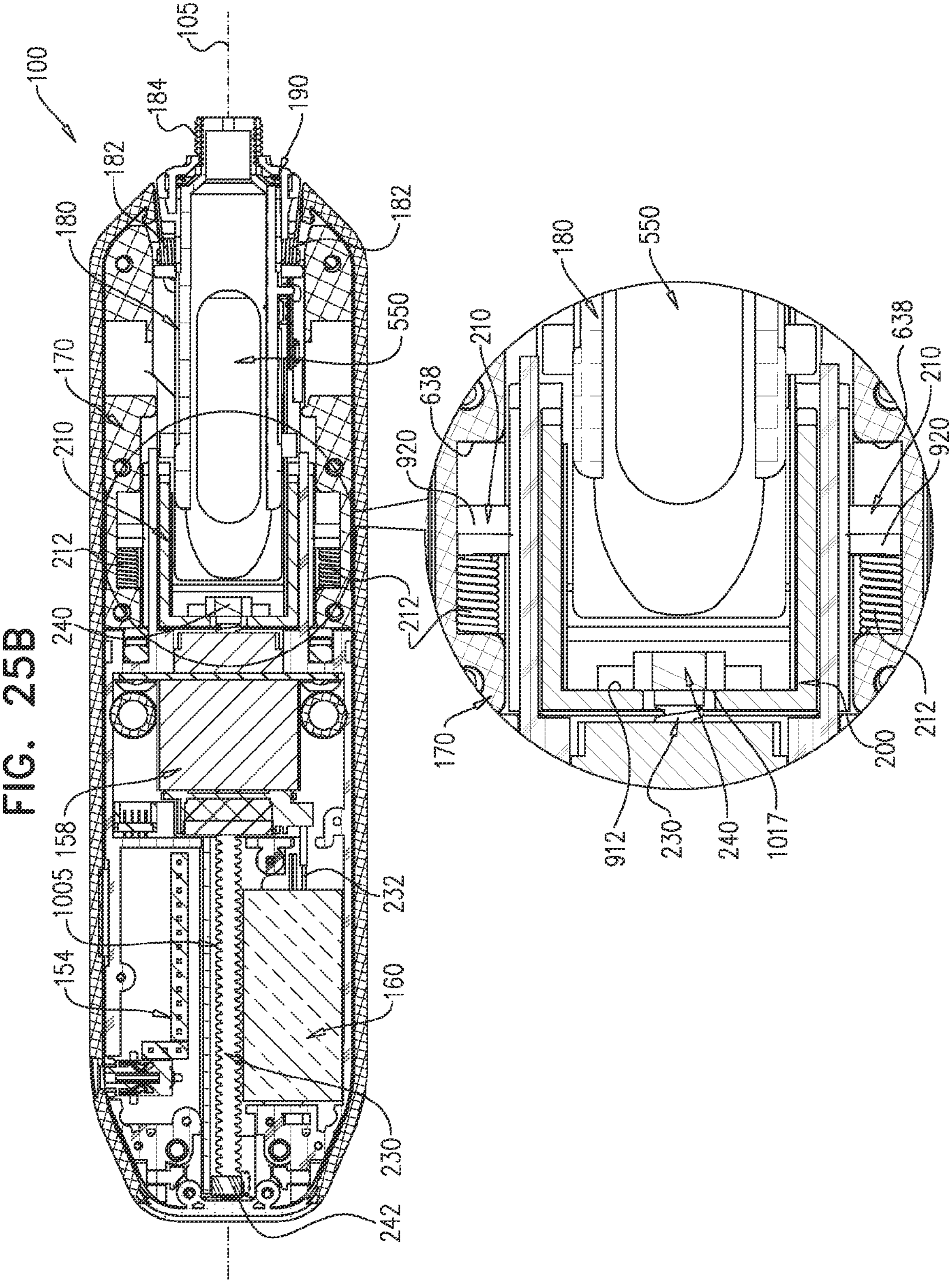

Reference is now made to FIGS. 24A-24B, which are two simplified pictorial illustrations of the MUCI 100 of FIGS. 1A-21B operated by a user, in a second pre-cartridge insertion operative orientation and to FIGS. 25A-25B, which are simplified sectional illustrations, taken generally along lines A-A and B-B respectively in FIG. 24A in the second pre-cartridge insertion operative orientation.

In FIGS. 24A-24B, the MUCI 100 is shown in the second pre-cartridge insertion operative orientation, operated by a user. Preferably, in this second pre-cartridge insertion operative orientation, as seen in FIG. 24A, the user presses button 354 of the button defining element 112, which is identified on display 106 as "OPEN" and confirms his selection by pressing button 350, which is identified on display 106 as "YES". The user can visually inspect the contents of cartridge enclosure assembly 130 through transparent window 564, which forms part of pivot mount element 180. There is no medicament cartridge mounted into the cartridge enclosure assembly 130 in this operative orientation.

As seen in FIGS. 25A-25B, in the second pre-cartridge insertion operative orientation, as compared with FIGS. 23A-23C, which illustrate the first pre-cartridge insertion operative orientation, moveable subassembly 1005 of piston drive subassembly 220 along with cartridge enclosure assembly latch element 210 are displaced rearwardly along longitudinal axis 105 by means of force transmission between the electrical motor 158 and the plunger rod element 230.

The mutual orientations of the various elements described in FIGS. 23A-23C remain essentially the same, other than as specifically set forth hereinbelow:

It is seen particularly in FIG. 25A that in this second pre-cartridge insertion operative orientation, the locking subassembly 200 being positioned in the unlocked operative orientation, as described in detail hereinabove, with reference to FIGS. 21A-21B. It is seen in FIGS. 25A-25B that the cartridge enclosure assembly 130 is still momentarily disposed in its closed operative orientation.

It is a particular feature of an embodiment of the present invention that as specifically seen in FIGS. 25A & 25B, axial position of the moveable subassembly 1005 of the piston drive subassembly 220 with respect to cartridge enclosure assembly 130 defines the operative orientation of locking subassembly 200.

Once the user pressed the button identified as "OPEN" on the display 106 and confirmed his selection, signal was provided to the system to activate the electrical motor 158, such that the moveable subassembly 1005 of the piston drive subassembly 220 is retracted rearwardly along longitudinal axis 105 to a pre-determined longitudinal extent, which positions the locking subassembly 200 in its unlocked operative orientation. During the rearward displacement of the moveable subassembly 1005, it pulls cartridge enclosure assembly latch element 210 rearwardly and thus urging the locking subassembly 200 to its unlocked operative orientation.

The unlocked operative orientation of the locking subassembly 200, which subsequently enables the cartridge enclosure assembly 130 to assume its open operative orientation, is defined by the following spatial relationships:

As specifically seen in FIG. 25A, pivot mount element 180 is no more prevented from pivoting relative to cartridge enclosure assembly chassis 170 to assume an open operative orientation under the force of torsion springs 182, due to the fact that cut-out 892 formed between upper portion 870 and bottom portion 872 of first and second arms 852, 854 of cartridge enclosure assembly latch element 210 is now disengaged from and slightly rearwardly spaced from locking snap elements 722 of pivot mount element 180.

As specifically seen in FIG. 25B, the cartridge enclosure assembly latch element 210 is fully displaced rearwardly with respect to cartridge enclosure assembly chassis 170, thus unlocking the locking subassembly 200.

It is seen that cartridge enclosure assembly latch element 210 is positioned in this fully rearwardly displaced positioned by means of force that is applied thereon by piston contact element 240, which is fixedly attached to plunger rod element 230. Specifically, rearwardly facing surface 1017 of piston contact element 240 engages forwardly facing surface 912 of base wall portion 850 of cartridge enclosure assembly latch element 210. Due to this engagement and the position of the moveable subassembly 1005 in this operative orientation, side protrusions 920 of cartridge enclosure assembly latch element 210 are fully spaced rearwardly from rearwardly facing end surfaces 638 of cartridge enclosure assembly chassis 170 and the springs 212 are fully compressed.

Cartridge enclosure assembly state sensor 784 is preferably disposed in an untriggered state, resulting from disengagement with upwardly facing protrusion 898 of protrusion 890 of cartridge enclosure assembly latch element 210, which indicates that pivot mount element 180 is disposed in its open operative orientation.

Additionally seen in FIG. 25A that the anti-rotation element 242 which is fixedly coupled to the rearward end 1002 of plunger rod element 230 now engages the home position sensor 980, which is mounted onto main PCB assembly 152, thus preventing further rearward axial displacement of the plunger rod element 230, even if a signal is provided to the electrical motor 158 which urges axial displacement of the plunger rod element 230. It is appreciated that alternatively, plunger rod element 230 could be stopped before engagement with home position sensor 980 by means of providing an appropriate signal to the electrical motor 158, thus home position sensor 980 serves as a safety mechanism.

Figure 26:
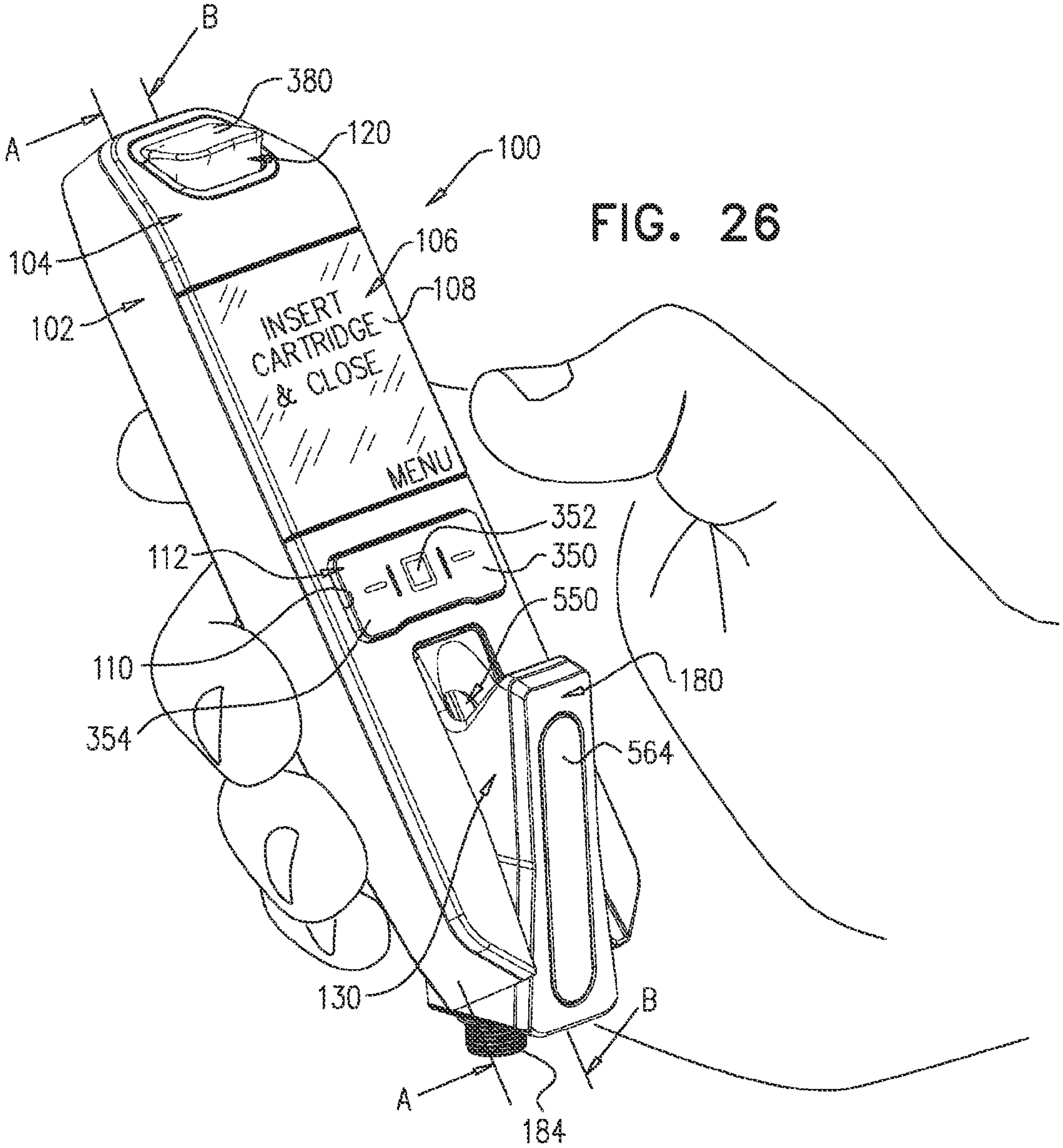
FIG. 26 is a simplified pictorial illustration of the MUCI of FIGS. 1A & 1B operated by a user, in a third pre-cartridge insertion operative orientation.
Figure 27A:
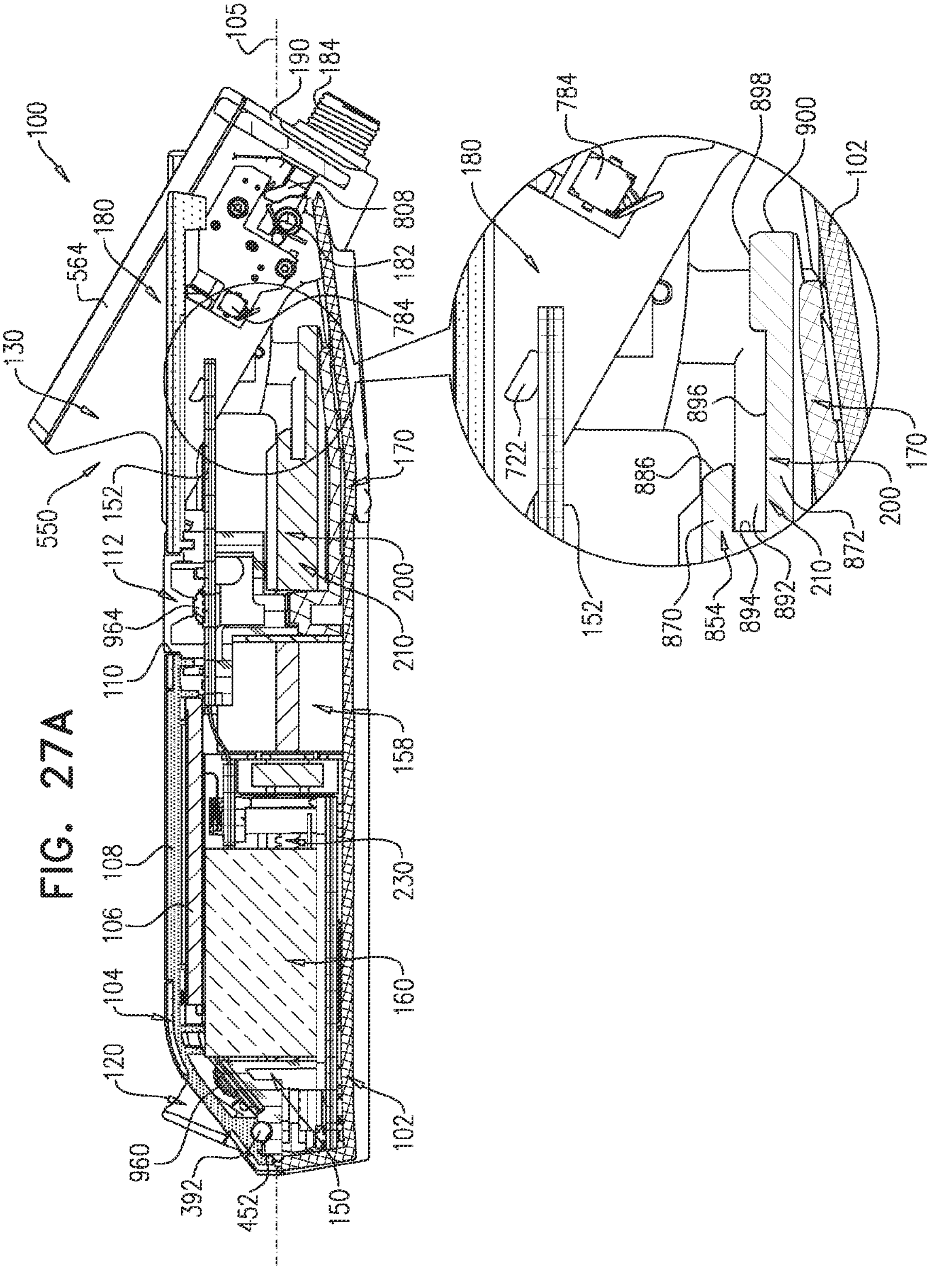
FIGS. 27A-27B are simplified sectional illustrations, taken generally along lines A-A and B-B respectively in FIG. 26 in the third pre-cartridge insertion operative orientation.
Figure 27B:
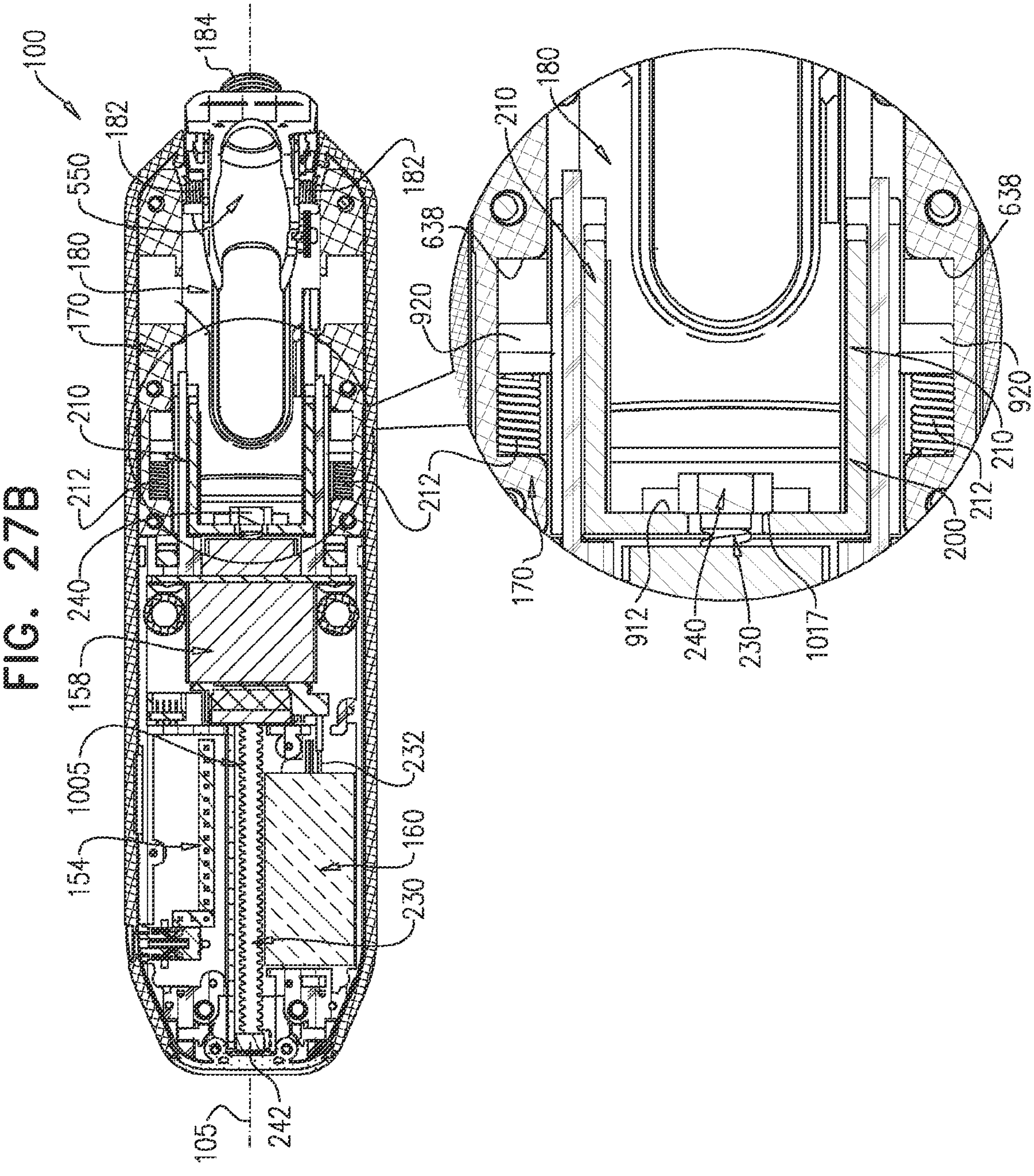

Reference is now made to FIG. 26, which is a simplified pictorial illustration of the MUCI 100 of FIGS. 1A-21B operated by a user, in a third pre-cartridge insertion operative orientation and to FIGS. 27A-27B, which are simplified sectional illustrations, taken generally along lines A-A and B-B respectively in FIG. 26 in the third pre-cartridge insertion operative orientation.

In FIG. 26, the MUCI 100 is shown in the third pre-cartridge insertion operative orientation, operated by a user. Preferably, in this third pre-cartridge insertion operative orientation, as seen in FIG. 26, the cartridge enclosure assembly 130 is positioned in its open operative orientation. There is no medicament cartridge mounted into the cartridge enclosure assembly 130 in this operative orientation.

As seen in FIGS. 27A-27B, in the third pre-cartridge insertion operative orientation, as compared with FIGS. 25A-25B, the pivot mount element 180 is pivoted with respect to cartridge enclosure assembly chassis 170, thus positioning the cartridge enclosure assembly 130 in open operative orientation.

The mutual orientations of the various elements described in FIGS. 25A-25B remain essentially the same, other than as specifically set forth hereinbelow:

It is seen particularly in FIGS. 27A-27B that in this third pre-cartridge insertion operative orientation, the locking subassembly 200 being still positioned in the unlocked operative orientation, as described in detail hereinabove, with reference to FIGS. 21A-21B. It is seen in FIGS. 27A-27B that the cartridge enclosure assembly 130 is now disposed in the open operative orientation.

Following the unlocking of the locking subassembly 200, as described in particular hereinabove with reference to FIGS. 25A-25B, opening of the cartridge enclosure assembly 130 is permitted and is defined by the fact that the pivot mount element 180 has pivoted relative to cartridge enclosure assembly chassis 170 to assume an open operative orientation under the force of torsion springs 182, which are preferably normally biasing the pivot mount element 180 to its open operative orientation.

Figure 28A:
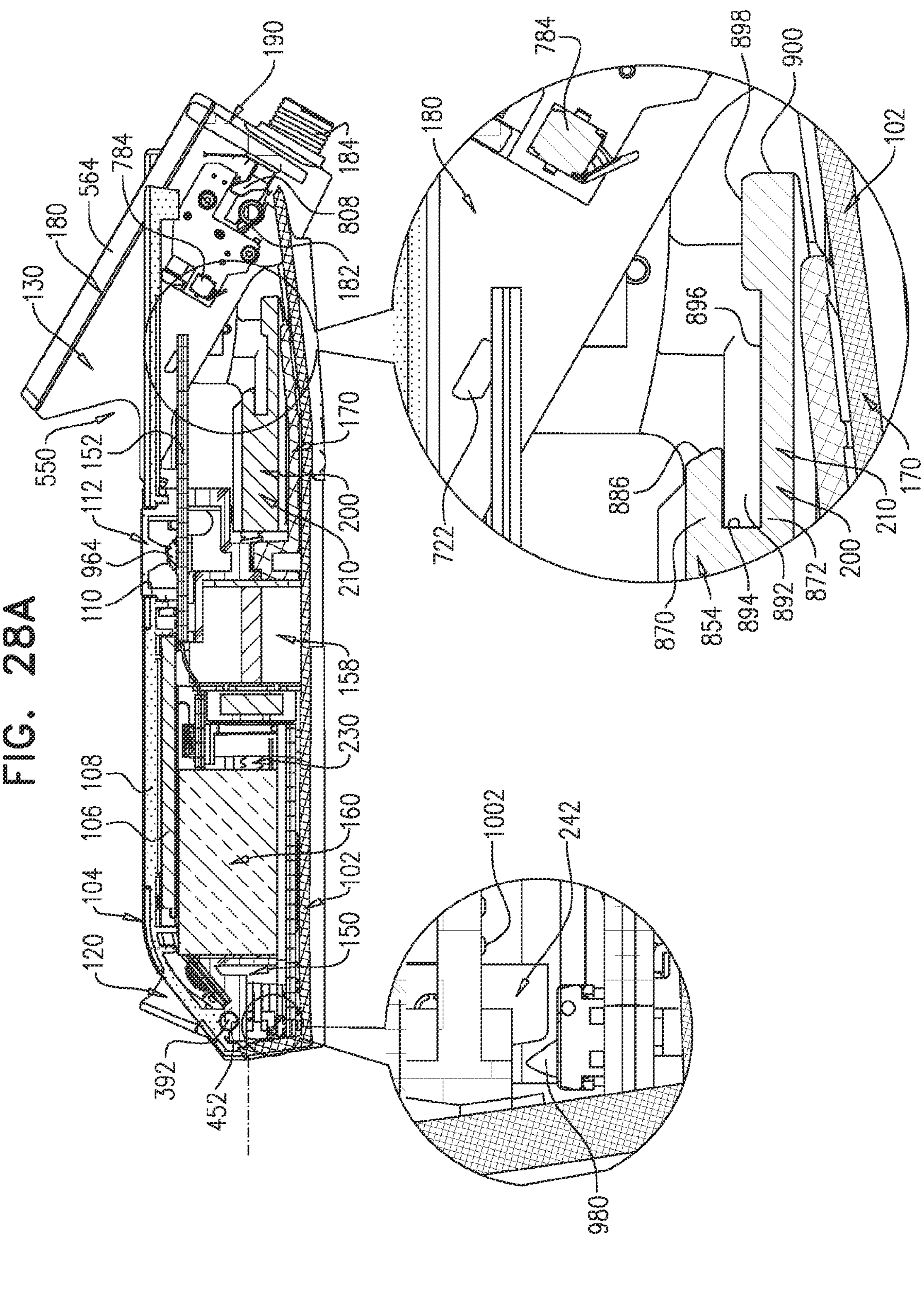
FIGS. 28A-28B are simplified sectional illustrations, taken generally along lines A-A and B-B respectively in FIG. 26 in a fourth pre-cartridge insertion operative orientation.
Figure 28B:
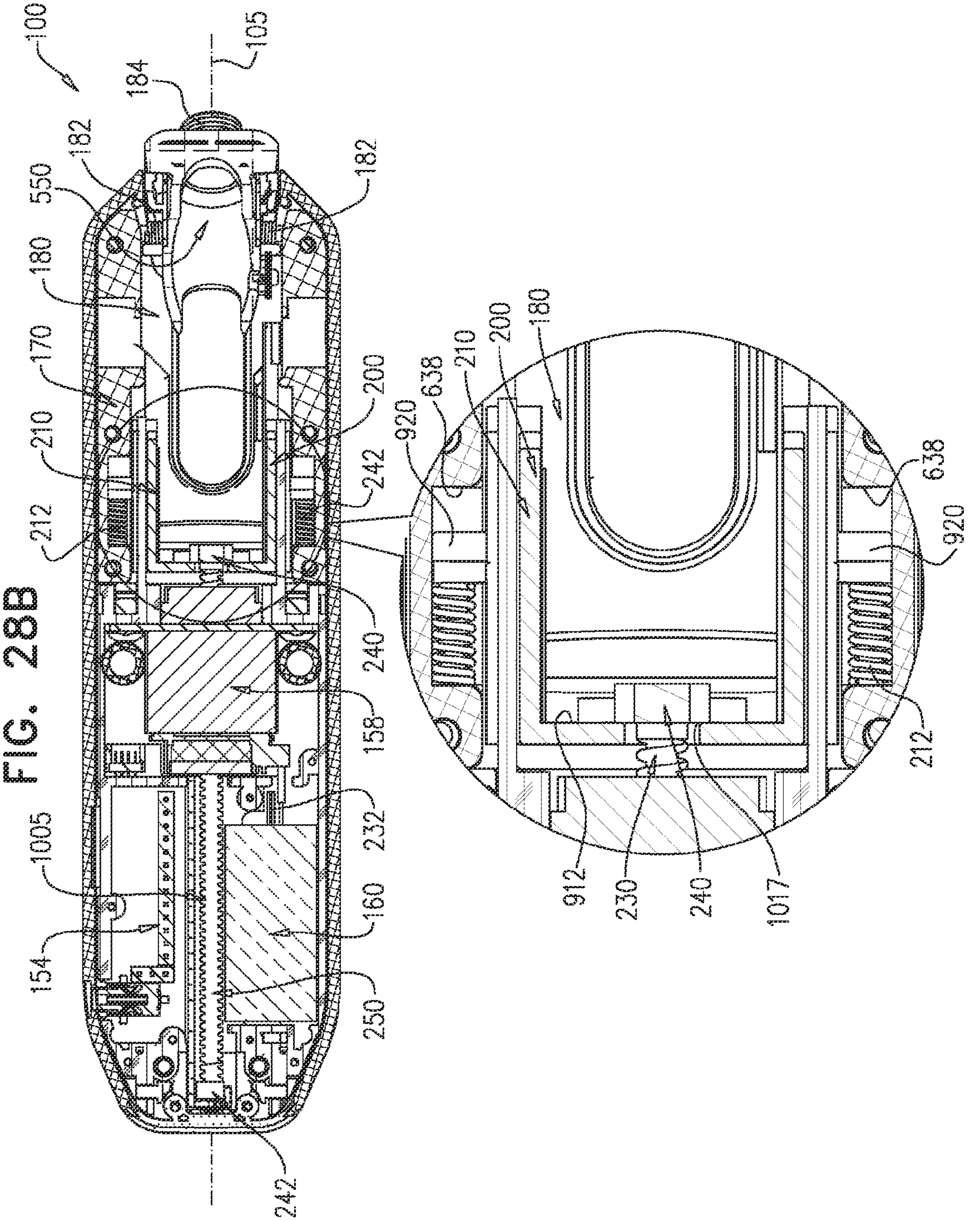

Reference is now made to FIGS. 28A-28B, which are simplified sectional illustrations, taken generally along lines A-A and B-B respectively in FIG. 26 in a fourth pre-cartridge insertion operative orientation.

It is seen in FIGS. 28A-28B that preferably immediately upon opening of the pivot mount element 180, as illustrated and described with reference to FIGS. 27A-27B, the moveable subassembly 1005 of the piston drive subassembly 220 is slightly displaced axially forwardly to the intermediate operative orientation thereof, which defines the snapped operative orientation of the locking subassembly 200, ready for closing the cartridge enclosure assembly 130.

In FIGS. 28A-28B, the MUCI 100 is shown in the fourth pre-cartridge insertion operative orientation, there is no medicament cartridge mounted into the cartridge enclosure assembly 130 in this operative orientation.

As seen in FIGS. 28A-28B, in the fourth pre-cartridge insertion operative orientation, as compared with FIGS. 27A-27B, which illustrate the third pre-cartridge insertion operative orientation, moveable subassembly 1005 along with cartridge enclosure assembly latch element 210 are displaced forwardly along longitudinal axis 105.

The mutual orientations of the various elements described in FIGS. 27A-27B remain essentially the same, other than as specifically set forth hereinbelow:

During the forward displacement of the plunger rod element 230, the cartridge enclosure assembly latch element 210 is permitted to be displaced forwardly to the same longitudinal extent as the moveable subassembly 1005, under the biasing force of springs 212.

The locking subassembly 200 is still disposed in the unlocked operative orientation, and the pivot mount element 180 is still disposed in the open operative orientation however the cut-out 892 formed between upper portion 870 and bottom portion 872 of first and second arms 852, 854 of cartridge enclosure assembly latch element 210 is now less rearwardly spaced from locking snap elements 722 of pivot mount element 180.

As specifically seen in FIGS. 28A-28B, the cartridge enclosure assembly latch element 210 is slightly forwardly displaced with respect to cartridge enclosure assembly chassis 170.

Due to forward displacement of the moveable subassembly 1005 of the piston drive subassembly 1005 in this operative orientation, side protrusions 920 of cartridge enclosure assembly latch element 210 are less spaced rearwardly from rearwardly facing end surfaces 638 of cartridge enclosure assembly chassis 170 and the springs 212 are less compressed.

It is specifically seen in FIG. 28A that the anti-rotation element 242 which is fixedly coupled to the rearward end 1002 of plunger rod element 230 is now preferably disengaged from home position sensor 980, which is mounted onto main PCB assembly 152.

Figure 29:
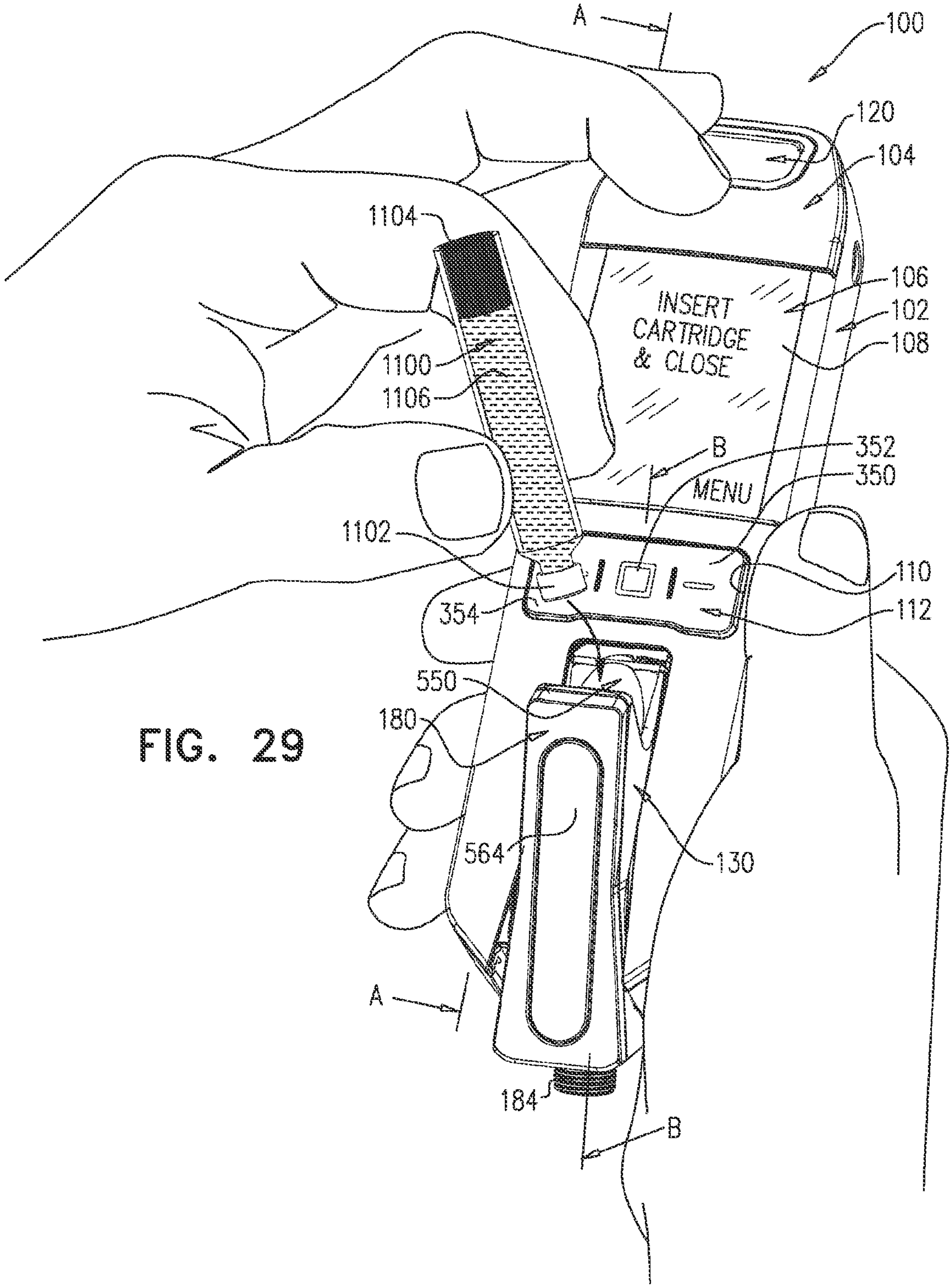
FIG. 29 is a simplified pictorial illustration of the MUCI of FIGS. 1A & 1B operated by a user, in a fifth pre-cartridge insertion operative orientation.
Figure 30A:
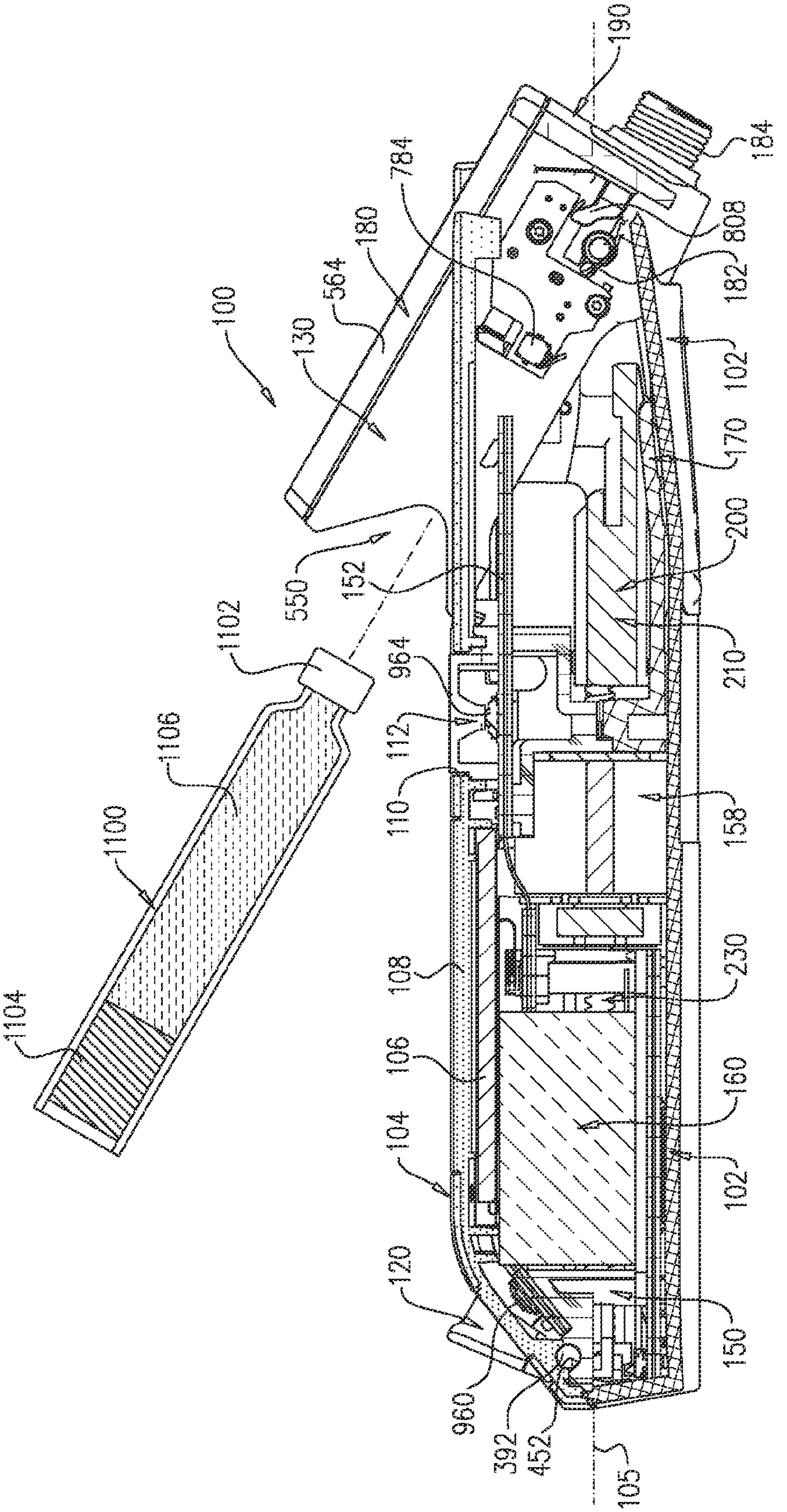
FIGS. 30A-30B are simplified sectional illustrations, taken generally along lines A-A and B-B respectively in FIG. 29 in the fifth pre-cartridge insertion operative orientation.
Figure 30B:
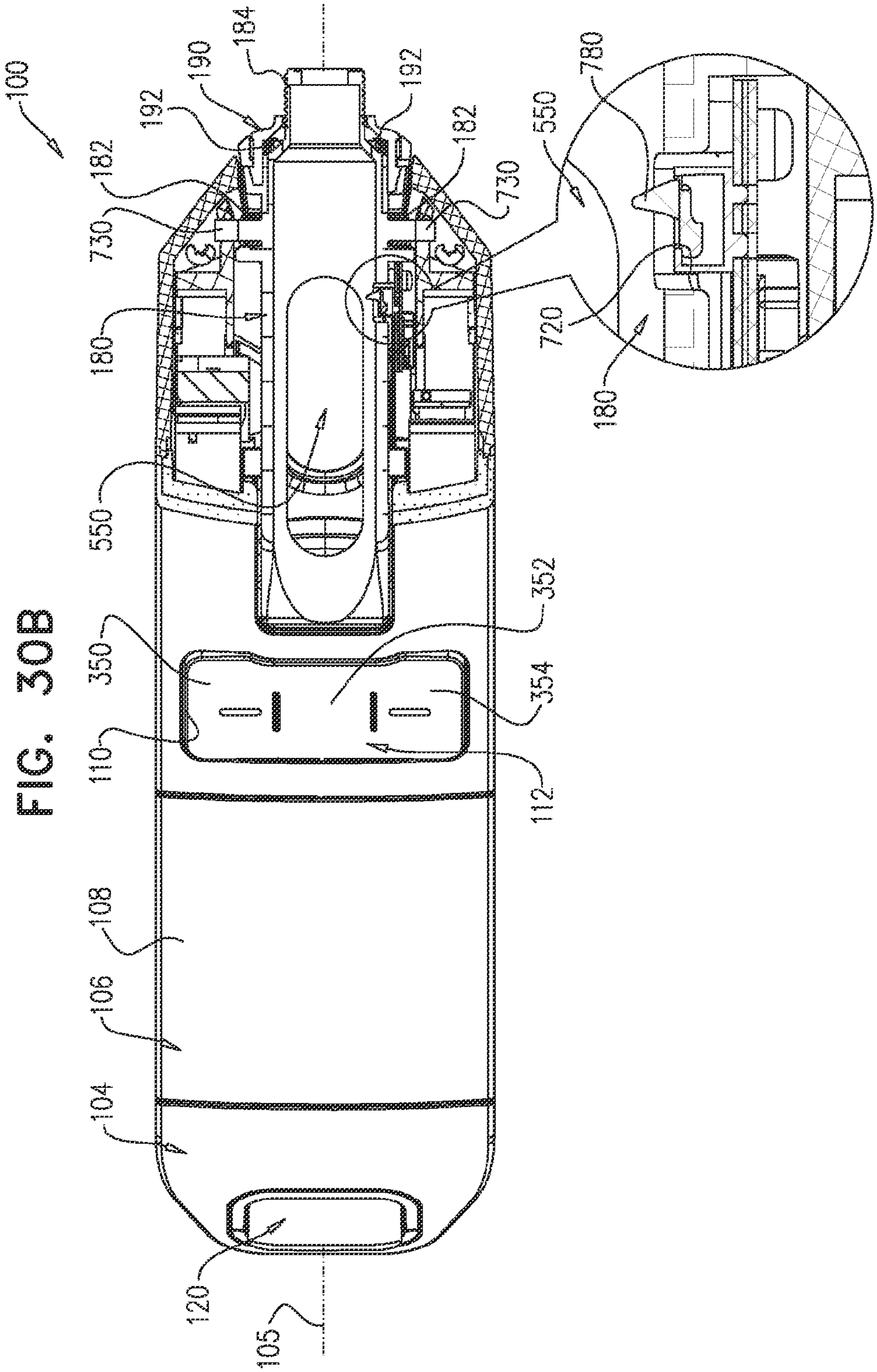

Reference is now made to FIG. 29, which is a simplified pictorial illustration of the MUCI 100 of FIGS. 1A-21B operated by a user, in a fifth pre-cartridge insertion operative orientation and to FIGS. 30A-30B, which are simplified sectional illustrations, taken generally along lines A-A and B-B respectively in FIG. 29 in the fifth pre-cartridge insertion operative orientation.

In FIG. 29, the MUCI 100 is shown in the fifth pre-cartridge insertion operative orientation, operated by a user. Preferably, in this fifth pre-cartridge insertion operative orientation, as seen in FIG. 29, the cartridge enclosure assembly 130 is positioned in its open operative orientation and the user is about to insert a medicament cartridge 1100 into the inner volume 550 of pivot mount element 180. Medicament cartridge 1100 is preferably cylindrical and circularly symmetric and preferably includes a septum 1102 at its forward end and a piston 1104 at its rearward end. Piston 1104 is configured to confine medicament 1106 which is contained within the inner volume of the medicament cartridge 1100.

As seen in FIGS. 30A-30B, in the fifth pre-cartridge insertion operative orientation, as compared with FIGS. 28A-28B, all mutual orientations of the various elements remain essentially the same, other than the fact that the user is ready to insert the medicament cartridge 1100 into the inner volume 550 of the pivot mount element 180.

It is particularly seen in FIG. 30B that cartridge sensor 780 preferably partially protrudes through opening 720 of pivot mount element 180 and is preferably disposed in an untriggered state, since there is no engagement with any element. Untriggered state of cartridge sensor 780 indicates that there is no medicament cartridge mounted into the cartridge enclosure assembly 130 in this operative orientation.

Figure 31:
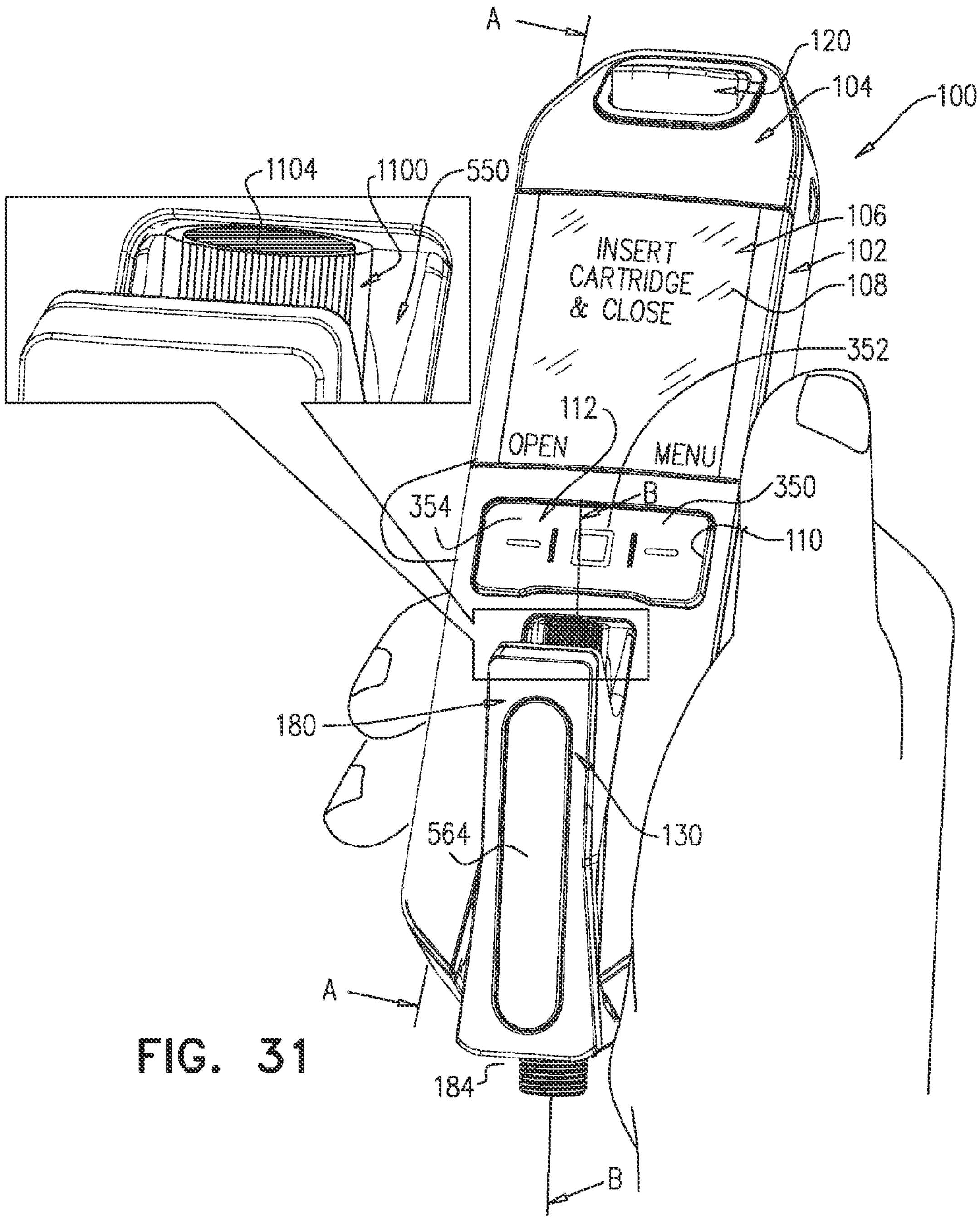
FIG. 31 is a simplified pictorial illustration of the MUCI of FIGS. 1A & 1B operated by a user, in a first cartridge insertion operative orientation.
Figure 32A:
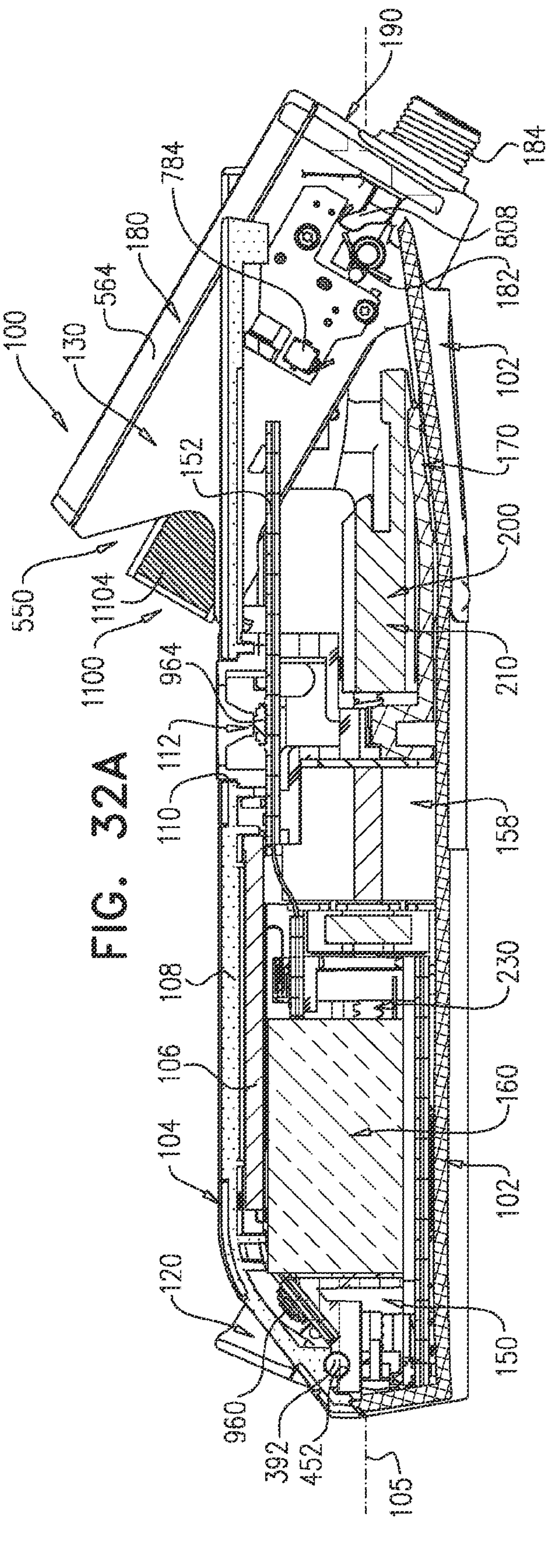
FIGS. 32A-32B are simplified sectional illustrations, taken generally along lines A-A and B-B respectively in FIG. 31 in the first cartridge insertion operative orientation.
Figure 32B:
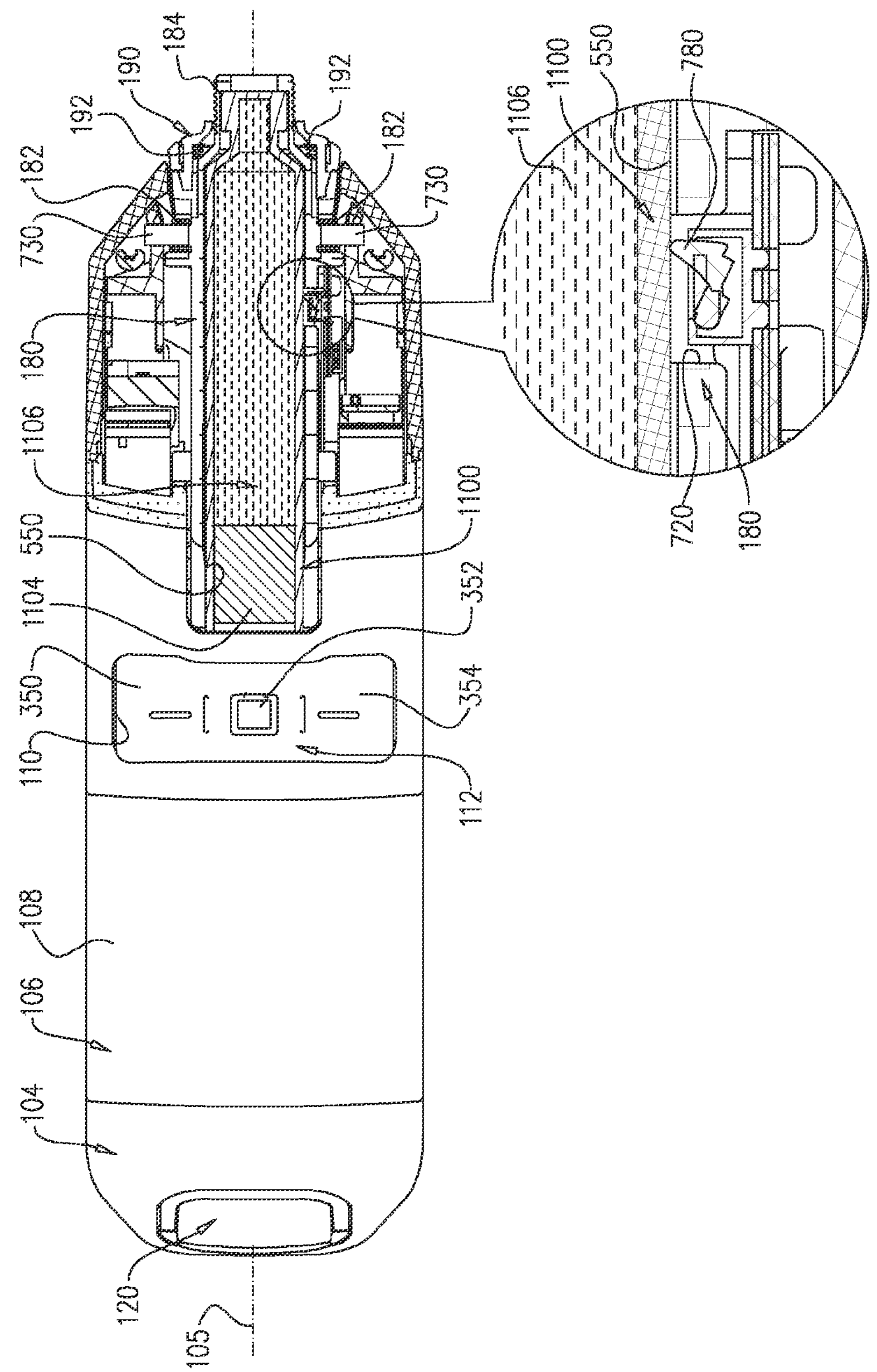

Reference is now made to FIG. 31, which is a simplified pictorial illustration of the MUCI 100 of FIGS. 1A-21B operated by a user, in a first cartridge insertion operative orientation and to FIGS. 32A-32B, which are simplified sectional illustrations, taken generally along lines A-A and B-B respectively in FIG. 31 in the first cartridge insertion operative orientation.

In FIG. 31, the MUCI 100 is shown in the first cartridge insertion operative orientation, operated by a user. Preferably, in this first cartridge insertion operative orientation, as seen in FIG. 31, the cartridge enclosure assembly 130 is positioned in its open operative orientation and the user has inserted a medicament cartridge 1100 into the inner volume 550 of pivot mount element 180.

The mutual orientations of the various elements described in FIGS. 30A-30B remain essentially the same, other than as specifically set forth hereinbelow:

It is particularly seen in FIG. 32B that cartridge sensor 780 preferably partially protrudes through opening 720 of pivot mount element 180 and is now preferably disposed in triggered state, due to engagement of the cartridge sensor 780 with the outer surface of medicament cartridge 1100, thus indicating that there is a medicament cartridge mounted into the cartridge enclosure assembly 130 in this operative orientation.

Figure 33:
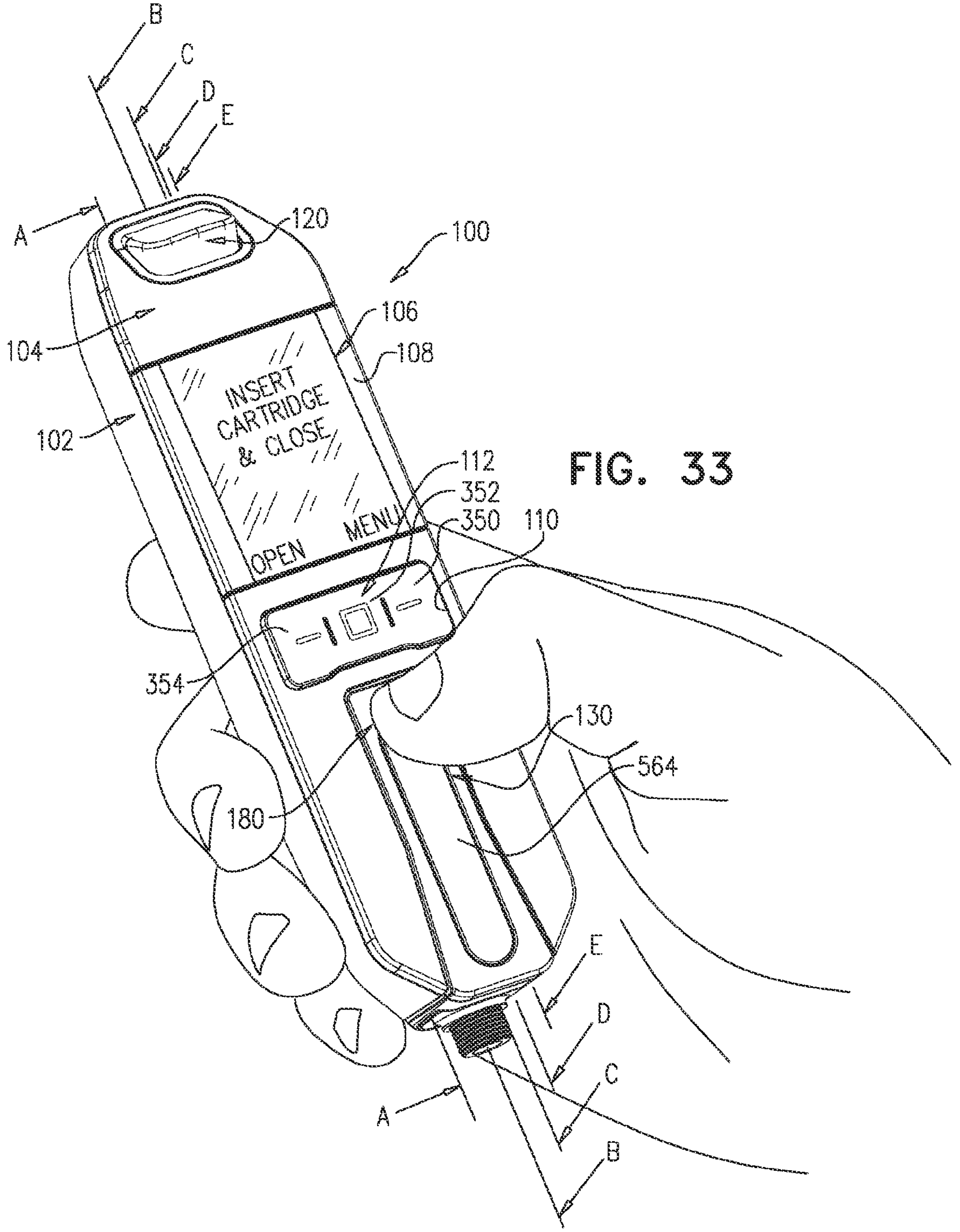
FIG. 33 is a simplified pictorial illustration of the MUCI of FIGS. 1A-21B operated by a user, in a second cartridge insertion operative orientation.
Figure 34A:
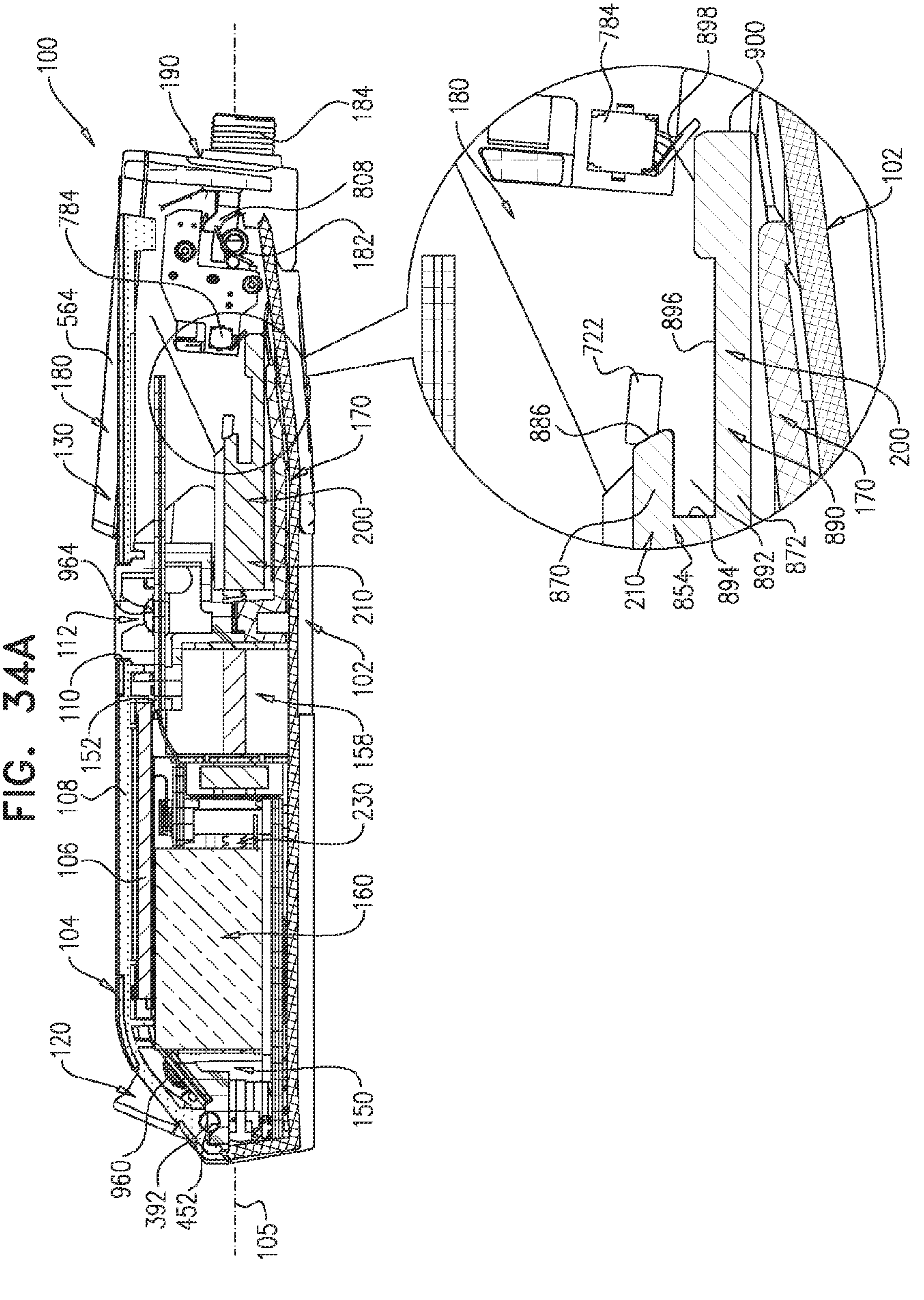
FIGS. 34A-34B are simplified sectional illustrations, taken generally along lines A-A and B-B respectively in FIG. 33 in a first stage of the second cartridge insertion operative orientation.
Figure 34B:
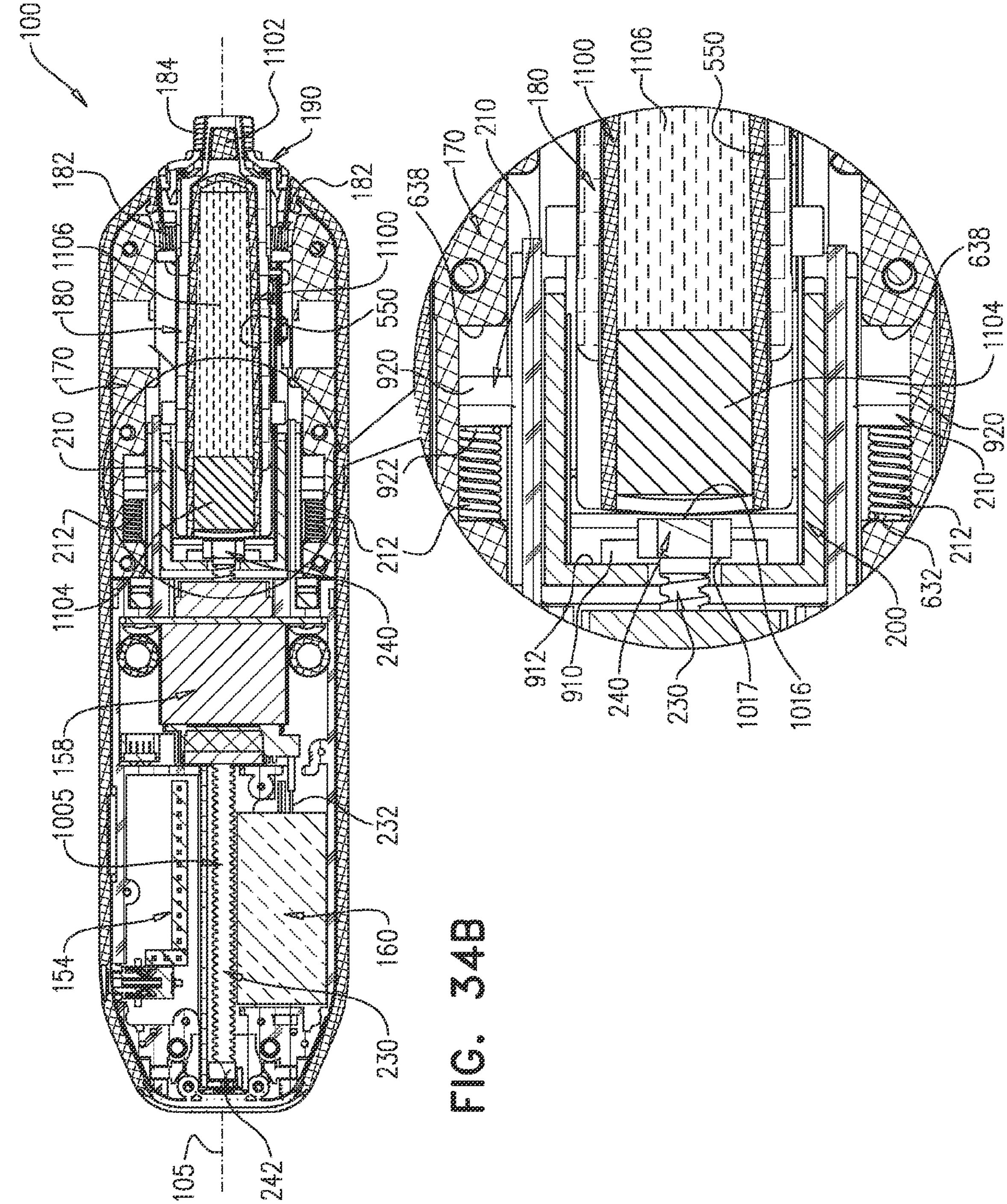

Reference is now made to FIG. 33, which is a simplified pictorial illustration of the MUCI of FIGS. 1A-21B operated by a user, in a second cartridge insertion operative orientation and to FIGS. 34A-34B, which are simplified sectional illustrations, taken generally along lines A-A and B-B respectively in FIG. 33 in a first stage of the second cartridge insertion operative orientation.

In FIG. 33, the MUCI 100 is shown in the second cartridge insertion operative orientation, operated by a user. Preferably, in this orientation, as seen in FIG. 33, the cartridge enclosure assembly 130 is positioned in the closed operative orientation following pivoting of the pivot mount element 180 inwardly, with respect to cartridge enclosure assembly chassis 170, following insertion of medicament cartridge 1100 and pressing on the pivot mount element 180 by the user.

It is noted that FIGS. 34A-39E, which are further described in detail hereinbelow, illustrate various intermediate stages during the closing of the pivot mount element 180 by the user.

It is seen specifically in FIGS. 34A-34B that the moveable subassembly 1005 of the piston drive subassembly 220 is positioned in the intermediate operative orientation, preferably identical to its operative orientation in FIGS. 28A-28B, 30A-30B and in FIGS. 32A-32B and the pivot mount element 180 is positioned in a first intermediate closing stage.

The mutual orientations of the various elements described in FIGS. 34A-34B remain essentially the same as in FIGS. 32A-32B, other than as specifically set forth hereinbelow:

The medicament cartridge 1100 is inserted into the inner volume 550 of pivot mount element 180.

It is seen particularly in FIGS. 34A-34B that in this first stage of the second cartridge insertion operative orientation, the locking subassembly 200 being now positioned in a first snapping operative orientation, where the displacement of the pivot mount element 180 by the user urges rearward displacement of the cartridge enclosure assembly latch element 210 against the force of springs 212.

It is appreciated that there is a range of axial positions of the cartridge enclosure assembly latch element 210, which defines the snapped operative orientation of locking subassembly 200.

Pivot mount element 180 is pivoted relative to cartridge enclosure assembly chassis 170 to assume the closed operative orientation against the urging of torsion springs 182.

It is seen that rearwardly facing surface 1017 of piston contact element 240 does not engage forwardly facing surface 912 of base wall portion 850 of cartridge enclosure assembly latch element 210.

It is specifically seen in FIG. 34A that in this first stage of the second cartridge insertion operative orientation, locking snap elements 722 of pivot mount element 180 initially engage forwardly facing tapered surfaces 886 of upper portions 870 of arms 852 and 854 of cartridge enclosure assembly latch element 210 and are not yet received within cut-out 892 formed between upper portion 870 and bottom portion 872 of first and second arms 852, 854 of cartridge enclosure assembly latch element 210.

As specifically seen in FIG. 34B, the cartridge enclosure assembly latch element 210 is positioned slightly rearwardly as compared with FIGS. 32A-32B, due to engagement between 886 thereof with 722 of 180, and the locking subassembly 200 is disposed in its first snapping operative orientation.

Cartridge enclosure assembly state sensor 784 is preferably disposed in untriggered state, resulting from disengagement with upwardly facing protrusion 898 of protrusion 890 of cartridge enclosure assembly latch element 210, which indicates that pivot mount element 180 is disposed in its open operative orientation.

Figure 35A:
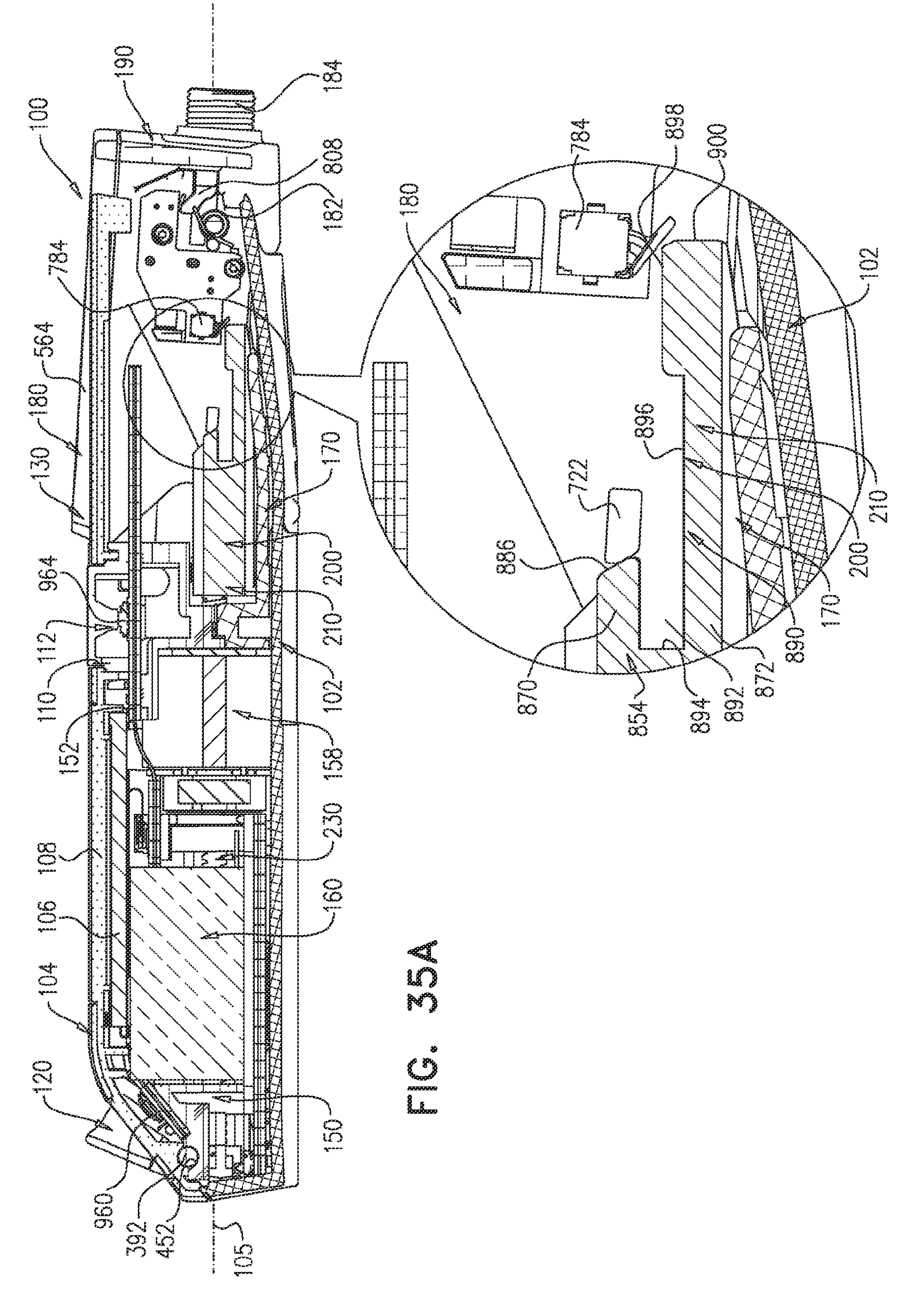
FIGS. 35A-35B are simplified sectional illustrations, taken generally along lines A-A and B-B respectively in FIG. 33 in a second stage of the second cartridge insertion operative orientation.
Figure 35B:
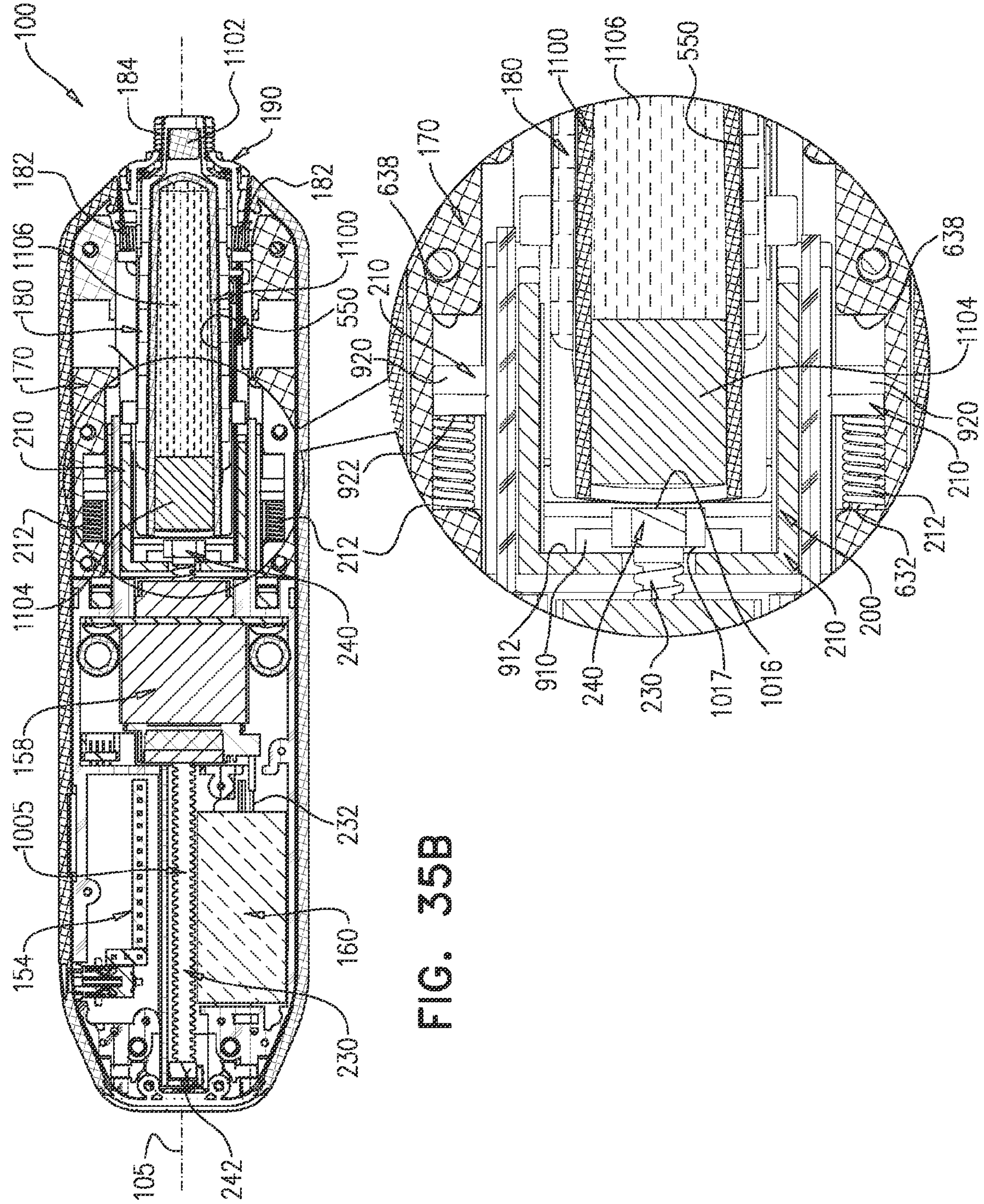

Reference is now made to FIGS. 35A-35B, which are simplified sectional illustrations, taken generally along lines A-A and B-B respectively in FIG. 33 in a second stage of the second cartridge insertion operative orientation.

It is seen specifically in FIGS. 35A-35B that the moveable subassembly 1005 of the piston drive subassembly 220 is positioned in the intermediate operative orientation, preferably identical to its operative orientation in FIGS. 34A-34B and the pivot mount element 180 is further pivoted inwardly against the urging of torsion springs 182 and is now positioned in a second intermediate closing stage.

The mutual orientations of the various elements described in FIGS. 35A-35B remain essentially the same as in FIGS. 34A-34B, other than as specifically set forth hereinbelow:

It is seen particularly in FIGS. 35A-35B that in this second stage of the second cartridge insertion operative orientation, the locking subassembly 200 being now positioned in a second snapping operative orientation, where the displacement of the pivot mount element 180 by the user urges further rearward displacement of the cartridge enclosure assembly latch element 210 against the force of springs 212.

It is specifically seen in FIG. 35A that in this second stage of the second cartridge insertion operative orientation, locking snap elements 722 of pivot mount element 180 further engage forwardly facing tapered surfaces 886 of upper portions 870 of arms 852 and 854 of cartridge enclosure assembly latch element 210 and are not yet received within cut-out 892 formed between upper portion 870 and bottom portion 872 of first and second arms 852, 854 of cartridge enclosure assembly latch element 210. Locking snap elements 722 urge the cartridge enclosure assembly latch element 210 rearwardly.

As specifically seen in FIG. 35B, the cartridge enclosure assembly latch element 210 is positioned slightly rearwardly as compared with FIGS. 34A-34B, due to engagement between 886 thereof with 722 of 180, and the locking subassembly 200 is disposed in its second snapping operative orientation.

Figure 36A:
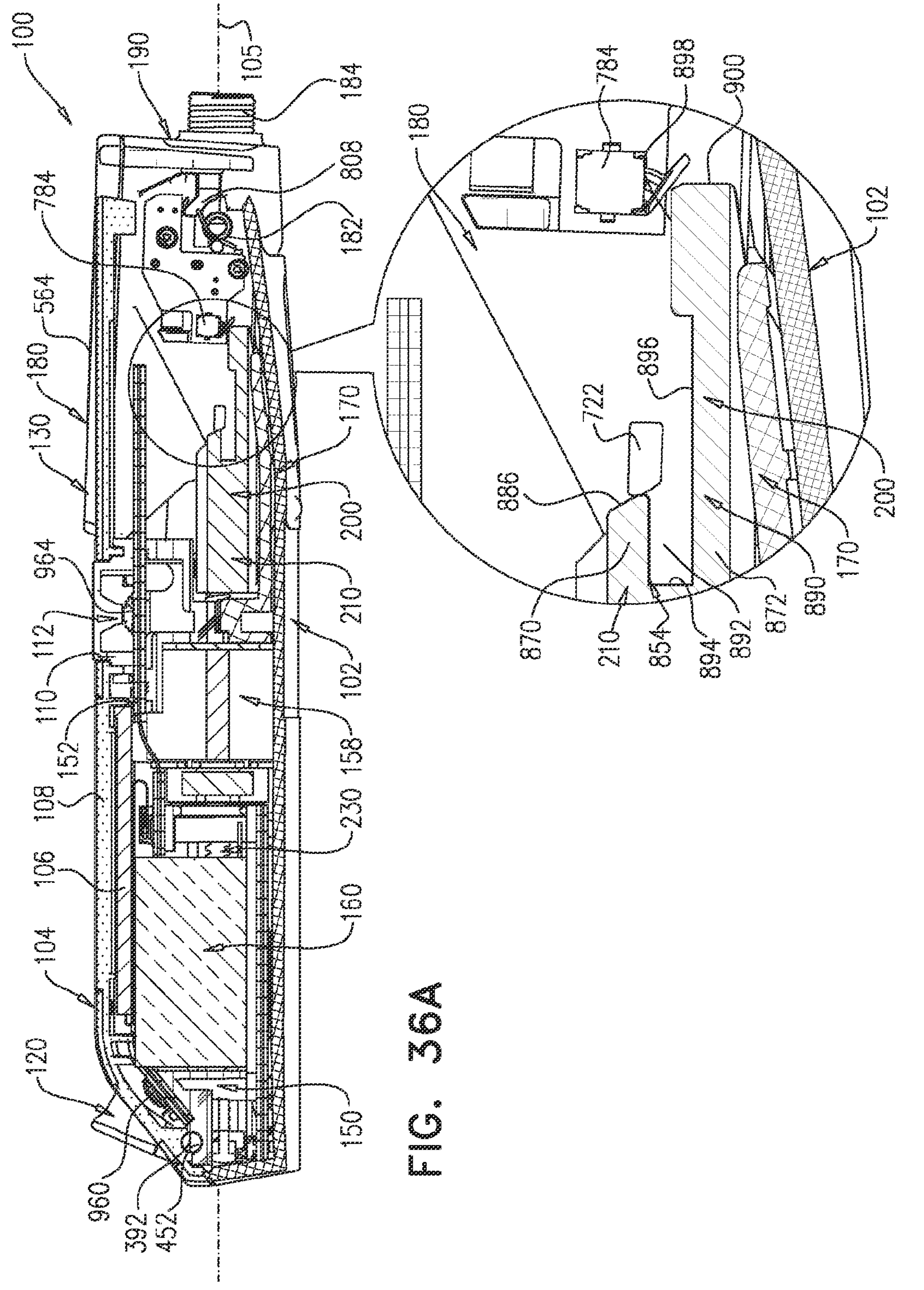
FIGS. 36A-36B are simplified sectional illustrations, taken generally along lines A-A and B-B respectively in FIG. 33 in a third stage of the second cartridge insertion operative orientation.
Figure 36B:
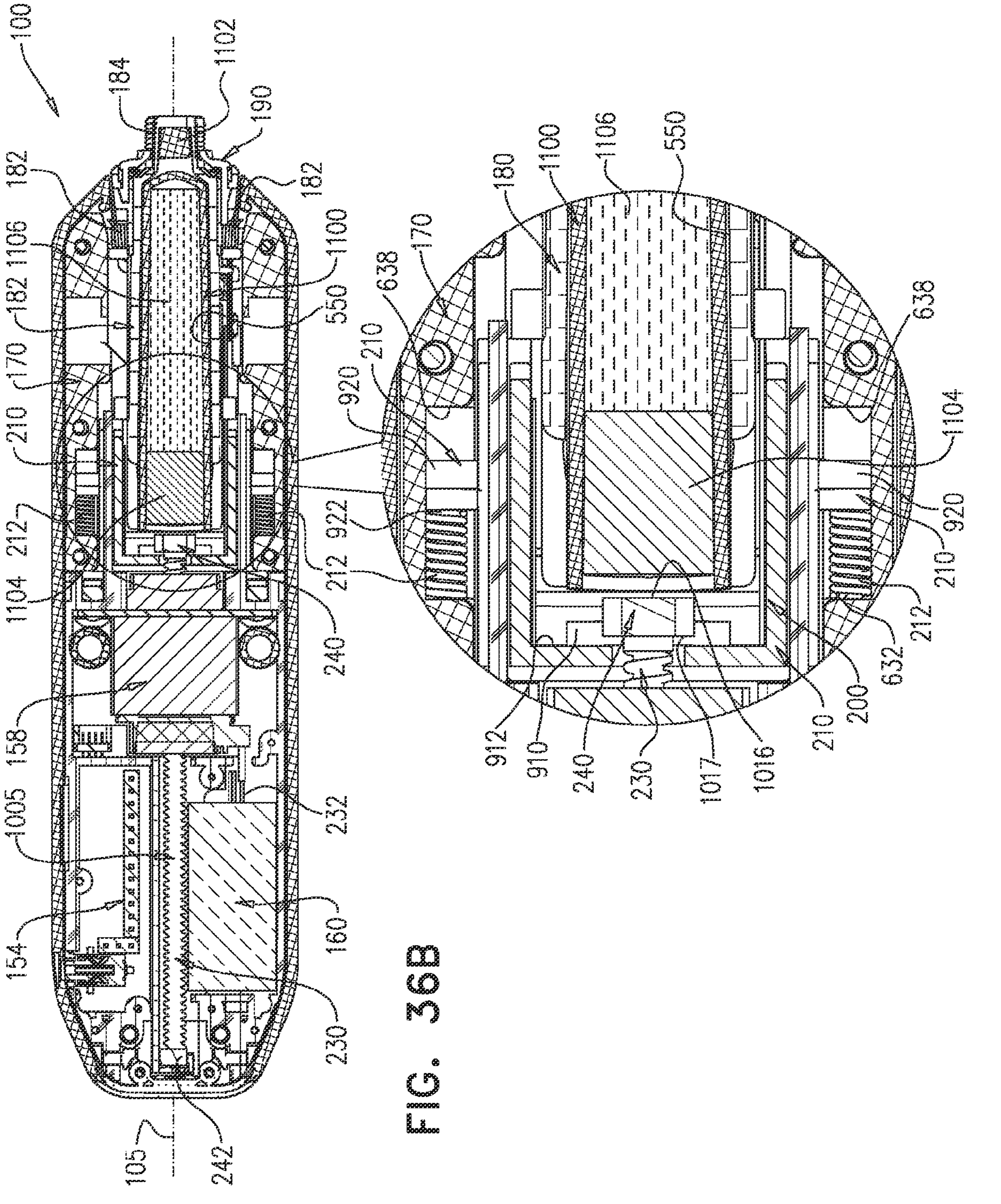

Reference is now made to FIGS. 36A-36B, which are simplified sectional illustrations, taken generally along lines A-A and B-B respectively in FIG. 33 in a third stage of the second cartridge insertion operative orientation.

It is seen specifically in FIGS. 36A-36B that the moveable subassembly 1005 of the piston drive subassembly 220 is positioned in the intermediate operative orientation, preferably identical to its operative orientation in FIGS. 35A-35B and the pivot mount element 180 is further pivoted inwardly against the urging of torsion springs 182 and is now positioned in a third intermediate closing stage.

The mutual orientations of the various elements described in FIGS. 36A-36B remain essentially the same as in FIGS. 35A-35B, other than as specifically set forth hereinbelow:

It is seen particularly in FIGS. 36A-36B that in this third stage of the second cartridge insertion operative orientation, the locking subassembly 200 being now positioned in a third snapping operative orientation, where the displacement of the pivot mount element 180 by the user urges even further rearward displacement of the cartridge enclosure assembly latch element 210 against the force of springs 212.

It is specifically seen in FIG. 36A that in this third stage of the second cartridge insertion operative orientation, locking snap elements 722 of pivot mount element 180 even further engage forwardly facing tapered surfaces 886 of upper portions 870 of arms 852 and 854 of cartridge enclosure assembly latch element 210 and are not yet received within cut-out 892 formed between upper portion 870 and bottom portion 872 of first and second arms 852, 854 of cartridge enclosure assembly latch element 210. Locking snap elements 722 urge the cartridge enclosure assembly latch element 210 rearwardly.

As specifically seen in FIG. 36B, the cartridge enclosure assembly latch element 210 is positioned slightly rearwardly as compared with FIGS. 35A-35B, due to further engagement between 886 thereof with 722 of 180, and the locking subassembly 200 is disposed in its third snapping operative orientation.

Figure 37A:
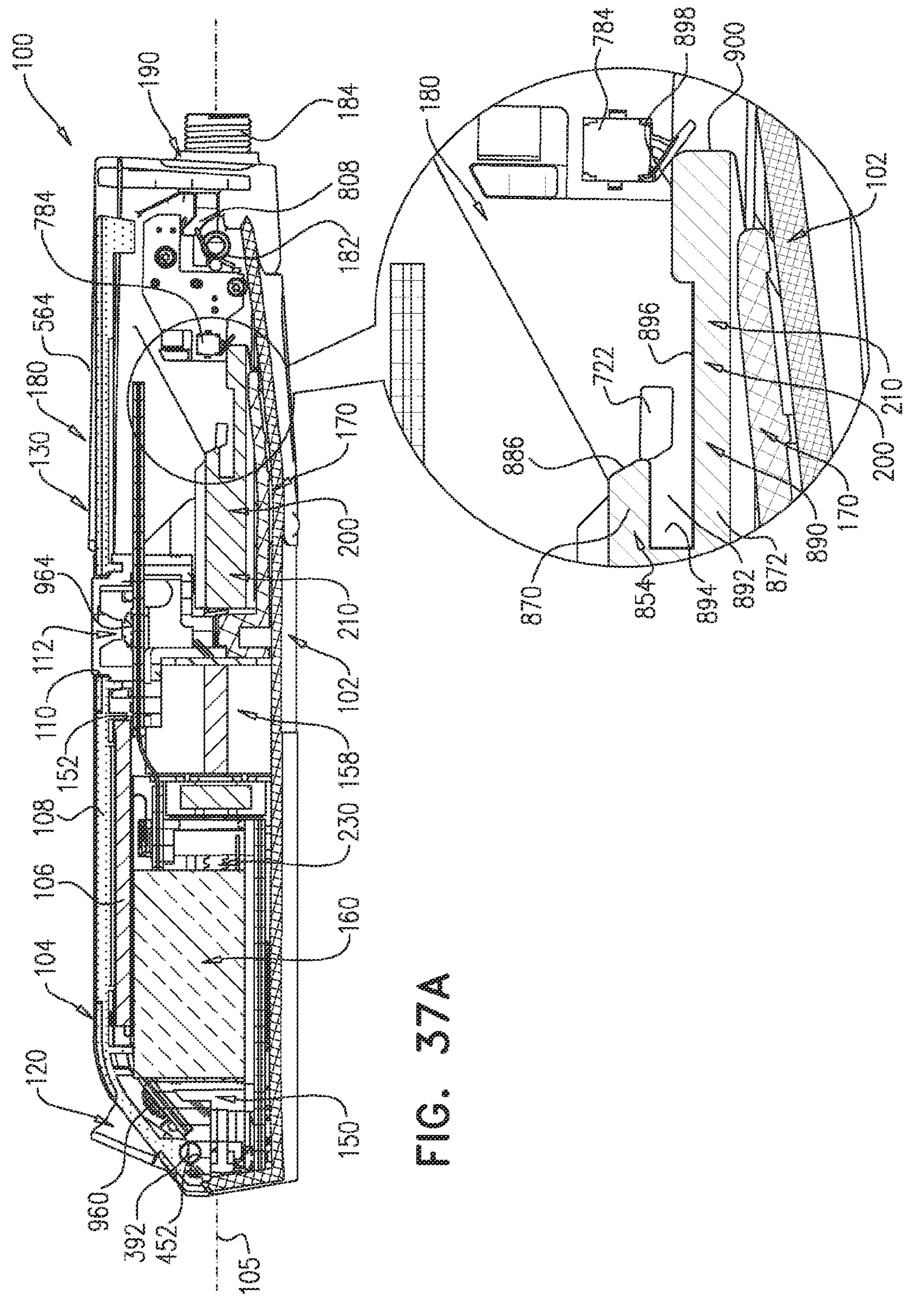
FIGS. 37A-37B are simplified sectional illustrations, taken generally along lines A-A and B-B respectively in FIG. 33 in a fourth stage of the second cartridge insertion operative orientation.
Figure 37B:
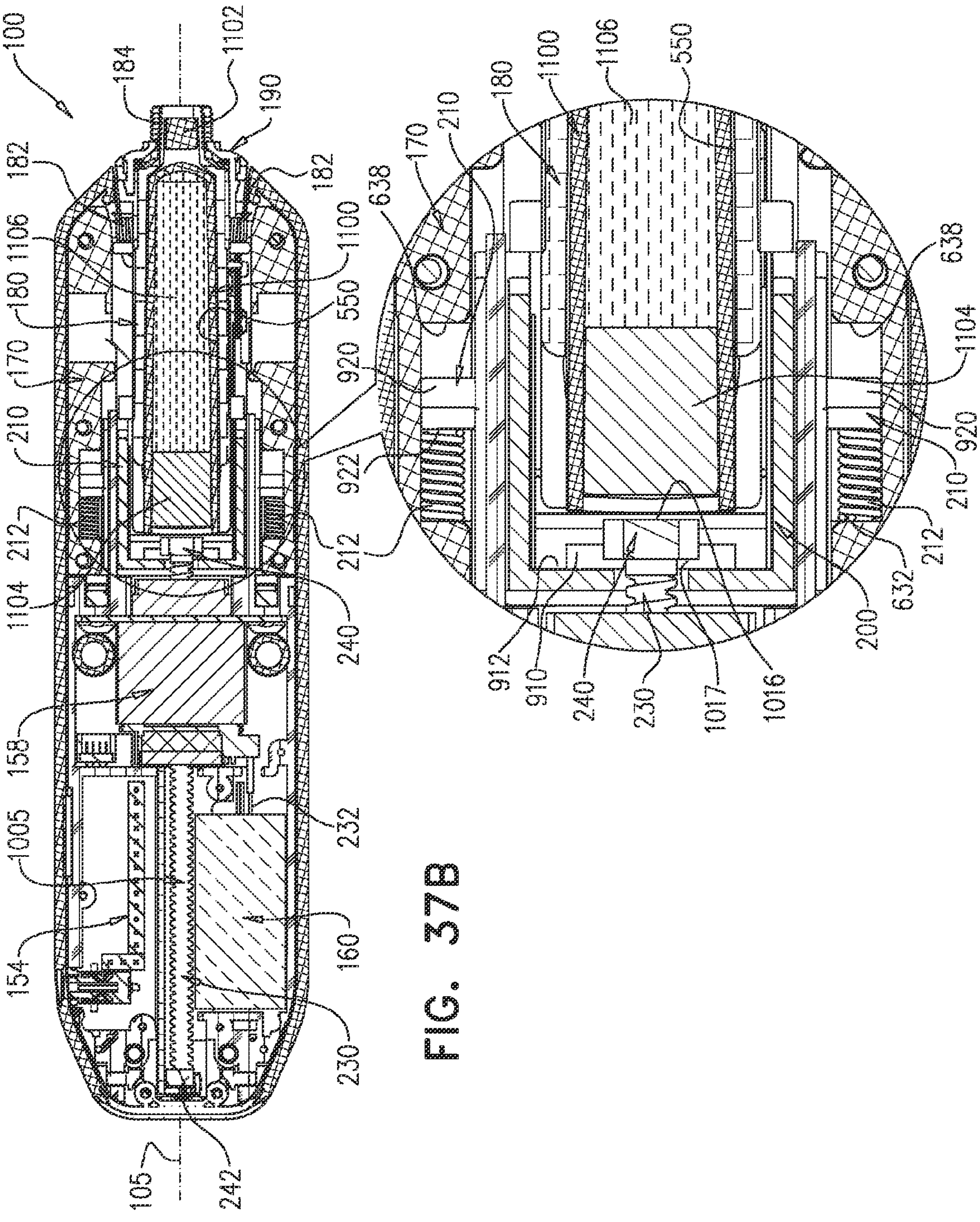

Reference is now made to FIGS. 37A-37B, which are simplified sectional illustrations, taken generally along lines A-A and B-B respectively in FIG. 33 in a fourth stage of the second cartridge insertion operative orientation.

It is seen specifically in FIGS. 37A-37B that the moveable subassembly 1005 of the piston drive subassembly 220 is positioned in the intermediate operative orientation, preferably identical to its operative orientation in FIGS. 36A-36B and the pivot mount element 180 is yet further pivoted inwardly against the urging of torsion springs 182 and is now positioned in a fourth intermediate closing stage.

The mutual orientations of the various elements described in FIGS. 37A-37B remain essentially the same as in FIGS. 36A-36B, other than as specifically set forth hereinbelow:

It is seen particularly in FIGS. 37A-37B that in this fourth stage of the second cartridge insertion operative orientation, the locking subassembly 200 being now positioned in a fourth snapping operative orientation, where the displacement of the pivot mount element 180 by the user urges yet further rearward displacement of the cartridge enclosure assembly latch element 210 against the force of springs 212.

It is specifically seen in FIG. 37A that in this fourth stage of the second cartridge insertion operative orientation, locking snap elements 722 of pivot mount element 180 even further engage forwardly facing tapered surfaces 886 of upper portions 870 of arms 852 and 854 of cartridge enclosure assembly latch element 210 and are nearly received within cut-out 892 formed between upper portion 870 and bottom portion 872 of first and second arms 852, 854 of cartridge enclosure assembly latch element 210. Locking snap elements 722 urge the cartridge enclosure assembly latch element 210 rearwardly.

As specifically seen in FIG. 37B, the cartridge enclosure assembly latch element 210 is positioned slightly rearwardly as compared with FIGS. 36A-36B, due to yet further engagement between 886 thereof with 722 of 180, and the locking subassembly 200 is disposed in its third snapping operative orientation.

Figure 38A:
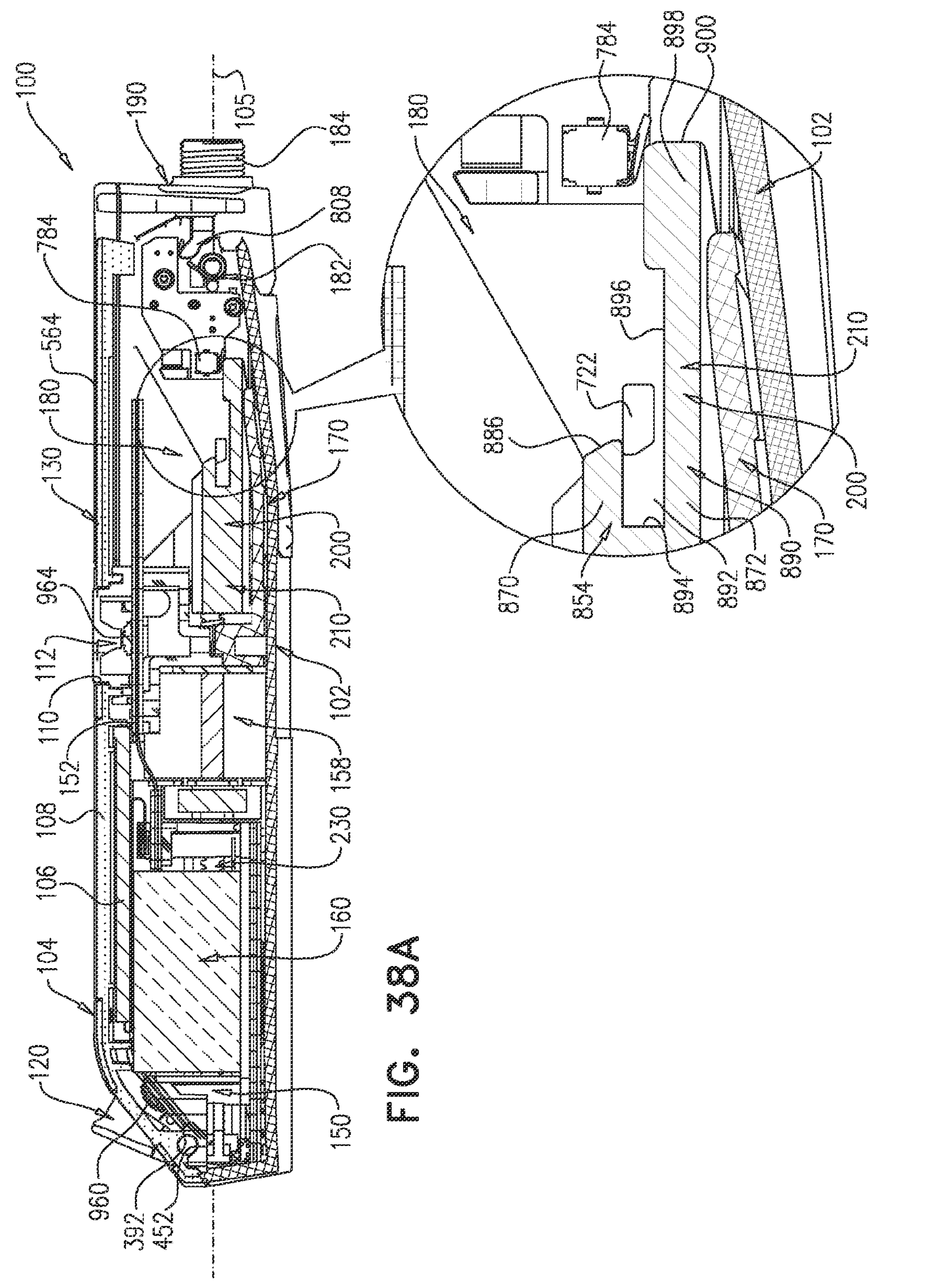
FIGS. 38A-38B are simplified sectional illustrations, taken generally along lines A-A and B-B respectively in FIG. 33 in a fifth stage of the second cartridge insertion operative orientation.
Figure 38B:
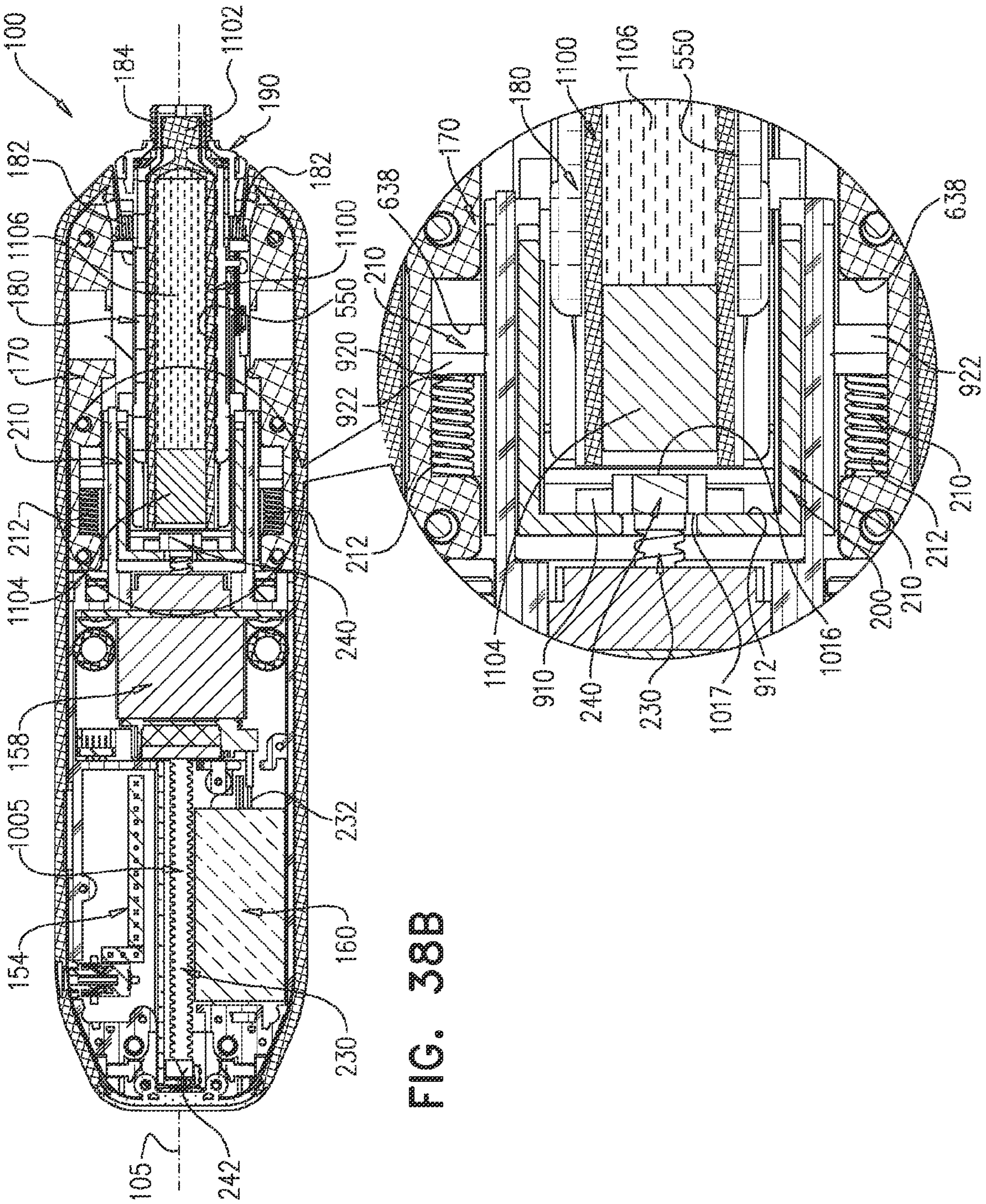

Reference is now made to FIGS. 38A-38B, which are simplified sectional illustrations, taken generally along lines A-A and B-B respectively in FIG. 33 in a fifth stage of the second cartridge insertion operative orientation.

It is seen specifically in FIGS. 38A-38B that the moveable subassembly 1005 of the piston drive subassembly 220 is positioned in the intermediate operative orientation, preferably identical to its operative orientation in FIGS. 37A-37B and the pivot mount element 180 is now positioned in its closed operative orientation.

The mutual orientations of the various elements described in FIGS. 38A-38B remain essentially the same as in FIGS. 37A-37B, other than as specifically set forth hereinbelow:

It is seen particularly in FIGS. 38A-38B that in this fifth stage of the second cartridge insertion operative orientation, the locking subassembly 200 being now positioned in the snapped operative orientation. It is appreciated that there is a range of axial positions of the cartridge enclosure assembly latch element 210, which define the snapped operative orientation of locking subassembly 200.

It is seen that rearwardly facing surface 1017 of piston contact element 240 now engages forwardly facing surface 912 of base wall portion 850 of cartridge enclosure assembly latch element 210 and the springs 212 are less compressed now.

The rearward end of medicament cartridge 1100 does not engage arc-shaped protrusion 910 of cartridge enclosure assembly latch element 210.

It is specifically seen in FIG. 38A that in this fifth stage of the second cartridge insertion operative orientation, locking snap elements 722 of pivot mount element 180 disengage forwardly facing tapered surfaces 886 of upper portions 870 of arms 852 and 854 of cartridge enclosure assembly latch element 210 and are now received within cut-out 892. Locking snap elements 722 do not urge the cartridge enclosure assembly latch element 210 rearwardly anymore, thus cartridge enclosure assembly latch element 210 is displaced forwardly up to engagement of forwardly facing surface 912 and rearwardly facing surface 1017 of piston contact element 240.

It is seen in FIG. 38A that forwardly facing surfaces 894 of cartridge enclosure assembly latch element 210 are rearwardly spaced from locking snap elements 722 of pivot mount element 180.

As specifically seen in FIG. 38B, the cartridge enclosure assembly latch element 210 is positioned slightly more forwardly as compared to FIGS. 37A-37B, and the locking subassembly 200 is now positioned in the range of axial positions, which defines the snapped operative orientation of locking subassembly 200.

Cartridge enclosure assembly state sensor 784 is now disposed in triggered state, resulting from engagement with upwardly facing protrusion 898 of protrusion 890 of cartridge enclosure assembly latch element 210, which indicates that pivot mount element 180 is now positioned in its closed operative orientation.

Reference is now made to FIGS. 39A-39E, which are simplified sectional illustrations, taken generally along lines A-A, B-B, C-C, D-D and E-E respectively in FIG. 33 in a sixth stage of the second cartridge insertion operative orientation.

It is appreciated that in this sixth stage of the second cartridge insertion operative orientation, the cartridge enclosure assembly 130 is disposed in its closed operative orientation and the moveable subassembly 1005 of the piston drive subassembly 220 is displaced axially forwardly along longitudinal axis 105 as compared to FIGS. 38A-38B, urging the cartridge enclosure assembly latch element 210 to be displaced forwardly as well, under the biasing force of springs 212.

Figure 39A:
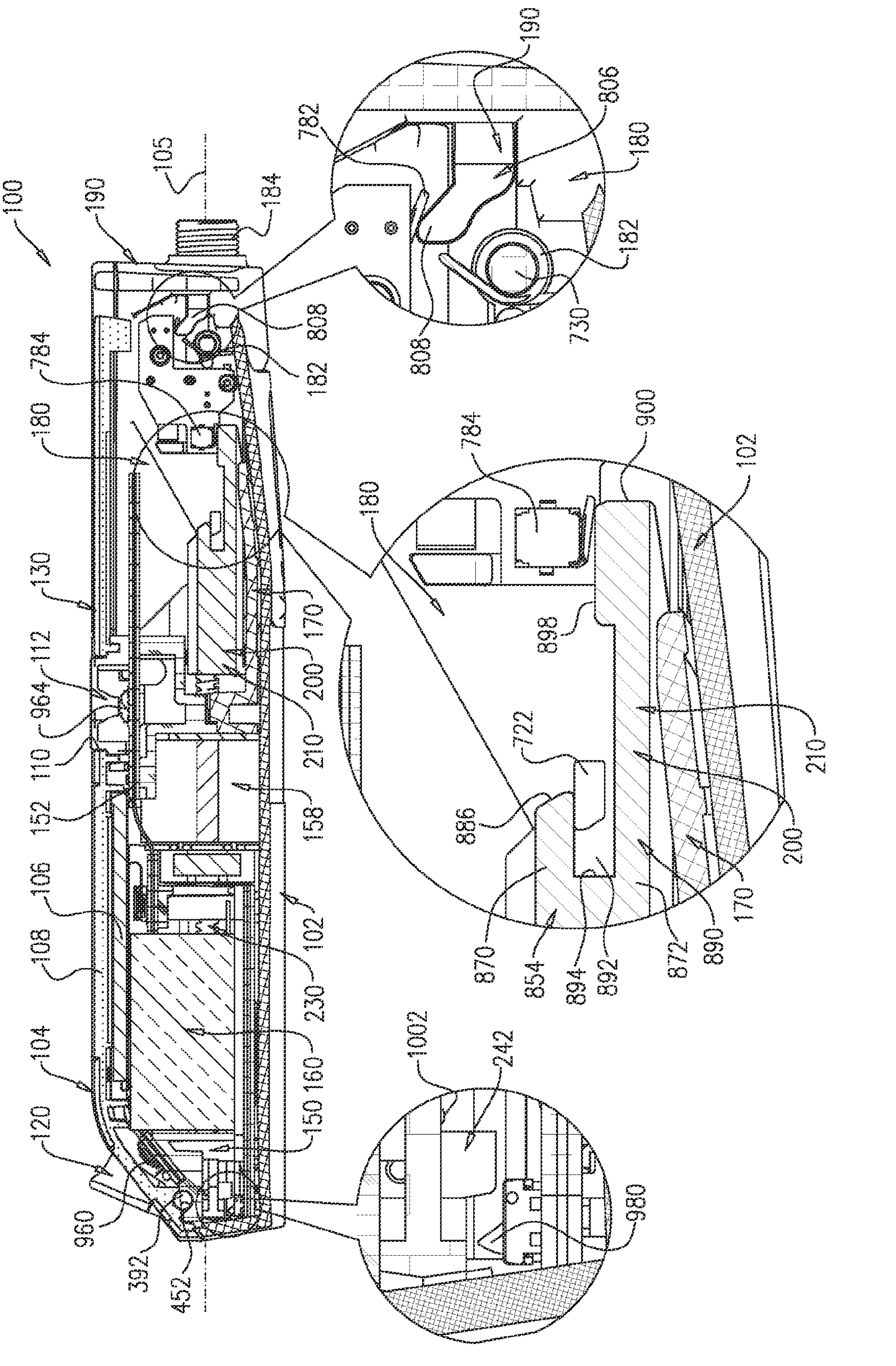
FIGS. 39A-39E are simplified sectional illustrations, taken generally along lines A-A, B-B, C-C, D-D and E-E respectively in FIG. 33 in a sixth stage of the second cartridge insertion operative orientation.
Figure 39B:
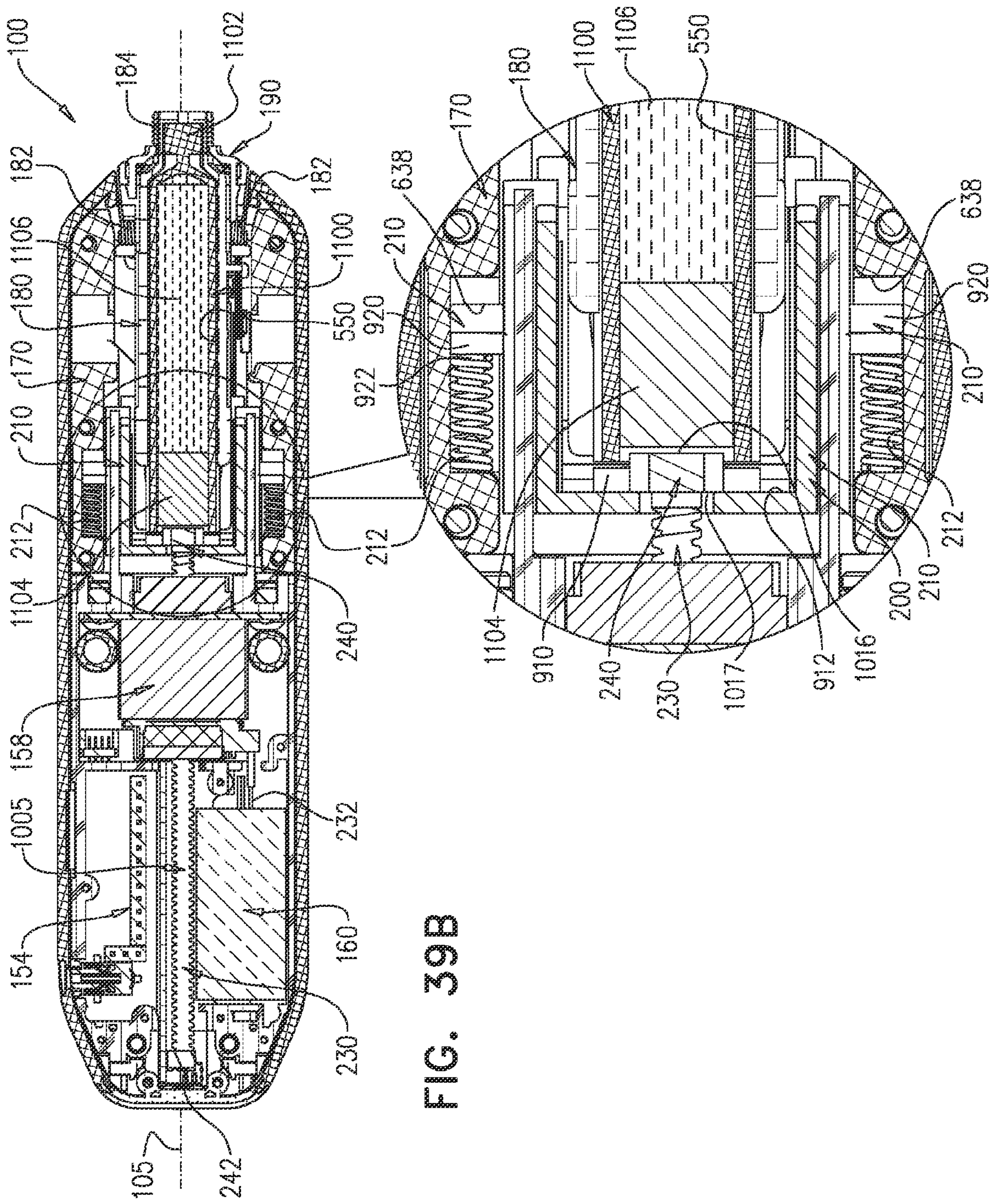

The mutual orientations of the various elements described in FIGS. 39A-39E remain essentially the same as in FIGS. 38A-38B, other than as specifically set forth hereinbelow:

It is seen particularly in FIGS. 39A-39B that in this sixth stage of the second cartridge insertion operative orientation, the locking subassembly 200 being positioned in the locked operative orientation. It is appreciated that there is a range of axial positions of the cartridge enclosure assembly latch element 210, which define the locked operative orientation of locking subassembly 200.

Pivot mount element 180 is positioned in the closed operative orientation in this sixth stage of the second cartridge insertion operative orientation.

It is seen that rearwardly facing surface 1017 of piston contact element 240 engages forwardly facing surface 912 of base wall portion 850 of cartridge enclosure assembly latch element 210 and the springs 212 are less compressed as compared to FIGS. 38A-38B.

The rearward end of medicament cartridge 1100 now nearly engages arc-shaped protrusion 910 of cartridge enclosure assembly latch element 210.

It is specifically seen in FIG. 39A that in this sixth stage of the second cartridge insertion operative orientation, locking snap elements 722 of pivot mount element 180 are received within cut-out 892. It is seen in FIG. 39A that forwardly facing surfaces 894 of cartridge enclosure assembly latch element 210 are less rearwardly spaced from locking snap elements 722 of pivot mount element 180.

As specifically seen in FIG. 39B, the cartridge enclosure assembly latch element 210 is positioned slightly more forwardly as compared to FIGS. 38A-38B, and is positioned in the range of axial positions, which defines the locked operative orientation of locking subassembly 200.

Cartridge enclosure assembly state sensor 784 is disposed in triggered state, resulting from engagement with upwardly facing protrusion 898 of protrusion 890 of cartridge enclosure assembly latch element 210, which indicates that the pivot mount element 180 is disposed in its closed operative orientation.

It is additionally seen in FIG. 39A that the anti-rotation element 242, which is fixedly coupled to the rearward end 1002 of plunger rod element 230, is forwardly spaced from home position sensor 980, which is mounted onto main PCB assembly 152, thus permitting rearward axial displacement of the plunger rod element 230, if an appropriate signal is provided to the electrical motor 158 which urges axial displacement of the plunger rod element 230.

It is additionally seen in FIG. 39A that needle sensor 782 is preferably disposed in triggered state, resulting from engagement with engagement portion 808 of needle presence responsive element 190, which indicates that needle is not mounted onto externally threaded end 184 of pivot mount element 180 in this operative orientation.

Figure 39C:
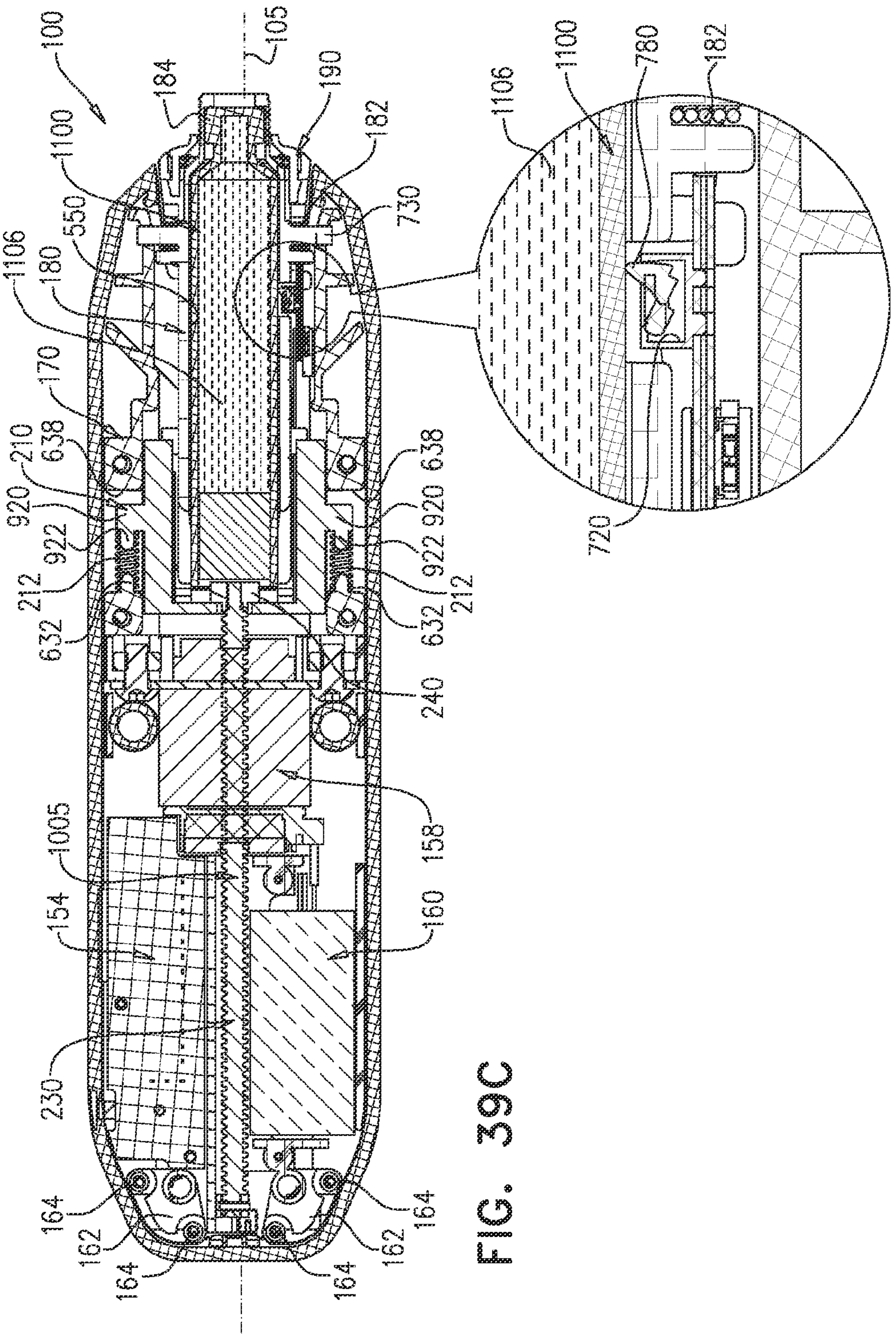

It is particularly seen in FIG. 39C that cartridge sensor 780 preferably partially protrudes through opening 720 of pivot mount element 180 and is preferably disposed in triggered state, resulting from the engagement of cartridge sensor 780 with the outer surface of medicament cartridge 1100. Triggered state of cartridge sensor 780 indicates to MUCI 100 that medicament cartridge 1100 is mounted into the cartridge enclosure assembly 130 in this operative orientation.

Figure 39D:
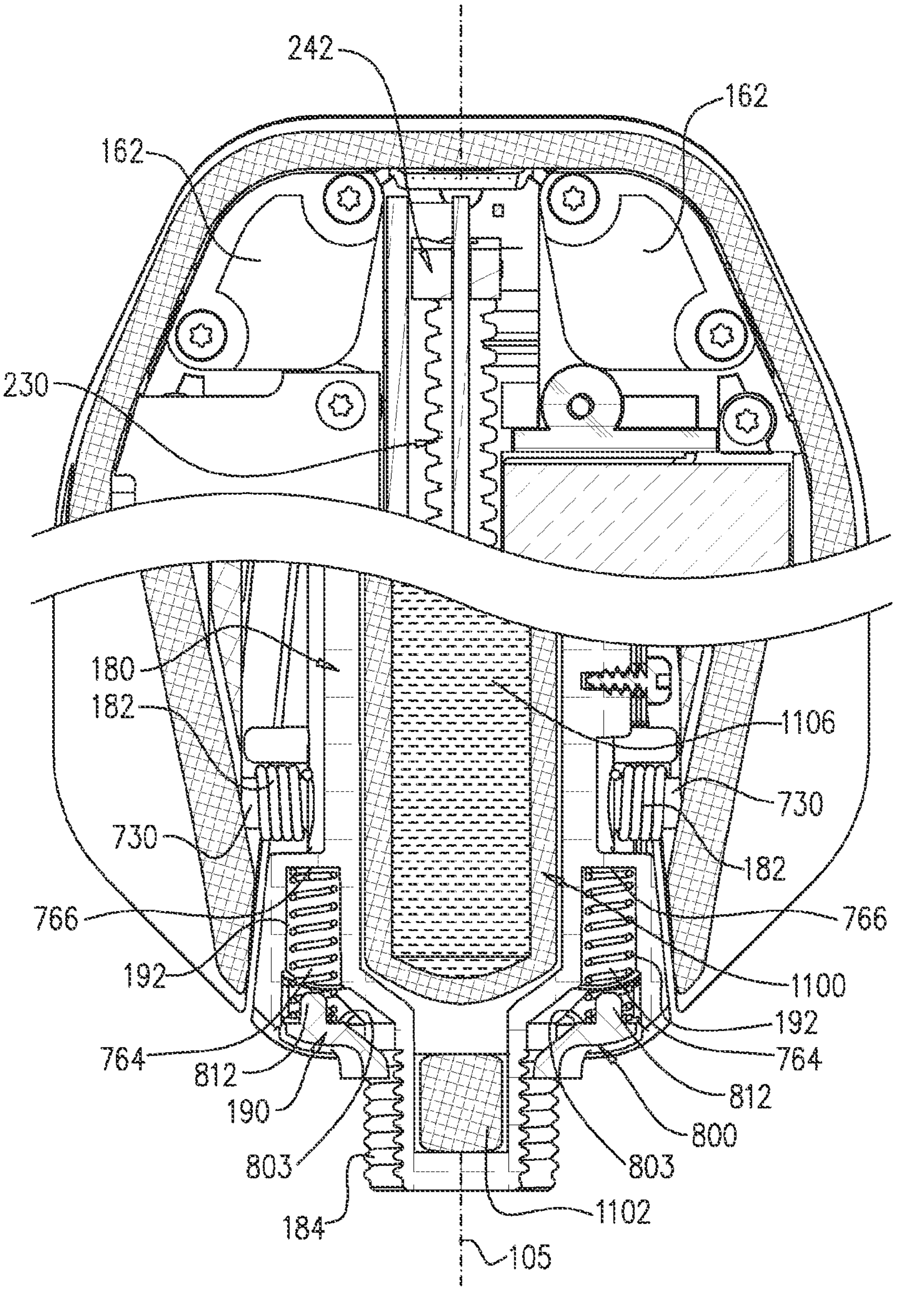
Figure 39E:
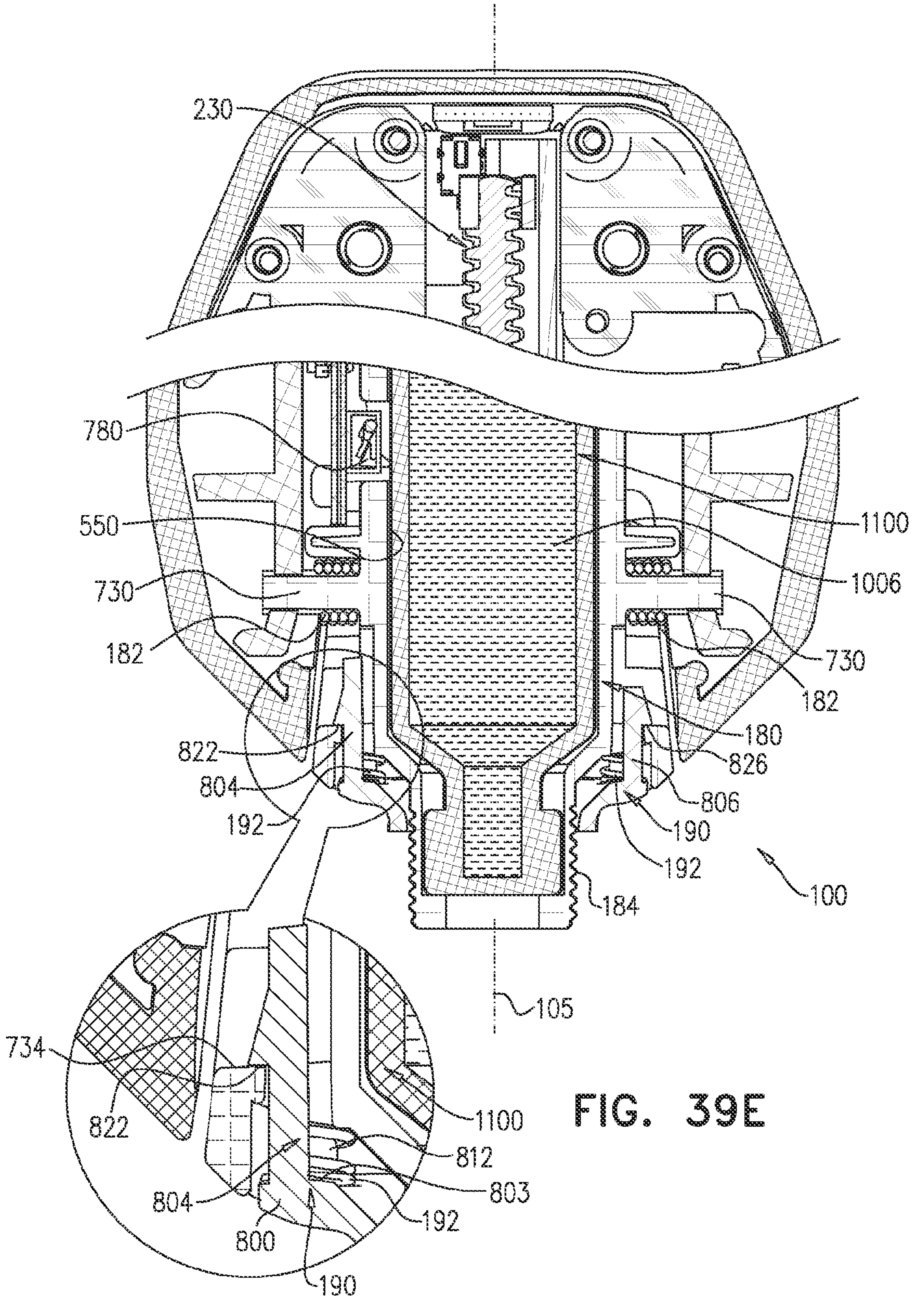

It is specifically seen in FIGS. 39D-39E that needle presence responsive element 190 is disposed in its inactivated forward operative orientation, since no needle is attached to outwardly threaded end 184 of pivot mount element 180.

The inactivated forward operative orientation of needle presence responsive element 190 is defined by the following spatial relationships:

The rearwardly facing surface 803 of flat wall portion 800 of needle presence responsive element 190 supports one end of springs 192 and is forwardly spaced from forwardly facing edge 766 of pivot mount element 180, which supports the other end of springs 192. Springs 192 are pre-loaded in this operative orientation and urge the needle presence responsive element 190 to extend forwardly.

Forwardly facing shoulder surfaces 822 and 826 of snap protrusions 804 and 806 of needle presence responsive element 190 engage rearwardly facing shoulder surfaces 734 of pivot mount element 180, which prevent detachment of the needle presence responsive element 190 from pivot mount element 180.

Figure 40:
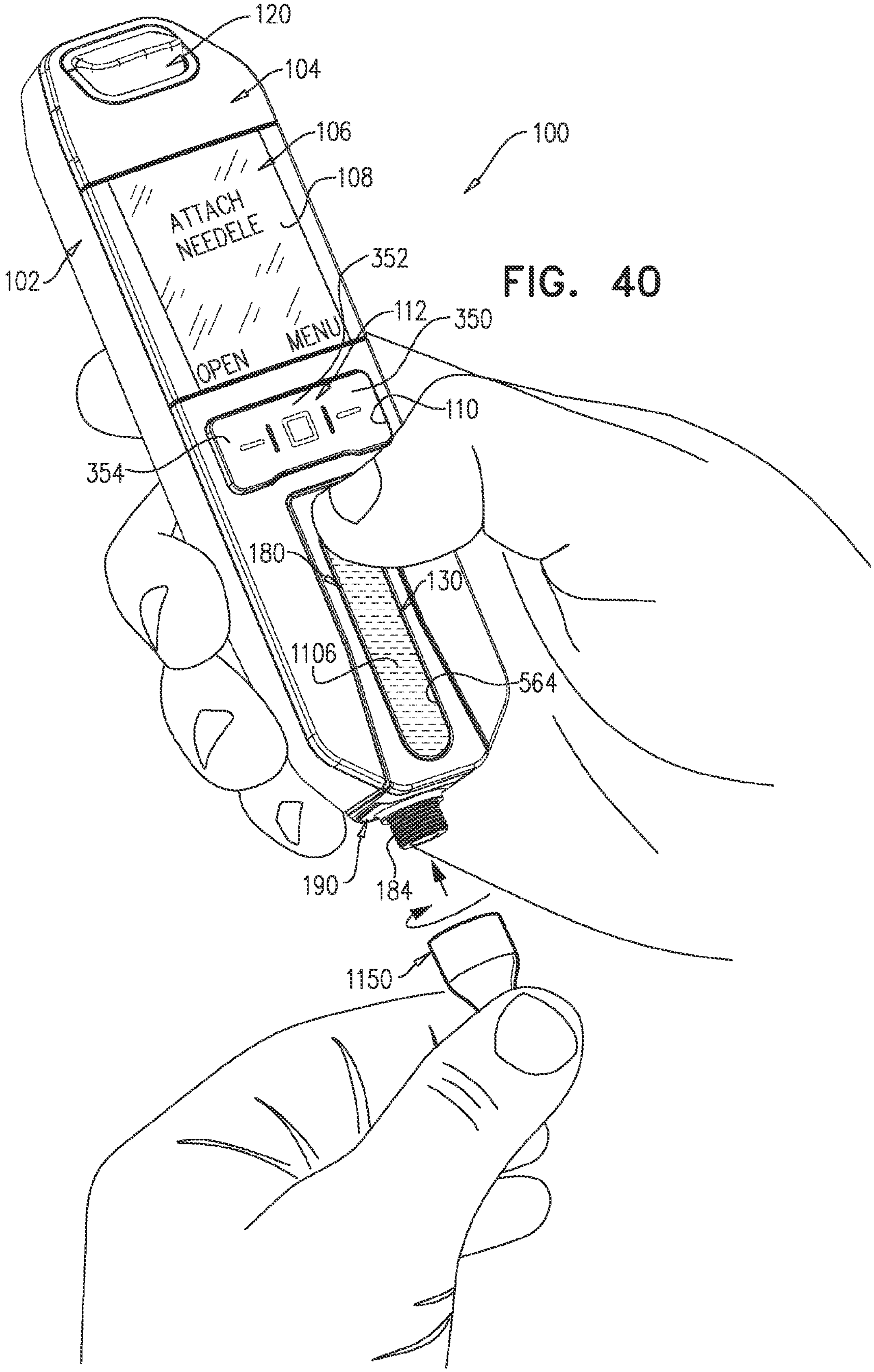
FIG. 40 is a simplified pictorial illustration of the MUCI of FIGS. 1A-21B operated by a user, in a needle attachment operative orientation.

Reference is now made to FIG. 40, which is a simplified pictorial illustration of the MUCI 100 of FIGS. 1A-21B operated by a user, in a needle attachment operative orientation.

It is seen in FIG. 40 that display 106 instructs the user to attach a needle and the user is about to connect a needle assembly 1150 to the externally threaded end 184 of pivot mount element 180 of the MUCI 100.

Figure 41:
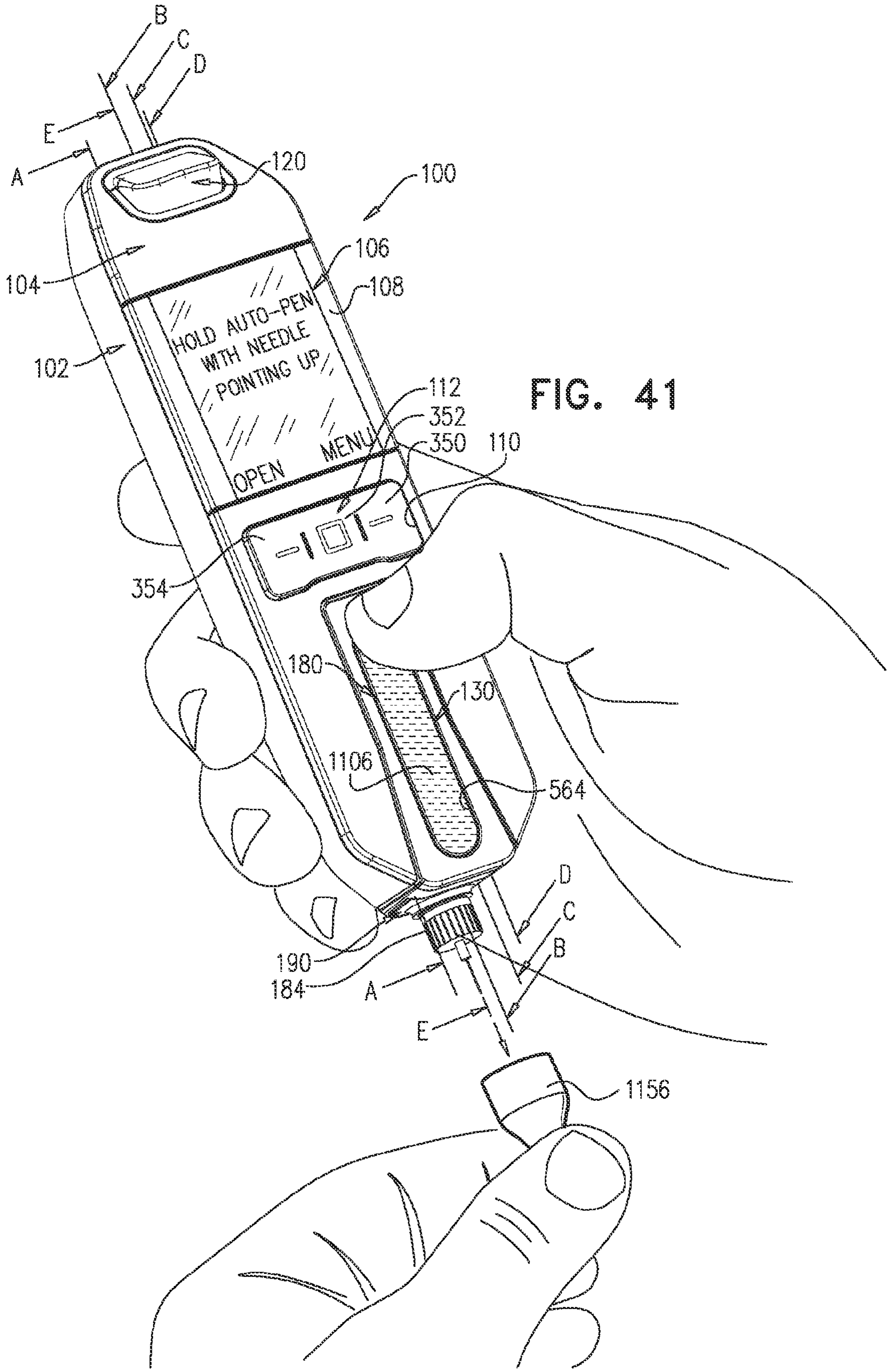
FIG. 41 is a simplified pictorial illustration of the MUCI of FIGS. 1A-21B operated by a user, in a first priming operative orientation.

Reference is now made to FIG. 41, which is a simplified pictorial illustration of the MUCI 100 of FIGS. 1A & 1B operated by a user, in a first priming operative orientation and to FIGS. 42A-42E, which are simplified sectional illustrations, taken generally along lines A-A, B-B, C-C, D-D and E-E respectively in FIG. 41 in the first priming operative orientation.

In FIG. 41, MUCI 100 is shown in the first priming operative orientation, operated by a user. It is seen in this operative orientation that a needle 1152 is fixedly attached to a needle hub 1154, which is preferably threadably attached to the external threaded end 184 of the pivot mount element 180. It is appreciated that needle 1152 and needle hub 1154 preferably form part of the needle assembly 1150. The user removes needle cover 1156 from the needle assembly 1150 in this operative orientation. It is appreciated that alternatively any other type of commercially available needle assembly or safety needle assembly can be attached to the MUCI 100.

The display 106 instructs the user to orient the injector with needle pointing up.

The user can visually inspect the contents of medicament cartridge 1100 through transparent window 564, which forms part of pivot mount element 180.

As seen in FIGS. 42A-42E, in the first priming operative orientation, as compared with FIGS. 39A-39F, which illustrate the sixth stage of the second cartridge insertion operative orientation, the needle assembly 1150 is attached to the MUCI 100.

Figure 42A:
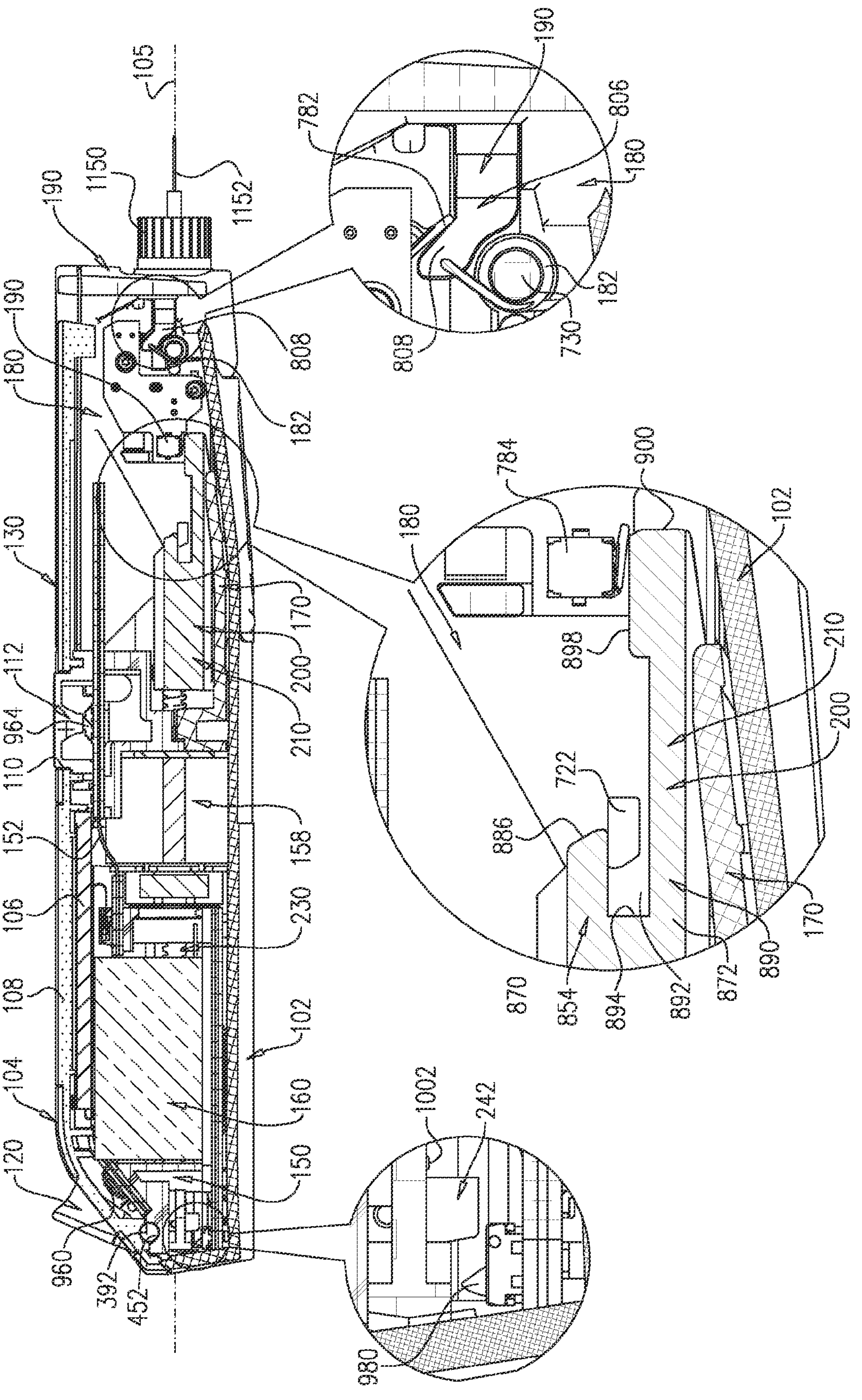
FIGS. 42A-42E are simplified sectional illustrations, taken generally along lines A-A, B-B, C-C, D-D and E-E respectively in FIG. 41 in the first priming operative orientation.

The mutual orientations of the various elements described in FIGS. 39A-39F remain essentially the same, other than as specifically set forth hereinbelow:

It is particularly seen in FIG. 42A that the needle sensor 782 is preferably disposed in an untriggered state, resulting from disengagement with engagement portion 808 of needle presence responsive element 190, which indicates that needle assembly 1150 is now mounted onto externally threaded end 184 of pivot mount element 180 in this operative orientation.

Figure 42B:
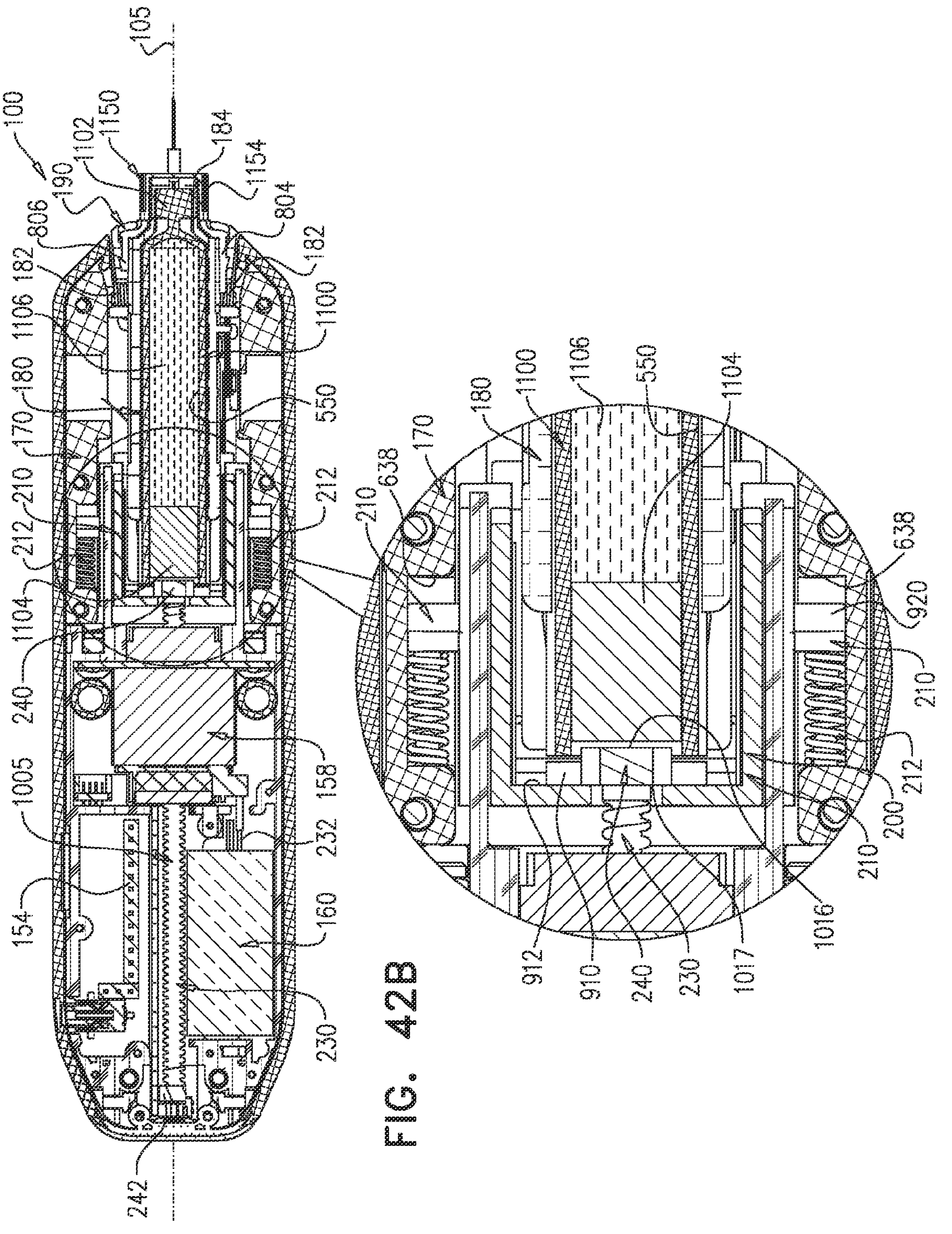
Figure 42C:
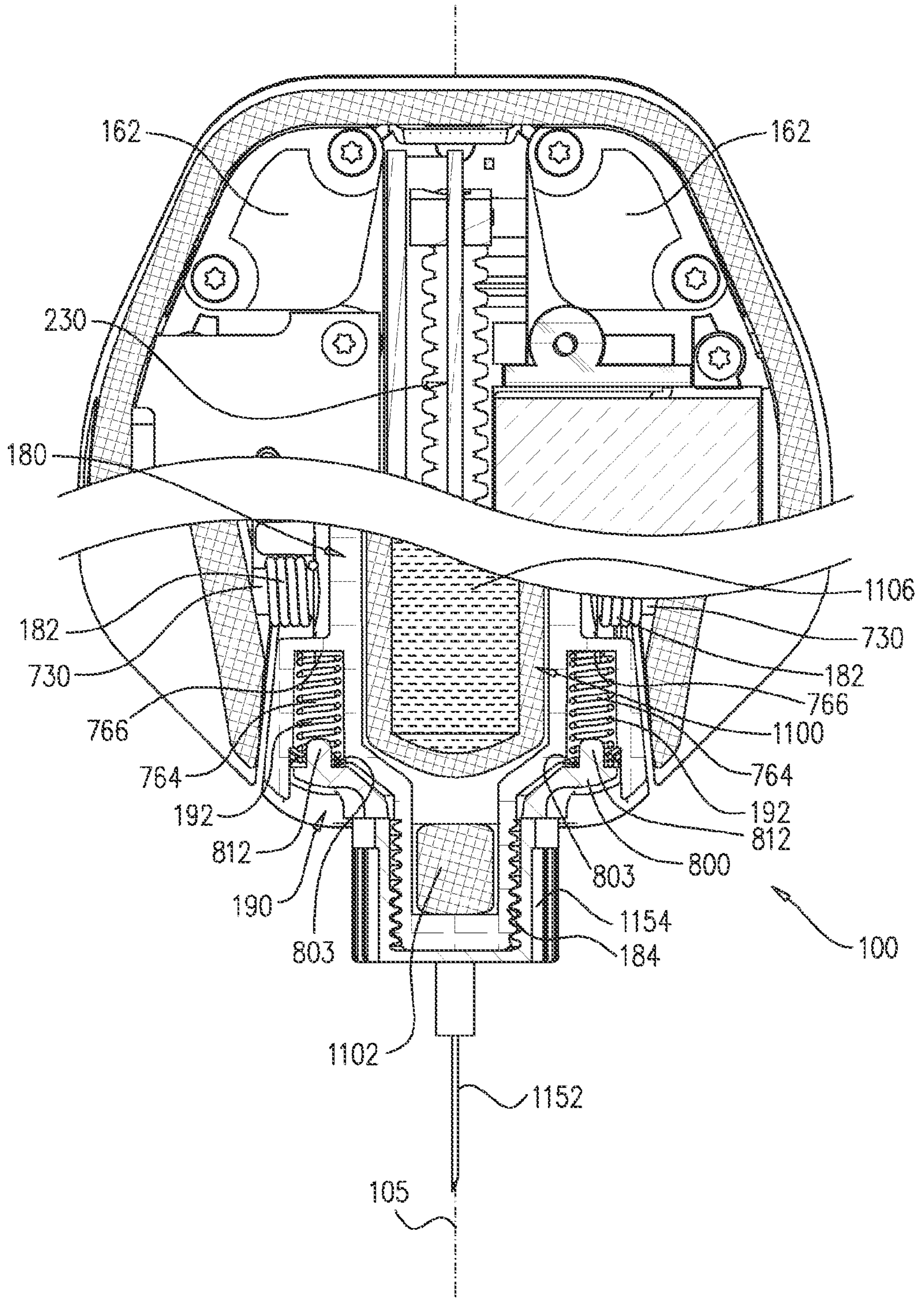
Figure 42D:
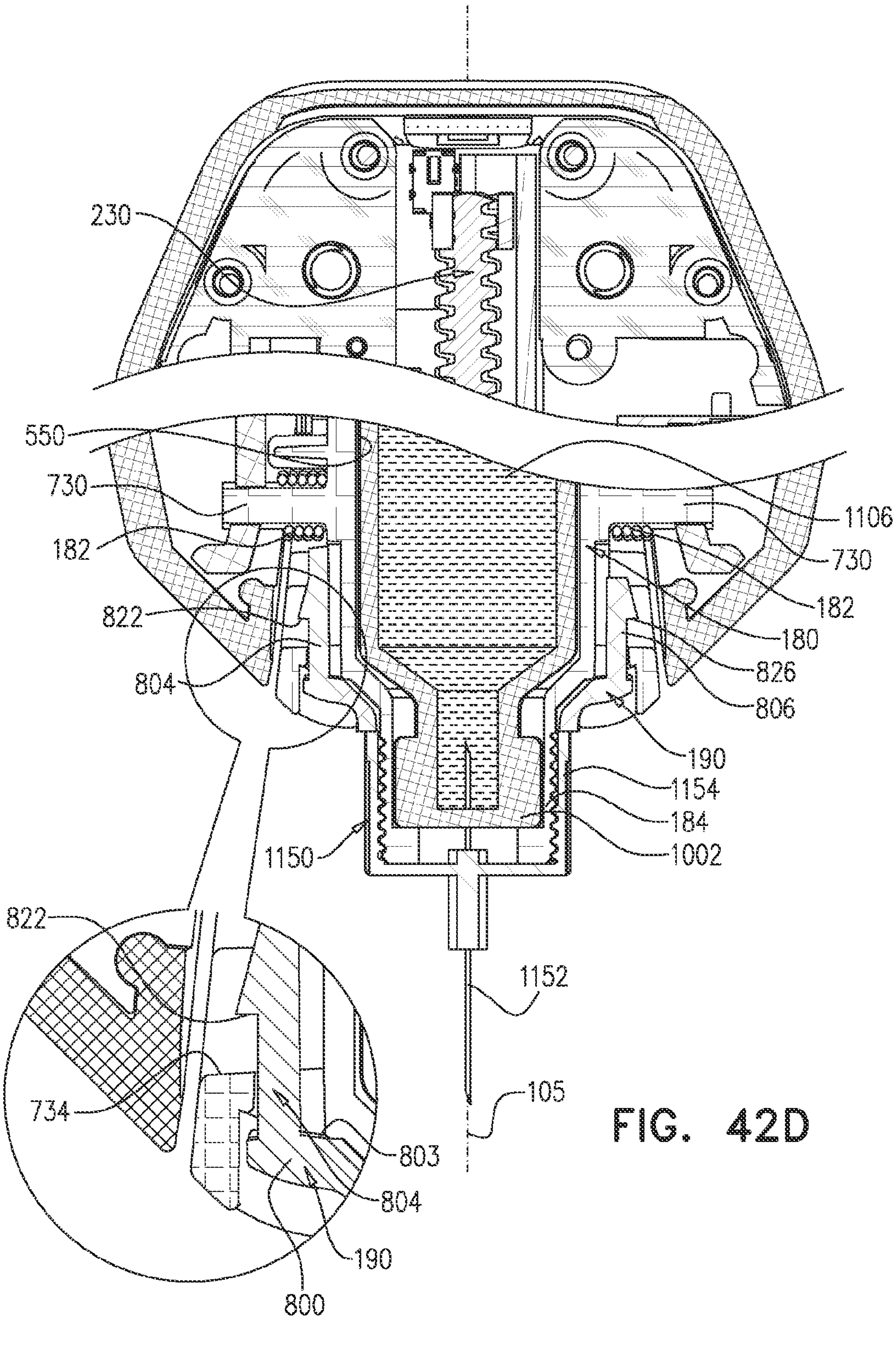

It is specifically seen in FIGS. 42C and 42D that needle presence responsive element 190 is preferably displaced rearwardly by the user against the force of springs 192 while attaching the needle assembly 1150 to the externally threaded end 184 of pivot mount element 180 and thus disengaging engagement portion 808 from needle sensor 782.

It is specifically seen in FIGS. 42C-42D that needle presence responsive element 190 is disposed in its activated rearward operative orientation, since needle assembly 1150 is now attached to outwardly threaded end 184 of pivot mount element 180.

The activated rearward operative orientation of needle presence responsive element 190 is defined by the following spatial relationships:

The rearwardly facing surface 803 of flat wall portion 800 of needle presence responsive element 190 is now less forwardly spaced from forwardly facing edge 766 of pivot mount element 180. Springs 192 are compressed in this operative orientation.

Forwardly facing shoulder surfaces 822 and 826 of snap protrusions 804 and 806 of needle presence responsive element 190 disengage and are now rearwardly spaced from rearwardly facing shoulder surfaces 734 of pivot mount element 180.

Figure 42E:
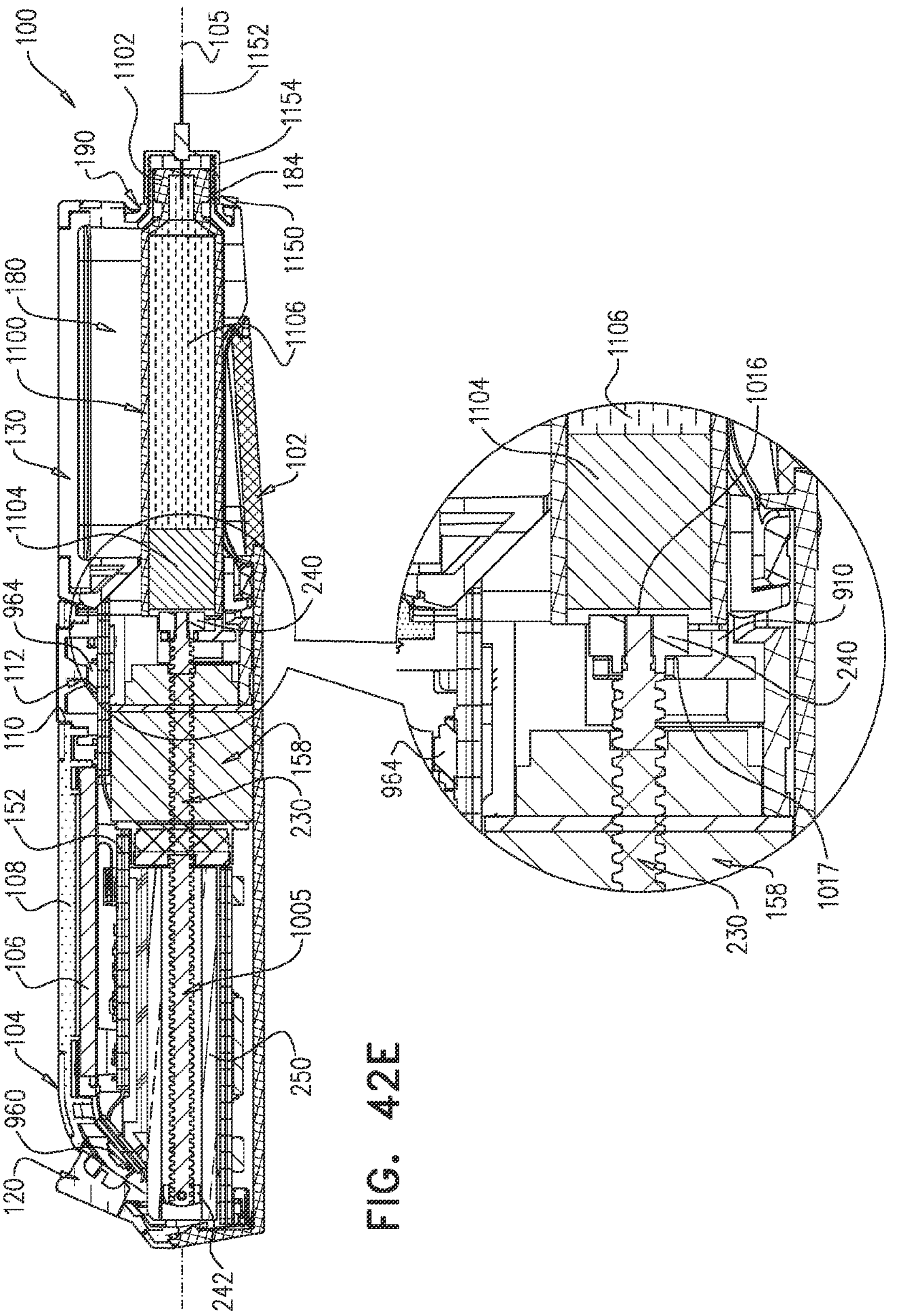

It is also seen in FIG. 42E that needle 1152 penetrates septum 1102 of the cartridge in this operative orientation and creates fluid flow passage between the inner volume of medicament cartridge 1100 and the atmosphere.

It is a particular feature of an embodiment of the present invention that as particularly seen in FIG. 42E, the forwardly facing surface 1016 of piston contact element 240 does not engage the rearward surface of the piston 1104 in this first priming operative orientation, thus the MUCI 100 is not ready for injection yet.

Figure 46:
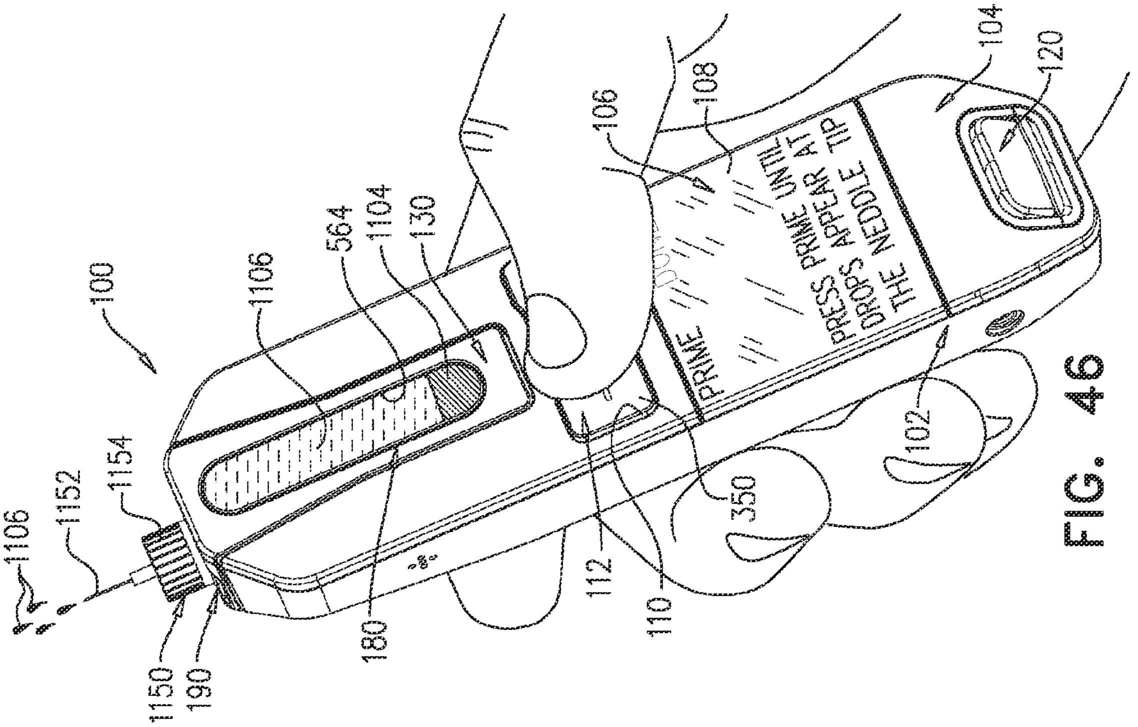
Figure 47:
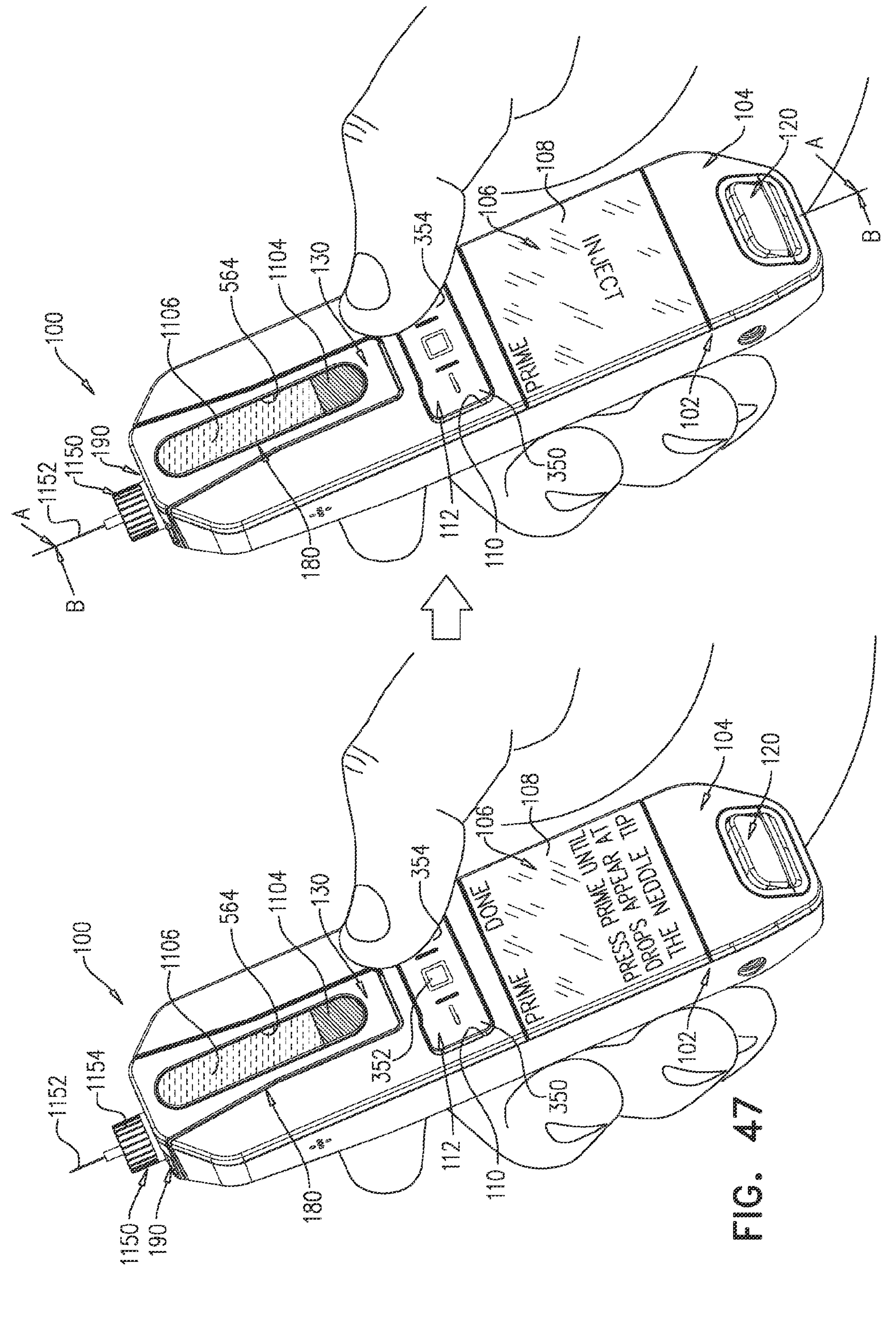
Figure 48A:
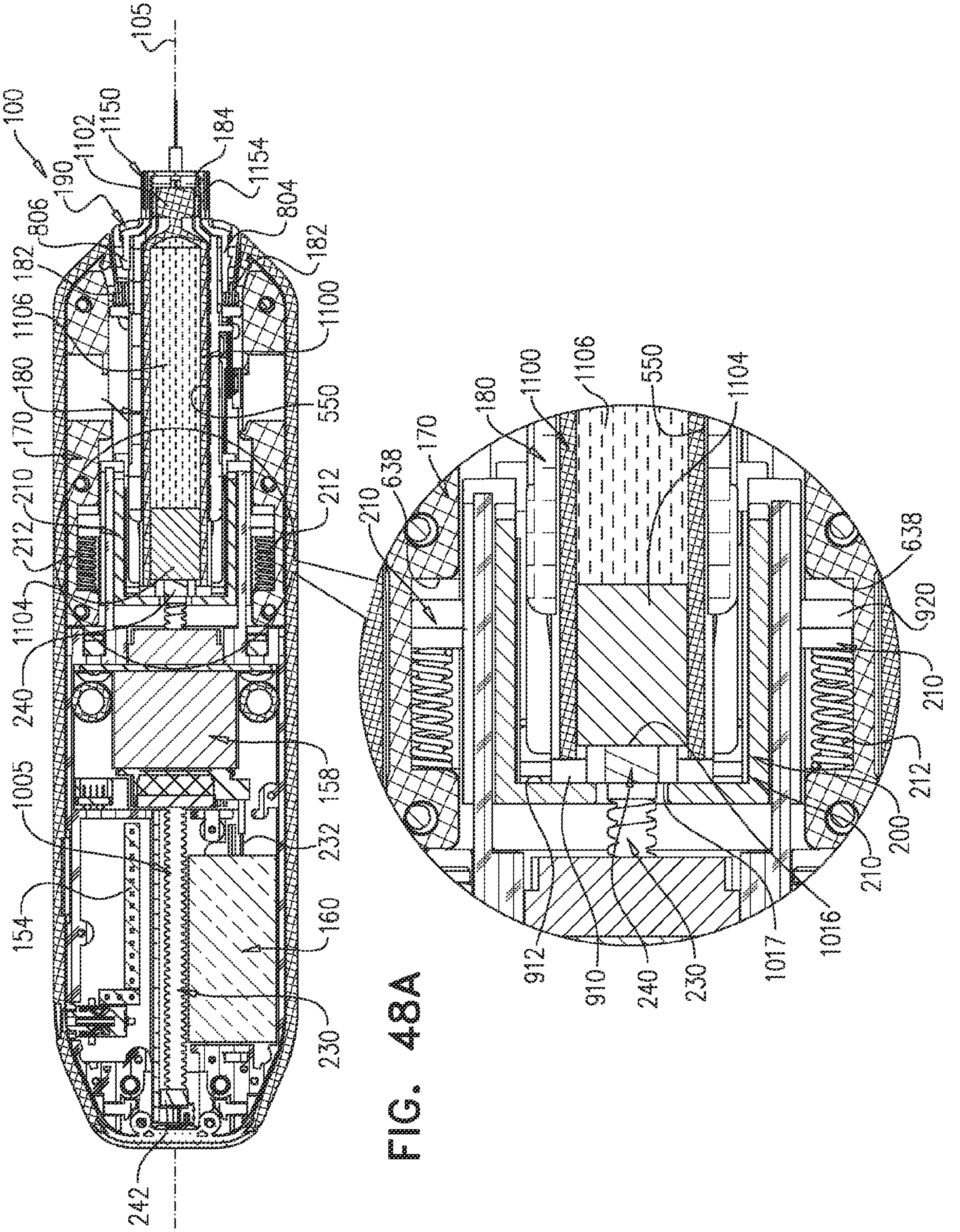
FIGS. 48A-48B are simplified sectional illustrations, taken generally along lines A-A and B-B respectively in FIG. 47 in the sixth priming operative orientation.
Figure 48B:
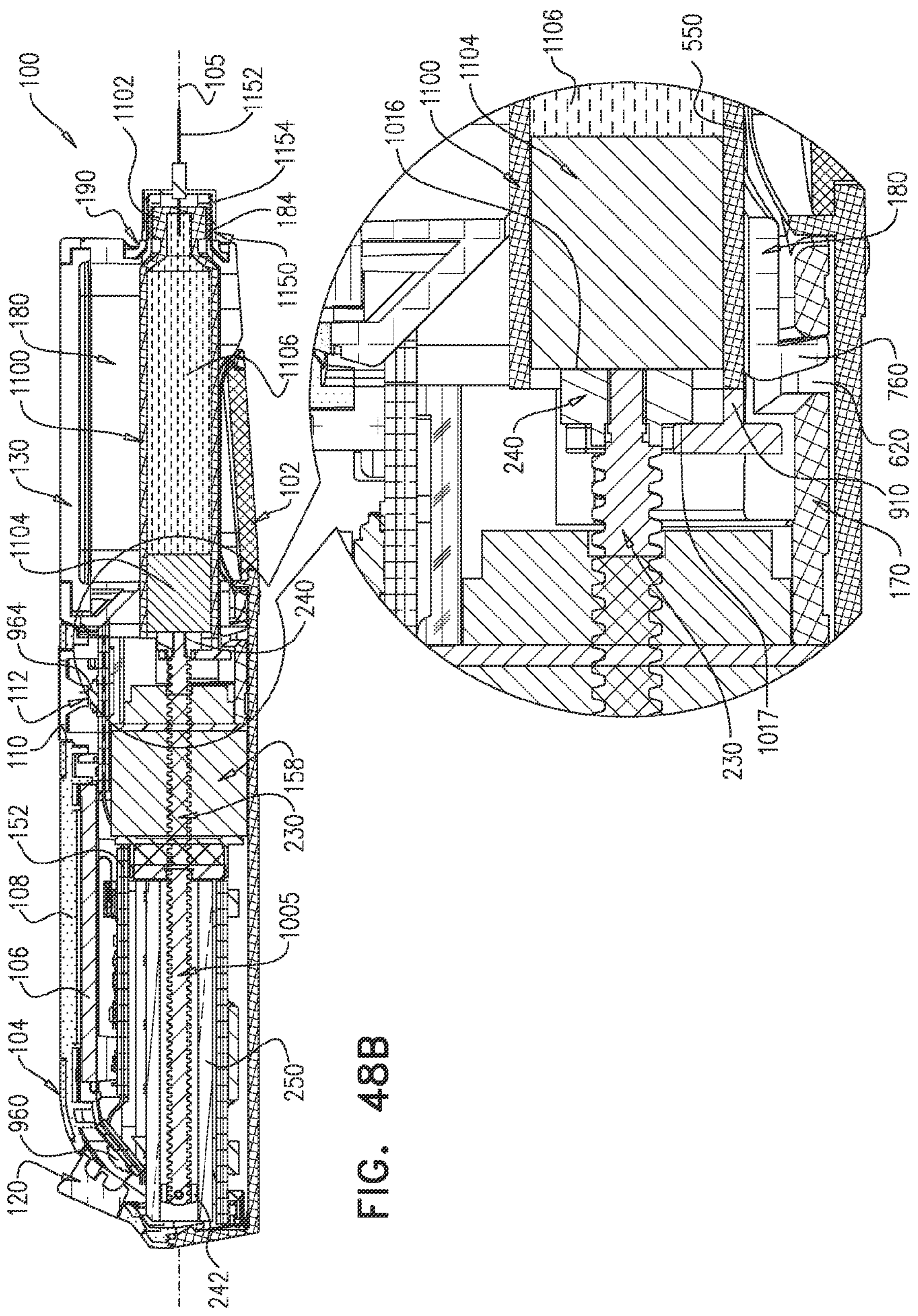

Reference is now made to FIGS. 43-47, which are simplified pictorial illustrations of the MUCI 100 of FIGS. 1A-21B operated by a user, in a second-sixth priming operative orientations respectively and to FIGS. 48A-48B, which are simplified sectional illustrations, taken generally along lines A-A and B-B respectively in FIG. 47 in the sixth priming operative orientation.

It is a particular feature of an embodiment of the present invention, as described hereinabove with reference to FIG. 42F, that before completion of the priming process, the MUCI 100 is not ready for injection, since there is no engagement between the piston contact element 240 and piston 1104, which is contained in medicament cartridge 1100. Any further forward linear displacement of the moveable subassembly 1005 after engagement of the piston contact element 240 and the piston 1104, produces a corresponding linear displacement of the piston 1104.

Figure 43:
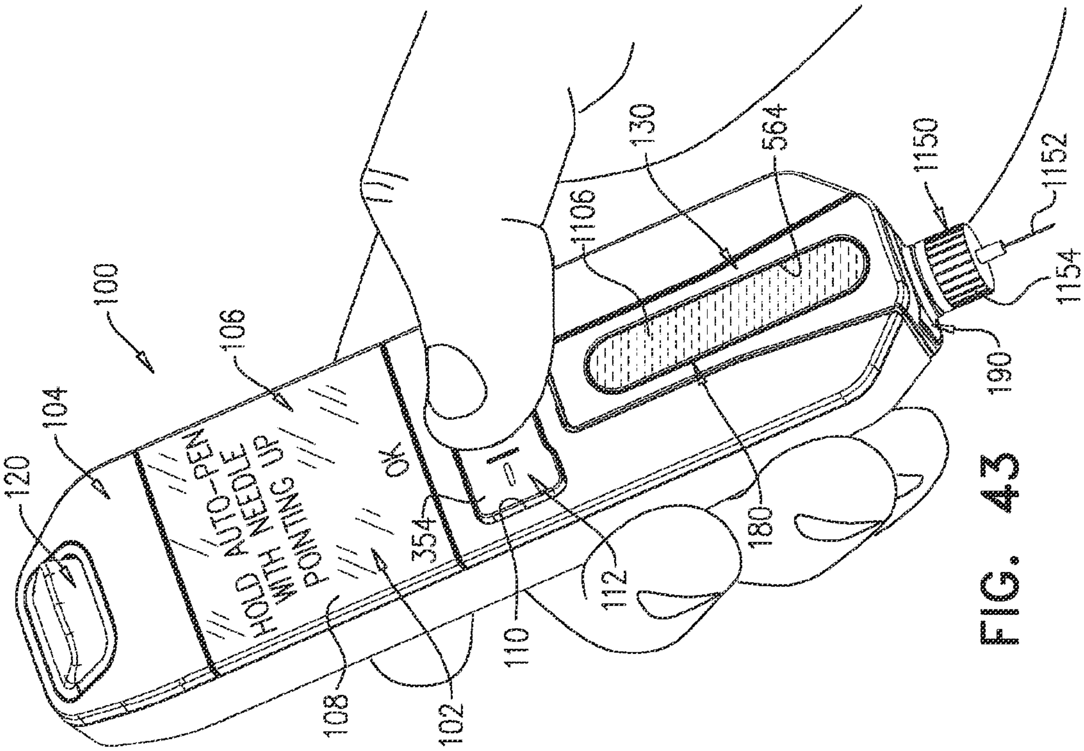

It is seen in FIG. 43 that following needle 1152 attachment to the MUCI 100, the MUCI 100 assumes its priming operative orientation and the display 106 instructs the user to orient injector with the needle 1152 pointing up. The user can exit this screen by means of waiting for a predetermined amount of time or by means of pressing button 352, identified as "OK" on the display 106.

Figure 44:
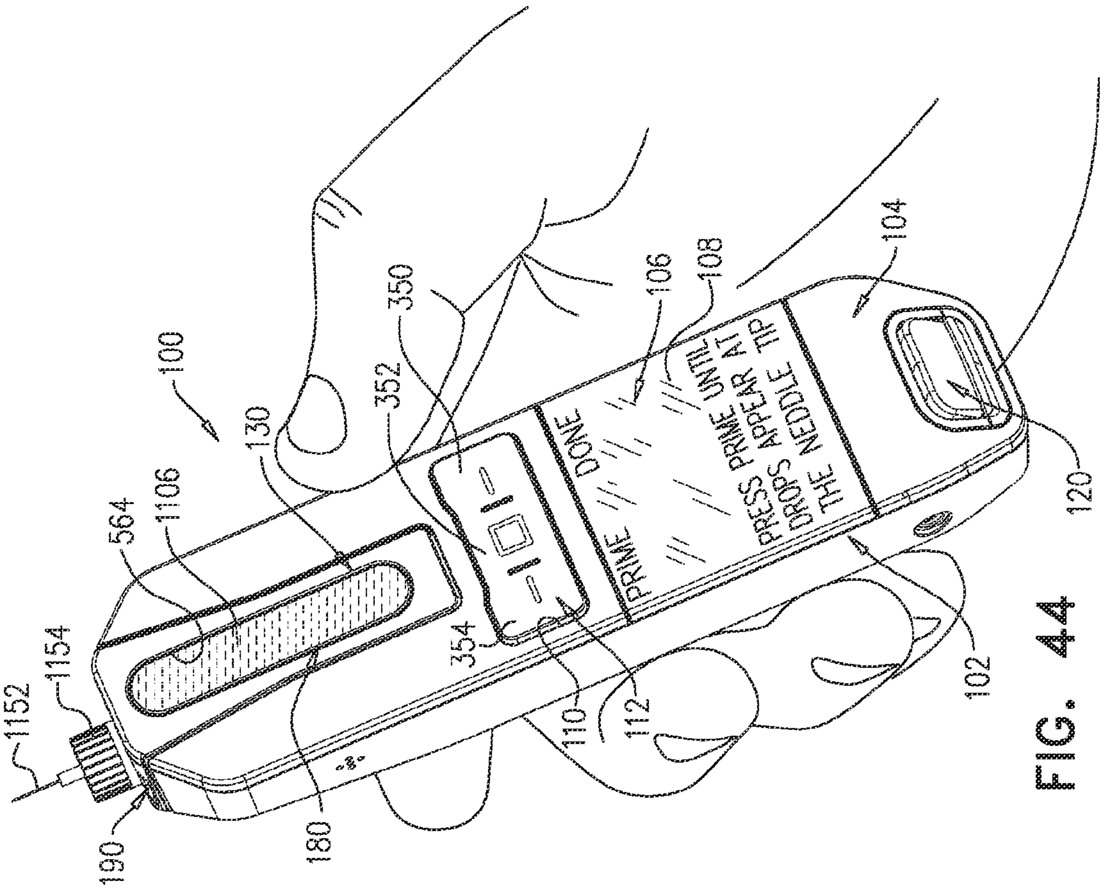
FIGS. 43-47 are simplified pictorial illustrations of the MUCI of FIGS. 1A-21B operated by a user, in a second-sixth priming operative orientations respectively.

It is a particular feature of an embodiment of the present invention that once the user orients the MUCI 100 with the needle 1152 pointing up and press button 352 identified on the display as "OK", the display 106 is preferably shifted by 180 degrees and instructs the user to press the button which is identified as "PRIME" on the display 106 until drops appear at the tip of needle 1152, as clearly seen in FIG. 44.

Figure 45:
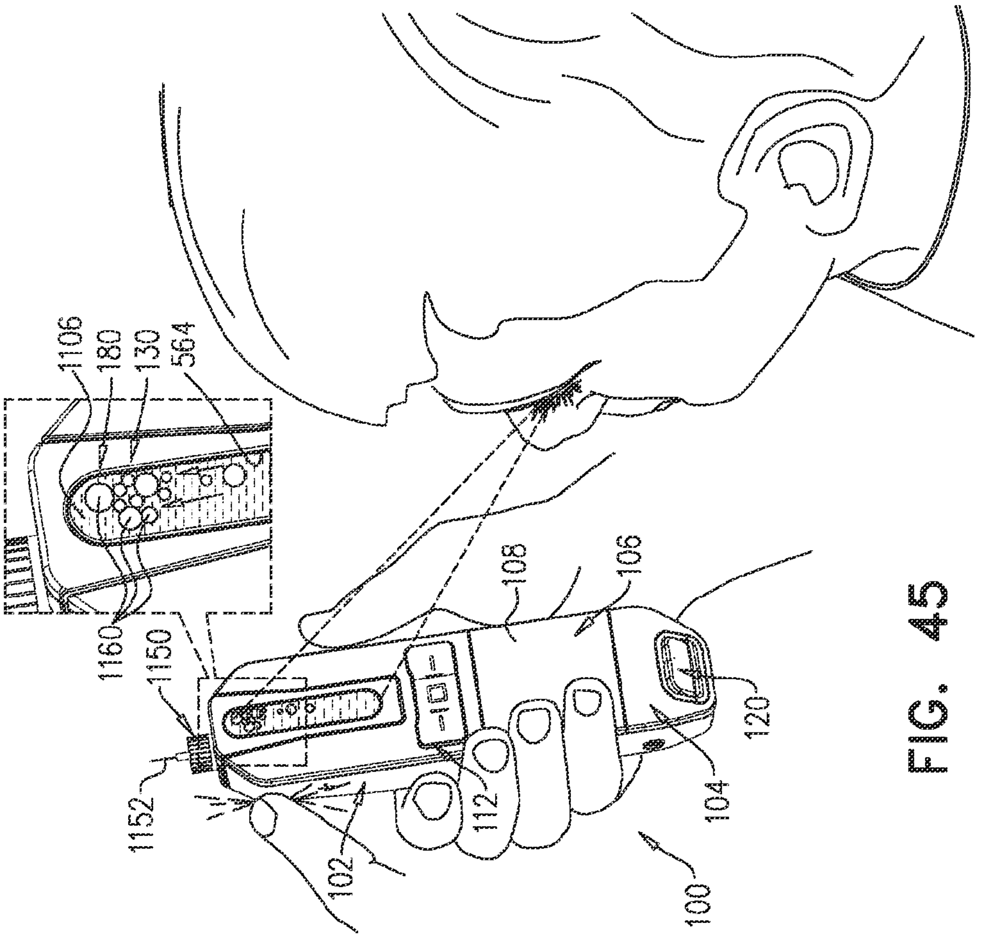

It is particularly seen in FIG. 45 that the user preferably taps the MUCI 100 to dislodge air bubbles 1160, which maybe present within the medicament 1106 contained in medicament cartridge 1100.

It is seen in FIG. 46 that the user presses the button identified as "PRIME" on the display 106 and as long as user continues pressing, the electrical motor 158 is operated to displace the piston 1104 upward within the medicament cartridge 1100.

It is noted that once the user observes a drop of medicament 1106 at the top of needle 1152, he stops pressing the button identified as "PRIME" on the display 106.

It is particularly seen in FIG. 47 that the user presses a different button, specifically button 354, identified on the display as "DONE" in order to confirm that the priming process is completed and then the display 106 instructs the user to inject, while it is a particular feature of an embodiment of the present invention that the display 106 has shifted back by 180 degrees at this stage.

It is appreciated that the priming process preferably continues as long as the user presses button 350, which is identified as "PRIME" on the display. Alternatively, the control system can define a condition where the priming process will be stopped even if the user did not release the button indicated as "PRIME" on the screen. This condition may include a certain amount of medicament 1106 ejected from the medicament cartridge 1100 or a predetermined pressure threshold exerted on the piston contact element 240.

As seen in FIGS. 48A-48B, in the sixth priming operative orientation, as compared with FIGS. 42A-42F, which illustrate the first priming operative orientation, the moveable subassembly 1005 of the piston drive subassembly 220, and particularly piston contact element 240, engages the piston 1104 contained in the medicament cartridge 1100. Any further forward linear displacement of the moveable subassembly 1005 now produces a corresponding linear displacement of the piston 1104.

It is a particular feature of an embodiment of the present invention that the initiation of injection is permitted only after the priming process is completed in order to enable the control system of the MUCI 100 to identify the exact amount of medication ejected from the medicament cartridge 1100. This exact identification is provided by the fact that the injection is initiated only when the priming process is completed. The user indicates to the control system that the priming was completed by pressing button 354, which is identified as "DONE" on display 106 as seen in FIG. 47, once he sees drops of liquid at the tip of needle 1152, which indicate that the piston contact element 240 engaged the piston 1104 and displaced it forwardly within the medicament cartridge 1100. Initiation of injection is only permitted once this signal is provided by the user, indicating completion of priming process, in order to prevent counting of moveable subassembly 1005 advancement during the period of time in which there is no engagement between piston contact element 240 and the piston 1104, which does not result in ejection of medication 1106 from the medicament cartridge 1100.

It is appreciated that in accordance with an embodiment of the present invention, confirmation of completion of the priming process by the user, or alternatively, automatic check of priming completion by the control system, can be defined as a condition for initiating injection. Such automatic check of priming completion may include identification of change in resistance to operate the electric motor 158, thus indicating that the piston contact element 240 engaged the piston 1104 within the medicament cartridge 1100.

The mutual orientations of the various elements described in FIGS. 48A-48B remain essentially the same as described in FIGS. 42B & 42F, other than as specifically set forth hereinbelow:

Piston contact element 240 is now supported between the piston 1104 and the cartridge enclosure assembly latch element 210, such that the forward facing surface 1016 of piston contact element 240 engages the piston 1104 and the rearward facing surface 1017 of piston contact element 240 engages the forwardly facing surface 912 of cartridge enclosure assembly latch element 210, thus the MUCI 100 is now ready for injection upon receiving the appropriate signal from the control system, as described further hereinbelow.

The rearward edge of medicament cartridge 1100 engages arc-shaped protrusion 910 of the cartridge enclosure assembly latch element 210 in order to support and align the medicament cartridge 1100.

It is noted that the moveable subassembly 1005 of the piston drive subassembly 220 is now displaced slightly forwardly with respect to the position thereof as shown in FIGS. 42A-42F. The moveable subassembly 1005 was displaced axially forwardly along longitudinal axis 105 as long as the user pressed on the button indicated as "PRIME" on the display 106. In this operative orientation, it is seen that the cartridge enclosure assembly latch element 210 was displaced forwardly along with the moveable subassembly 1005 under the biasing force of springs 212 up to engagement of arc-shaped protrusion 910 with medicament cartridge 1100, which is the most forward position of the cartridge enclosure assembly latch element 210. Further forward displacement of the moveable subassembly 1005, as described in detail hereinbelow, drives the piston contact element 240 forwardly away from arc shaped protrusion 910 of the cartridge enclosure assembly latch element 210.

Figure 49:
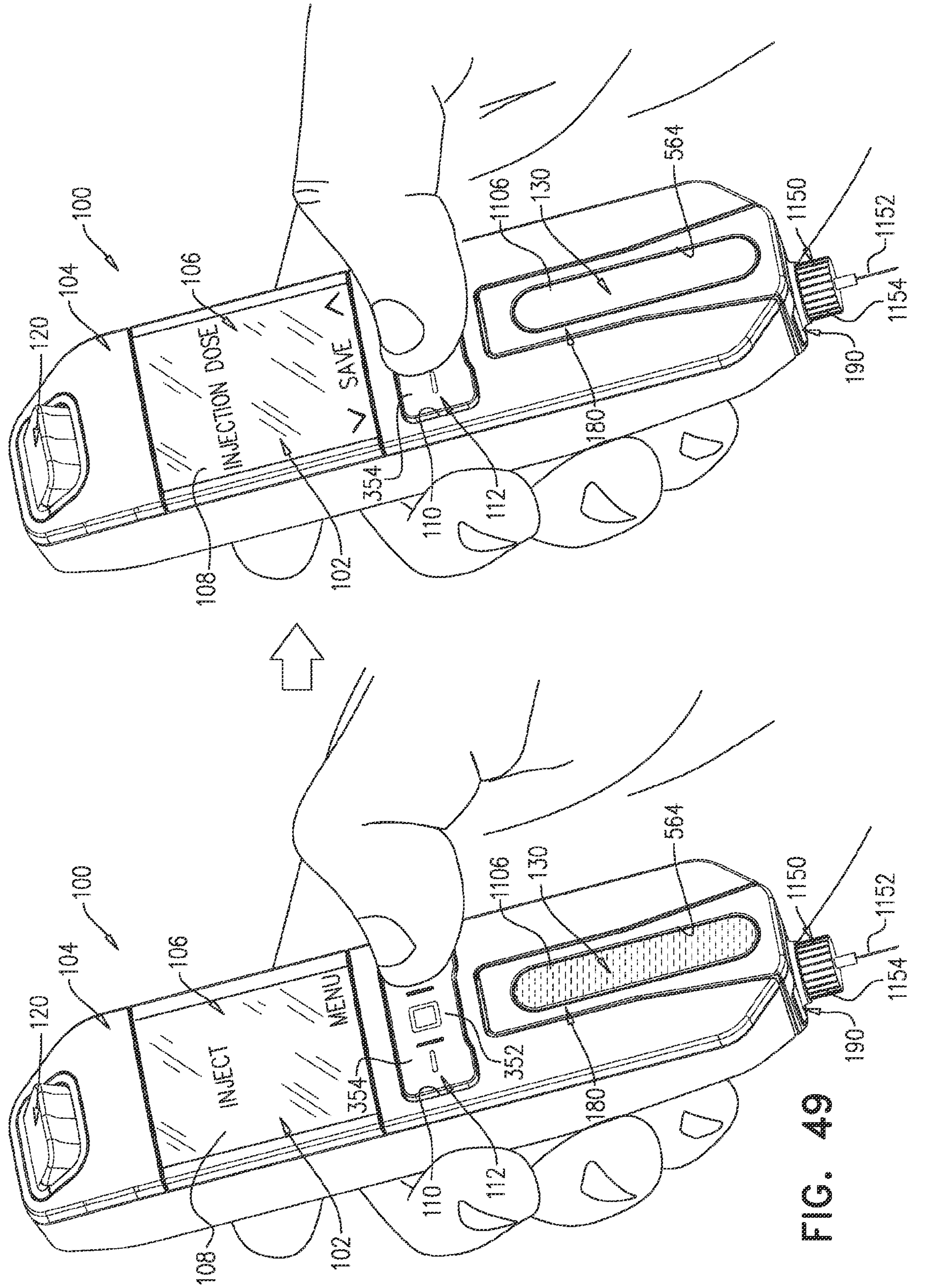
FIGS. 49-51 are simplified pictorial illustrations of the MUCI of FIGS. 1A-21B operated by a user, in a first-third injection preparation operative orientations respectively.
Figure 50:
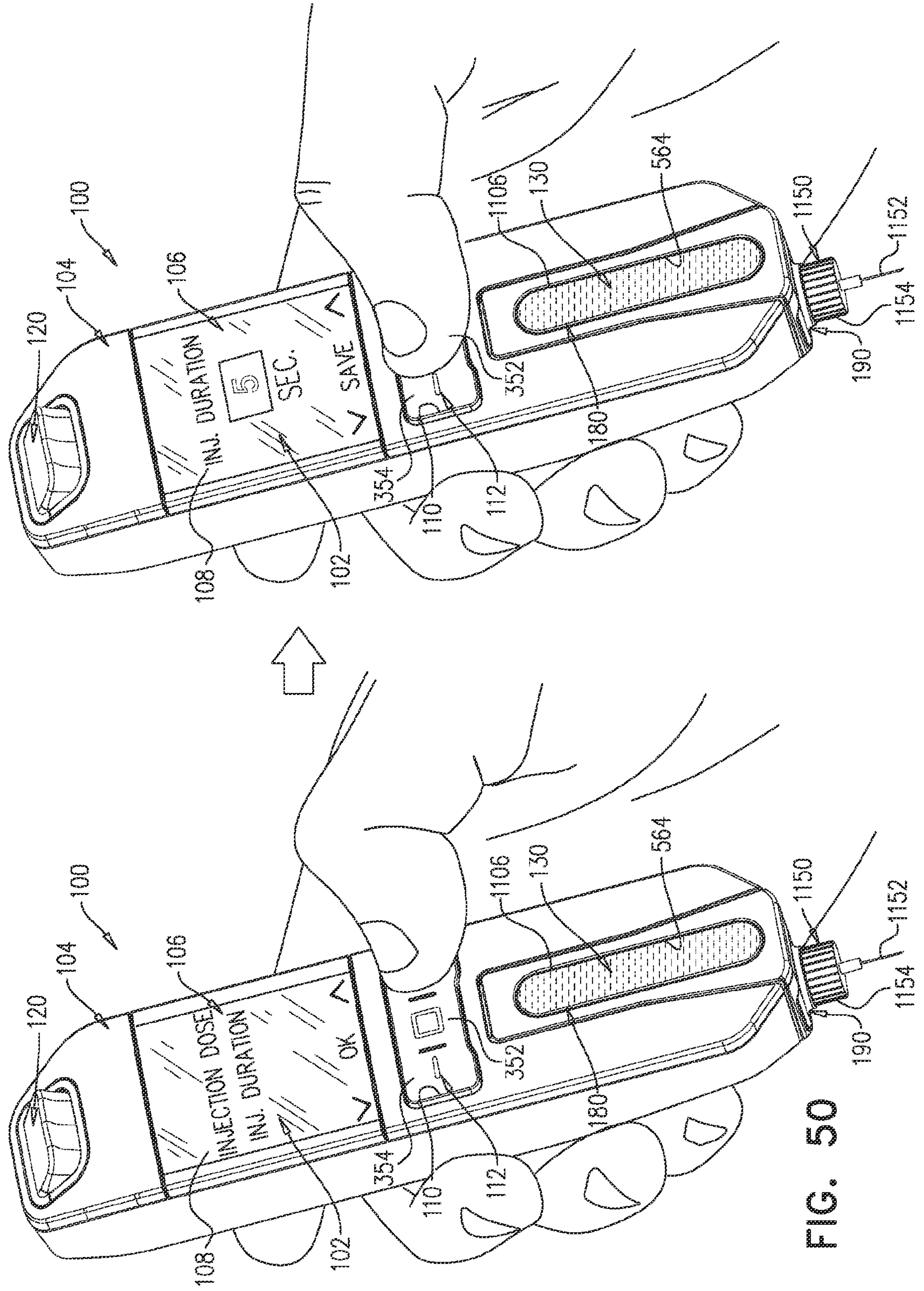
Figure 51:
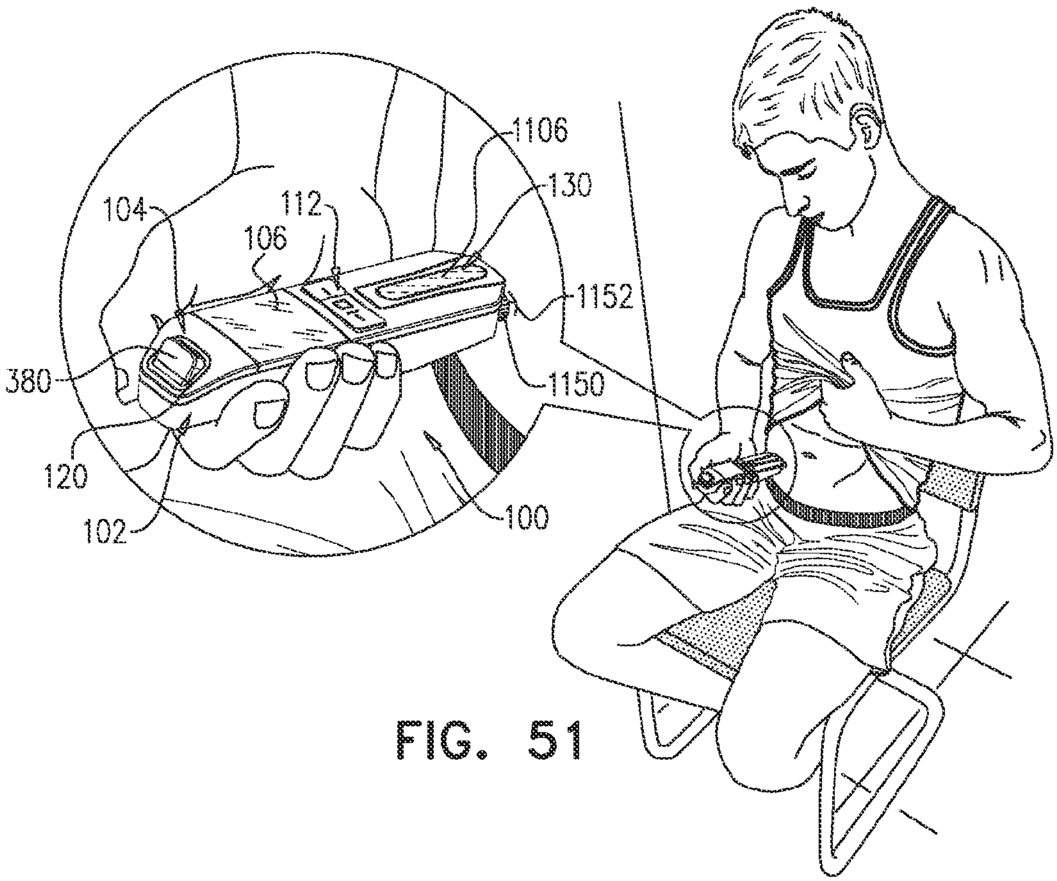

Reference is now made to FIGS. 49-51, which are simplified pictorial illustrations of the MUCI 100 of FIGS. 1A-21B operated by a user, in a first-third injection preparation operative orientations respectively.

It is seen in FIG. 49 that the user orients the injector with the needle 1152 pointing down and preferably presses button 350, identified as "MENU" in the display 106. It is further seen in FIGS. 49 & 50 that the user preferably presses at least one of buttons 350, 352 and 354, as a result screen appears which enables selection of injection dose and injection duration.

It is seen in FIG. 51 that the user inserts needle 1152 at an injection site on a body of the user.

Figure 52:
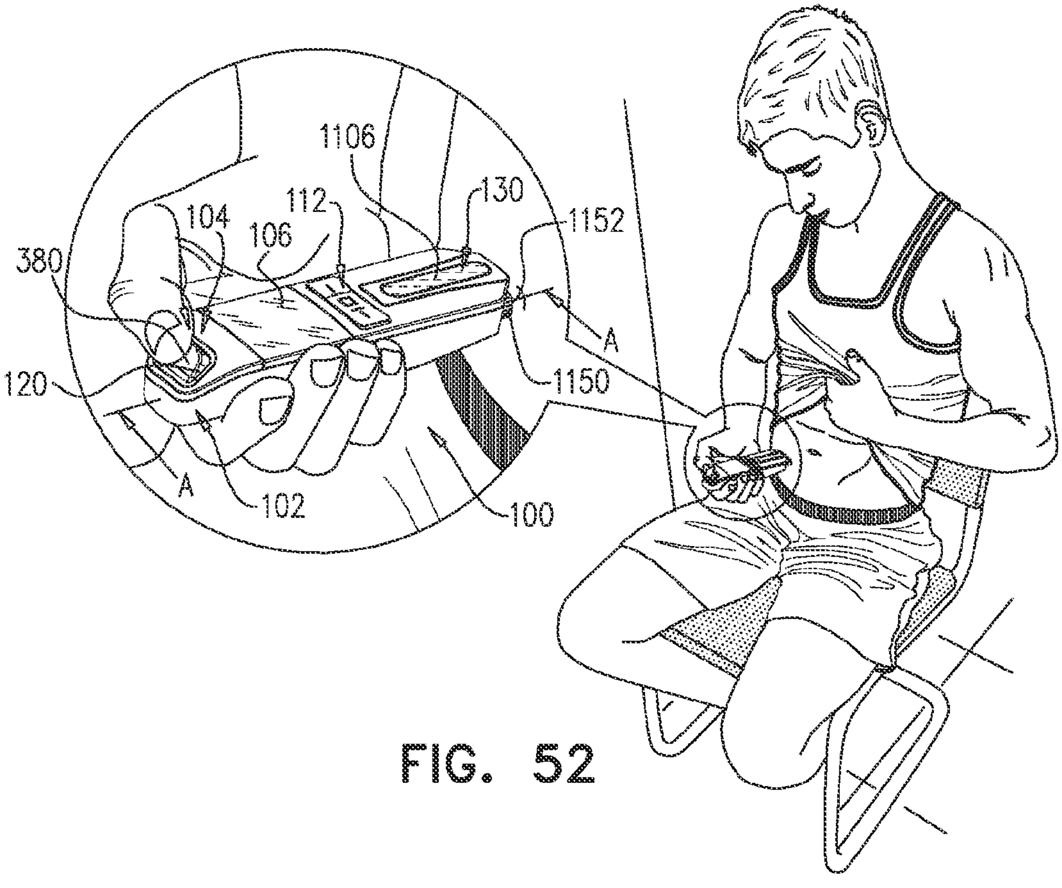
FIG. 52 is a simplified pictorial illustrations of the MUCI of FIGS. 1A-21B operated by a user, in an initiation of injection operative orientation.
Figure 53:
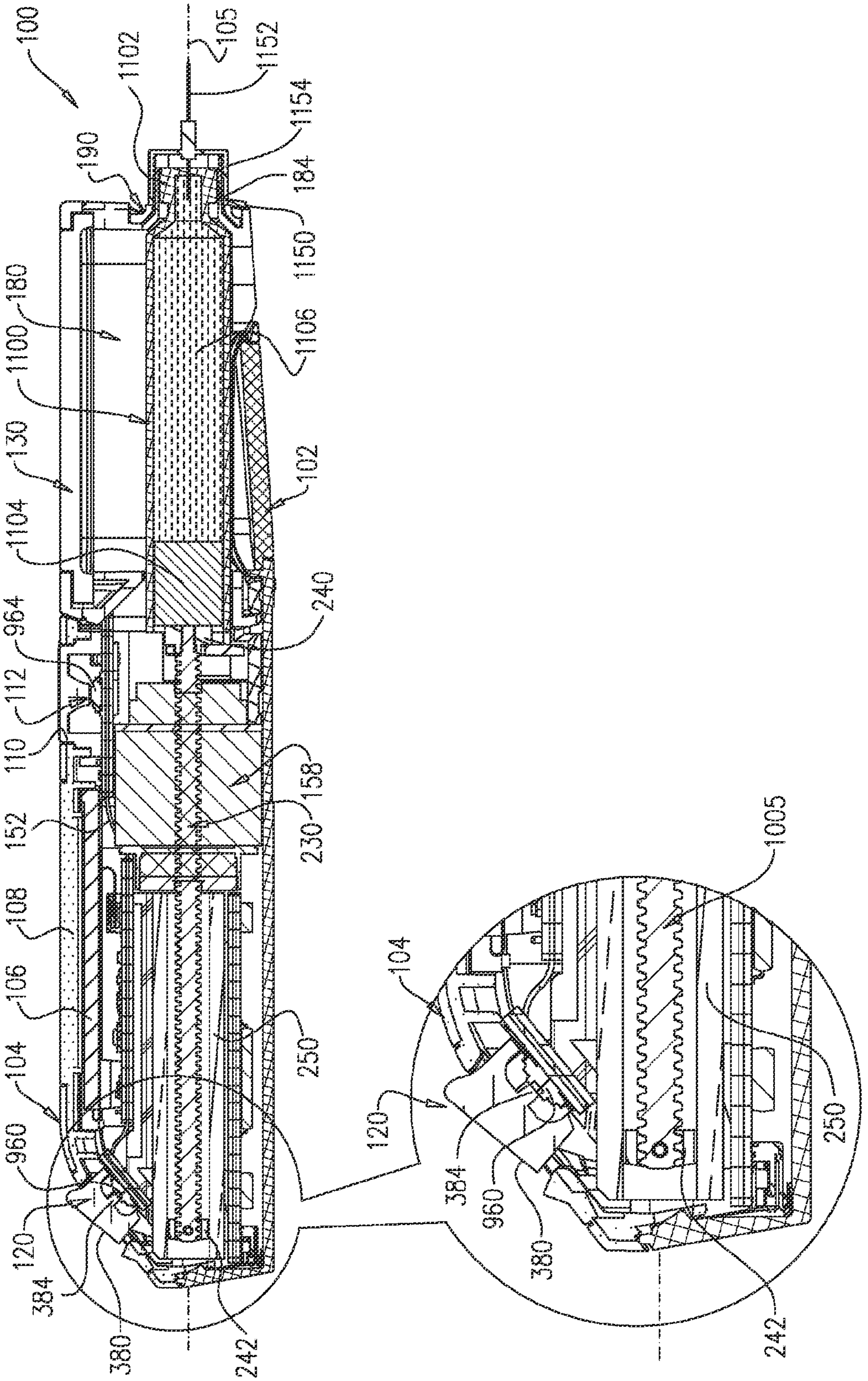
FIG. 53 is a simplified sectional illustration, taken generally along lines A-A in FIG. 52 in the initiation of injection operative orientation.

Reference is now made to FIG. 52, which is a simplified pictorial illustrations of the MUCI 100 of FIGS. 1A-21B operated by a user, in an initiation of injection operative orientation and to FIG. 53, which is a simplified sectional illustration, taken generally along lines A-A in FIG. 52 in the initiation of injection operative orientation.

It is seen in FIG. 52 that the user presses on the outer surface 380 of injection button element 120 to initiate ejection of medicament 1106 from the medicament cartridge 1100.

The mutual orientations of the various elements described in FIGS. 48A-48B remain essentially the same, other than as specifically set forth hereinbelow:

It is seen in FIG. 53 that upon pressing on the outer surface 380 of injection button element 120, the injection button element 120 is pivoted about pivoting axis 394, such that protrusion 384 engages injection button microswitch 960, which in turn transfers signal to the control system of the MUCI 100, to initiate injection by means of electrical motor 158 advancing the moveable subassembly 1005 of the piston drive subassembly 220 by a distance which precisely corresponds to the selected dose and at a rate which precisely corresponds to the selected injection duration.

It is seen in FIG. 53 that piston contact element 240 engages piston 1104, such that the forward facing surface 1016 of piston contact element 240 engages the piston 1104, thus the MUCI 100 is now ready for injection.

Figure 54:
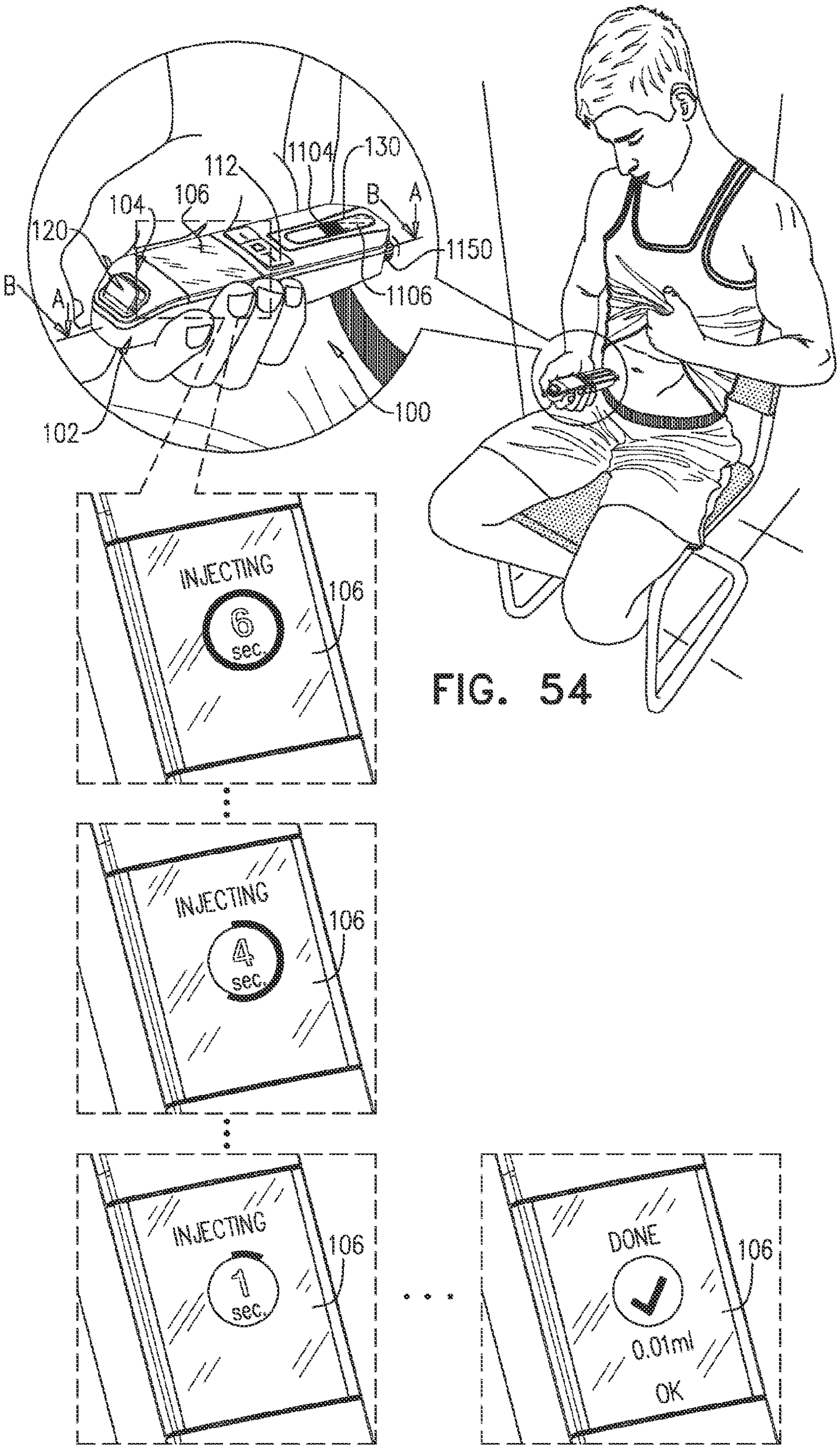
FIG. 54 is a simplified pictorial illustrations of the MUCI of FIGS. 1A-21B operated by a user, in an injection operative orientation.
Figure 55A:
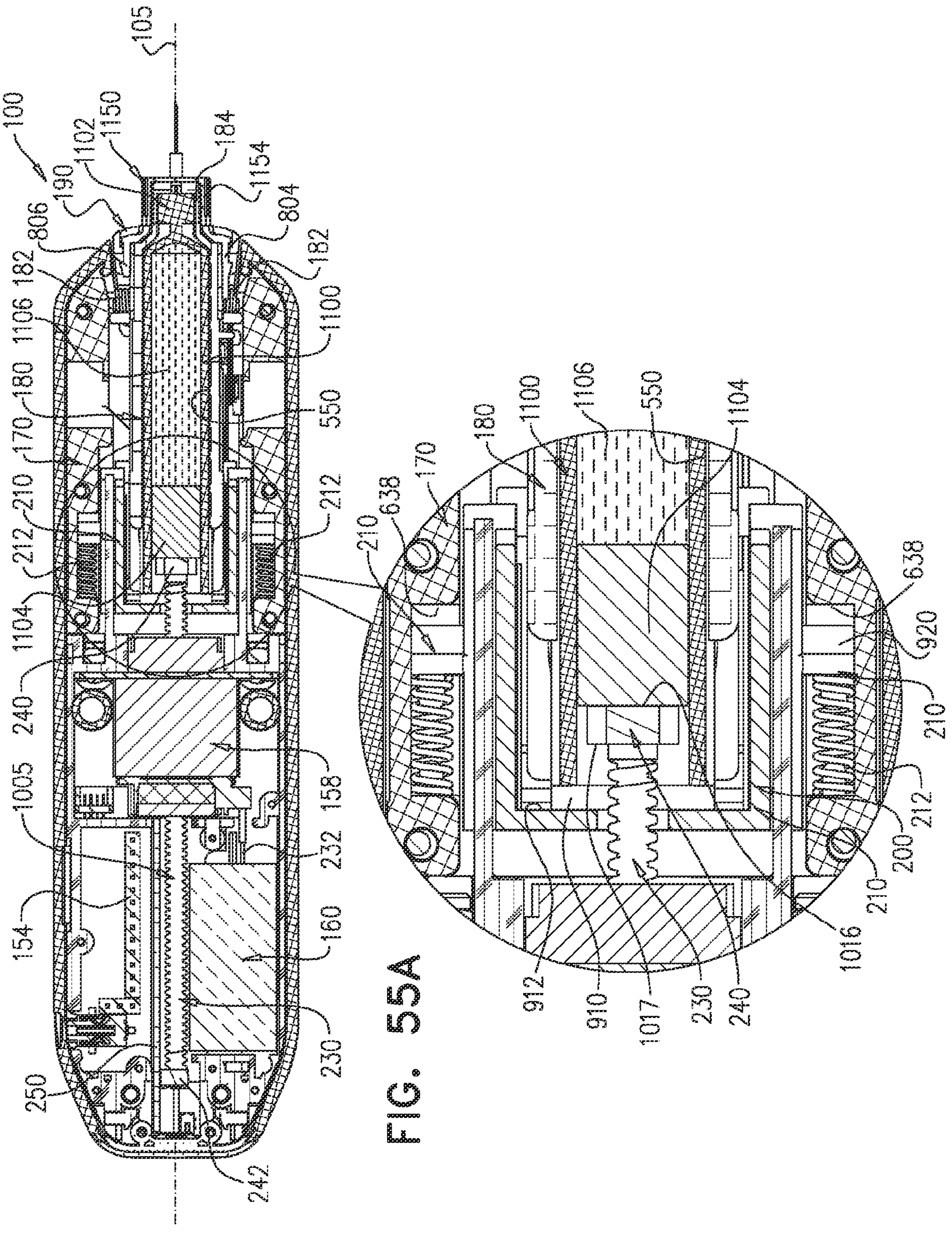
FIGS. 55A-55B are simplified sectional illustrations, taken generally along lines A-A and B-B respectively in FIG. 54 in the injection operative orientation.
Figure 55B:
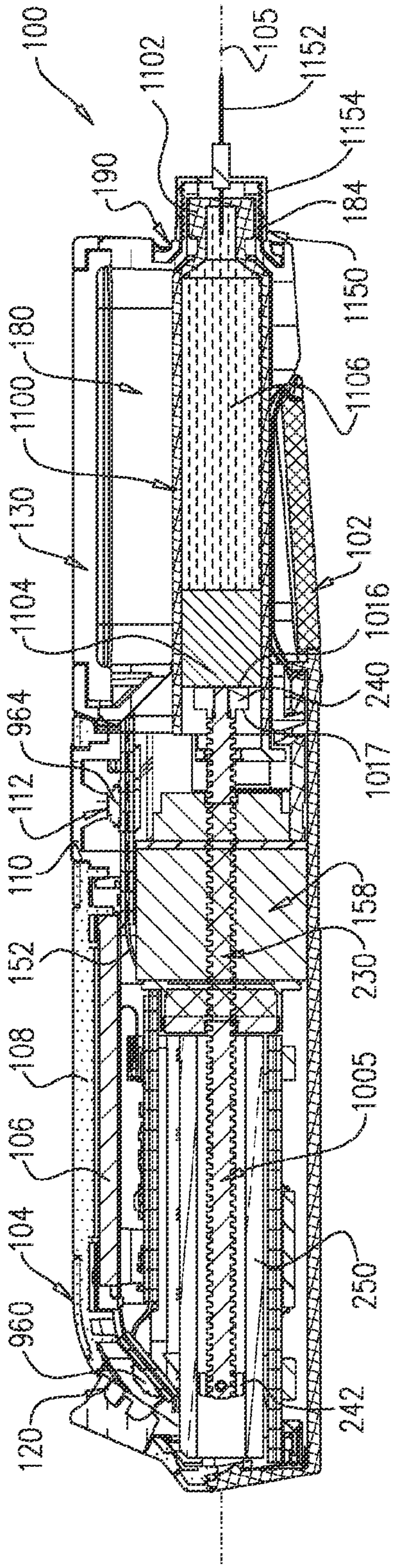
Figure 56A:
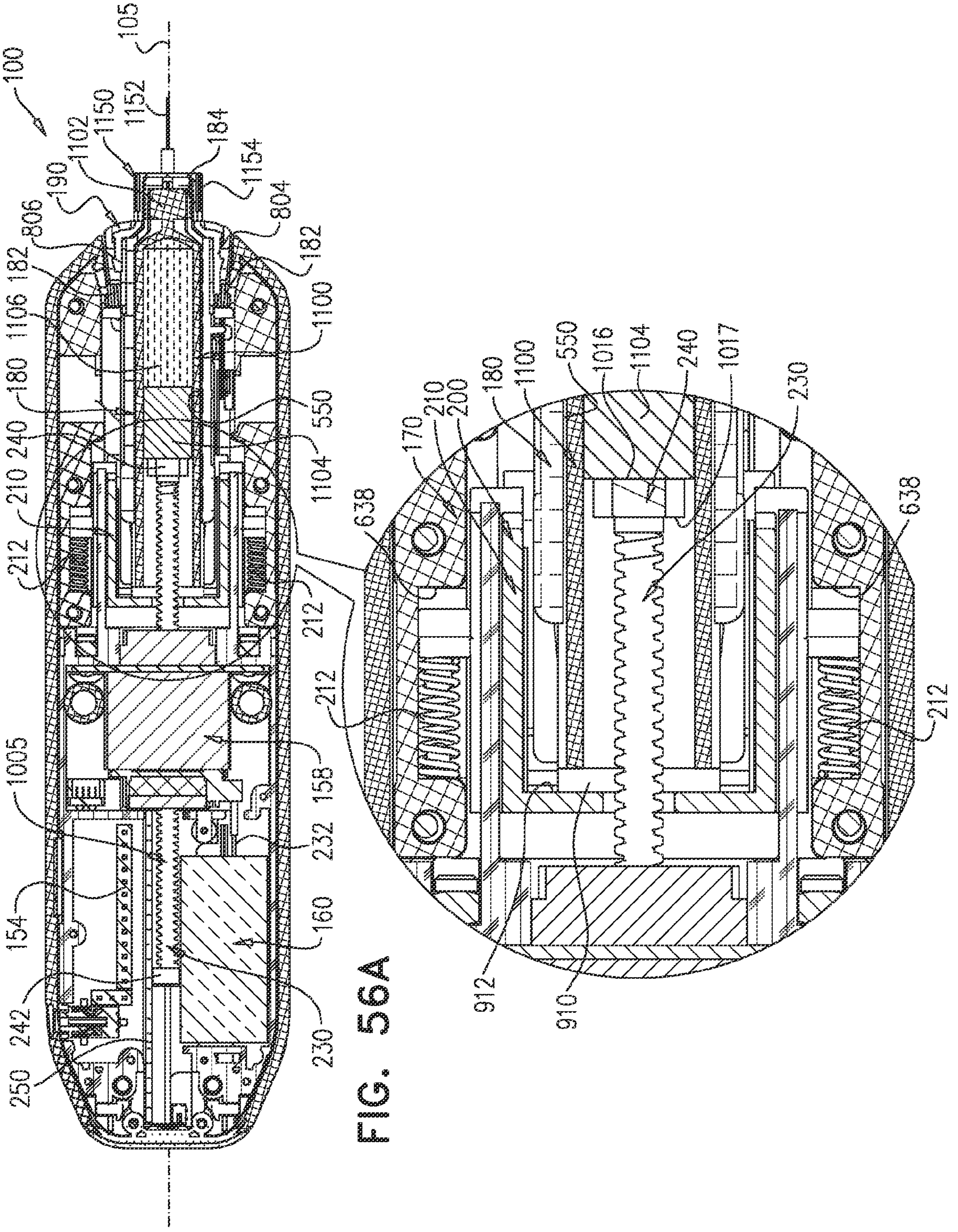
FIGS. 56A-56B are simplified sectional illustrations, taken generally along lines A-A and B-B respectively in FIG. 54 in an end of injection operative orientation.
Figure 56B:
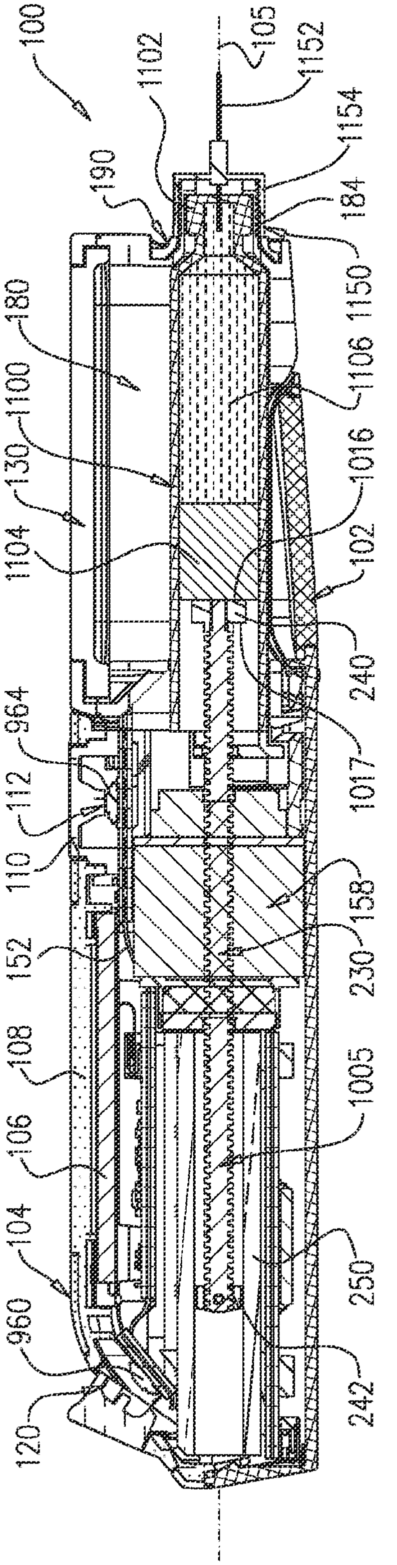

Reference is now made to FIG. 54, which is a simplified pictorial illustrations of the MUCI 100 of FIGS. 1A-21B operated by a user, in an injection operative orientation and to FIGS. 55A-55B, which are simplified sectional illustrations, taken generally along lines A-A and B-B respectively in FIG. 54 in the injection operative orientation. Reference is additionally made to FIGS. 56A-56B, which are simplified sectional illustrations, taken generally along lines A-A and B-B respectively in FIG. 54 in an end of injection operative orientation.

It is seen in FIG. 54 that following pressing the injection button element 120, display 106 shows a countdown of the duration of injection.

It is seen in FIGS. 54-56B that the injection button element 120 is now released.

It is seen that in FIGS. 55A-55B, the mutual orientations of the various elements described in FIGS. 48A-48B remain essentially the same, other than as specifically set forth hereinbelow:

In this injection operative orientation, it is seen that the cartridge enclosure assembly latch element 210 engages the medicament cartridge 1100 and the moveable subassembly 1005 of piston drive subassembly 220 is displaced forwardly along longitudinal axis 105, while driving the piston contact element 240 forwardly away from arc shaped protrusion 910 of the cartridge enclosure assembly latch element 210.

It is seen in FIGS. 55A-55B that moveable subassembly 1005 is displaced forwardly along track element 250 and piston contact element 240 drives piston 1104 forwardly within medicament cartridge 1100 to a first longitudinal extent, which results in ejection of a certain amount of medicament 1106 from the medicament cartridge 1100.

It is seen that in FIGS. 56A-56B, the mutual orientations of the various elements described in FIGS. 55A-55B remain essentially the same, other than as specifically set forth hereinbelow:

FIGS. 56A-56B show the end of injection operative orientation of the MUCI 100.

It is seen in FIGS. 56A-56B that moveable subassembly 1005 of piston drive subassembly 220 is displaced more forwardly along track element 250 while driving piston contact element 240 more forwardly away from arc shaped protrusion 910 of the cartridge enclosure assembly latch element 210. Piston contact element 240 drives piston 1104 forwardly within medicament cartridge 1100 to a second longitudinal extent, which is greater than the first longitudinal extent, and which results in ejection of the selected dose of medicament 1106 from medicament cartridge 1100.

Reference is now made to FIGS. 57-60B, which are simplified pictorial illustrations of the MUCI 100 of FIGS. 1A-21B operated by a user, in a first-fifth end of injection operative orientations respectively.

Figure 57:
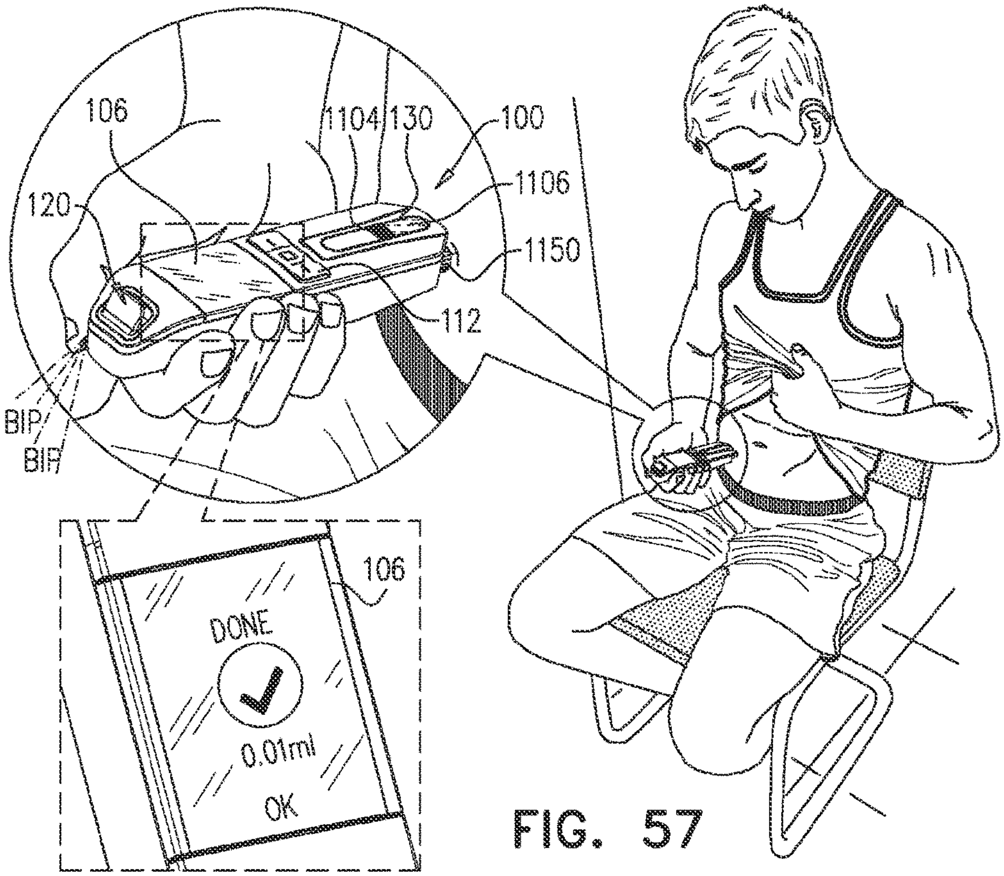
FIGS. 57-60B are simplified pictorial illustrations of the MUCI of FIGS. 1A-21B operated by a user, in a first-fifth end of injection operative orientations respectively.
Figure 58:
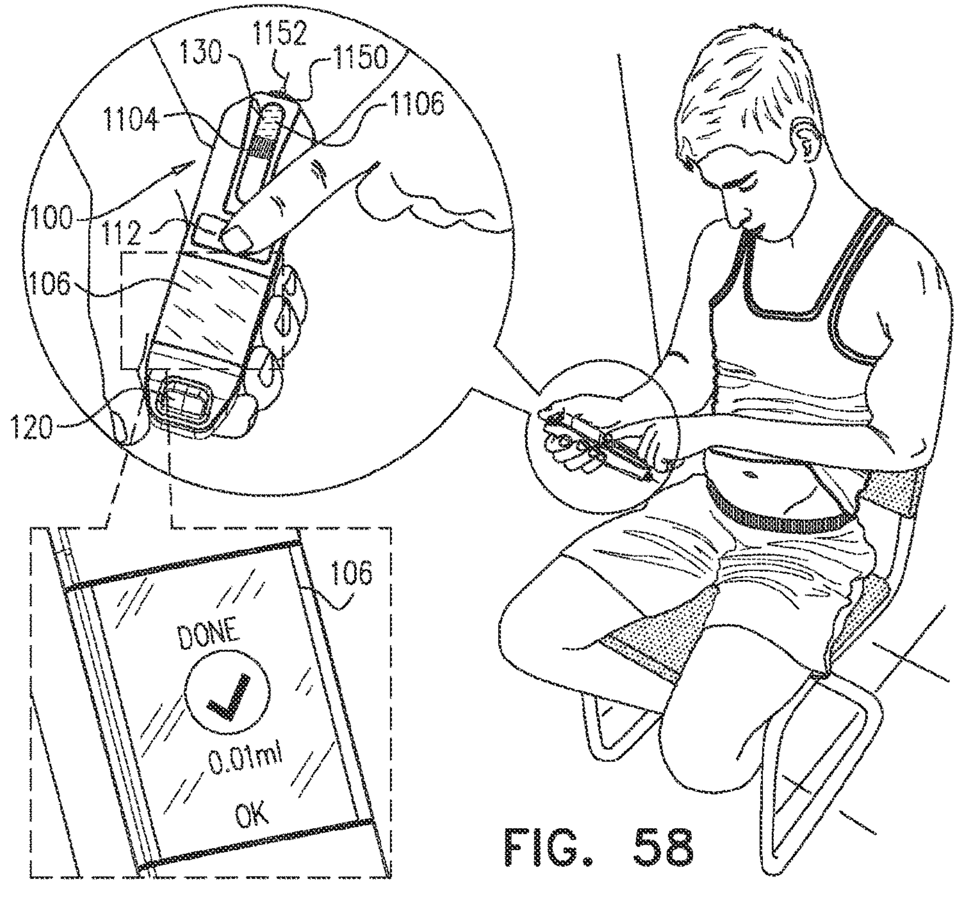

It is seen in FIG. 57 that the display 106 indicates to the user that the injection is completed and the MUCI 100 may also provide a corresponding audial indication to the user. It is seen in FIG. 58 that upon the indication provided in FIG. 57, the user removes the MUCI 100 from the injection site and the display 106 indicates the quantity of medicament 1106 injected. The user presses a button, which is indicated as "OK" on the display 106.

Figure 59:
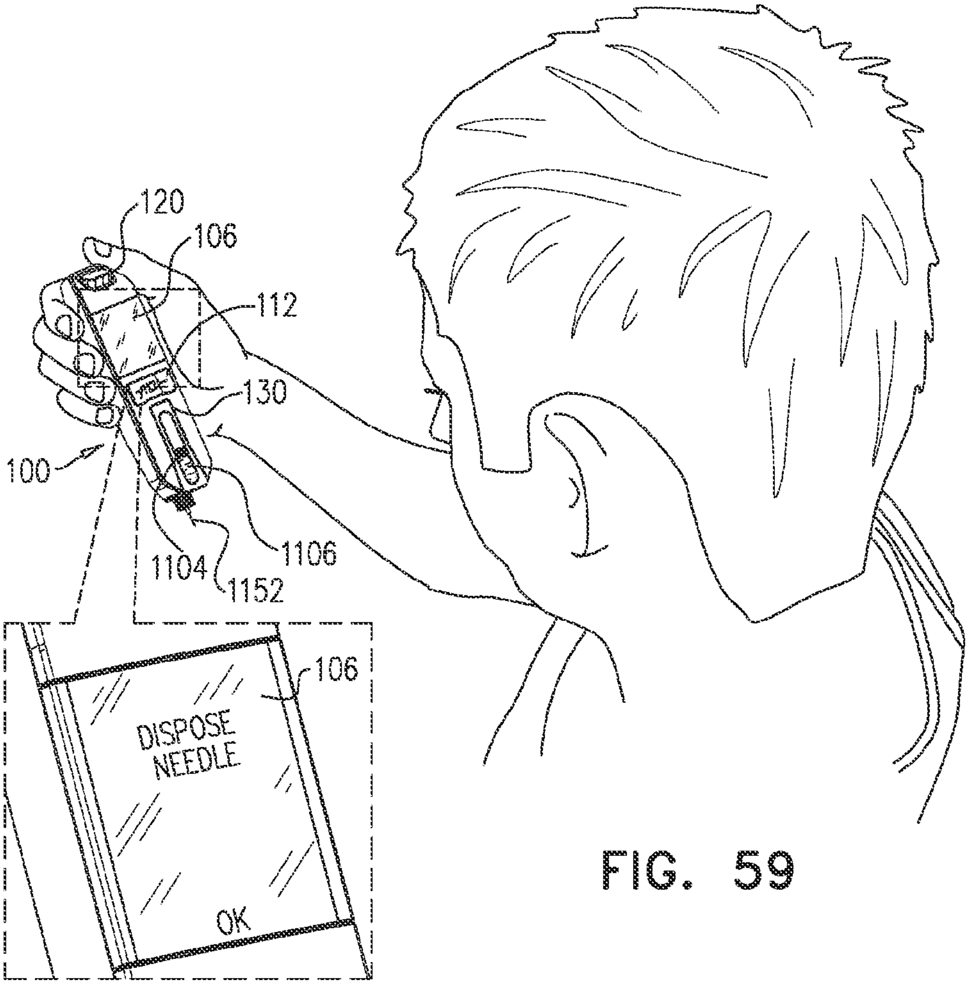

It is seen in FIG. 59 that the display 106 instructs the user to dispose of needle 1152.

Figure 60A:
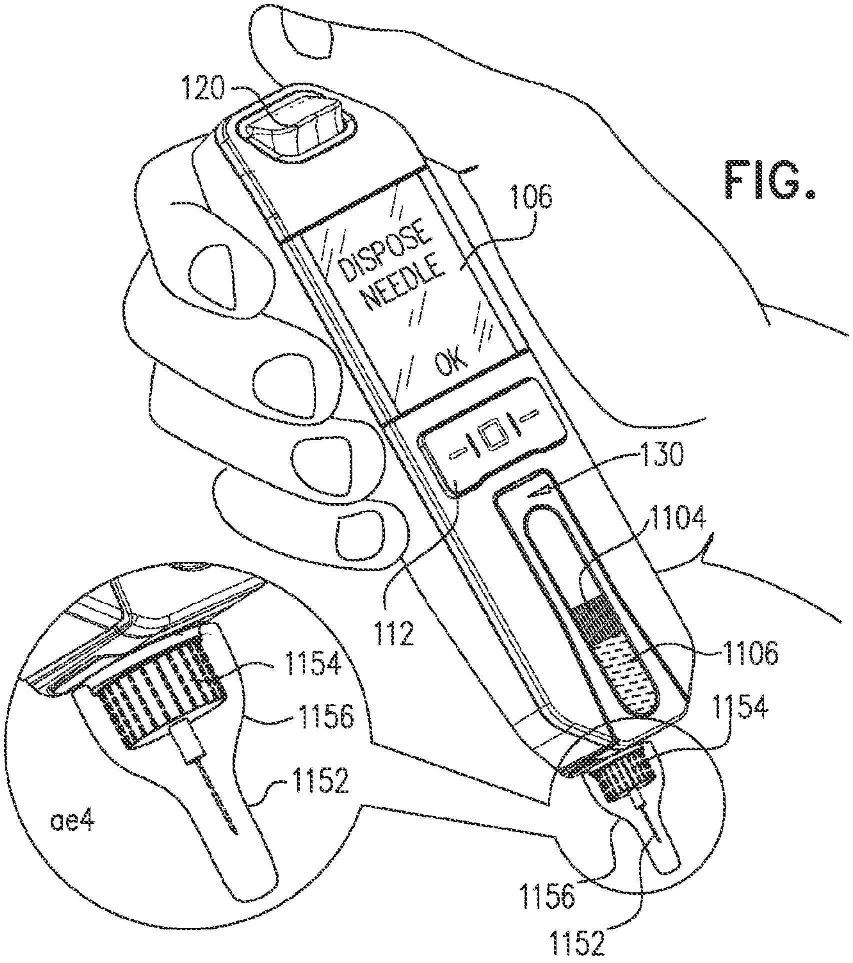

It is further seen in FIG. 60A that the user presses a button which is indicated as "OK" on display 106. Following this action, if the needle 1152 was not disposed, the MUCI 100 is ready for use for injecting an additional dosage of medicament 1106 using the same needle 1152. Alternatively, the user can cover the needle 1152 using needle cover 1156 and then dispose the needle assembly 1150 as shown further in FIG. 60B.

Figure 60B:
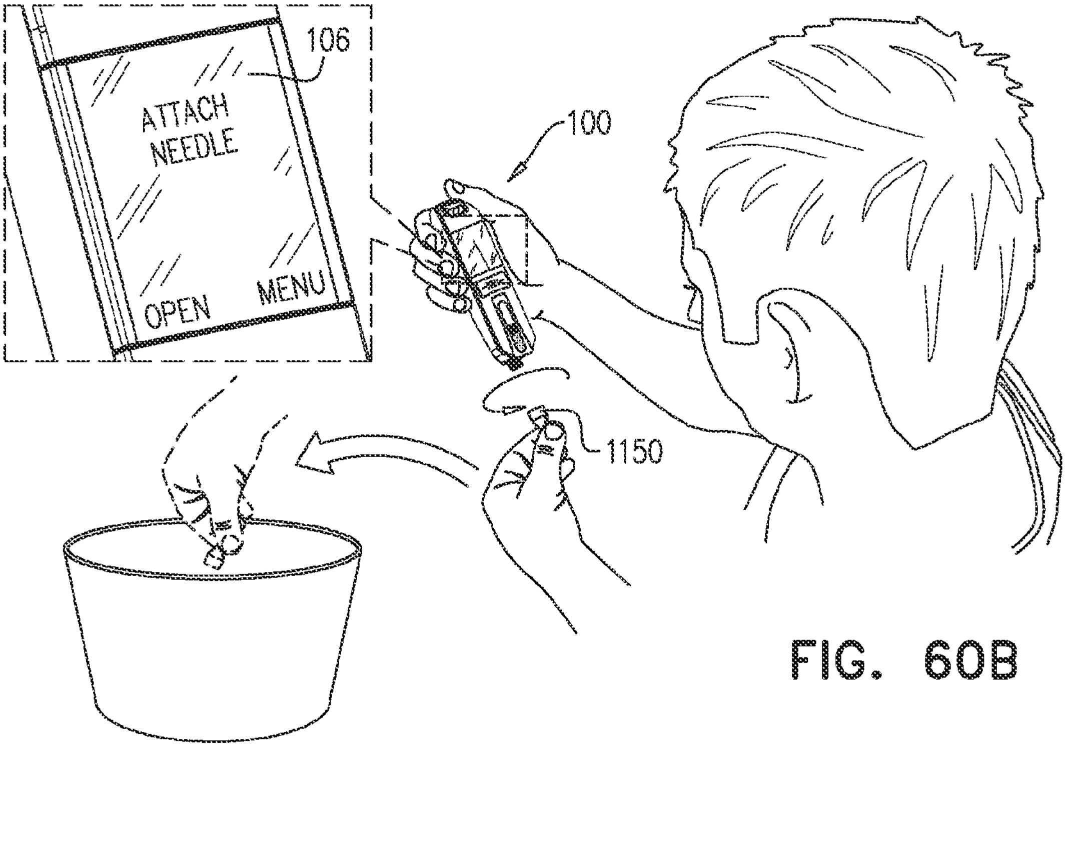
Figure 61A:
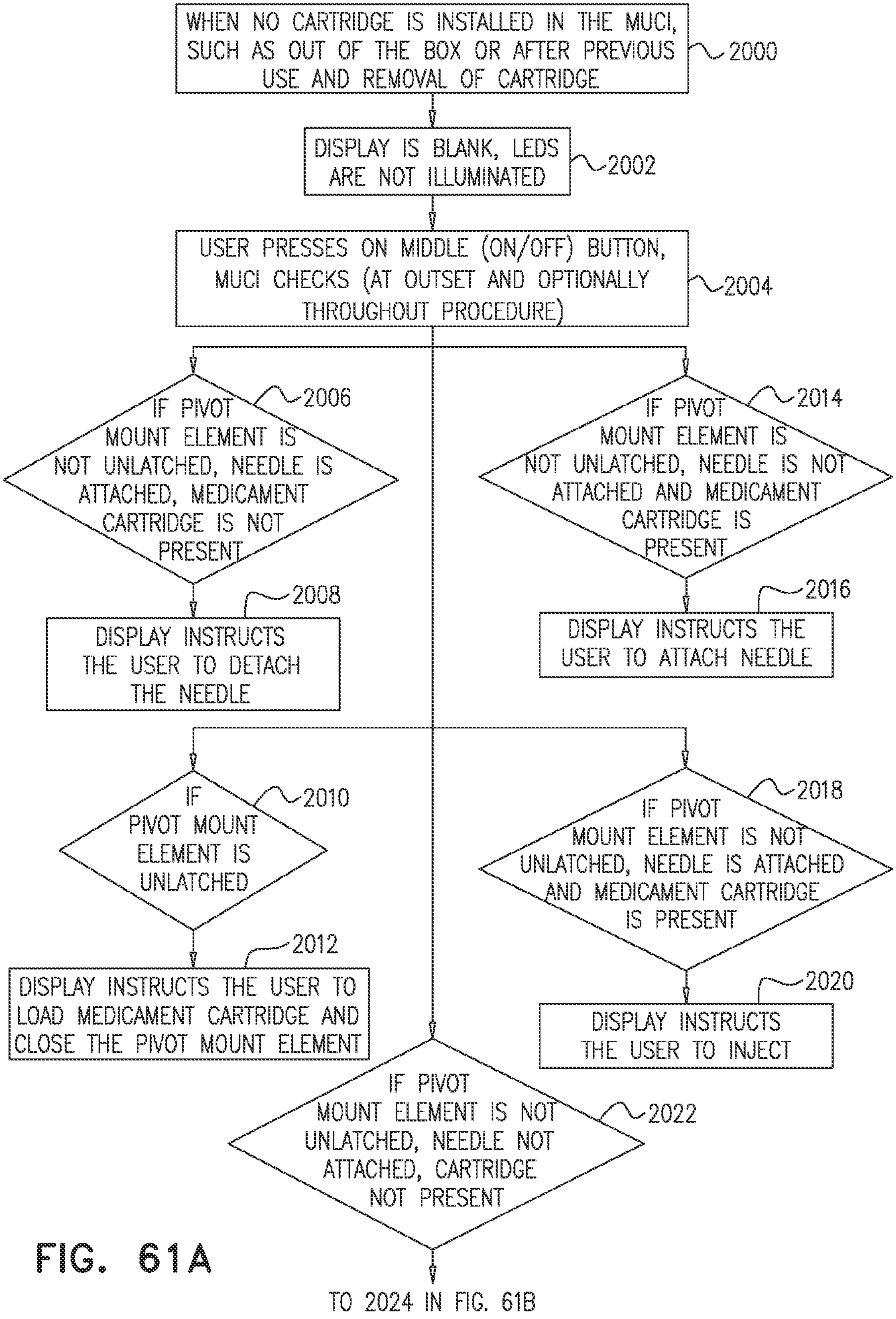
FIGS. 61A-61H are together a simplified flowchart illustrating operation of the electronic control assembly of the MUCI of FIGS. 1-21B.
Figure 61B:
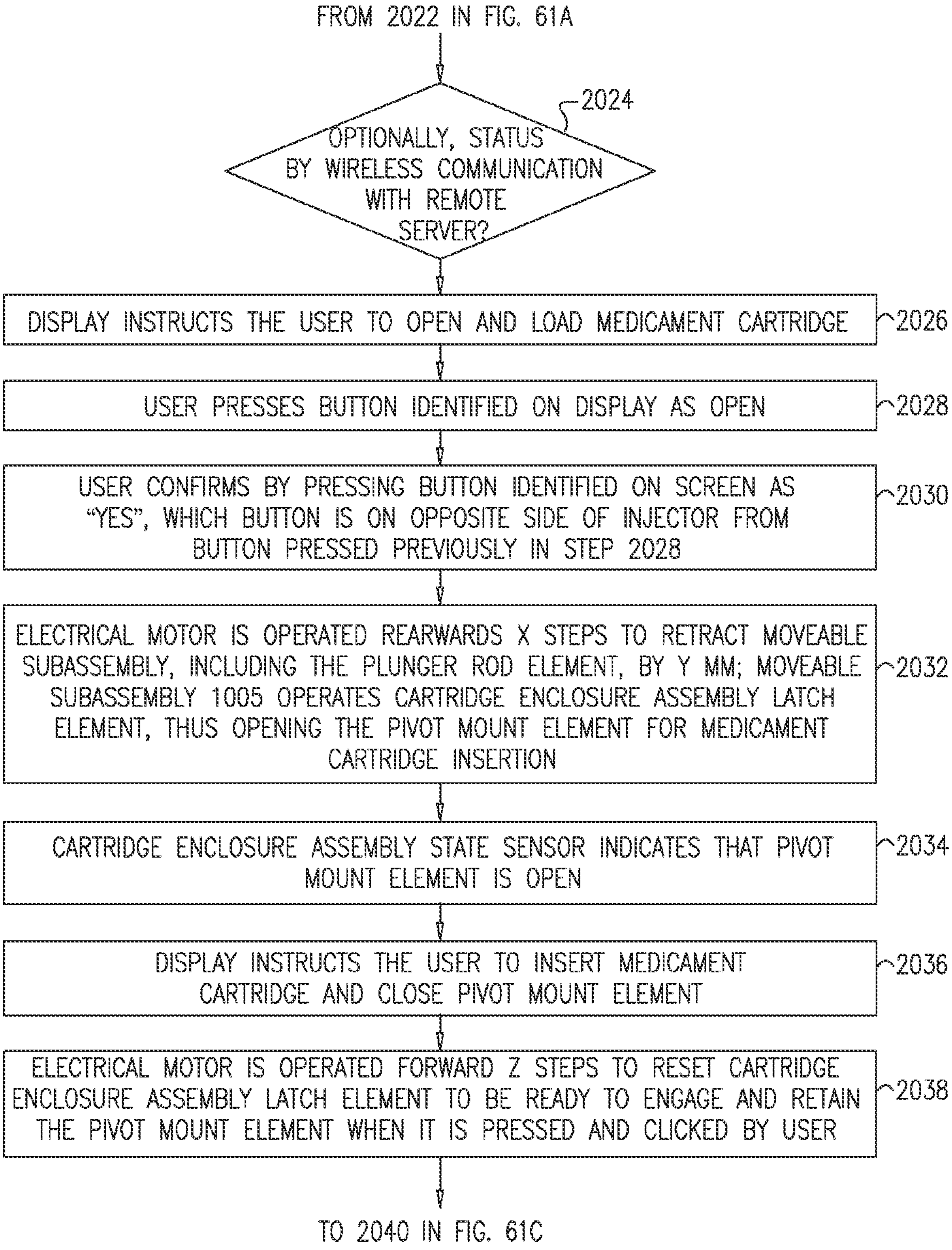
Figure 61C:
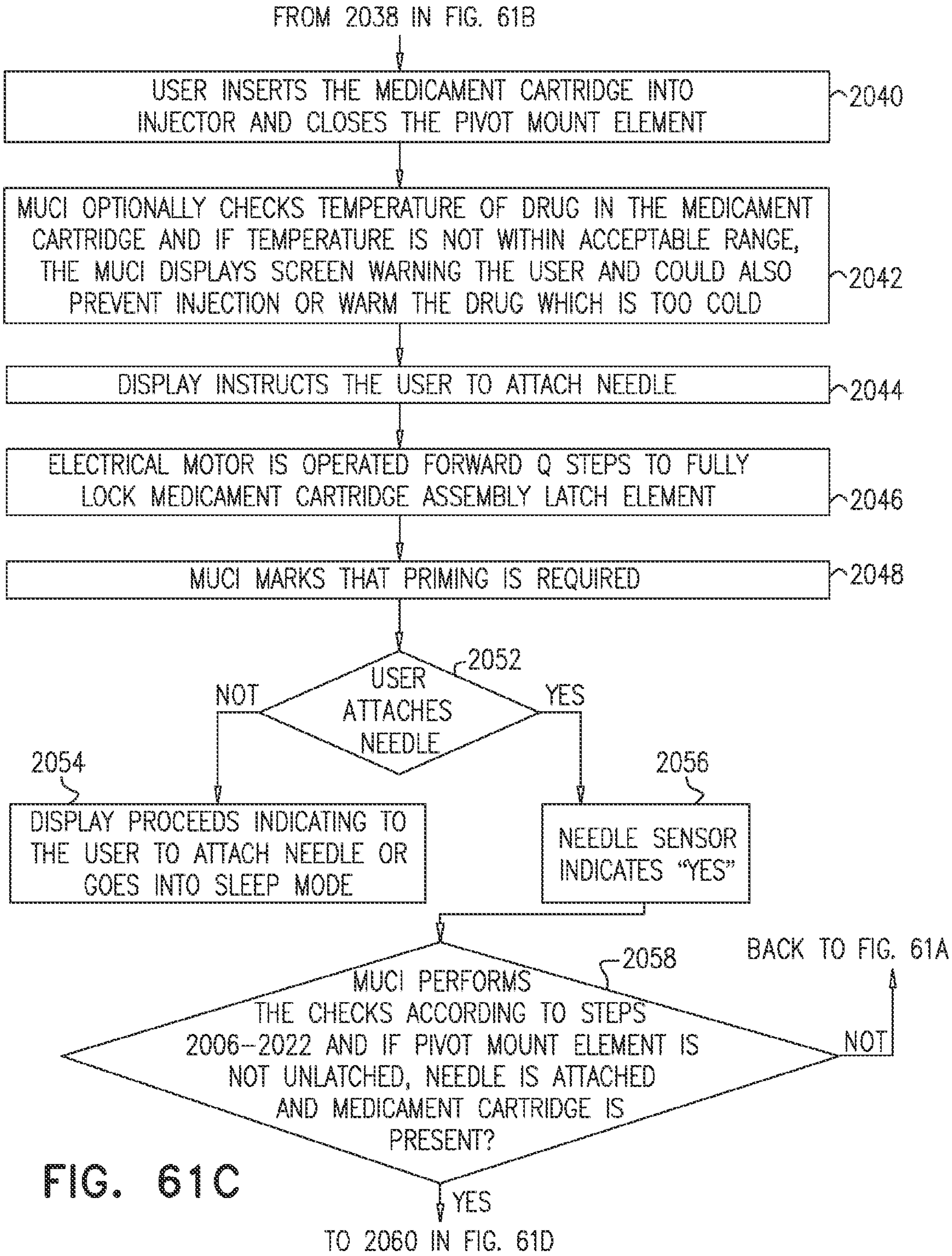
Figure 61D:
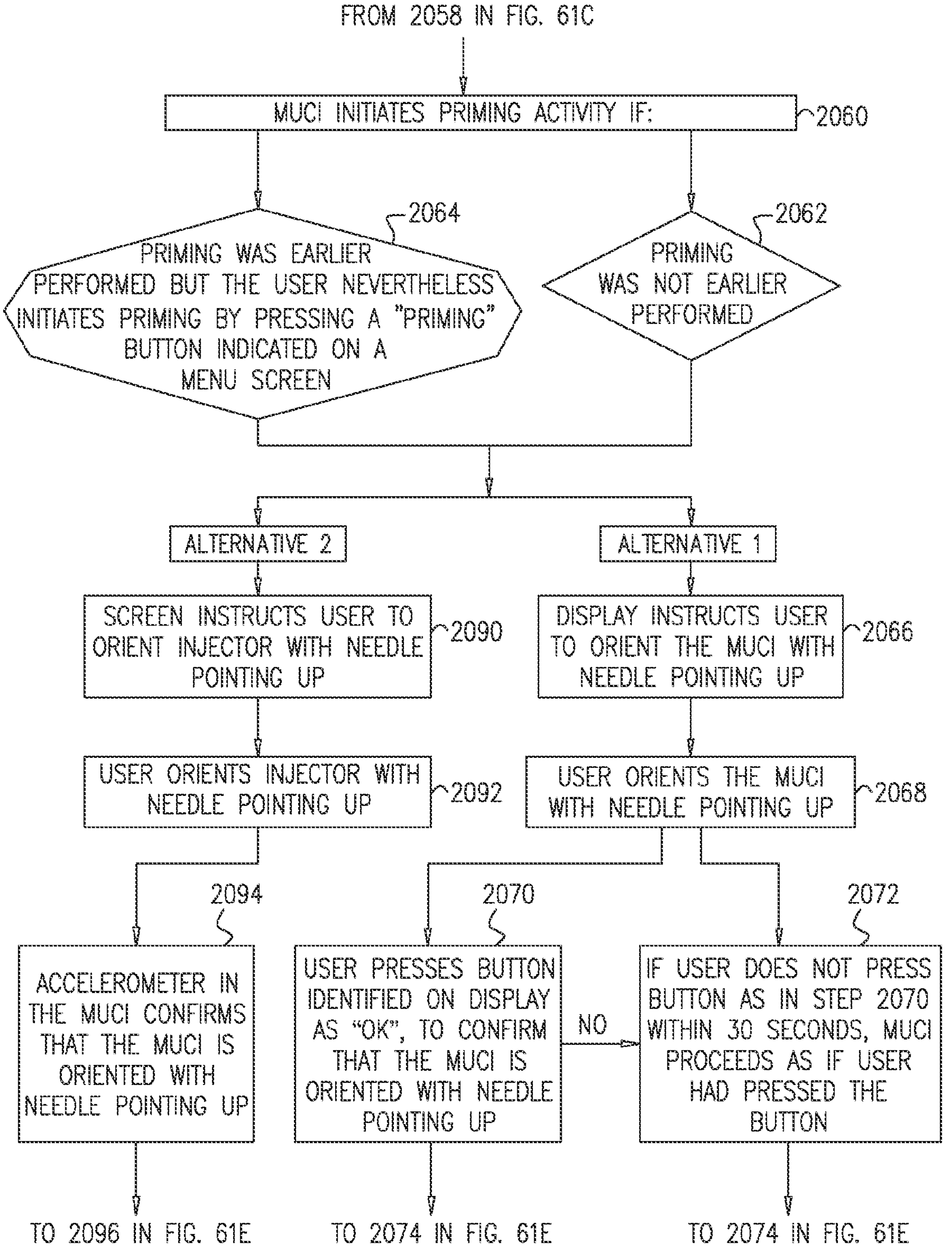
Figure 61E:
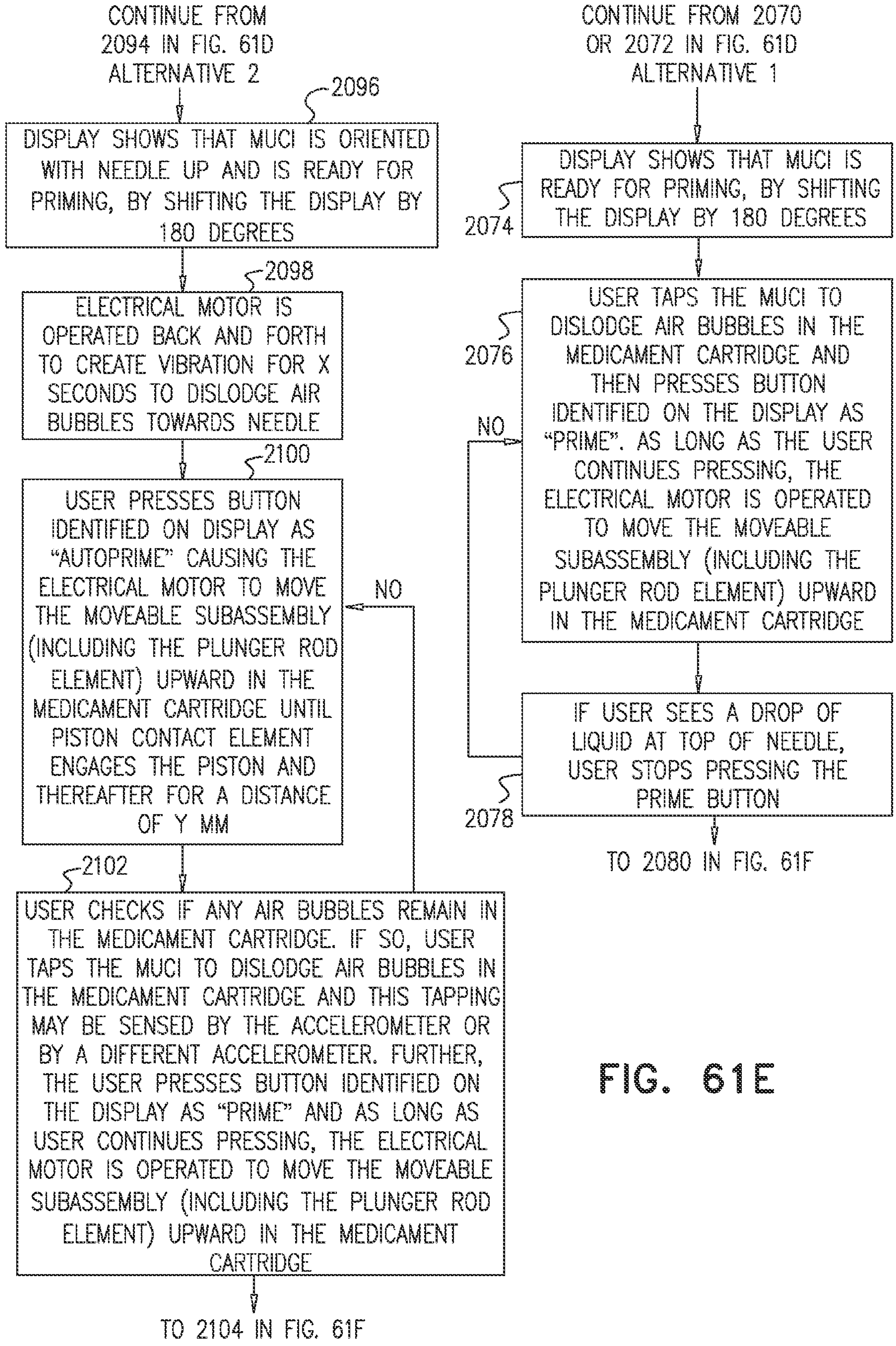
Figure 61F:
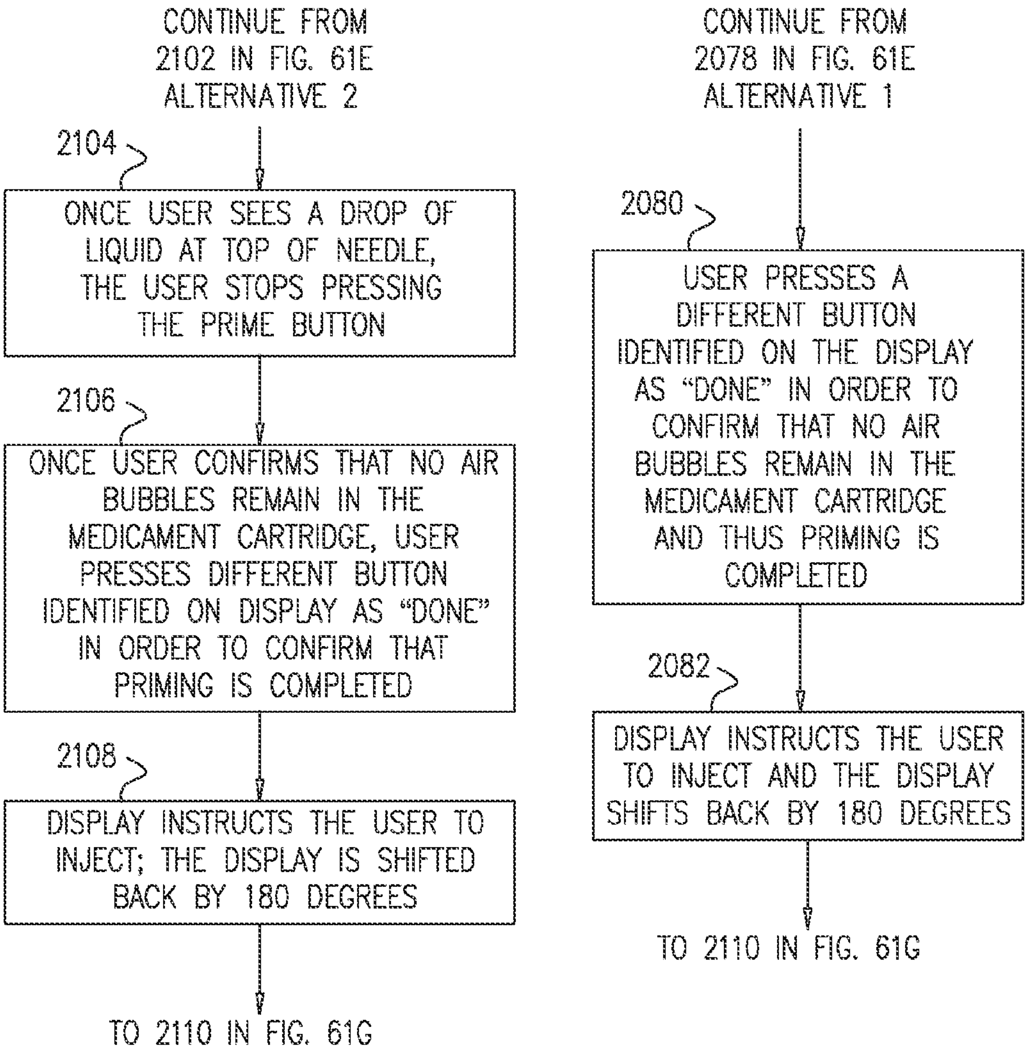
Figure 61G:
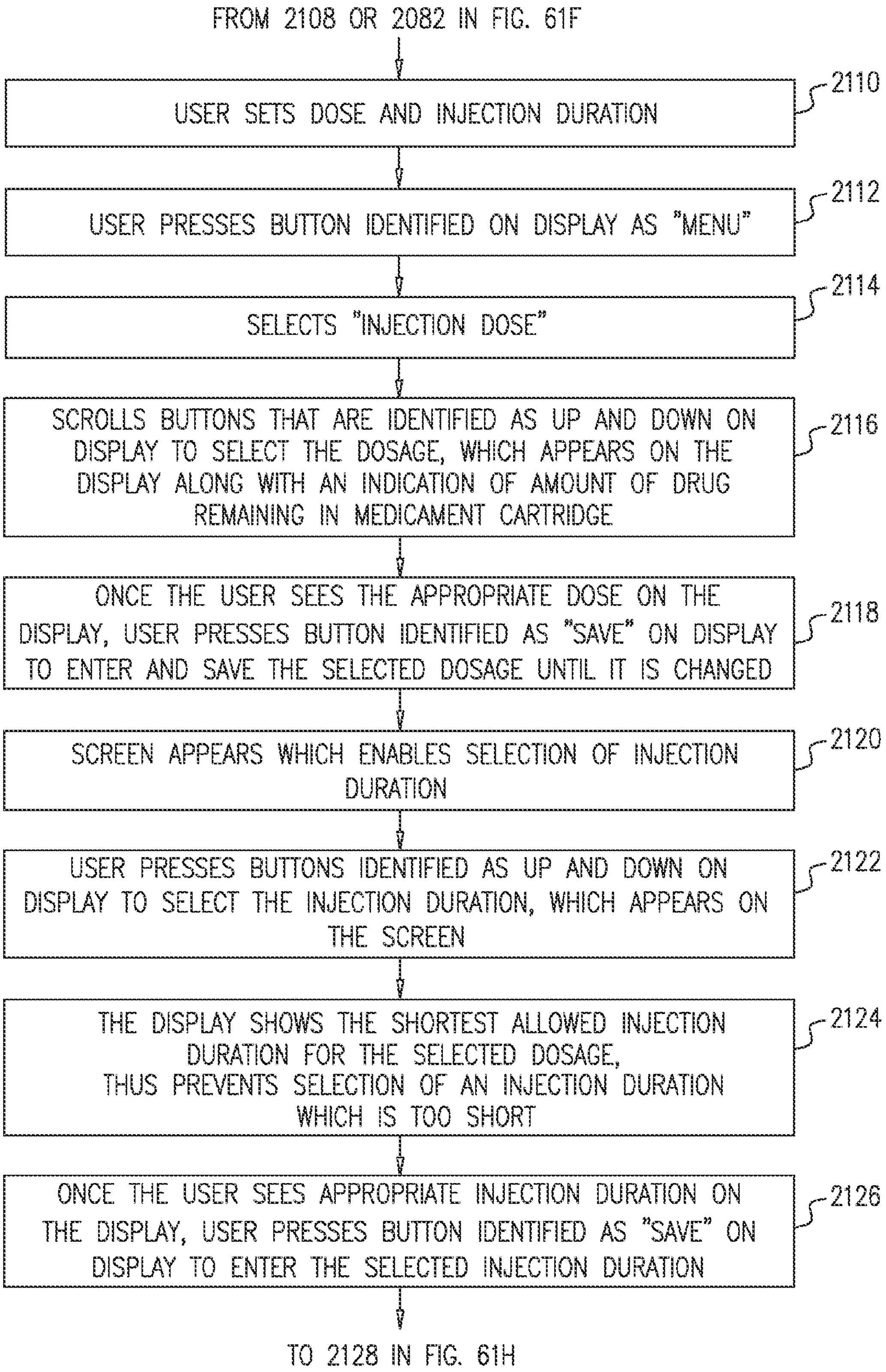
Figure 61H:
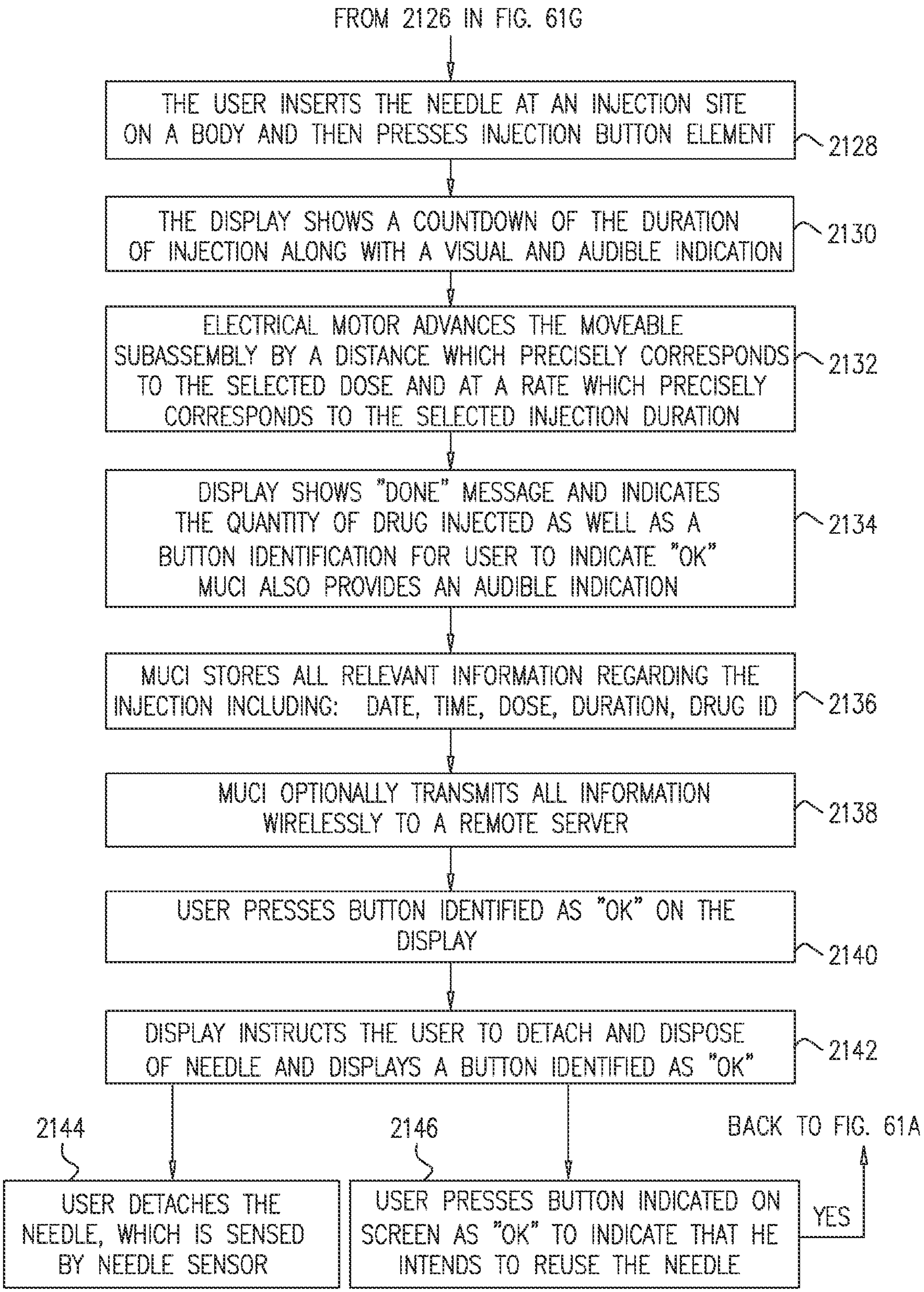

In FIG. 60B it is seen that the needle assembly 1150 along with needle cover 1156 are detached from the MUCI 100 and disposed of. It is appreciated that in this operative orientation, the needle sensor 782 assumes its triggered state, which indicates that no needle is attached to the MUCI 100, thus the display 106 instructs the user to attach needle.

It is noted that the MUCI 100 as shown in FIG. 60B is now ready for an additional injection of a medicament dose, as explained in detail hereinabove with reference to FIGS. 48A-60B. Alternatively, the user can remove the medicament cartridge 1100 from the MUCI 100 and insert it later on or insert a new medicament cartridge as described in detail with reference to FIGS. 22-60B.

It is a particular feature of an embodiment of the present invention that the MUCI 100 optionally includes a manually operable opener for the pivot mount element 180, which is operative to permit opening of the pivot mount element 180 under low-battery conditions. The electrical motor 158 is operative under low-battery conditions to operate the cartridge enclosure assembly latch element 210, such as to displace it longitudinally rearwardly, so as to enable opening of the pivot mount element 180 by the manually operable opener.

It is a further particular feature of an embodiment of the present invention that the medicament cartridge 1100, which is cylindrical and circularly symmetric, optionally bears an RFID transducer fixed thereto and containing information relating to the medicament. The MUCI 100 further has and an RFID communication antenna disposed within the main housing portion 102 and top housing portion 104 for communicating with the RFID transducer on the medicament cartridge 1100. The RFID communication antenna is operative to communicate with the RFID transducer irrespective of the rotational orientation of the medicament cartridge 1100 within the cartridge enclosure assembly 130. The RFID communication antenna is optionally a V-shaped antenna. The MUCI 100 may be operated at least partially based on information received from the RFID transducer.

It is a yet further particular feature of an embodiment of the present invention that optionally initiation of medicament injection is enabled only upon an indication related to at least partial performance of priming function.

Reference is now made to FIGS. 61A-61H, which are together a simplified flowchart illustrating operation of the electronic control assembly of the MUCI 100 of FIGS. 1A-21B).

Preferably, as shown in step 2000, when no cartridge is installed in the MUCI 100, such as out of the box or after previous use and removal of cartridge, the screen is blank and LEDs are not illuminated, as shown in step 2002 until the user presses on middle (on/off) button as seen in step 2004 and the MUCI 100 performs various checks (at outset and optionally throughout procedure), which are described hereinbelow in steps 2006 to 2022 and accordingly instructs the user.

Specifically, as shown in step 2006, the MUCI 100 checks whether the pivot mount element 180 is not unlatched, the needle 1152 is attached and medicament cartridge 1100 is not present. If all of the above conditions are fulfilled, then the display 1006 instructs the user to detach the needle 1152, as shown in step 2008.

Further, as shown in step 2010, the MUCI 100 checks whether the pivot mount element 180 is unlatched. Notwithstanding whether the needle 1152 is attached or whether the medicament cartridge 1100 is present, the display 1006 instructs the user to load medicament cartridge 1100 and close the pivot mount element 180, as shown in step 2012.

Yet further, as shown in step 2014, the MUCI 100 checks whether the pivot mount element 180 is not unlatched, the needle 1152 is not attached and medicament cartridge 1100 is present. If all of the above conditions are fulfilled, then the display 1006 instructs the user to attach needle 1152, as shown in step 2016.

Still further, as shown in step 2018, the MUCI 100 checks whether the pivot mount element 180 is not unlatched, the needle 1152 is attached and medicament cartridge 1100 is present. If all of the above conditions are fulfilled, then the display 1006 instructs the user to inject, as shown in step 2020.

Further specifically, as shown in step 2022, the MUCI 100 checks whether the pivot mount element 180 is not unlatched, the needle 1152 is not attached and medicament cartridge 1100 is not present. If all of the above conditions are fulfilled, then the status of the MUCI 100 is optionally shared with a remote server by wireless communication, as shown in step 2024 and the display 1006 instructs the user to open and load medicament cartridge 1100, as shown in step 2026.

Further, as shown in step 2028, the user presses button 354 identified on display 1006 as open and thereafter, as shown in step 2030, the user confirms by pressing button 350 identified on screen as "YES", which button is on opposite side of injector from button 354, pressed previously as shown in step 2028.

Following the pressing on button 350, the electrical motor 158 is operated rearwards x steps to retract moveable subassembly 1005, including the plunger rod element 230, by y mm (optionally using encoder either on the electrical motor or on motor-driven plunger rod element), and the moveable subassembly 1005 in turn operates a cartridge enclosure assembly latch element 210, thus opening the pivot mount element 180 for medicament cartridge 1100 insertion, as shown in step 2032.

Once the pivot mount element 180 is opened, the following occurs:

Cartridge enclosure assembly state sensor 784 indicates that the pivot mount element 180 is open, as shown in step 2034; The display 1006 instructs the user to insert medicament cartridge and close pivot mount element 180, as shown in step 2036; and the electrical motor 158 is operated forward z steps to reset cartridge enclosure assembly latch element to be ready to engage and retain the pivot mount element 180 when it is pressed and clicked by the user, as shown in step 2038.

Further, as shown in step 2040, the user inserts the medicament cartridge 1100 into injector and closes the pivot mount element 180, as shown in step 2040.

Following the insertion of the medicament cartridge 1100 by the user, the MUCI 100 optionally checks temperature of medicament in the medicament cartridge 1100 and if temperature is not within acceptable range, the MUCI 100 displays screen warning the user and could also prevent injection—further option—could warm the medicament which is too cold, as shown in step 2042 and then the display 106 instructs the user to attach needle 1152, as shown in step 2044. If one of the above conditions is not fulfilled, then the MUCI 100 instructs the user according to FIG. 61A.

Following step 2044, the electrical motor 158 is operated forward q steps to fully lock medicament cartridge assembly latch element 210, as shown in step 2046 and the MUCI 100 marks that priming is required, as shown in step 2048.

It is further seen in step 2052, that the user now should attach the needle 1152. If the user does not attach needle 1152, then the display 106 proceeds indicating to the user to attach needle 1552 or goes into sleep mode after a predetermined amount of time, as shown in step 2054. If the user attaches the needle 1152, then the needle sensor 782 indicates "YES", as shown in step 2056, and the MUCI 100 performs the checks according to steps 2006-2022 and if pivot mount element 180 is latched and needle 1152 is attached and medicament cartridge 1100 is present, as shown in step 2058, then the MUCI proceeds to step 2060, which is detailed further hereinbelow. If one of the above conditions is not fulfilled, then the MUCI 100 instructs the user according to FIG. 61A.

It is shown in step 2060 that the MUCI 100 initiates priming activity in two different cases. The first one is shown in step 2062, when priming was not earlier performed. The second one is shown in step 2064 when priming was earlier performed but the user nevertheless initiates priming by pressing "priming" button indicated on a menu screen.

Preferably, there are at least two alternatives for performing the priming process.

In accordance with a first alternative, it is shown in step 2066 that the display 106 instructs user to orient the MUCI 100 with needle 1152 pointing up. Further, the user orients the MUCI 100 with needle 1152 pointing up as shown in step 2068. Further, the user may press button identified on display 106 as "OK", to confirm that the MUCI 100 is oriented with needle 1152 pointing up, as shown in step 2070 or if the user does not press button as in step 2070 within 30 seconds, the MUCI 100 proceeds as if user had pressed the button, as shown in step 2072.

Further, display 106 shows that the MUCI 100, which is oriented with needle 1152 up, is ready for priming, by shifting the display 106 by 180 degrees as shown in step 2074.

Following step 2074, the user taps the MUCI 100 to dislodge air bubbles 1160 in the medicament cartridge 1100 and then presses button identified on the display 106 as "PRIME" and as long as the user continues pressing, the electrical motor 158 is operated to move the moveable subassembly 1005 upward in the medicament cartridge 1100, as shown in step 2076.

Once the user sees a drop of liquid at top of needle 1152, user stops pressing the prime button as shown in step 2078. If user still sees air bubbles 1160 in the medicament cartridge 1100, user repeats steps 2076 and 2078 until no air bubbles 1160 remain in the medicament cartridge 1100.

Further, it is shown in step 2080 that the user presses a different button identified on the display 106 as "DONE" in order to confirm that no air bubbles 1160 remain in the medicament cartridge 1100 and thus priming is completed, thus the display 106 instructs the user to inject and the display 106 shifts back by 180 degrees, as shown in step 2082.

In accordance with a second alternative, it is shown in step 2090 that the display 106 instructs the user to orient the MUCI 100 with needle pointing up. Further, the user orients the MUCI 100 with needle 1152 pointing up as shown in step 2092 and accelerometer (not shown) in the MUCI 100 confirms that the MUCI 100 is oriented with needle 1152 pointing up, following which the display 106 shows that the MUCI 100 oriented with needle 1152 up is ready for priming, by shifting the display 106 by 180 degrees, as shown in steps 2094 and 2096.

It is further shown in step 2098 that the electrical motor 158 is operated back and forth to create vibration for x seconds to dislodge air bubbles 1160 towards needle 1152. Preferably, as further shown in step 2100, the user presses button identified on display 106 as "AUTOPRIME" causing the electrical motor 158 to move the moveable subassembly 1005 upward in the medicament cartridge 1100 until the piston contact element 240 engages the piston 1104 and thereafter for a distance of y mm.

As is seen in step 2102, the user now checks to see if any air bubbles 1160 remain in the medicament cartridge. If so, user taps the MUCI 100 to dislodge air bubbles 1160 in the medicament cartridge 1100 and this tapping may be sensed by the accelerometer or by a different accelerometer. Further, the user presses button identified on the display 106 as "PRIME" and as long as user continues pressing, the electrical motor 158 is operated to move the moveable subassembly 105 upward in the medicament cartridge 1100. If air bubbles 1160 are still present in the medicament cartridge 1100, user repeats steps 2100 and 2102 until no air bubbles 1160 remain in the medicament cartridge 1100.

Further seen in step 2104 that once the user sees a drop of liquid at top of needle 1152, the user stops pressing the prime button. Once user confirms that no air bubbles 1160 remain in the medicament cartridge 1100, user presses different button identified on display 106 as "DONE" in order to confirm that priming is completed, as shown in step 2106. Further, the display 106 instructs the user to inject and the display 106 is shifted back by 180 degrees, as shown in step 2108.

Following the completion of the priming procedure, the user sets dose and injection duration, as shown in step 2110. The setting of dose and injection duration preferably includes the steps which are detailed hereinbelow in steps 2112-2126.

As shown in step 2112, the user presses button 350 identified on display 106 as "MENU" and selects "INJECTION DOSE" by scrolling with menu buttons up & down as shown in step 2114 and then presses buttons 350/354, that are identified as up and down on display 106 to select the dosage, which appears on the display 106 along with an indication of amount of medicament remaining in medicament cartridge 1100, as shown in step 2116.

Once the user sees the appropriate dose on the display 106, user presses button 352 identified as "SAVE" on display 106 to enter and save the selected dosage until it is changed, as shown in step 2118.

Step 2120 show that display 106 appears which enables selection of injection duration, then the user presses buttons 350/354 identified as up and down on display 106 to select the injection duration, which appears on the screen, as shown in step 2122.

It is a particular feature of an embodiment of the present invention as is shown in step 2124 that the MUCI 100 does not permit the user to select an injection duration which is too short, the display 106 shows the shortest allowed injection duration for the selected dosage. This function allows controlling the injection speed and preventing setting of injection speed above a pre-determined threshold, which could be harmful for the user.

Once the user sees the appropriate injection duration on the display 106, user presses button 352 identified as "SAVE" on display 106 to enter the selected injection duration, as shown in step 2126.

Once the setting stage is completed, the user preferably inserts the needle 1152 at an injection site on a body up to the hilt and then presses injection button element 120 preferably with his thumb, as shown in step 2128. Pressing the injection button element 120 produces two results: the display 106 shows a countdown of the duration of injection, preferably along with an audible indication and a visual indication, such as LEDs illuminating around the injection button element 120, as shown in step 2130 and the electrical motor 158 advances the moveable subassembly 1005 by a distance which precisely corresponds to the selected dose and at a rate which precisely corresponds to the selected injection duration, as shown in step 2132.

Preferably, the display 106 then shows a "DONE" message and indicates the quantity of medicament injected as well as a button identification for user to indicate "OK", as shown in step 2134 and the MUCI 100 also provides an audible indication at the end of injection process. It is shown in step 2136 that the MUCI 100 stores all relevant information regarding the injection including: date, time, dose, duration, medicament id. The MUCI 100 may optionally transmit all such information wirelessly to a remote server, as shown in step 2138.

Following injection completion, the user preferably presses button 352, identified as "OK" on the display 106, as shown in step 2140, then the display 106 instructs the user to detach and dispose of needle 1152 and displays a button identified as "OK", as shown in step 2142.

At this stage, the user has two alternatives to choose from: the first alternative is shown in step 2144, when the user detaches needle 1152, which is sensed by needle sensor 782; the second alternative is shown in step 2146, when the user presses button 352 indicated on screen as "OK" to indicate that he intends to reuse needle 1152.

It is appreciated that at this stage the MUCI 100 is ready for an additional injection.

It will be appreciated by persons skilled in the art that the present invention is not limited by what has been particularly shown and described hereinabove. Rather the present invention includes both combinations and subcombinations of various features described herein and improvements and variations which would occur to persons skilled in the art upon reading the foregoing description and which are not in the prior art.

The invention claimed is:

1. A computer-controlled injector for use with a medicament cartridge and comprising:

a housing including a medicament cartridge receiving volume and a medicament cartridge insertion and removal opening communicating with said medicament cartridge receiving volume;

a pivot mount element mounted onto said housing for selectably enabling access to said medicament cartridge receiving volume via said opening;

a mechanical latch selectably locking said pivot mount element in a closed operative orientation;

a computer interactive user interface including a display and user input facility, said computer interactive user interface providing a prompt to said user to perform opening of said pivot mount element and requiring a confirmatory user input to initiate said opening;

and an injection drive mechanism including a computer-controlled motor for driving a piston, forming part of said medicament cartridge, for injecting a medicament, said computer-controlled motor also being operative for operating said mechanical latch in response to operation of said user input.

2. The computer-controlled injector according to claim 1 and also comprising a moveable subassembly, which is linearly displaceable by said computer-controlled motor for linearly displacing said piston, said moveable subassembly including a mechanical latch engagement portion which engages said mechanical latch when said moveable subassembly is at a predetermined linear position with respect to said medicament cartridge.

3. The computer-controlled injector according to claim 2 and wherein said mechanical latch engagement portion unlatches said mechanical latch, thereby allowing opening of said pivot mount element, only when said moveable subassembly is entirely retracted from said medicament cartridge.

4. The computer-controlled injector according to claim 2 and wherein when said moveable subassembly is disposed in a forward operative orientation, said mechanical latch is latched and urges said pivot mount element to assume said closed operative orientation; when said moveable subassembly is disposed in a rearward operative orientation, said mechanical latch is unlatched and urges said pivot mount element to assume an open operative orientation and when said moveable subassembly is disposed in an intermediate operative orientation, said mechanical latch urges said pivot mount element to assume a snapped operative orientation.

5. The computer-controlled injector according to claim 1 and also comprising a biasing element operative to open said pivot mount element except when said pivot mount element is locked in said closed operative orientation by said mechanical latch.

6. The computer-controlled injector according to claim 1 and wherein said pivot mount element is pivotably mounted onto said housing.

7. The computer-controlled injector according to claim 1 and wherein said pivot mount element comprises a threaded portion for mounting of a needle assembly thereon.

8. The computer-controlled injector according to claim 1 and also comprising a needle presence responsive element, configured to be coupled to said pivot mount element, and being axially displaceable, thereby indicating mounting of a needle assembly to said pivot mount element.

9. The computer-controlled injector according to claim 1 and wherein said mechanical latch is biased to be positioned in a locked operative orientation by the biasing force of a biasing element.

10. The computer-controlled injector according to claim 1 and also comprising a PCB assembly including at least one of: a cartridge sensor, which is configured to indicate whether said medicament cartridge is inserted into said medicament cartridge receiving volume, a needle sensor, which is configured to indicate whether a needle assembly is mounted to said pivot mount element, and a cartridge enclosure assembly state sensor, which is configured to indicate whether said pivot mount element is disposed in an open or a closed operative orientation.

11. A computer-controlled injector for use with a medicament cartridge and comprising:

a housing including a medicament cartridge receiving volume and a medicament cartridge insertion and removal opening communicating with said medicament cartridge receiving volume;

a pivot mount element mounted onto said housing for selectably enabling access to said medicament cartridge receiving volume via said opening;

a computer interactive user interface including a display and user input facility, said computer interactive user interface providing a prompt to said user to perform opening of said pivot mount element; and requiring a confirmatory user input to initiate said opening; and an injection drive mechanism including a computer-controlled motor for driving a piston, forming part of said medicament cartridge, for injecting a medicament, said computer-controlled motor also being operative for enabling opening of said pivot mount element in response to operation of said user input facility.

12. The computer-controlled injector according to claim 11 and also comprising a moveable subassembly, which is linearly displaceable by said computer-controlled motor for linearly displacing said piston, said moveable subassembly including a mechanical latch engagement portion which engages said mechanical latch when said moveable subassembly is at a predetermined linear position with respect to said medicament cartridge.

13. The computer-controlled injector according to claim 11 and also comprising a biasing element operative to open said pivot mount element except when said pivot mount element is locked in said closed operative orientation by said mechanical latch.

14. The computer-controlled injector according to claim 11 and also comprising a needle presence responsive element, configured to be coupled to said pivot mount element, and being axially displaceable, thereby indicating mounting of a needle assembly to said pivot mount element.

15. The computer-controlled injector according to claim 11 and wherein said mechanical latch is biased to be positioned in a locked operative orientation by the biasing force of a biasing element.

16. A computer-controlled injection method for use with a medicament cartridge and an injector including:

a housing including a medicament cartridge receiving volume and a medicament cartridge insertion and removal opening communicating with said medicament cartridge receiving volume;

a pivot mount element mounted onto said housing for selectably enabling access to said medicament cartridge receiving volume via said opening, said pivot mount element being normally open unless latched closed;

a computer interactive user interface including a display and user input facility, said computer interactive user interface providing a prompt to said user to perform opening of said pivot mount element and requiring a confirmatory user input to initiate said opening; and an injection drive mechanism including a computer-controlled motor for driving a piston, forming part of said medicament cartridge, for injecting a medicament, the method comprising: operating said computer-controlled motor for permitting said pivot mount element to assume a biased open operational orientation to permit insertion of said medicament cartridge into said medicament cartridge receiving volume;

thereafter, manually pushing the pivot mount element to a closed position;

thereafter, automatically operating said computer-controlled motor to lock said pivot mount element in said closed position, thereby preventing opening of said pivot mount element;

thereafter, operating said computer-controlled motor for driving said piston; thereafter, operating said user input facility to enable opening of said pivot mount element by said computer-controlled motor.

17. The computer-controlled injection method according to claim 16 and wherein operating said computer-controlled motor comprises positioning of a mechanical latch in an unlocked operative orientation for permitting said pivot mount element to assume said biased open operational orientation.

18. The computer-controlled injection method according to claim 17 and also comprising employing a biasing element operative to open said pivot mount element except when said pivot mount element is locked in said closed operative orientation by said mechanical latch.

19. The computer-controlled injection method according to claim 16 and also comprising a needle presence responsive element, configured to be coupled to said pivot mount element, and being axially displaceable, thereby indicating mounting of a needle assembly to said pivot mount element.

20. The computer-controlled injection method according to claim 16 and also comprising a PCB assembly including at least one of a cartridge sensor, which is configured to indicate whether said medicament cartridge is inserted into said medicament cartridge receiving volume, a needle sensor, which is configured to indicate whether a needle assembly is mounted to said pivot mount element, and a cartridge enclosure assembly state sensor, which is configured to indicate whether said pivot mount element is disposed in an open or a closed operative orientation.

* * * * *